US012662477B2

(12) United States Patent
Siddiqui et al.

(10) Patent No.: US 12,662,477 B2
(45) **Date of Patent: *Jun. 23, 2026**

(54) SUBSTITUTED PYRAZOLE COMPOUNDS AND METHODS OF USING THEM FOR TREATMENT OF HYPERPROLIFERATIVE DISEASES

(71) Applicant: Bantam Pharmaceutical, LLC, New York, NY (US)

(72) Inventors: M. Arshad Siddiqui, Newton, MA (US); Stephane Ciblat, Montreal (CA); Martin Dery, Montreal (CA); Lea Constantineau-Forget, Montreal (CA); Chantal Grand-Maitre, Boisbriand (CA); Nicolas Bruneau-Latour, Ste. Genevieve (CA); Gerald W. Shipps, Boston, MA (US); Alan B. Cooper, Kenilworth, NJ (US); Vibha Oza, Acton, MA (US); Matthew J. Kostura, Hillsborough, NC (US); Michael Luther, Andover, MA (US); Jedd Levine, Litchfield, CT (US)

(73) Assignee: Bantam Pharmaceutical, LLC, New York, NY (US)

( * ) Notice: Subject to any disclaimer, the term of this patent is extended or adjusted under 35 U.S.C. 154(b) by 387 days.

This patent is subject to a terminal disclaimer.

(21) Appl. No.: 17/741,153

(22) Filed: May 10, 2022

(65) Prior Publication Data

US 2023/0076820 A1 Mar. 9, 2023

Related U.S. Application Data

(63) Continuation of application No. 16/465,136, filed as application No. PCT/US2017/063774 on Nov. 29, 2017, now Pat. No. 11,325,903.

(Continued)

(51) Int. Cl.
*C07D 417/14* (2006.01)
*A61K 31/4155* (2006.01)
(Continued)

(52) U.S. Cl.
CPC ............ *C07D 417/14* (2013.01); *A61P 35/00* (2018.01); *C07D 403/04* (2013.01); *C07D 417/04* (2013.01); *C07D 451/02* (2013.01)

(58) Field of Classification Search
CPC .. C07D 417/14; C07D 417/04; C07D 403/04; A61K 31/4155; A61K 31/426; A61K 31/427; A61K 31/4196; A61P 35/00
See application file for complete search history.

(56) References Cited

U.S. PATENT DOCUMENTS

| | | | |
|---|---|---|---|
| 6,468,979 | B1 | 10/2002 | Pellacini |
| 6,649,636 | B1 | 11/2003 | Ando |

(Continued)

FOREIGN PATENT DOCUMENTS

| | | | |
|---|---|---|---|
| EP | 2264017 | A1 | 12/2010 |
| EP | 2275414 | B1 | 6/2015 |

(Continued)

OTHER PUBLICATIONS

Anand et al., Curcumin and Cancer: An “old-age” disease with an “age-old” solution, Cancer Letters, vol. 267, No. 1, Aug. 18, 2008, pp. 133-164.

(Continued)

*Primary Examiner* — Kamal A Saeed
*Assistant Examiner* — Sagar Patel
(74) *Attorney, Agent, or Firm* — McDonnell Boehnen Hulbert & Berghoff LLP

(57) ABSTRACT

Disclosed are compounds useful, for example, in methods of treating hyperproliferative disorders such as cancer, methods of arresting the cell cycle in cancer cells, methods of inhibiting glutathione synthesis in cancer cells, and associated compounds for use and uses in medicaments. In certain embodiments, the methods, uses and compounds are provided with reference to compounds of the structural formulae (Continued)

-continued

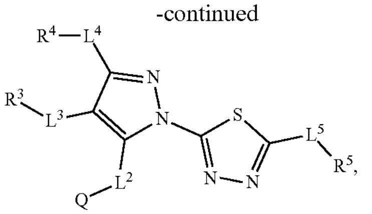

and

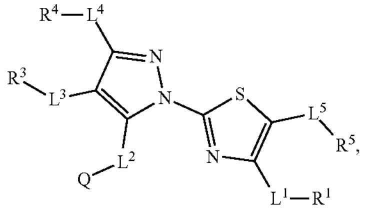

in which $R^1$, $L^1$, $L^2$, Q, $L^3$, $R^3$, $L^4$, $R^4$, $L^5$, and $R^5$ are as described herein. In certain embodiments, compounds disclosed herein are especially active against cancers having a mutant KRAS gene.

22 Claims, 5 Drawing Sheets

Related U.S. Application Data

(60) Provisional application No. 62/428,271, filed on Nov. 30, 2016.

(51) Int. Cl.

| | |
|---|---|
| *A61K 31/4196* | (2006.01) |
| *A61K 31/426* | (2006.01) |
| *A61K 31/427* | (2006.01) |
| *A61P 35/00* | (2006.01) |
| *C07D 403/04* | (2006.01) |
| *C07D 417/04* | (2006.01) |
| *C07D 451/02* | (2006.01) |

(56) References Cited

U.S. PATENT DOCUMENTS

| | | | | |
|---|---|---|---|---|
| 10,537,558 | B2 | 1/2020 | Siddiqui | |
| 11,325,903 | B2 * | 5/2022 | Siddiqui .............. | A61K 31/427 |
| 2003/0220356 | A1 | 11/2003 | Ibrahim | |
| 2011/0028493 | A1 | 2/2011 | Matsunaga | |
| 2015/0274717 | A1 | 10/2015 | Patane | |
| 2020/0261424 | A1 | 8/2020 | Siddiqui | |
| 2022/0162204 | A1 * | 5/2022 | Cooper ................ | A61K 31/427 |

FOREIGN PATENT DOCUMENTS

| | | | | |
|---|---|---|---|---|
| WO | 2004089303 | A2 | 10/2004 | |
| WO | 2004094395 | A2 | 11/2004 | |
| WO | 2007138110 | A2 | 12/2007 | |
| WO | 2008121861 | W | 10/2008 | |
| WO | 2009027393 | A2 | 3/2009 | |
| WO | 2014066304 | A1 | 5/2014 | |
| WO | 2015144290 | W | 10/2015 | |
| WO | 2016169886 | W | 10/2016 | |
| WO | 2016196644 | W | 12/2016 | |
| WO | WO-2016196644 | A1 * | 12/2016 | ........... A61K 31/427 |

OTHER PUBLICATIONS

International Search Report mailed Mar. 6, 2018 for International Application No. PCT/US2017/063774 filed Nov. 29, 2017, 3 pages.

PUBCHEM, 4-{4-fluorophenyl)-1-[4-4{4-fluorophenyl)-1, 3-thiazol-2-yl]-1 Hpyrazol-5-amine, Jul. 11, 2005, pp. 1-7.

Rida et al., "Synthesis of novel benzofuran and related benzimidazole derivatives for evaluation of in vitro anti-HIV-1, anticancer and antimicrobial activities," Archives of Pharmacal Research., vol. 29, No. 10, Oct. 1, 2006, pp. 826-833.

Jadhav et al., Oriental Journal of Chemistry, 2015, pp. 967-972, vol. 31, No. 2.

Duan et al., Bioorganic & Medicinal Chemistry: A Tetrahedron Publication For The Rapid Dissemination of Full Original Research Papers and Critical Review on Biomolecular Chemistry, Medicinal Chemistry and Related Disciplines, 2015, pp. 611-6117, vol. 23, No. 18, NL.

* cited by examiner

DMSO

Serum Starvation

Test Compound

SUBSTITUTED PYRAZOLE COMPOUNDS AND METHODS OF USING THEM FOR TREATMENT OF HYPERPROLIFERATIVE DISEASES

CROSS-REFERENCE TO RELATED APPLICATIONS

This application is a continuation of U.S. patent application Ser. No. 16/465,136, filed May 29, 2019, which is a U.S. National Stage filing of International Patent Application no. PCT/US2017/063774, filed Nov. 29, 2017, which claims the benefit of priority of U.S. Provisional Patent Application No. 62/428,271, filed Nov. 30, 2016, each of which is hereby incorporated herein by reference in its entirety.

BACKGROUND OF THE DISCLOSURE

Field

This disclosure relates to the field of compounds, pharmaceutical compositions comprising them, and methods of using the compounds and compositions. This disclosure relates more particularly to methods for using certain compounds for the treatment of hyperproliferative disorders such as cancer.

Technical Background

Cancer, an uncontrolled proliferation of cells, is a multifactorial disease characterized by tumor formation, growth, and in some instances, metastasis. In the United States this year, over 1.5 million people will be diagnosed with cancer, and more than 500,000 people will die from cancer. Overall it is estimated that at least one in three people will develop some form of cancer during their lifetime. There are more than 200 different histopathological types of cancer, with breast, lung, colorectal, and prostate accounting for over half of all new cases in the U.S. Current cancer therapies vary depending upon the localization and stage of the cancer but generally include a combination of surgery, systemic therapy, radiation therapy, and chemotherapy. Despite the effort that has been devoted to the development of anti-cancer strategies, many of them remain unefficacious for specific cancers.

The uncontrolled cell proliferation that represents the essence of cancer involves not only deregulated control of cell proliferation but also corresponding adjustments of energy metabolism in order to fuel cell growth and division. The reprogramming of cell metabolism is emerging as an important molecular hallmark of cancer cells. Under aerobic conditions, normal cells process glucose, first to pyruvate via glycolysis in the cytosol and thereafter to carbon dioxide in the mitochondria; under anaerobic conditions, glycolysis is favored and relatively little pyruvate is dispatched to the oxygen-consuming mitochondria. When growth factors and nutrients are abundant, oncogenic signaling pathways direct enhanced metabolism leading to increased synthesis of macromolecules such as lipids, proteins and nucleic acids. The net effect is the support of cell growth and proliferation. During tumor formation, however, a harsh, anoxic, nutrient deprived environment exists that challenges the cell and its ability to maintain metabolic homeostasis. Cancer cells can reprogram their glucose metabolism, and thus their energy production, by limiting their energy metabolism largely to glycolysis, which was seen by early biochemists as primitive and inefficient. Despite these early beliefs, the metabolic signatures of cancer cells are not passive responses to damaged mitochondria, but result from oncogene-directed metabolic reprogramming required to support anabolic growth. Oncogene mutations that allow for increased and more efficient utilization of scarce nutrients present unique targets in treatment of cancer.

SUMMARY OF THE DISCLOSURE

In one aspect, the disclosure provides compounds having any of structural formulae (Ia)-(Ie):

(Ia)

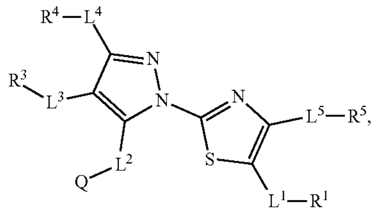

(Ib)

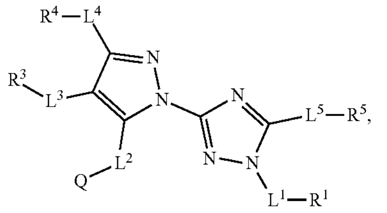

(Ic)

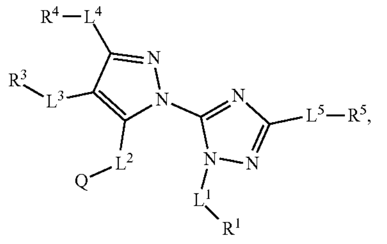

(Id)

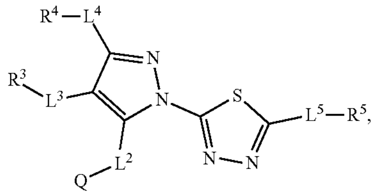

(Ie)

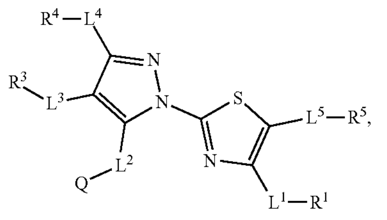

optionally in the form of a pharmaceutically acceptable salt or N-oxide, and/or a solvate or hydrate, wherein $L^1$ is selected from the group consisting of a bond, —C(O)—, —S—, —$S(O)_{1-2}$—, —O—, —$NR^6$—, —C(O)$NR^6$—, —$NR^6$C(O)—, —C(S)$NR^6$—, —$NR^6$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}$ $NR^6$— and —$NR^6$$S(O)_{1-2}$—;

$R^1$ is selected from the group consisting of hydrogen, $C_1$-$C_8$ alkyl, $C_1$-$C_8$ alkenyl and $C_1$-$C_8$ alkynyl, each unsubstituted or fluorinated, cycloalkyl and heterocycloalkyl, each optionally substituted with 1-2 $R^{1E}$, and phenyl and monocyclic heteroaryl, each optionally substituted with 1-5 $R^{1E}$, in which each $R^{1E}$ is independently selected from oxo, optionally-substituted $C_1$-$C_4$ alkyl, $C_1$-$C_4$ fluoroalkyl, halogen, —CN, $SF^3$, —$N_3$, —C(O)$R^{1F}$, —S$R^{1F}$, —$S(O)_{1-2}R^{1F}$, —O$R^{1F}$, —$(OCH_2CH_2O)_n$—$R^{1G}$ in which n is 1-4, —N($R^{1G}$)C(O)$CH_2$—O—$(CH_2CH_2O)_nR^{1G}$ in which n is 0-3, —C(O)N$R^{1G}$$(CH_2CH_2O)_nR^{1G}$, —N$R^{1G}R^{1F}$ and —C(O)$R^{1F}$;

each $R^{1F}$ is independently selected from H, $C_1$-$C_3$ alkyl and $C_1$-$C_3$ fluoroalkyl and each $R^{1G}$ is independently selected from H and $C_1$-$C_3$ alkyl;

$L^2$ is selected from the group consisting of a bond, —$CH_2$—, —$CH(CH_3)$— or —$CH_2CH_2$—;

Q is selected from the group consisting of H, —$CH_2OH$, —C(O)OH, —C(O)O$R^{2A}$, —C(O)N$R^{2B}R^{2A}$, —C(O)N$R^{2B}$$S(O)_2R^{2A}$, —C(O)N$R^{2B}$$S(O)_2$N$R^{2B}R^{2A}$, —O(O)$R^{2A}$, —$S(O)_2$OH, —P(O)$(OH)_2$, —C(OH)$(CF_3)_2$, $S(O)_2$ $R^{2A}$, —N($R^{2B}$)$S(O)_2R^{2A}$, —$S(O)_2$N$R^{2B}R^{2A}$, —C(O)NHOH, —C(O)NH—O($C_1$-$C_3$ alkyl), and —CO(NH)CN, in which each $R^{2A}$ is independently selected from H and $C_1$-$C_3$ alkyl, and each $R^{2B}$ is independently selected from H and $C_1$-$C_3$ alkyl;

$L^3$ is a bond, —C(O)—, —S—, —$S(O)_{1-2}$—, —O—, —N$R^6$—, —$CH_2$—, —$CH(CH_3)(OH)$— or —CH(OH)—;

$R^3$ is aryl or heteroaryl each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$, in which each $L^{3C}$ is a bond, methylene, ethylene, —C(O)—, —S—, —$S(O)_{1-2}$—, —O— or —N$R^{3G}$—, each $R^{3D}$ is independently selected from oxo optionally-substituted $C_1$-$C_4$ alkyl, $C_1$-$C_4$ fluoroalkyl, halogen, —CN, $SF_5$, —$N_3$, —C(O)$R^{3F}$, —S$R^{3F}$, —$S(O)_{1-2}R^{3F}$, —O$R^{3F}$, —N$R^{3G}R^{3F}$, —C(O)$R^{3F}$, —C(O)N$R^{3G}R^{3F}$, —N$R^{3G}$C(O)$R^{3F}$, —C(S)N$R^{3G}R^{3F}$, —N$R^{3G}$C(S)$R^{3F}$, —C(O)O$R^{3F}$, —OC(O)$R^{3F}$, —C(O)S$R^{3F}$, —SC(O)$R^{3F}$, —C(S)O$R^{3F}$, —OC(S)$R^{3F}$, —C(S)S$R^{3F}$, —SC(S)$R^{3F}$, —$S(O)_{1-2}$O$R^{3F}$, —O$S(O)_{1-2}R^{3F}$, $S(O)_{1-2}$N$R^{3G}R^{3F}$ and —N$R^{3G}$$S(O)_{1-2}R^{3F}$;

each $R^{3E}$ is independently selected from oxo, optionally-substituted $C_1$-$C_4$ alkyl, $C_1$-$C_4$ fluoroalkyl, halogen, —CN, $SF_5$, —$N_3$, —C(O)$R^{3F}$, —S$R^{3F}$, —$S(O)_{1-2}R^{3F}$, O$R^{3F}$, —N$R^{3G}R^{3F}$, —C(O)$R^{3F}$, —C(O)N$R^{3G}R^{3F}$, —N$R^{3G}$C(O)$R^{3F}$, —C(S)N$R^{3G}R^{3F}$, —N$R^{3G}$C(S)$R^{3F}$, —C(O)O$R^{3F}$, —OC(O)$R^{3F}$, —C(O)S$R^{3F}$, —SC(O)$R^{3F}$, —C(S)O$R^{3F}$, —OC(S)$R^{3F}$, —C(S)S$R^{3F}$, —SC(S)$R^{3F}$, —$S(O)_{1-2}$O$R^{3F}$, —O$S(O)_{1-2}R^{3F}$, —$S(O)_{1-2}$N$R^{3G}R^{3F}$, —N$R^{3G}$$S(O)_{1-2}R^{3F}$;

each $R^{3F}$ is independently selected from H, $C_1$-$C_3$ alkyl and $C_1$-$C_3$ fluoroalkyl and each $R^{3G}$ is independently selected from H and $C_1$-$C_3$ alkyl, $C_1$-$C_3$ fluoroalkyl;

$L^4$ is selected from the group consisting of a bond, —C(O)—, —S—, —$S(O)_{1-2}$—, —O—, —N$R^6$—, —C(O)N$R^6$—, —N$R^6$C(O)—, —C(S)N$R^6$—, —N$R^6$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}$N$R^6$— and —N$R^6$$S(O)_{1-2}$—;

$R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl;

$L^5$ is a bond, —C(O)—, —S—, —$S(O)_{1-2}$—, —O—, —N$R^6$—, —$CH_2CH_2$—, —CH═CH—, —C≡C—, —$CH_2$—, —$CH(CH_3)(OH)$— or —CH(OH)—; and $R^5$ is aryl, heteroaryl, cycloalkyl or heterocycloalkyl, each (i) optionally substituted with a single substituent selected from -$L^{5C}$-(phenyl optionally substituted with 1-5 $R^{5D}$), -$L^{5C}$-(monocyclic heteroaryl optionally substituted with 1-5 $R^{5D}$), and -$L^{5C}$-(monocyclic cycloalkyl optionally substituted with 1-5 $R^{5D}$), -$L^{5C}$-(monocyclic heterocycloalkyl optionally substituted with 1-5 $R^{5D}$) and (ii) optionally substituted with 1-5 $R^{5E}$, in which each $L^{5C}$ is a bond, methylene, ethylene, —C(O)—, —S—, —$S(O)_{1-2}$—, —O— or —N$R^{3G}$—;

each $R^{5D}$ is independently selected from oxo, optionally-substituted $C_1$-$C_4$ alkyl, $C_1$-$C_4$ fluoroalkyl, halogen, —CN, $SF_5$, —$N_3$, —C(O)$R^{3F}$, —S$R^{3F}$, —$S(O)_{1-2}R^{3F}$, —O$R^{3F}$, —N$R^{3G}R^{3F}$, —C(O)$R^{3F}$, —C(O)N$R^{3G}R^{3F}$, —N$R^{3G}$C(O)$R^{3F}$, —C(S)N$R^{3G}R^{3F}$, —N$R^{3G}$C(S)$R^{3F}$, —C(O)O$R^{3F}$, —OC(O)$R^{3F}$, —C(O)S$R^{3F}$, —SC(O)$R^{3F}$, —C(S)O$R^{3F}$, —OC(S)$R^{3F}$, —C(S)S$R^{3F}$, —SC(S)$R^{3F}$, —$S(O)_{1-2}$O$R^{3F}$, —O$S(O)_{1-2}R^{3F}$, —$S(O)_{1-2}$N$R^{3G}R^{3F}$ and —N$R^{3G}$$S(O)_{1-2}R^{3F}$;

each $R^{5E}$ is independently selected from oxo, optionally-substituted $C_1$-$C_4$ alkyl, $C_1$-$C_4$ fluoroalkyl, halogen, —CN, —$SF_5$, —$N_3$, —C(O)$R^{5F}$, —S$R^{5F}$, —$S(O)_{1-2}R^{5F}$, —O$R^{5F}$, —N$R^{5G}R^{5F}$, —C(O)$R^{5F}$, —C(O)N$R^{5G}R^{5F}$, —N$R^{5G}$C(O)$R^{5F}$, —C(S)N$R^{5G}R^{5F}$, —N$R^{1G}$C(S)$R^{5F}$, —C(O)O$R^{5F}$, —OC(O)$R^{5F}$, —C(O)S$R^{5F}$, —SC(O)$R^{5F}$, —C(S)O$R^{5F}$, —OC(S)$R^{5F}$, —C(S)S$R^{5F}$, —SC(S)$R^{5F}$, —$S(O)_{1-2}$O$R^{5F}$, —O$S(O)_{1-2}R^{5F}$, $S(O)_{1-2}$N$R^{5G}R^{5F}$ and —N$R^{5G}$$S(O)_{1-2}R^{5F}$;

each $R^{5F}$ is independently selected from H, $C_1$-$C_3$ alkyl and $C_1$-$C_3$ fluoroalkyl and each $R^{5G}$ is independently selected from H and $C_1$-$C_3$ alkyl;

wherein each $R^6$ is selected from the group consisting of hydrogen, $C_1$-$C_3$ alkyl and —C(O)($C_1$-$C_3$ alkyl));

each optionally substituted alkyl, alkenyl and alkynyl is unsubstituted, fluorinated or substituted with one or two hydroxyl groups;

each cycloalkyl has 3-10 ring carbons and is unsaturated or partially unsaturated, and optionally includes one or two fused cycloalkyl rings, each fused ring having 3-8 ring members;

each heterocylcloalkyl has 3-10 ring members and 1-3 heteroatoms independently selected from nitrogen, oxygen and sulfur and is unsaturated or partially unsaturated, and optionally includes one or two fused cycloalkyl rings, each having 3-8 ring members;

each aryl is a phenyl or a naphthyl, and optionally includes one or two fused cycloalkyl or heterocycloalkyl rings, each fused cycloalkyl or heterocycloalkyl ring having 4-8 ring members;

each heteroaryl is a 5-6 membered monocyclic heteroaryl ring having 1-4 heteroatoms independently selected from nitrogen, oxygen and sulfur or a 8-10 membered bicyclic heteroaryl having 1-5 heteroatoms independently selected from nitrogen, oxygen or sulfur, and optionally includes one or two fused cycloalkyl or heterocycloalkyl rings, each fused cycloalkyl or heterocycloalkyl ring having 4-8 ring members.

In certain such embodiments, each and every optionally substituted alkyl, alkylene, alkenyl, alkenylene, alkynyl and alkynylene is unsubstituted or fluorinated. For example, in certain such embodiments, each and every optionally substituted alkyl, alkylene, alkenyl, alkenylene, alkynyl and alkynylene is unsubstituted.

In another aspect, the disclosure provides pharmaceutical compositions comprising a compound as described herein.

In another aspect, the disclosure provides a method for treating a hyperproliferative disorder such as cancer in a subject in need thereof. The method includes administering to the subject an effective amount of a compound as described herein.

In another aspect, the disclosure provides compounds as described herein for use in treating hyperproliferative disorders such as cancer.

In another aspect, the disclosure provides the use of a compound as described herein for the preparation of a medicament for the treatment of a hyperproliferative disorder such as cancer.

In certain embodiments of the various aspects of the disclosure, the hyperproliferative disorder is a hematopoietic cancer. In certain alternative embodiments of the disclosure, the hyperproliferative disorder is a solid tumor.

In certain embodiments of the various aspects of the disclosure, the hyperproliferative disorder is a cancer (e.g., a solid tumor such as a colorectal cancer, a lung cancer or a pancreatic cancer) having a mutant KRAS gene, e.g., a heterozygous mutant KRAS gene.

Another aspect of the disclosure provides a method for inhibiting cell cycle progression in a cancer cell. The method includes contacting the cancer cell with an effective amount of a compound as described herein. In certain such embodiments, the cancer cell is a hematopoietic cancer cell. In other such embodiments, the cancer cell is a cancer cell of a solid tumor (e.g., a pancreatic cancer, a lung cancer, or a colorectal cancer). In certain such embodiments, the cancer cell has a heterozygous mutant KRAS gene. Cell cycle progression can be inhibited, for example, at the G0/G1 phase.

Another aspect of the disclosure provides a method for inducing apoptosis of a cancer cell. The method includes contacting the cancer cell with an effective amount of a compound as described herein. In certain such embodiments, the cancer cell is a hematopoietic cancer cell.

Another aspect of the disclosure provides a method for inducing cytotoxic effect of a cancer cell. The method includes contacting the cancer cell with an effective amount of a compound as described herein. In certain such embodiments, the cancer cell is a hematopoietic cancer cell. In other such embodiments, the cancer cell is a cancer cell of a solid tumor (e.g., a pancreatic cancer, a lung cancer, or a colorectal cancer). In certain such embodiments, the cancer cell has a heterozygous mutant KRAS gene.

Another aspect of the disclosure provides a method for inhibiting glutathione synthesis in a cancer cell. The method includes contacting the cancer cell with an effective amount of a compound as described herein. In certain such embodiments, the cancer cell is a hematopoietic cancer cell. In other such embodiments, the cancer cell is a cancer cell of a solid tumor (e.g., a pancreatic cancer, a lung cancer, or a colorectal cancer). In certain such embodiments, the cancer cell has a heterozygous mutant KRAS gene.

In certain embodiments, the compound used in the methods, compounds and uses described herein is a compound of any of the structural formulae (I) below:

Other aspects and embodiments of the disclosure are evident in view of the detailed description provided herein.

All publications referenced herein are hereby incorporated herein by reference in their entirety to the extent they are not inconsistent with the specific disclosure provided herein.

DETAILED DESCRIPTION

Figure 1:
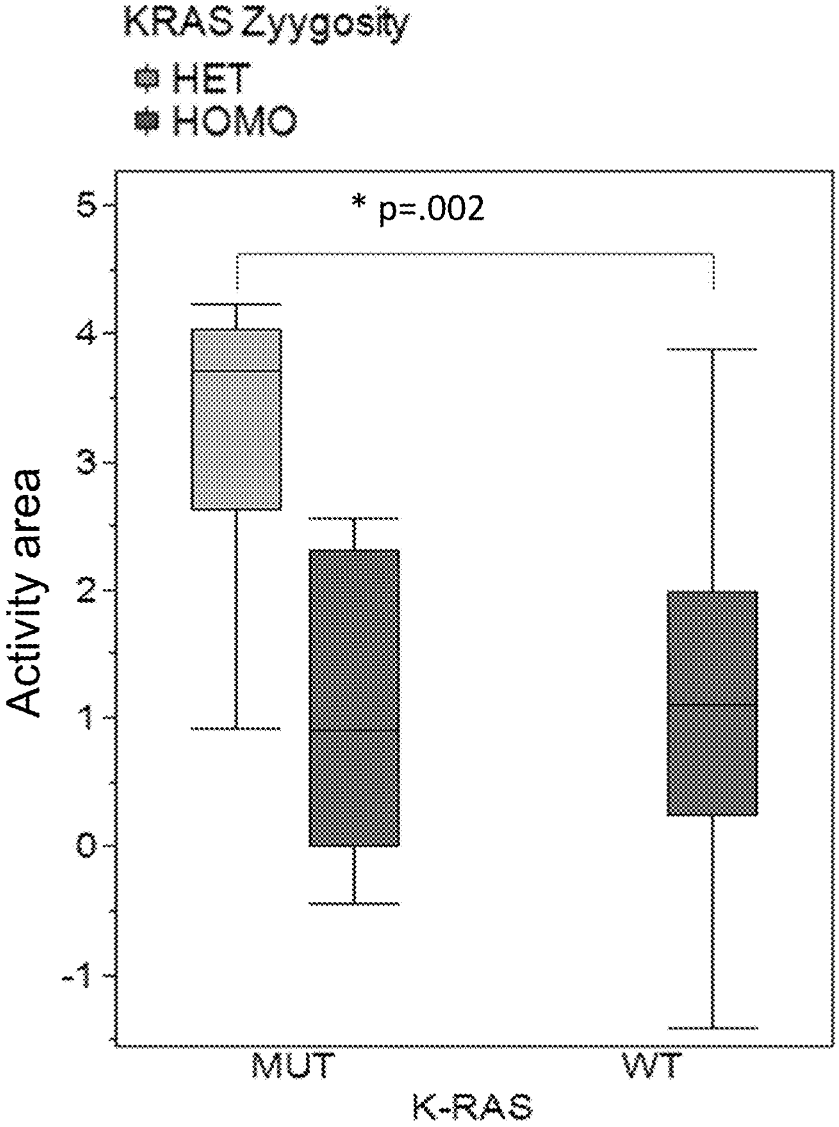
FIG. 1 is a bar graph showing responsiveness of cell lines to treatment with a test compound of the broad disclosure with respect to KRAS genotype and KRAS zygosity of the cell lines.

In one aspect, the disclosure provides methods, compounds and uses for treating a variety of hyperproliferative disorders using a compound as described herein. The compound can be defined generically as with respect to any of formulae (Ia), (Ib), (Ic) and (Id) above, or in various subgenera compounds in which the structural formula, $R^1$, $L^1$, $L^2$, Q, $L^3$, $R^3$, $L^4$, $R^4$, $L^5$, and $R^5$ are optionally independently selected from the groups (Ia) et seq., (1a) et seq., (2a) et seq., (3a) et seq., (4a) et seq., (5a) et seq., (6a) et seq., (7a) et seq., (8a) et seq., (9a) et seq., and (10a) et seq., defined hereinbelow (e.g., wherein the compound is of a structural formula as defined in any combination of the embodiments below):

In certain embodiments of the compounds as otherwise described herein, the compound has one of the following structural formulae:

(Ia);

(Ib);

(Ic);

(Id);

(Ie).

In certain embodiments of the compounds as otherwise described herein, $R^1$ is selected from one of the following groups (1a)-(1k):

(1a) $R^1$ is selected from the group consisting of hydrogen, optionally substituted $C_1$-$C_8$ alkyl and cycloalkyl optionally substituted with 1-5 $R^{1E}$;

(1b) $R^1$ is hydrogen;

(1c) $R^1$ is optionally substituted $C_1$-$C_8$ alkyl;

(1d) $R^1$ is unsubstituted $C_1$-$C_8$ alkyl or fluorinated $C_1$-$C_8$ alkyl, e.g., propyl or butyl;

(1e) $R^1$ is unsubstituted cycloalkyl;

(1f) $R^1$ is optionally substituted $C_1$-$C_8$ alkenyl;

(1g) $R^1$ is phenyl optionally substituted with 1-5 $R^E$.

(1h) $R^1$ is propyl, butyl, or butenyl;

(1i) $R^1$ is trifluoromethyl-substituted phenyl, methoxy-substituted phenyl or fluoro-substituted phenyl.

(1j) $R^1$ is phenyl substituted with —$(OCH_2CH_2O)_n$—$R^{1G}$ in which n is 1-4, —$N(R^{1G})C(O)CH_2$—O—$(CH_2CH_2O)_nR^{1G}$ in which n is 0-3, or —$C(O)NR^{1G}(CH_2CH_2O)_nR^{1G}$;

(1k) $R^1$ is hydroxymethyl, methoxymethyl, hydroxyethyl or methoxyethyl. In certain such embodiments, each optionally substituted alkyl of $R^1$ (including those of $R^{1E}$) is unsubstituted or fluorinated. For example, in certain such embodiments each optionally substituted alkyl, alkenyl and alkynyl of $R^1$ (including those of $R^{1E}$) is unsubstituted.

In certain embodiments of the compounds as otherwise described herein, $L^1$ is selected from one of the following groups (2a)-(2e)

(2a) $L^1$ is a bond, —S—, —S(O)— or —$S(O)_2$—;

(2b) $L^1$ is selected from a bond, —$CH_2$—, —$CH(CH_3)$—, —$CH_2CH_2$—, —C(O)—, —S—, —$S(O)_{1-2}$—, —O—, and —$NR^6$—;

(2c) $L^1$ is —O— or —S—.

(2d) $L^1$ is a bond (e.g., when $R^1$ is (1d), (1f), (1g), (1i), (1j) or (1k) above);

(2e) $L^1$ is —$NR^6$—.

In certain embodiments of the compounds as otherwise described herein, $L^2$ is selected from one of the following groups (3a)-(3c)

(3a) $L^2$ is —$CH_2$—, —$CH(CH_3)$— or —$CH_2CH_2$—;

(3b) $L^2$ is a bond;

(3c) $L^2$ is a bond or —$CH_2$—.

In certain embodiments of the compounds as otherwise described herein, Q is selected from one of the following groups (4a)-(4d)

(4a) Q is selected from the group consisting of —$CH_2OH$, —C(O)OH, —$C(O)OR^{2A}$, —$C(O)NR^{2B}R^{2A}$, —$C(O)NR^{2B}S(O)_2R^{2A}$, —$C(O)NR^{2B}S(O)_2NR^{2B}R^{2A}$, —$(O)R^{2A}$, —$S(O)_2OH$, —$P(O)(OH)_2$, —$C(OH)(CF_3)_2$, $S(O)_2R^{2A}$, —$N(R^{2B})S(O)_2R^{2A}$, —$S(O)_2NR^{2B}R^{2A}$, —C(O)NH—O($C_1$-$C_3$ alkyl), —C(O)NHOH and —CO(NH)CN;

(4b) Q is selected from the group consisting of —$CH_2OH$, —C(O)OH, —$C(O)OR^{2A}$, —$C(O)NR^{2B}R^{2A}$, —$C(O)NR^2BS(O)_2R^{2A}$, —$C(O)NR^2BS(O)_2NR^{2B}R^{2A}$, —$(O)R^{2A}$, —$S(O)_20H$, —$P(O)(OH)_2$.

(4c) Q is —$CH_2OH$, —C(O)OH or —$C(O)OR^{2A}$;

(4d) Q is —COOH.

In certain embodiments of the compounds as otherwise described herein, $L^3$ is selected from one of the following groups (5a)-(5c)

(5a) $L^3$ is a bond, —C(O)—, —S—, —$S(O)_{1-2}$—, —O—, —$NR^6$—, —$CH_2$—, —$CH(CH_3)(OH)$— or —CH(OH)—;

(5b) $L^3$ is a bond;

(5c) $L^3$ is a bond, —$CH_2$—, —$CH(CH_3)(OH)$— or —CH(OH)—.

In certain embodiments of the compounds as otherwise described herein, $R^3$ is selected from one of the following groups (6a)-(6k)

(6a) $R^3$ is aryl (e.g., phenyl) or heteroaryl (e.g., monocyclic heteroaryl) each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$ (6b) $R^3$ is aryl (e.g., a phenyl, a benzodioxole, or a dihydro-1H-isoquinoline) optionally substituted with 1-5 $R^{3E}$;

(6c) $R^3$ is aryl (e.g., a phenyl, a benzodioxole, or a dihydro-1H-isoquinoline) (i) substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$;

(6d) $R^3$ is aryl (e.g., a phenyl, a benzodioxole, or a dihydro-1H-isoquinoline) (i) substituted with a single substituent selected from -$L^{3C}$-(phenyl optionally substituted with 1-5 $R^{3D}$), -$L^{3C}$-(monocyclic heteroaryl optionally substituted with 1-5 $R^{3D}$), -$L^{3C}$-(monocyclic cycloalkyl optionally substituted with 1-5 $R^{3D}$), -$L^{3C}$-(monocyclic heterocycloalkyl optionally substituted with 1-5 $R^{3D}$) and (ii) optionally substituted with 1-5 $R^{3E}$;

(6e) $R^3$ is as defined in (6a)-(6d), wherein the aryl is not substituted with any $R^{3E}$;

(6f) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) optionally substituted with 1-5 $R^{3E}$;

(6g) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$;

(6h) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -$L^{3C}$-(phenyl optionally substituted with 1-5 $R^{3D}$), -$L^{3C}$-(monocyclic heteroaryl optionally substituted with 1-5 $R^{3D}$), -$L^{3C}$-(monocyclic cycloalkyl optionally substituted with 1-5 $R^{3D}$), -$L^{3C}$-(monocyclic heterocycloalkyl optionally substituted with 1-5 $R^{3D}$) and (ii) optionally substituted with 1-5 $R^{3E}$;

(6i) $R^3$ is as defined in (6f)-(6h), wherein the heteroaryl is not substituted with any $R^{3E}$;

(6j) $R^3$ is selected from the group consisting of: phenyl, benzodioxolyl, dihydro-1H-isoquinolinyl, imidazolyl, oxazolyl, isoxazolyl, isothiazolyl, thiazolyl, pyridinyl, and pyrazinyl, pyridonyl, thiadiazolyl, pyrazolopyrimidinyl, pyrazolopyridinyl, benzofuranyl, indolyl, imidazopyridinyl, pyrazolyl, triazolopyridinyl, benzimidazolyl, a benzimidazolyl, a thienyl, a benzothienyl, a furanyl and pyrimidinyl, each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$ (6k) $R^3$ is selected from the group consisting of phenyl and monocyclic heteroaryl (e.g., pyridyl, pyrazolyl), optionally substituted with 1-5 $R^{3E}$.

In certain such embodiments, each optionally substituted alkyl, alkenyl and alkynyl of $R^3$ (including those of $R^{3D}$ and $R^{3E}$) is unsubstituted or fluorinated. For example, in certain such embodiments each optionally substituted alkyl, alkenyl and alkynyl of $R^3$ (including those of $R^{3D}$ and $R^{3E}$) is unsubstituted. In certain such embodiments, $L^{3C}$ is methylene or —O—. In certain such embodiments, the optional number of R3E substituents is 1-3, or 1-2.

In certain embodiments of the compounds as otherwise described herein, $R^4$ is selected from one of the following groups (7a)-(7d)

(7a) $R^4$ is hydrogen;

(7b) $R^4$ is optionally substituted $C_1$-$C_8$ alkyl, optionally-substituted $C_1$-$C_8$ alkenyl or optionally substituted $C_1$-$C_8$ alkynyl;

(7c) $R^4$ is hydrogen or unsubstituted $C_1$-$C_6$ alkyl;

(7d) $R^4$ is unsubstituted $C_1$-$C_3$ alkyl.

In certain such embodiments, each optionally substituted alkyl, alkenyl and alkynyl of $R^4$ is unsubstituted or fluorinated. For example, in certain such embodiments each optionally substituted alkyl, alkenyl and alkynyl of $R^4$ is unsubstituted.

In certain embodiments of the compounds as otherwise described herein, $L^4$ is selected from one of the following groups (8a)-(8c)

(8a) $L^4$ is selected from a bond, —C(O)—, —S—, —$S(O)_{12}$—, —O—, and —$NR^6$—;

(8b) $L^4$ is a bond;

(8c) $L^4$ is —O— (e.g., when $R^4$ is any of (7a), (7b), (7c) or (7d) above).

In certain embodiments of the compounds as otherwise described herein, $L^5$ is selected from one of the following groups (9a)-(9c)

(9a) $L^5$ is a bond, —C(O)—, —S—, —$S(O)_{12}$—, —O—, —$NR^6$—, —$CH_2CH_2$—, —$CH_2$—, —$CH(CH_3)(OH)$— or —CH(OH)—;

(9b) $L^5$ is a bond;

(9c) $L^5$ is a bond, —O—, —S—, —C(O)— or —$S(O)_{1-2}$—.

In certain embodiments of the compounds as otherwise described herein, $R^5$ is selected from one of the following groups (21o)-(21g)

(10a) $R^5$ is aryl (e.g., phenyl) or heteroaryl (e.g., an isoxazolyl, a pyridyl, an imidazopyridyl, a pyrazolyl), each optionally substituted with 1-5 $R^{5E}$;

(10b) $R^5$ is phenyl optionally substituted with 1-5 $R^{5E}$;

(10c) $R^5$ is selected from the group consisting of phenyl, isoxazolyl, pyridyl, imidazopyridyl, and pyrazolyl, each optionally substituted with 1-5 $R^{5E}$.

(10d) $R^5$ is phenyl substituted with a single substituent selected from -$L^{5C}$-(phenyl optionally substituted with 1-5 $R^{5D}$), -$L^{5C}$-(monocyclic heteroaryl optionally substituted with 1-5 $R^{5D}$), and -$L^{5C}$-(monocyclic cycloalkyl optionally substituted with 1-5 $R^{5D}$) -$L^{5C}$-(monocyclic heterocycloalkyl optionally substituted with 1-5 $R^{5D}$) and (ii) optionally substituted with 1-5 $R^{5E}$;

(10e) $R^5$ is phenyl substituted with a single -$L^{5C}$-(monocyclic heteroaryl optionally substituted with 1-5 $R^{5D}$) substituent and (ii) optionally substituted with 1-5 $R^{5E}$;

(10f) $R^5$ is phenyl substituted with a single -$L^{5C}$-(monocyclic heterocycloalkyl optionally substituted with 1-5 $R^{5D}$) substituent and (ii) optionally substituted with 1-5 $R^{5E}$;

(10g) (10d), (10e) or (10f) above, in which $L^{5C}$ is a bond;

(10h) (10d), (10e) or (10f) above, in which $L^{5C}$ is —O— or —C(O)—;

(10i) $R^5$ is heterocycloalkyl optionally substituted with 1-5 $R^{5E}$;

(10j) $R^5$ is heterocycloalkyl substituted with a single -$L^{5C}$-(monocyclic cycloalkyl optionally substituted with 1-5 $R^{5D}$) substituent and (ii) optionally substituted with 1-5 $R^{5E}$;

(10j) (10h) or (10i) above, in which the heterocycloalkyl is a nitrogen-containing heterocycloalkyl, attached to the -$L^5$- through a nitrogen atom;

(10k) (10h), (10i) or (10j) above, in which the heterocycloalkyl is monocyclic;

(10l) (10h), (10i) or (10j) above, in which the heterocycloalkyl is bicyclic;

(10m) any of (10h)-(10l) above, in which the heterocycloalkyl is saturated;

(10n) $R^5$ is cycloalkyl optionally substituted with 1-5 $R^{5E}$;

(10o) (10n) above, in which the cycloalkyl is substituted with 1-5 $R^{5E}$;

(10p) (10n) or (10o) above, in which the cycloalkyl is monocyclic;

(10q) any of (10n), (10o) or (10p) above, in which the cycloalkyl is saturated; In certain such embodiments, each optionally substituted alkyl, alkenyl and alkynyl of $R^5$ (including those of $R^{5D}$ and $R^{5E}$) is unsubstituted or fluorinated. For example, in certain such embodiments each optionally substituted alkyl, alkenyl and alkynyl of $R^5$ (including those of $R^{5D}$ and $R^{5E}$) is unsubstituted.

Various particular embodiments nos. 1-1024 of compounds for use in the methods, compounds and uses of the disclosure include compounds of formula (I), each as defined in each of the following rows (or a pharmaceutically acceptable salt or N-oxide thereof, or a solvate or hydrate thereof), wherein each entry is a group number as defined above:

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 1 | (Ia)-(Id) | (1a) | (2a) | (3c) | (4a) | (5b) | (6a) | (7a), (7b) | (8a) | (9a) | (10a) |
| 2 | (Ia)-(Id) | (1a) | (2a) | (3c) | (4a) | (5b) | (6a) | (7a), (7b) | (8a) | (9a) | (10c) |
| 3 | (Ia)-(Id) | (1a) | (2a) | (3c) | (4a) | (5b) | (6a) | (7a), (7b) | (8a) | (9b) | (10a) |
| 4 | (Ia)-(Id) | (1a) | (2a) | (3c) | (4a) | (5b) | (6a) | (7a), (7b) | (8a) | (9b) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 5 | (Ia)-(Id) | (1a) | (2a) | (3c) | (4a) | (5b) | (6a) | (7d) | (8a) | (9a) | (10a) |
| 6 | (Ia)-(Id) | (1a) | (2a) | (3c) | (4a) | (5b) | (6a) | (7d) | (8a) | (9a) | (10c) |
| 7 | (Ia)-(Id) | (1a) | (2a) | (3c) | (4a) | (5b) | (6a) | (7d) | (8a) | (9b) | (10a) |
| 8 | (Ia)-(Id) | (1a) | (2a) | (3c) | (4a) | (5b) | (6a) | (7d) | (8a) | (9b) | (10c) |
| 9 | (Ia)-(Id) | (1a) | (2a) | (3c) | (4a) | (5b) | (6k) | (7a), (7b) | (8a) | (9a) | (10a) |
| 10 | (Ia)-(Id) | (1a) | (2a) | (3c) | (4a) | (5b) | (6k) | (7a), (7b) | (8a) | (9a) | (10c) |
| 11 | (Ia)-(Id) | (1a) | (2a) | (3c) | (4a) | (5b) | (6k) | (7a), (7b) | (8a) | (9b) | (10a) |
| 12 | (Ia)-(Id) | (1a) | (2a) | (3c) | (4a) | (5b) | (6k) | (7a), (7b) | (8a) | (9b) | (10c) |
| 13 | (Ia)-(Id) | (1a) | (2a) | (3c) | (4a) | (5b) | (6k) | (7d) | (8a) | (9a) | (10a) |
| 14 | (Ia)-(Id) | (1a) | (2a) | (3c) | (4a) | (5b) | (6k) | (7d) | (8a) | (9a) | (10c) |
| 15 | (Ia)-(Id) | (1a) | (2a) | (3c) | (4a) | (5b) | (6k) | (7d) | (8a) | (9b) | (10a) |
| 16 | (Ia)-(Id) | (1a) | (2a) | (3c) | (4a) | (5b) | (6k) | (7d) | (8a) | (9b) | (10c) |
| 17 | (Ia)-(Id) | (1a) | (2a) | (3c) | (4a) | (5a) | (6a) | (7a), (7b) | (8a) | (9a) | (10a) |
| 18 | (Ia)-(Id) | (1a) | (2a) | (3c) | (4a) | (5a) | (6a) | (7a), (7b) | (8a) | (9a) | (10c) |
| 19 | (Ia)-(Id) | (1a) | (2a) | (3c) | (4a) | (5a) | (6a) | (7a), (7b) | (8a) | (9b) | (10a) |
| 20 | (Ia)-(Id) | (1a) | (2a) | (3c) | (4a) | (5a) | (6a) | (7a), (7b) | (8a) | (9b) | (10c) |
| 21 | (Ia)-(Id) | (1a) | (2a) | (3c) | (4a) | (5a) | (6a) | (7d) | (8a) | (9a) | (10a) |
| 22 | (Ia)-(Id) | (1a) | (2a) | (3c) | (4a) | (5a) | (6a) | (7d) | (8a) | (9a) | (10c) |
| 23 | (Ia)-(Id) | (1a) | (2a) | (3c) | (4a) | (5a) | (6a) | (7d) | (8a) | (9b) | (10a) |
| 24 | (Ia)-(Id) | (1a) | (2a) | (3c) | (4a) | (5a) | (6a) | (7d) | (8a) | (9b) | (10c) |
| 25 | (Ia)-(Id) | (1a) | (2a) | (3c) | (4a) | (5a) | (6k) | (7a), (7b) | (8a) | (9a) | (10a) |
| 26 | (Ia)-(Id) | (1a) | (2a) | (3c) | (4a) | (5a) | (6k) | (7a), (7b) | (8a) | (9a) | (10c) |
| 27 | (Ia)-(Id) | (1a) | (2a) | (3c) | (4a) | (5a) | (6k) | (7a), (7b) | (8a) | (9b) | (10a) |
| 28 | (Ia)-(Id) | (1a) | (2a) | (3c) | (4a) | (5a) | (6k) | (7a), (7b) | (8a) | (9b) | (10c) |
| 29 | (Ia)-(Id) | (1a) | (2a) | (3c) | (4a) | (5a) | (6k) | (7d) | (8a) | (9a) | (10a) |
| 30 | (Ia)-(Id) | (1a) | (2a) | (3c) | (4a) | (5a) | (6k) | (7d) | (8a) | (9a) | (10c) |
| 31 | (Ia)-(Id) | (1a) | (2a) | (3c) | (4a) | (5a) | (6k) | (7d) | (8a) | (9b) | (10a) |
| 32 | (Ia)-(Id) | (1a) | (2a) | (3c) | (4a) | (5a) | (6k) | (7d) | (8a) | (9b) | (10c) |
| 33 | (Ia)-(Id) | (1a) | (2a) | (3c) | (4d) | (5b) | (6a) | (7a), (7b) | (8a) | (9a) | (10a) |
| 34 | (Ia)-(Id) | (1a) | (2a) | (3c) | (4d) | (5b) | (6a) | (7a), (7b) | (8a) | (9a) | (10c) |
| 35 | (Ia)-(Id) | (1a) | (2a) | (3c) | (4d) | (5b) | (6a) | (7a), (7b) | (8a) | (9b) | (10a) |
| 36 | (Ia)-(Id) | (1a) | (2a) | (3c) | (4d) | (5b) | (6a) | (7a), (7b) | (8a) | (9b) | (10c) |
| 37 | (Ia)-(Id) | (1a) | (2a) | (3c) | (4d) | (5b) | (6a) | (7d) | (8a) | (9a) | (10a) |
| 38 | (Ia)-(Id) | (1a) | (2a) | (3c) | (4d) | (5b) | (6a) | (7d) | (8a) | (9a) | (10c) |
| 39 | (Ia)-(Id) | (1a) | (2a) | (3c) | (4d) | (5b) | (6a) | (7d) | (8a) | (9b) | (10a) |
| 40 | (Ia)-(Id) | (1a) | (2a) | (3c) | (4d) | (5b) | (6a) | (7d) | (8a) | (9b) | (10c) |
| 41 | (Ia)-(Id) | (1a) | (2a) | (3c) | (4d) | (5b) | (6k) | (7a), (7b) | (8a) | (9a) | (10a) |
| 42 | (Ia)-(Id) | (1a) | (2a) | (3c) | (4d) | (5b) | (6k) | (7a), (7b) | (8a) | (9a) | (10c) |
| 43 | (Ia)-(Id) | (1a) | (2a) | (3c) | (4d) | (5b) | (6k) | (7a), (7b) | (8a) | (9b) | (10a) |
| 44 | (Ia)-(Id) | (1a) | (2a) | (3c) | (4d) | (5b) | (6k) | (7a), (7b) | (8a) | (9b) | (10c) |
| 45 | (Ia)-(Id) | (1a) | (2a) | (3c) | (4d) | (5b) | (6k) | (7d) | (8a) | (9a) | (10a) |
| 46 | (Ia)-(Id) | (1a) | (2a) | (3c) | (4d) | (5b) | (6k) | (7d) | (8a) | (9a) | (10c) |
| 47 | (Ia)-(Id) | (1a) | (2a) | (3c) | (4d) | (5b) | (6k) | (7d) | (8a) | (9b) | (10a) |
| 48 | (Ia)-(Id) | (1a) | (2a) | (3c) | (4d) | (5b) | (6k) | (7d) | (8a) | (9b) | (10c) |
| 49 | (Ia)-(Id) | (1a) | (2a) | (3c) | (4d) | (5a) | (6a) | (7a), (7b) | (8a) | (9a) | (10a) |
| 50 | (Ia)-(Id) | (1a) | (2a) | (3c) | (4d) | (5a) | (6a) | (7a), (7b) | (8a) | (9a) | (10c) |
| 51 | (Ia)-(Id) | (1a) | (2a) | (3c) | (4d) | (5a) | (6a) | (7a), (7b) | (8a) | (9b) | (10a) |
| 52 | (Ia)-(Id) | (1a) | (2a) | (3c) | (4d) | (5a) | (6a) | (7a), (7b) | (8a) | (9b) | (10c) |
| 53 | (Ia)-(Id) | (1a) | (2a) | (3c) | (4d) | (5a) | (6a) | (7d) | (8a) | (9a) | (10a) |
| 54 | (Ia)-(Id) | (1a) | (2a) | (3c) | (4d) | (5a) | (6a) | (7d) | (8a) | (9a) | (10c) |
| 55 | (Ia)-(Id) | (1a) | (2a) | (3c) | (4d) | (5a) | (6a) | (7d) | (8a) | (9b) | (10a) |
| 56 | (Ia)-(Id) | (1a) | (2a) | (3c) | (4d) | (5a) | (6a) | (7d) | (8a) | (9b) | (10c) |
| 57 | (Ia)-(Id) | (1a) | (2a) | (3c) | (4d) | (5a) | (6k) | (7a), (7b) | (8a) | (9a) | (10a) |
| 58 | (Ia)-(Id) | (1a) | (2a) | (3c) | (4d) | (5a) | (6k) | (7a), (7b) | (8a) | (9a) | (10c) |
| 59 | (Ia)-(Id) | (1a) | (2a) | (3c) | (4d) | (5a) | (6k) | (7a), (7b) | (8a) | (9b) | (10a) |
| 60 | (Ia)-(Id) | (1a) | (2a) | (3c) | (4d) | (5a) | (6k) | (7a), (7b) | (8a) | (9b) | (10c) |
| 61 | (Ia)-(Id) | (1a) | (2a) | (3c) | (4d) | (5a) | (6k) | (7d) | (8a) | (9a) | (10a) |
| 62 | (Ia)-(Id) | (1a) | (2a) | (3c) | (4d) | (5a) | (6k) | (7d) | (8a) | (9a) | (10c) |
| 63 | (Ia)-(Id) | (1a) | (2a) | (3c) | (4d) | (5a) | (6k) | (7d) | (8a) | (9b) | (10a) |
| 64 | (Ia)-(Id) | (1a) | (2a) | (3c) | (4d) | (5a) | (6k) | (7d) | (8a) | (9b) | (10c) |
| 65 | (Ia)-(Id) | (1a) | (2a) | (3b) | (4a) | (5b) | (6a) | (7a), (7b) | (8a) | (9a) | (10a) |
| 66 | (Ia)-(Id) | (1a) | (2a) | (3b) | (4a) | (5b) | (6a) | (7a), (7b) | (8a) | (9a) | (10c) |
| 67 | (Ia)-(Id) | (1a) | (2a) | (3b) | (4a) | (5b) | (6a) | (7a), (7b) | (8a) | (9b) | (10a) |
| 68 | (Ia)-(Id) | (1a) | (2a) | (3b) | (4a) | (5b) | (6a) | (7a), (7b) | (8a) | (9b) | (10c) |
| 69 | (Ia)-(Id) | (1a) | (2a) | (3b) | (4a) | (5b) | (6a) | (7d) | (8a) | (9a) | (10a) |
| 70 | (Ia)-(Id) | (1a) | (2a) | (3b | (4a) | (5b) | (6a) | (7d) | (8a) | (9a) | (10c) |
| 71 | (Ia)-(Id) | (1a) | (2a) | (3b) | (4a) | (5b) | (6a) | (7d) | (8a) | (9b) | (10a) |
| 72 | (Ia)-(Id) | (1a) | (2a) | (3b) | (4a) | (5b) | (6a) | (7d) | (8a) | (9b) | (10c) |
| 73 | (Ia)-(Id) | (1a) | (2a) | (3b) | (4a) | (5b) | (6k) | (7a), (7b) | (8a) | (9a) | (10a) |
| 74 | (Ia)-(Id) | (1a) | (2a) | (3b) | (4a) | (5b) | (6k) | (7a), (7b) | (8a) | (9a) | (10c) |
| 75 | (Ia)-(Id) | (1a) | (2a) | (3b) | (4a) | (5b) | (6k) | (7a), (7b) | (8a) | (9b) | (10a) |
| 76 | (Ia)-(Id) | (1a) | (2a) | (3b) | (4a) | (5b) | (6k) | (7a), (7b) | (8a) | (9b) | (10c) |
| 77 | (Ia)-(Id) | (1a) | (2a) | (3b) | (4a) | (5b) | (6k) | (7d) | (8a) | (9a) | (10a) |
| 78 | (Ia)-(Id) | (1a) | (2a) | (3b) | (4a) | (5b) | (6k) | (7d) | (8a) | (9a) | (10c) |
| 79 | (Ia)-(Id) | (1a) | (2a) | (3b) | (4a) | (5b) | (6k) | (7d) | (8a) | (9b) | (10a) |
| 80 | (Ia)-(Id) | (1a) | (2a) | (3b) | (4a) | (5b) | (6k) | (7d) | (8a) | (9b) | (10c) |
| 81 | (Ia)-(Id) | (1a) | (2a) | (3b) | (4a) | (5a) | (6a) | (7a), (7b) | (8a) | (9a) | (10a) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 82 | (Ia)-(Id) | (1a) | (2a) | (3b) | (4a) | (5a) | (6a) | (7a), (7b) | (8a) | (9a) | (10c) |
| 83 | (Ia)-(Id) | (1a) | (2a) | (3b) | (4a) | (5a) | (6a) | (7a), (7b) | (8a) | (9b) | (10a) |
| 84 | (Ia)-(Id) | (1a) | (2a) | (3b) | (4a) | (5a) | (6a) | (7a), (7b) | (8a) | (9b) | (10c) |
| 85 | (Ia)-(Id) | (1a) | (2a) | (3b) | (4a) | (5a) | (6a) | (7d) | (8a) | (9a) | (10a) |
| 86 | (Ia)-(Id) | (1a) | (2a) | (3b) | (4a) | (5a) | (6a) | (7d) | (8a) | (9a) | (10c) |
| 87 | (Ia)-(Id) | (1a) | (2a) | (3b) | (4a) | (5a) | (6a) | (7d) | (8a) | (9b) | (10a) |
| 88 | (Ia)-(Id) | (1a) | (2a) | (3b) | (4a) | (5a) | (6a) | (7d) | (8a) | (9b) | (10c) |
| 89 | (Ia)-(Id) | (1a) | (2a) | (3b) | (4a) | (5a) | (6k) | (7a), (7b) | (8a) | (9a) | (10a) |
| 90 | (Ia)-(Id) | (1a) | (2a) | (3b) | (4a) | (5a) | (6k) | (7a), (7b) | (8a) | (9a) | (10c) |
| 91 | (Ia)-(Id) | (1a) | (2a) | (3b) | (4a) | (5a) | (6k) | (7a), (7b) | (8a) | (9b) | (10a) |
| 92 | (Ia)-(Id) | (1a) | (2a) | (3b) | (4a) | (5a) | (6k) | (7a), (7b) | (8a) | (9b) | (10c) |
| 93 | (Ia)-(Id) | (1a) | (2a) | (3b) | (4a) | (5a) | (6k) | (7d) | (8a) | (9a) | (10a) |
| 94 | (Ia)-(Id) | (1a) | (2a) | (3b) | (4a) | (5a) | (6k) | (7d) | (8a) | (9a) | (10c) |
| 95 | (Ia)-(Id) | (1a) | (2a) | (3b) | (4a) | (5a) | (6k) | (7d) | (8a) | (9b) | (10a) |
| 96 | (Ia)-(Id) | (1a) | (2a) | (3b) | (4a) | (5a) | (6k) | (7d) | (8a) | (9b) | (10c) |
| 97 | (Ia)-(Id) | (1a) | (2a) | (3b) | (4d) | (5b) | (6a) | (7a), (7b) | (8a) | (9a) | (10a) |
| 98 | (Ia)-(Id) | (1a) | (2a) | (3b) | (4d) | (5b) | (6a) | (7a), (7b) | (8a) | (9a) | (10c) |
| 99 | (Ia)-(Id) | (1a) | (2a) | (3b) | (4d) | (5b) | (6a) | (7a), (7b) | (8a) | (9b) | (10a) |
| 100 | (Ia)-(Id) | (1a) | (2a) | (3b) | (4d) | (5b) | (6a) | (7a), (7b) | (8a) | (9b) | (10c) |
| 101 | (Ia)-(Id) | (1a) | (2a) | (3b) | (4d) | (5b) | (6a) | (7d) | (8a) | (9a) | (10a) |
| 102 | (Ia)-(Id) | (1a) | (2a) | (3b) | (4d) | (5b) | (6a) | (7d) | (8a) | (9a) | (10c) |
| 103 | (Ia)-(Id) | (1a) | (2a) | (3b) | (4d) | (5b) | (6a) | (7d) | (8a) | (9b) | (10a) |
| 104 | (Ia)-(Id) | (1a) | (2a) | (3b) | (4d) | (5b) | (6a) | (7d) | (8a) | (9b) | (10c) |
| 105 | (Ia)-(Id) | (1a) | (2a) | (3b) | (4d) | (5b) | (6k) | (7a), (7b) | (8a) | (9a) | (10a) |
| 106 | (Ia)-(Id) | (1a) | (2a) | (3b) | (4d) | (5b) | (6k) | (7a), (7b) | (8a) | (9a) | (10c) |
| 107 | (Ia)-(Id) | (1a) | (2a) | (3b) | (4d) | (5b) | (6k) | (7a), (7b) | (8a) | (9b) | (10a) |
| 108 | (Ia)-(Id) | (1a) | (2a) | (3b) | (4d) | (5b) | (6k) | (7a), (7b) | (8a) | (9b) | (10c) |
| 109 | (Ia)-(Id) | (1a) | (2a) | (3b) | (4d) | (5b) | (6k) | (7d) | (8a) | (9a) | (10a) |
| 110 | (Ia)-(Id) | (1a) | (2a) | (3b) | (4d) | (5b) | (6k) | (7d) | (8a) | (9a) | (10c) |
| 111 | (Ia)-(Id) | (1a) | (2a) | (3b) | (4d) | (5b) | (6k) | (7d) | (8a) | (9b) | (10a) |
| 112 | (Ia)-(Id) | (1a) | (2a) | (3b) | (4d) | (5b) | (6k) | (7d) | (8a) | (9b) | (10c) |
| 113 | (Ia)-(Id) | (1a) | (2a) | (3b) | (4d) | (5a) | (6a) | (7a), (7b) | (8a) | (9a) | (10a) |
| 114 | (Ia)-(Id) | (1a) | (2a) | (3b) | (4d) | (5a) | (6a) | (7a), (7b) | (8a) | (9a) | (10c) |
| 115 | (Ia)-(Id) | (1a) | (2a) | (3b) | (4d) | (5a) | (6a) | (7a), (7b) | (8a) | (9b) | (10a) |
| 116 | (Ia)-(Id) | (1a) | (2a) | (3b) | (4d) | (5a) | (6a) | (7a), (7b) | (8a) | (9b) | (10c) |
| 117 | (Ia)-(Id) | (1a) | (2a) | (3b) | (4d) | (5a) | (6a) | (7d) | (8a) | (9a) | (10a) |
| 118 | (Ia)-(Id) | (1a) | (2a) | (3b) | (4d) | (5a) | (6a) | (7d) | (8a) | (9a) | (10c) |
| 119 | (Ia)-(Id) | (1a) | (2a) | (3b) | (4d) | (5a) | (6a) | (7d) | (8a) | (9b) | (10a) |
| 120 | (Ia)-(Id) | (1a) | (2a) | (3b) | (4d) | (5a) | (6a) | (7d) | (8a) | (9b) | (10c) |
| 121 | (Ia)-(Id) | (1a) | (2a) | (3b) | (4d) | (5a) | (6k) | (7a), (7b) | (8a) | (9a) | (10a) |
| 122 | (Ia)-(Id) | (1a) | (2a) | (3b) | (4d) | (5a) | (6k) | (7a), (7b) | (8a) | (9a) | (10c) |
| 123 | (Ia)-(Id) | (1a) | (2a) | (3b) | (4d) | (5a) | (6k) | (7a), (7b) | (8a) | (9b) | (10a) |
| 124 | (Ia)-(Id) | (1a) | (2a) | (3b) | (4d) | (5a) | (6k) | (7a), (7b) | (8a) | (9b) | (10c) |
| 125 | (Ia)-(Id) | (1a) | (2a) | (3b) | (4d) | (5a) | (6k) | (7d) | (8a) | (9a) | (10a) |
| 126 | (Ia)-(Id) | (1a) | (2a) | (3b) | (4d) | (5a) | (6k) | (7d) | (8a) | (9a) | (10c) |
| 127 | (Ia)-(Id) | (1a) | (2a) | (3b) | (4d) | (5a) | (6k) | (7d | (8a) | (9b) | (10a) |
| 128 | (Ia)-(Id) | (1a) | (2a) | (3b) | (4d) | (5a) | (6k) | (7d) | (8a) | (9b) | (10c) |
| 129 | (Ia)-(Id) | (1a) | (2b) | (3c) | (4a) | (5b) | (6a) | (7a), (7b) | (8a) | (9a) | (10a) |
| 130 | (Ia)-(Id) | (1a) | (2b) | (3c) | (4a) | (5b) | (6a) | (7a), (7b) | (8a) | (9a) | (10c) |
| 131 | (Ia)-(Id) | (1a) | (2b) | (3c) | (4a) | (5b) | (6a) | (7a), (7b) | (8a) | (9b) | (10a) |
| 132 | (Ia)-(Id) | (1a) | (2b) | (3c) | (4a) | (5b) | (6a) | (7a), (7b) | (8a) | (9b) | (10c) |
| 133 | (Ia)-(Id) | (1a) | (2b) | (3c) | (4a) | (5b) | (6a) | (7d) | (8a) | (9a) | (10a) |
| 134 | (Ia)-(Id) | (1a) | (2b) | (3c) | (4a) | (5b) | (6a) | (7d) | (8a) | (9a) | (10c) |
| 135 | (Ia)-(Id) | (1a) | (2b) | (3c) | (4a) | (5b) | (6a) | (7d) | (8a) | (9b) | (10a) |
| 136 | (Ia)-(Id) | (1a) | (2b) | (3c) | (4a) | (5b) | (6a) | (7d) | (8a) | (9b) | (10c) |
| 137 | (Ia)-(Id) | (1a) | (2b) | (3c) | (4a) | (5b) | (6k) | (7a), (7b) | (8a) | (9a) | (10a) |
| 138 | (Ia)-(Id) | (1a) | (2b) | (3c) | (4a) | (5b) | (6k) | (7a), (7b) | (8a) | (9a) | (10c) |
| 139 | (Ia)-(Id) | (1a) | (2b) | (3c) | (4a) | (5b) | (6k) | (7a), (7b) | (8a) | (9b) | (10a) |
| 140 | (Ia)-(Id) | (1a) | (2b) | (3c) | (4a) | (5b) | (6k) | (7a), (7b) | (8a) | (9b) | (10c) |
| 141 | (Ia)-(Id) | (1a) | (2b) | (3c) | (4a) | (5b) | (6k) | (7d) | (8a) | (9a) | (10a) |
| 142 | (Ia)-(Id) | (1a) | (2b) | (3c) | (4a) | (5b) | (6k) | (7d) | (8a) | (9a) | (10c) |
| 143 | (Ia)-(Id) | (1a) | (2b) | (3c) | (4a) | (5b) | (6k) | (7d) | (8a) | (9b) | (10a) |
| 144 | (Ia)-(Id) | (1a) | (2b) | (3c) | (4a) | (5b) | (6k) | (7d) | (8a) | (9b) | (10c) |
| 145 | (Ia)-(Id) | (1a) | (2b) | (3c) | (4a) | (5a) | (6a) | (7a), (7b) | (8a) | (9a) | (10a) |
| 146 | (Ia)-(Id) | (1a) | (2b) | (3c) | (4a) | (5a) | (6a) | (7a), (7b) | (8a) | (9a) | (10c) |
| 147 | (Ia)-(Id) | (1a) | (2b) | (3c) | (4a) | (5a) | (6a) | (7a), (7b) | (8a) | (9b) | (10a) |
| 148 | (Ia)-(Id) | (1a) | (2b) | (3c) | (4a) | (5a) | (6a) | (7a), (7b) | (8a) | (9b) | (10c) |
| 149 | (Ia)-(Id) | (1a) | (2b) | (3c) | (4a) | (5a) | (6a) | (7d) | (8a) | (9a) | (10a) |
| 150 | (Ia)-(Id) | (1a) | (2b) | (3c) | (4a) | (5a) | (6a) | (7d) | (8a) | (9a) | (10c) |
| 151 | (Ia)-(Id) | (1a) | (2b) | (3c) | (4a) | (5a) | (6a) | (7d) | (8a) | (9b) | (10a) |
| 152 | (Ia)-(Id) | (1a) | (2b) | (3c) | (4a) | (5a) | (6a) | (7d) | (8a) | (9b) | (10c) |
| 153 | (Ia)-(Id) | (1a) | (2b) | (3c) | (4a) | (5a) | (6k) | (7a), (7b) | (8a) | (9a) | (10a) |
| 154 | (Ia)-(Id) | (1a) | (2b) | (3c) | (4a) | (5a) | (6k) | (7a), (7b) | (8a) | (9a) | (10c) |
| 155 | (Ia)-(Id) | (1a) | (2b) | (3c) | (4a) | (5a) | (6k) | (7a), (7b) | (8a) | (9b) | (10a) |
| 156 | (Ia)-(Id) | (1a) | (2b) | (3c) | (4a) | (5a) | (6k) | (7a), (7b) | (8a) | (9b) | (10c) |
| 157 | (Ia)-(Id) | (1a) | (2b) | (3c) | (4a) | (5a) | (6k) | (7d) | (8a) | (9a) | (10a) |
| 158 | (Ia)-(Id) | (1a) | (2b) | (3c) | (4a) | (5a) | (6k) | (7d) | (8a) | (9a) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 159 | (Ia)-(Id) | (1a) | (2b) | (3c) | (4a) | (5a) | (6k) | (7d) | (8a) | (9b) | (10a) |
| 160 | (Ia)-(Id) | (1a) | (2b) | (3c) | (4a) | (5a) | (6k) | (7d) | (8a) | (9b) | (10c) |
| 161 | (Ia)-(Id) | (1a) | (2b) | (3c) | (4d) | (5b) | (6a) | (7a), (7b) | (8a) | (9a) | (10a) |
| 162 | (Ia)-(Id) | (1a) | (2b) | (3c) | (4d) | (5b) | (6a) | (7a), (7b) | (8a) | (9a) | (10c) |
| 163 | (Ia)-(Id) | (1a) | (2b) | (3c) | (4d) | (5b) | (6a) | (7a), (7b) | (8a) | (9b) | (10a) |
| 164 | (Ia)-(Id) | (1a) | (2b) | (3c) | (4d) | (5b) | (6a) | (7a), (7b) | (8a) | (9b) | (10c) |
| 165 | (Ia)-(Id) | (1a) | (2b) | (3c) | (4d) | (5b) | (6a) | (7d) | (8a) | (9a) | (10a) |
| 166 | (Ia)-(Id) | (1a) | (2b) | (3c) | (4d) | (5b) | (6a) | (7d) | (8a) | (9a) | (10c) |
| 167 | (Ia)-(Id) | (1a) | (2b) | (3c) | (4d) | (5b) | (6a) | (7d) | (8a) | (9b) | (10a) |
| 168 | (Ia)-(Id) | (1a) | (2b) | (3c) | (4d) | (5b) | (6a) | (7d) | (8a) | (9b) | (10c) |
| 169 | (Ia)-(Id) | (1a) | (2b) | (3c) | (4d) | (5b) | (6k) | (7a), (7b) | (8a) | (9a) | (10a) |
| 170 | (Ia)-(Id) | (1a) | (2b) | (3c) | (4d) | (5b) | (6k) | (7a), (7b) | (8a) | (9a) | (10c) |
| 171 | (Ia)-(Id) | (1a) | (2b) | (3c) | (4d) | (5b) | (6k) | (7a), (7b) | (8a) | (9b) | (10a) |
| 172 | (Ia)-(Id) | (1a) | (2b) | (3c) | (4d) | (5b) | (6k) | (7a), (7b) | (8a) | (9b) | (10c) |
| 173 | (Ia)-(Id) | (1a) | (2b) | (3c) | (4d) | (5b) | (6k) | (7d) | (8a) | (9a) | (10a) |
| 174 | (Ia)-(Id) | (1a) | (2b) | (3c) | (4d) | (5b) | (6k) | (7d) | (8a) | (9a) | (10c) |
| 175 | (Ia)-(Id) | (1a) | (2b) | (3c) | (4d) | (5b) | (6k) | (7d) | (8a) | (9b) | (10a) |
| 176 | (Ia)-(Id) | (1a) | (2b) | (3c) | (4d) | (5b) | (6k) | (7d) | (8a) | (9b) | (10c) |
| 177 | (Ia)-(Id) | (1a) | (2b) | (3c) | (4d) | (5a) | (6a) | (7a), (7b) | (8a) | (9a) | (10a) |
| 178 | (Ia)-(Id) | (1a) | (2b) | (3c) | (4d) | (5a) | (6a) | (7a), (7b) | (8a) | (9a) | (10c) |
| 179 | (Ia)-(Id) | (1a) | (2b) | (3c) | (4d) | (5a) | (6a) | (7a), (7b) | (8a) | (9b) | (10a) |
| 180 | (Ia)-(Id) | (1a) | (2b) | (3c) | (4d) | (5a) | (6a) | (7a), (7b) | (8a) | (9b) | (10c) |
| 181 | (Ia)-(Id) | (1a) | (2b) | (3c) | (4d) | (5a) | (6a) | (7d) | (8a) | (9a) | (10a) |
| 182 | (Ia)-(Id) | (1a) | (2b) | (3c) | (4d) | (5a) | (6a) | (7d) | (8a) | (9a) | (10c) |
| 183 | (Ia)-(Id) | (1a) | (2b) | (3c) | (4d) | (5a) | (6a) | (7d) | (8a) | (9b) | (10a) |
| 184 | (Ia)-(Id) | (1a) | (2b) | (3c) | (4d) | (5a) | (6a) | (7d) | (8a) | (9b) | (10c) |
| 185 | (Ia)-(Id) | (1a) | (2b) | (3c) | (4d) | (5a) | (6k) | (7a), (7b) | (8a) | (9a) | (10a) |
| 186 | (Ia)-(Id) | (1a) | (2b) | (3c) | (4d) | (5a) | (6k) | (7a), (7b) | (8a) | (9a) | (10c) |
| 187 | (Ia)-(Id) | (1a) | (2b) | (3c) | (4d) | (5a) | (6k) | (7a), (7b) | (8a) | (9b) | (10a) |
| 188 | (Ia)-(Id) | (1a) | (2b) | (3c) | (4d) | (5a) | (6k) | (7a), (7b) | (8a) | (9b) | (10c) |
| 189 | (Ia)-(Id) | (1a) | (2b) | (3c) | (4d) | (5a) | (6k) | (7d) | (8a) | (9a) | (10a) |
| 190 | (Ia)-(Id) | (1a) | (2b) | (3c) | (4d) | (5a) | (6k) | (7d) | (8a) | (9a) | (10c) |
| 191 | (Ia)-(Id) | (1a) | (2b) | (3c) | (4d) | (5a) | (6k) | (7d) | (8a) | (9b) | (10a) |
| 192 | (Ia)-(Id) | (1a) | (2b) | (3c) | (4d) | (5a) | (6k) | (7d) | (8a) | (9b) | (10c) |
| 193 | (Ia)-(Id) | (1a) | (2b) | (3b) | (4a) | (5b) | (6a) | (7a), (7b) | (8a) | (9a) | (10a) |
| 194 | (Ia)-(Id) | (1a) | (2b) | (3b) | (4a) | (5b) | (6a) | (7a), (7b) | (8a) | (9a) | (10c) |
| 195 | (Ia)-(Id) | (1a) | (2b) | (3b) | (4a) | (5b) | (6a) | (7a), (7b) | (8a) | (9b) | (10a) |
| 196 | (Ia)-(Id) | (1a) | (2b) | (3b) | (4a) | (5b) | (6a) | (7a), (7b) | (8a) | (9b) | (10c) |
| 197 | (Ia)-(Id) | (1a) | (2b) | (3b) | (4a) | (5b) | (6a) | (7d) | (8a) | (9a) | (10a) |
| 198 | (Ia)-(Id) | (1a) | (2b) | (3b) | (4a) | (5b) | (6a) | (7d) | (8a) | (9a) | (10c) |
| 199 | (Ia)-(Id) | (1a) | (2b) | (3b) | (4a) | (5b) | (6a) | (7d) | (8a) | (9b) | (10a) |
| 200 | (Ia)-(Id) | (1a) | (2b) | (3b) | (4a) | (5b) | (6a) | (7d) | (8a) | (9b) | (10c) |
| 201 | (Ia)-(Id) | (1a) | (2b) | (3b) | (4a) | (5b) | (6k) | (7a), (7b) | (8a) | (9a) | (10a) |
| 202 | (Ia)-(Id) | (1a) | (2b) | (3b) | (4a) | (5b) | (6k) | (7a), (7b) | (8a) | (9a) | (10c) |
| 203 | (Ia)-(Id) | (1a) | (2b) | (3b) | (4a) | (5b) | (6k) | (7a), (7b) | (8a) | (9b) | (10a) |
| 204 | (Ia)-(Id) | (1a) | (2b) | (3b) | (4a) | (5b) | (6k) | (7a), (7b) | (8a) | (9b) | (10c) |
| 205 | (Ia)-(Id) | (1a) | (2b) | (3b) | (4a) | (5b) | (6k) | (7d) | (8a) | (9a) | (10a) |
| 206 | (Ia)-(Id) | (1a) | (2b) | (3b) | (4a) | (5b) | (6k) | (7d) | (8a) | (9a) | (10c) |
| 207 | (Ia)-(Id) | (1a) | (2b) | (3b) | (4a) | (5b) | (6k) | (7d) | (8a) | (9b) | (10a) |
| 208 | (Ia)-(Id) | (1a) | (2b) | (3b) | (4a) | (5b) | (6k) | (7d) | (8a) | (9b) | (10c) |
| 209 | (Ia)-(Id) | (1a) | (2b) | (3b) | (4a) | (5a) | (6a) | (7a), (7b) | (8a) | (9a) | (10a) |
| 210 | (Ia)-(Id) | (1a) | (2b) | (3b) | (4a) | (5a) | (6a) | (7a), (7b) | (8a) | (9a) | (10c) |
| 211 | (Ia)-(Id) | (1a) | (2b) | (3b) | (4a) | (5a) | (6a) | (7a), (7b) | (8a) | (9b) | (10a) |
| 212 | (Ia)-(Id) | (1a) | (2b) | (3b) | (4a) | (5a) | (6a) | (7a), (7b) | (8a) | (9b) | (10c) |
| 213 | (Ia)-(Id) | (1a) | (2b) | (3b) | (4a) | (5a) | (6a) | (7d) | (8a) | (9a) | (10a) |
| 214 | (Ia)-(Id) | (1a) | (2b) | (3b) | (4a) | (5a) | (6a) | (7d) | (8a) | (9a) | (10c) |
| 215 | (Ia)-(Id) | (1a) | (2b) | (3b) | (4a) | (5a) | (6a) | (7d) | (8a) | (9b) | (10a) |
| 216 | (Ia)-(Id) | (1a) | (2b) | (3b) | (4a) | (5a) | (6a) | (7d) | (8a) | (9b) | (10c) |
| 217 | (Ia)-(Id) | (1a) | (2b) | (3b) | (4a) | (5a) | (6k) | (7a), (7b) | (8a) | (9a) | (10a) |
| 218 | (Ia)-(Id) | (1a) | (2b) | (3b) | (4a) | (5a) | (6k) | (7a), (7b) | (8a) | (9a) | (10c) |
| 219 | (Ia)-(Id) | (1a) | (2b) | (3b) | (4a) | (5a) | (6k) | (7a), (7b) | (8a) | (9b) | (10a) |
| 220 | (Ia)-(Id) | (1a) | (2b) | (3b) | (4a) | (5a) | (6k) | (7a), (7b) | (8a) | (9b) | (10c) |
| 221 | (Ia)-(Id) | (1a) | (2b) | (3b) | (4a) | (5a) | (6k) | (7d) | (8a) | (9a) | (10a) |
| 222 | (Ia)-(Id) | (1a) | (2b) | (3b) | (4a) | (5a) | (6k) | (7d) | (8a) | (9a) | (10c) |
| 223 | (Ia)-(Id) | (1a) | (2b) | (3b) | (4a) | (5a) | (6k) | (7d) | (8a) | (9b) | (10a) |
| 224 | (Ia)-(Id) | (1a) | (2b) | (3b) | (4a) | (5a) | (6k) | (7d) | (8a) | (9b) | (10c) |
| 225 | (Ia)-(Id) | (1a) | (2b) | (3b) | (4d) | (5b) | (6a) | (7a), (7b) | (8a) | (9a) | (10a) |
| 226 | (Ia)-(Id) | (1a) | (2b) | (3b) | (4d) | (5b) | (6a) | (7a), (7b) | (8a) | (9a) | (10c) |
| 227 | (Ia)-(Id) | (1a) | (2b) | (3b) | (4d) | (5b) | (6a) | (7a), (7b) | (8a) | (9b) | (10a) |
| 228 | (Ia)-(Id) | (1a) | (2b) | (3b) | (4d) | (5b) | (6a) | (7a), (7b) | (8a) | (9b) | (10c) |
| 229 | (Ia)-(Id) | (1a) | (2b) | (3b) | (4d) | (5b) | (6a) | (7d) | (8a) | (9a) | (10a) |
| 230 | (Ia)-(Id) | (1a) | (2b) | (3b) | (4d) | (5b) | (6a) | (7d) | (8a) | (9a) | (10c) |
| 231 | (Ia)-(Id) | (1a) | (2b) | (3b) | (4d) | (5b) | (6a) | (7d) | (8a) | (9b) | (10a) |
| 232 | (Ia)-(Id) | (1a) | (2b) | (3b) | (4d) | (5b) | (6a) | (7d) | (8a) | (9b) | (10c) |
| 233 | (Ia)-(Id) | (1a) | (2b) | (3b) | (4d) | (5b) | (6k) | (7a), (7b) | (8a) | (9a) | (10a) |
| 234 | (Ia)-(Id) | (1a) | (2b) | (3b) | (4d) | (5b) | (6k) | (7a), (7b) | (8a) | (9a) | (10c) |
| 235 | (Ia)-(Id) | (1a) | (2b) | (3b) | (4d) | (5b) | (6k) | (7a), (7b) | (8a) | (9b) | (10a) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 236 | (Ia)-(Id) | (1a) | (2b) | (3b) | (4d) | (5b) | (6k) | (7a), (7b) | (8a) | (9b) | (10c) |
| 237 | (Ia)-(Id) | (1a) | (2b) | (3b) | (4d) | (5b) | (6k) | (7d) | (8a) | (9a) | (10a) |
| 238 | (Ia)-(Id) | (1a) | (2b) | (3b) | (4d) | (5b) | (6k) | (7d) | (8a) | (9a) | (10c) |
| 239 | (Ia)-(Id) | (1a) | (2b) | (3b) | (4d) | (5b) | (6k) | (7d) | (8a) | (9b) | (10a) |
| 240 | (Ia)-(Id) | (1a) | (2b) | (3b) | (4d) | (5b) | (6k) | (7d) | (8a) | (9b) | (10c) |
| 241 | (Ia)-(Id) | (1a) | (2b) | (3b) | (4d) | (5a) | (6a) | (7a), (7b) | (8a) | (9a) | (10a) |
| 242 | (Ia)-(Id) | (1a) | (2b) | (3b) | (4d) | (5a) | (6a) | (7a), (7b) | (8a) | (9a) | (10c) |
| 243 | (Ia)-(Id) | (1a) | (2b) | (3b) | (4d) | (5a) | (6a) | (7a), (7b) | (8a) | (9b) | (10a) |
| 244 | (Ia)-(Id) | (1a) | (2b) | (3b) | (4d) | (5a) | (6a) | (7a), (7b) | (8a) | (9b) | (10c) |
| 245 | (Ia)-(Id) | (1a) | (2b) | (3b) | (4d) | (5a) | (6a) | (7d) | (8a) | (9a) | (10a) |
| 246 | (Ia)-(Id) | (1a) | (2b) | (3b) | (4d) | (5a) | (6a) | (7d) | (8a) | (9a) | (10c) |
| 247 | (Ia)-(Id) | (1a) | (2b) | (3b) | (4d) | (5a) | (6a) | (7d) | (8a) | (9b) | (10a) |
| 248 | (Ia)-(Id) | (1a) | (2b) | (3b) | (4d) | (5a) | (6a) | (7d) | (8a) | (9b) | (10c) |
| 249 | (Ia)-(Id) | (1a) | (2b) | (3b) | (4d) | (5a) | (6k) | (7a), (7b) | (8a) | (9a) | (10a) |
| 250 | (Ia)-(Id) | (1a) | (2b) | (3b) | (4d) | (5a) | (6k) | (7a), (7b) | (8a) | (9a) | (10c) |
| 251 | (Ia)-(Id) | (1a) | (2b) | (3b) | (4d) | (5a) | (6k) | (7a), (7b) | (8a) | (9b) | (10a) |
| 252 | (Ia)-(Id) | (1a) | (2b) | (3b) | (4d) | (5a) | (6k) | (7a), (7b) | (8a) | (9b) | (10c) |
| 253 | (Ia)-(Id) | (1a) | (2b) | (3b) | (4d) | (5a) | (6k) | (7d) | (8a) | (9a) | (10a) |
| 254 | (Ia)-(Id) | (1a) | (2b) | (3b) | (4d) | (5a) | (6k) | (7d) | (8a) | (9a) | (10c) |
| 255 | (Ia)-(Id) | (1a) | (2b) | (3b) | (4d) | (5a) | (6k) | (7d) | (8a) | (9b) | (10a) |
| 256 | (Ia)-(Id) | (1a) | (2b) | (3b) | (4d) | (5a) | (6k) | (7d) | (8a) | (9b) | (10c) |
| 257 | (Ia)-(Id) | (1d) | (2a) | (3c) | (4a) | (5b) | (6a) | (7a), (7b) | (8a) | (9a) | (10a) |
| 258 | (Ia)-(Id) | (1d) | (2a) | (3c) | (4a) | (5b) | (6a) | (7a), (7b) | (8a) | (9a) | (10c) |
| 259 | (Ia)-(Id) | (1d) | (2a) | (3c) | (4a) | (5b) | (6a) | (7a), (7b) | (8a) | (9b) | (10a) |
| 260 | (Ia)-(Id) | (1d) | (2a) | (3c) | (4a) | (5b) | (6a) | (7a), (7b) | (8a) | (9b) | (10c) |
| 261 | (Ia)-(Id) | (1d) | (2a) | (3c) | (4a) | (5b) | (6a) | (7d) | (8a) | (9a) | (10a) |
| 262 | (Ia)-(Id) | (1d) | (2a) | (3c) | (4a) | (5b) | (6a) | (7d) | (8a) | (9a) | (10c) |
| 263 | (Ia)-(Id) | (1d) | (2a) | (3c) | (4a) | (5b) | (6a) | (7d) | (8a) | (9b) | (10a) |
| 264 | (Ia)-(Id) | (1d) | (2a) | (3c) | (4a) | (5b) | (6a) | (7d) | (8a) | (9b) | (10c) |
| 265 | (Ia)-(Id) | (1d) | (2a) | (3c) | (4a) | (5b) | (6k) | (7a), (7b) | (8a) | (9a) | (10a) |
| 266 | (Ia)-(Id) | (1d) | (2a) | (3c) | (4a) | (5b) | (6k) | (7a), (7b) | (8a) | (9a) | (10c) |
| 267 | (Ia)-(Id) | (1d) | (2a) | (3c) | (4a) | (5b) | (6k) | (7a), (7b) | (8a) | (9b) | (10a) |
| 268 | (Ia)-(Id) | (1d) | (2a) | (3c) | (4a) | (5b) | (6k) | (7a), (7b) | (8a) | (9b) | (10c) |
| 269 | (Ia)-(Id) | (1d) | (2a) | (3c) | (4a) | (5b) | (6k) | (7d) | (8a) | (9a) | (10a) |
| 270 | (Ia)-(Id) | (1d) | (2a) | (3c) | (4a) | (5b) | (6k) | (7d) | (8a) | (9a) | (10c) |
| 271 | (Ia)-(Id) | (1d) | (2a) | (3c) | (4a) | (5b) | (6k) | (7d) | (8a) | (9b) | (10a) |
| 272 | (Ia)-(Id) | (1d) | (2a) | (3c) | (4a) | (5b) | (6k) | (7d) | (8a) | (9b) | (10c) |
| 273 | (Ia)-(Id) | (1d) | (2a) | (3c) | (4a) | (5a) | (6a) | (7a), (7b) | (8a) | (9a) | (10a) |
| 274 | (Ia)-(Id) | (1d) | (2a) | (3c) | (4a) | (5a) | (6a) | (7a), (7b) | (8a) | (9a) | (10c) |
| 275 | (Ia)-(Id) | (1d) | (2a) | (3c) | (4a) | (5a) | (6a) | (7a), (7b) | (8a) | (9b) | (10a) |
| 276 | (Ia)-(Id) | (1d) | (2a) | (3c) | (4a) | (5a) | (6a) | (7a), (7b) | (8a) | (9b) | (10c) |
| 277 | (Ia)-(Id) | (1d) | (2a) | (3c) | (4a) | (5a) | (6a) | (7d) | (8a) | (9a) | (10a) |
| 278 | (Ia)-(Id) | (1d) | (2a) | (3c) | (4a) | (5a) | (6a) | (7d) | (8a) | (9a) | (10c) |
| 279 | (Ia)-(Id) | (1d) | (2a) | (3c) | (4a) | (5a) | (6a) | (7d) | (8a) | (9b) | (10a) |
| 280 | (Ia)-(Id) | (1d) | (2a) | (3c) | (4a) | (5a) | (6a) | (7d) | (8a) | (9b) | (10c) |
| 281 | (Ia)-(Id) | (1d) | (2a) | (3c) | (4a) | (5a) | (6k) | (7a), (7b) | (8a) | (9a) | (10a) |
| 282 | (Ia)-(Id) | (1d) | (2a) | (3c) | (4a) | (5a) | (6k) | (7a), (7b) | (8a) | (9a) | (10c) |
| 283 | (Ia)-(Id) | (1d) | (2a) | (3c) | (4a) | (5a) | (6k) | (7a), (7b) | (8a) | (9b) | (10a) |
| 284 | (Ia)-(Id) | (1d) | (2a) | (3c) | (4a) | (5a) | (6k) | (7a), (7b) | (8a) | (9b) | (10c) |
| 285 | (Ia)-(Id) | (1d) | (2a) | (3c) | (4a) | (5a) | (6k) | (7d) | (8a) | (9a) | (10a) |
| 286 | (Ia)-(Id) | (1d) | (2a) | (3c) | (4a) | (5a) | (6k) | (7d) | (8a) | (9a) | (10c) |
| 287 | (Ia)-(Id) | (1d) | (2a) | (3c) | (4a) | (5a) | (6k) | (7d) | (8a) | (9b) | (10a) |
| 288 | (Ia)-(Id) | (1d) | (2a) | (3c) | (4a) | (5a) | (6k) | (7d) | (8a) | (9b) | (10c) |
| 289 | (Ia)-(Id) | (1d) | (2a) | (3c) | (4d) | (5b) | (6a) | (7a), (7b) | (8a) | (9a) | (10a) |
| 290 | (Ia)-(Id) | (1d) | (2a) | (3c) | (4d) | (5b) | (6a) | (7a), (7b) | (8a) | (9a) | (10c) |
| 291 | (Ia)-(Id) | (1d) | (2a) | (3c) | (4d) | (5b) | (6a) | (7a), (7b) | (8a) | (9b) | (10a) |
| 292 | (Ia)-(Id) | (1d) | (2a) | (3c) | (4d) | (5b) | (6a) | (7a), (7b) | (8a) | (9b) | (10c) |
| 293 | (Ia)-(Id) | (1d) | (2a) | (3c) | (4d) | (5b) | (6a) | (7d) | (8a) | (9a) | (10a) |
| 294 | (Ia)-(Id) | (1d) | (2a) | (3c) | (4d) | (5b) | (6a) | (7d) | (8a) | (9a) | (10c) |
| 295 | (Ia)-(Id) | (1d) | (2a) | (3c) | (4d) | (5b) | (6a) | (7d) | (8a) | (9b) | (10a) |
| 296 | (Ia)-(Id) | (1d) | (2a) | (3c) | (4d) | (5b) | (6a) | (7d) | (8a) | (9b) | (10c) |
| 297 | (Ia)-(Id) | (1d) | (2a) | (3c) | (4d) | (5b) | (6k) | (7a), (7b) | (8a) | (9a) | (10a) |
| 298 | (Ia)-(Id) | (1d) | (2a) | (3c) | (4d) | (5b) | (6k) | (7a), (7b) | (8a) | (9a) | (10c) |
| 299 | (Ia)-(Id) | (1d) | (2a) | (3c) | (4d) | (5b) | (6k) | (7a), (7b) | (8a) | (9b) | (10a) |
| 300 | (Ia)-(Id) | (1d) | (2a) | (3c) | (4d) | (5b) | (6k) | (7a), (7b) | (8a) | (9b) | (10c) |
| 301 | (Ia)-(Id) | (1d) | (2a) | (3c) | (4d) | (5b) | (6k) | (7d) | (8a) | (9a) | (10a) |
| 302 | (Ia)-(Id) | (1d) | (2a) | (3c) | (4d) | (5b) | (6k) | (7d) | (8a) | (9a) | (10c) |
| 303 | (Ia)-(Id) | (1d) | (2a) | (3c) | (4d) | (5b) | (6k) | (7d) | (8a) | (9b) | (10a) |
| 304 | (Ia)-(Id) | (1d) | (2a) | (3c) | (4d) | (5b) | (6k) | (7d) | (8a) | (9b) | (10c) |
| 305 | (Ia)-(Id) | (1d) | (2a) | (3c) | (4d) | (5a) | (6a) | (7a), (7b) | (8a) | (9a) | (10a) |
| 306 | (Ia)-(Id) | (1d) | (2a) | (3c) | (4d) | (5a) | (6a) | (7a), (7b) | (8a) | (9a) | (10c) |
| 307 | (Ia)-(Id) | (1d) | (2a) | (3c) | (4d) | (5a) | (6a) | (7a), (7b) | (8a) | (9b) | (10a) |
| 308 | (Ia)-(Id) | (1d) | (2a) | (3c) | (4d) | (5a) | (6a) | (7a), (7b) | (8a) | (9b) | (10c) |
| 309 | (Ia)-(Id) | (1d) | (2a) | (3c) | (4d) | (5a) | (6a) | (7d) | (8a) | (9a) | (10a) |
| 310 | (Ia)-(Id) | (1d) | (2a) | (3c) | (4d) | (5a) | (6a) | (7d) | (8a) | (9a) | (10c) |
| 311 | (Ia)-(Id) | (1d) | (2a) | (3c) | (4d) | (5a) | (6a) | (7d) | (8a) | (9b) | (10a) |
| 312 | (Ia)-(Id) | (1d) | (2a) | (3c) | (4d) | (5a) | (6a) | (7d) | (8a) | (9b) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 313 | (Ia)-(Id) | (1d) | (2a) | (3c) | (4d) | (5a) | (6k) | (7a), (7b) | (8a) | (9a) | (10a) |
| 314 | (Ia)-(Id) | (1d) | (2a) | (3c) | (4d) | (5a) | (6k) | (7a), (7b) | (8a) | (9a) | (10c) |
| 315 | (Ia)-(Id) | (1d) | (2a) | (3c) | (4d) | (5a) | (6k) | (7a), (7b) | (8a) | (9b) | (10a) |
| 316 | (Ia)-(Id) | (1d) | (2a) | (3c) | (4d) | (5a) | (6k) | (7a), (7b) | (8a) | (9b) | (10c) |
| 317 | (Ia)-(Id) | (1d) | (2a) | (3c) | (4d) | (5a) | (6k) | (7d) | (8a) | (9a) | (10a) |
| 318 | (Ia)-(Id) | (1d) | (2a) | (3c) | (4d) | (5a) | (6k) | (7d) | (8a) | (9a) | (10c) |
| 319 | (Ia)-(Id) | (1d) | (2a) | (3c) | (4d) | (5a) | (6k) | (7d) | (8a) | (9b) | (10a) |
| 320 | (Ia)-(Id) | (1d) | (2a) | (3c) | (4d) | (5a) | (6k) | (7d) | (8a) | (9b) | (10c) |
| 321 | (Ia)-(Id) | (1d) | (2a) | (3b) | (4a) | (5b) | (6a) | (7a), (7b) | (8a) | (9a) | (10a) |
| 322 | (Ia)-(Id) | (1d) | (2a) | (3b) | (4a) | (5b) | (6a) | (7a), (7b) | (8a) | (9a) | (10c) |
| 323 | (Ia)-(Id) | (1d) | (2a) | (3b) | (4a) | (5b) | (6a) | (7a), (7b) | (8a) | (9b) | (10a) |
| 324 | (Ia)-(Id) | (1d) | (2a) | (3b) | (4a) | (5b) | (6a) | (7a), (7b) | (8a) | (9b) | (10c) |
| 325 | (Ia)-(Id) | (1d) | (2a) | (3b) | (4a) | (5b) | (6a) | (7d) | (8a) | (9a) | (10a) |
| 326 | (Ia)-(Id) | (1d) | (2a) | (3b) | (4a) | (5b) | (6a) | (7d) | (8a) | (9a) | (10c) |
| 327 | (Ia)-(Id) | (1d) | (2a) | (3b) | (4a) | (5b) | (6a) | (7d) | (8a) | (9b) | (10a) |
| 328 | (Ia)-(Id) | (1d) | (2a) | (3b) | (4a) | (5b) | (6a) | (7d) | (8a) | (9b) | (10c) |
| 329 | (Ia)-(Id) | (1d) | (2a) | (3b) | (4a) | (5b) | (6k) | (7a), (7b) | (8a) | (9a) | (10a) |
| 330 | (Ia)-(Id) | (1d) | (2a) | (3b) | (4a) | (5b) | (6k) | (7a), (7b) | (8a) | (9a) | (10c) |
| 331 | (Ia)-(Id) | (1d) | (2a) | (3b) | (4a) | (5b) | (6k) | (7a), (7b) | (8a) | (9b) | (10a) |
| 332 | (Ia)-(Id) | (1d) | (2a) | (3b) | (4a) | (5b) | (6k) | (7a), (7b) | (8a) | (9b) | (10c) |
| 333 | (Ia)-(Id) | (1d) | (2a) | (3b) | (4a) | (5b) | (6k) | (7d) | (8a) | (9a) | (10a) |
| 334 | (Ia)-(Id) | (1d) | (2a) | (3b) | (4a) | (5b) | (6k) | (7d) | (8a) | (9a) | (10c) |
| 335 | (Ia)-(Id) | (1d) | (2a) | (3b) | (4a) | (5b) | (6k) | (7d) | (8a) | (9b) | (10a) |
| 336 | (Ia)-(Id) | (1d) | (2a) | (3b) | (4a) | (5b) | (6k) | (7d) | (8a) | (9b) | (10c) |
| 337 | (Ia)-(Id) | (1d) | (2a) | (3b) | (4a) | (5a) | (6a) | (7a), (7b) | (8a) | (9a) | (10a) |
| 338 | (Ia)-(Id) | (1d) | (2a) | (3b) | (4a) | (5a) | (6a) | (7a), (7b) | (8a) | (9a) | (10c) |
| 339 | (Ia)-(Id) | (1d) | (2a) | (3b) | (4a) | (5a) | (6a) | (7a), (7b) | (8a) | (9b) | (10a) |
| 340 | (Ia)-(Id) | (1d) | (2a) | (3b) | (4a) | (5a) | (6a) | (7a), (7b) | (8a) | (9b) | (10c) |
| 341 | (Ia)-(Id) | (1d) | (2a) | (3b) | (4a) | (5a) | (6a) | (7d) | (8a) | (9a) | (10a) |
| 342 | (Ia)-(Id) | (1d) | (2a) | (3b) | (4a) | (5a) | (6a) | (7d) | (8a) | (9a) | (10c) |
| 343 | (Ia)-(Id) | (1d) | (2a) | (3b) | (4a) | (5a) | (6a) | (7d) | (8a) | (9b) | (10a) |
| 344 | (Ia)-(Id) | (1d) | (2a) | (3b) | (4a) | (5a) | (6a) | (7d) | (8a) | (9b) | (10c) |
| 345 | (Ia)-(Id) | (1d) | (2a) | (3b) | (4a) | (5a) | (6k) | (7a), (7b) | (8a) | (9a) | (10a) |
| 346 | (Ia)-(Id) | (1d) | (2a) | (3b) | (4a) | (5a) | (6k) | (7a), (7b) | (8a) | (9a) | (10c) |
| 347 | (Ia)-(Id) | (1d) | (2a) | (3b | (4a) | (5a) | (6k) | (7a), (7b) | (8a) | (9b) | (10a) |
| 348 | (Ia)-(Id) | (1d) | (2a) | (3b) | (4a) | (5a) | (6k) | (7a), (7b) | (8a) | (9b) | (10c) |
| 349 | (Ia)-(Id) | (1d) | (2a) | (3b) | (4a) | (5a) | (6k) | (7d) | (8a) | (9a) | (10a) |
| 350 | (Ia)-(Id) | (1d) | (2a) | (3b) | (4a) | (5a) | (6k) | (7d) | (8a) | (9a) | (10c) |
| 351 | (Ia)-(Id) | (1d) | (2a) | (3b) | (4a) | (5a) | (6k) | (7d) | (8a) | (9b) | (10a) |
| 352 | (Ia)-(Id) | (1d) | (2a) | (3b) | (4a) | (5a) | (6k) | (7d) | (8a) | (9b) | (10c) |
| 353 | (Ia)-(Id) | (1d) | (2a) | (3b) | (4d) | (5b) | (6a) | (7a), (7b) | (8a) | (9a) | (10a) |
| 354 | (Ia)-(Id) | (1d) | (2a) | (3b) | (4d) | (5b) | (6a) | (7a), (7b) | (8a) | (9a) | (10c) |
| 355 | (Ia)-(Id) | (1d) | (2a) | (3b) | (4d) | (5b) | (6a) | (7a), (7b) | (8a) | (9b) | (10a) |
| 356 | (Ia)-(Id) | (1d) | (2a) | (3b) | (4d) | (5b) | (6a) | (7a), (7b) | (8a) | (9b) | (10c) |
| 357 | (Ia)-(Id) | (1d) | (2a) | (3b) | (4d) | (5b) | (6a) | (7d) | (8a) | (9a) | (10a) |
| 358 | (Ia)-(Id) | (1d) | (2a) | (3b) | (4d) | (5b) | (6a) | (7d) | (8a) | (9a) | (10c) |
| 359 | (Ia)-(Id) | (1d) | (2a) | (3b) | (4d) | (5b) | (6a) | (7d) | (8a) | (9b) | (10a) |
| 360 | (Ia)-(Id) | (1d) | (2a) | (3b) | (4d) | (5b) | (6a) | (7d) | (8a) | (9b) | (10c) |
| 361 | (Ia)-(Id) | (1d) | (2a) | (3b) | (4d) | (5b) | (6k) | (7a), (7b) | (8a) | (9a) | (10a) |
| 362 | (Ia)-(Id) | (1d) | (2a) | (3b) | (4d) | (5b) | (6k) | (7a), (7b) | (8a) | (9a) | (10c) |
| 363 | (Ia)-(Id) | (1d) | (2a) | (3b) | (4d) | (5b) | (6k) | (7a), (7b) | (8a) | (9b) | (10a) |
| 364 | (Ia)-(Id) | (1d) | (2a) | (3b) | (4d) | (5b) | (6k) | (7a), (7b) | (8a) | (9b) | (10c) |
| 365 | (Ia)-(Id) | (1d) | (2a) | (3b) | (4d) | (5b) | (6k) | (7d) | (8a) | (9a) | (10a) |
| 366 | (Ia)-(Id) | (1d) | (2a) | (3b) | (4d) | (5b) | (6k) | (7d) | (8a) | (9a) | (10c) |
| 367 | (Ia)-(Id) | (1d) | (2a) | (3b) | (4d) | (5b) | (6k) | (7d) | (8a) | (9b) | (10a) |
| 368 | (Ia)-(Id) | (1d) | (2a) | (3b) | (4d) | (5b) | (6k) | (7d) | (8a) | (9b) | (10c) |
| 369 | (Ia)-(Id) | (1d) | (2a) | (3b) | (4d) | (5a) | (6a) | (7a), (7b) | (8a) | (9a) | (10a) |
| 370 | (Ia)-(Id) | (1d) | (2a) | (3b) | (4d) | (5a) | (6a) | (7a), (7b) | (8a) | (9a) | (10c) |
| 371 | (Ia)-(Id) | (1d) | (2a) | (3b) | (4d) | (5a) | (6a) | (7a), (7b) | (8a) | (9b) | (10a) |
| 372 | (Ia)-(Id) | (1d) | (2a) | (3b) | (4d) | (5a) | (6a) | (7a), (7b) | (8a) | (9b) | (10c) |
| 373 | (Ia)-(Id) | (1d) | (2a) | (3b) | (4d) | (5a) | (6a) | (7d) | (8a) | (9a) | (10a) |
| 374 | (Ia)-(Id) | (1d) | (2a) | (3b) | (4d) | (5a) | (6a) | (7d) | (8a) | (9a) | (10c) |
| 375 | (Ia)-(Id) | (1d) | (2a) | (3b) | (4d) | (5a) | (6a) | (7d) | (8a) | (9b) | (10a) |
| 376 | (Ia)-(Id) | (1d) | (2a) | (3b) | (4d) | (5a) | (6a) | (7d) | (8a) | (9b) | (10c) |
| 377 | (Ia)-(Id) | (1d) | (2a) | (3b) | (4d) | (5a) | (6k) | (7a), (7b) | (8a) | (9a) | (10a) |
| 378 | (Ia)-(Id) | (1d) | (2a) | (3b) | (4d) | (5a) | (6k) | (7a), (7b) | (8a) | (9a) | (10c) |
| 379 | (Ia)-(Id) | (1d) | (2a) | (3b) | (4d) | (5a) | (6k) | (7a), (7b) | (8a) | (9b) | (10a) |
| 380 | (Ia)-(Id) | (1d) | (2a) | (3b) | (4d) | (5a) | (6k) | (7a), (7b) | (8a) | (9b) | (10c) |
| 381 | (Ia)-(Id) | (1d) | (2a) | (3b) | (4d) | (5a) | (6k) | (7d) | (8a) | (9a) | (10a) |
| 382 | (Ia)-(Id) | (1d) | (2a) | (3b) | (4d) | (5a) | (6k) | (7d) | (8a) | (9a) | (10c) |
| 383 | (Ia)-(Id) | (1d) | (2a) | (3b) | (4d) | (5a) | (6k) | (7d) | (8a) | (9b) | (10a) |
| 384 | (Ia)-(Id) | (1d) | (2a) | (3b) | (4d) | (5a) | (6k) | (7d) | (8a) | (9b) | (10c) |
| 385 | (Ia)-(Id) | (1d) | (2b) | (3c) | (4a) | (5b) | (6a) | (7a), (7b) | (8a) | (9a) | (10a) |
| 386 | (Ia)-(Id) | (1d) | (2b) | (3c) | (4a) | (5b) | (6a) | (7a), (7b) | (8a) | (9a) | (10c) |
| 387 | (Ia)-(Id) | (1d) | (2b) | (3c) | (4a) | (5b) | (6a) | (7a), (7b) | (8a) | (9b) | (10a) |
| 388 | (Ia)-(Id) | (1d) | (2b) | (3c) | (4a) | (5b) | (6a) | (7a), (7b) | (8a) | (9b) | (10c) |
| 389 | (Ia)-(Id) | (1d) | (2b) | (3c) | (4a) | (5b) | (6a) | (7d | (8a) | (9a) | (10a) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 390 | (Ia)-(Id) | (1d) | (2b) | (3c) | (4a) | (5b) | (6a) | (7d) | (8a) | (9a) | (10c) |
| 391 | (Ia)-(Id) | (1d) | (2b) | (3c) | (4a) | (5b) | (6a) | (7d) | (8a) | (9b) | (10a) |
| 392 | (Ia)-(Id) | (1d) | (2b) | (3c) | (4a) | (5b) | (6a) | (7d) | (8a) | (9b) | (10c) |
| 393 | (Ia)-(Id) | (1d) | (2b) | (3c) | (4a) | (5b) | (6k) | (7a), (7b) | (8a | (9a) | (10a) |
| 394 | (Ia)-(Id) | (1d) | (2b) | (3c) | (4a) | (5b) | (6k) | (7a), (7b) | (8a) | (9a) | (10c) |
| 395 | (Ia)-(Id) | (1d) | (2b) | (3c) | (4a) | (5b) | (6k) | (7a), (7b) | (8a) | (9b) | (10a) |
| 396 | (Ia)-(Id) | (1d) | (2b) | (3c) | (4a) | (5b) | (6k) | (7a), (7b) | (8a) | (9b) | (10c) |
| 397 | (Ia)-(Id) | (1d) | (2b) | (3c) | (4a) | (5b) | (6k) | (7d) | (8a) | (9a) | (10a) |
| 398 | (Ia)-(Id) | (1d) | (2b) | (3c) | (4a) | (5b) | (6k) | (7d) | (8a) | (9a) | (10c) |
| 399 | (Ia)-(Id) | (1d) | (2b) | (3c) | (4a) | (5b) | (6k) | (7d) | (8a) | (9b) | (10a) |
| 400 | (Ia)-(Id) | (1d) | (2b) | (3c) | (4a) | (5b) | (6k) | (7d) | (8a) | (9b) | (10c) |
| 401 | (Ia)-(Id) | (1d) | (2b) | (3c) | (4a) | (5a) | (6a) | (7a), (7b) | (8a) | (9a) | (10a) |
| 402 | (Ia)-(Id) | (1d) | (2b) | (3c) | (4a) | (5a) | (6a) | (7a), (7b) | (8a) | (9a) | (10c) |
| 403 | (Ia)-(Id) | (1d) | (2b) | (3c) | (4a) | (5a) | (6a) | (7a), (7b) | (8a) | (9b) | (10a) |
| 404 | (Ia)-(Id) | (1d) | (2b) | (3c) | (4a) | (5a) | (6a) | (7a), (7b) | (8a) | (9b) | (10c) |
| 405 | (Ia)-(Id) | (1d) | (2b) | (3c) | (4a) | (5a) | (6a) | (7d) | (8a) | (9a) | (10a) |
| 406 | (Ia)-(Id) | (1d) | (2b) | (3c) | (4a) | (5a) | (6a) | (7d) | (8a) | (9a) | (10c) |
| 407 | (Ia)-(Id) | (1d) | (2b) | (3c) | (4a) | (5a) | (6a) | (7d) | (8a) | (9b) | (10a) |
| 408 | (Ia)-(Id) | (1d) | (2b) | (3c) | (4a) | (5a) | (6a) | (7d) | (8a) | (9b) | (10c) |
| 409 | (Ia)-(Id) | (1d) | (2b) | (3c) | (4a) | (5a) | (6k) | (7a), (7b) | (8a) | (9a) | (10a) |
| 410 | (Ia)-(Id) | (1d) | (2b) | (3c) | (4a) | (5a) | (6k) | (7a), (7b) | (8a) | (9a) | (10c) |
| 411 | (Ia)-(Id) | (1d) | (2b) | (3c) | (4a) | (5a) | (6k) | (7a), (7b) | (8a) | (9b) | (10a) |
| 412 | (Ia)-(Id) | (1d) | (2b) | (3c) | (4a) | (5a) | (6k) | (7a), (7b) | (8a) | (9b) | (10c) |
| 413 | (Ia)-(Id) | (1d) | (2b) | (3c) | (4a) | (5a) | (6k) | (7d) | (8a) | (9a) | (10a) |
| 414 | (Ia)-(Id) | (1d) | (2b) | (3c) | (4a) | (5a) | (6k) | (7d) | (8a) | (9a) | (10c) |
| 415 | (Ia)-(Id) | (1d) | (2b) | (3c) | (4a) | (5a) | (6k) | (7d) | (8a) | (9b) | (10a) |
| 416 | (Ia)-(Id) | (1d) | (2b) | (3c) | (4a) | (5a) | (6k) | (7d) | (8a) | (9b) | (10c) |
| 417 | (Ia)-(Id) | (1d) | (2b) | (3c) | (4d) | (5b) | (6a) | (7a), (7b) | (8a) | (9a) | (10a) |
| 418 | (Ia)-(Id) | (1d) | (2b) | (3c) | (4d) | (5b) | (6a) | (7a), (7b) | (8a) | (9a) | (10c) |
| 419 | (Ia)-(Id) | (1d) | (2b) | (3c) | (4d) | (5b) | (6a) | (7a), (7b) | (8a) | (9b) | (10a) |
| 420 | (Ia)-(Id) | (1d) | (2b) | (3c) | (4d) | (5b) | (6a) | (7a), (7b) | (8a) | (9b) | (10c) |
| 421 | (Ia)-(Id) | (1d) | (2b) | (3c) | (4d) | (5b) | (6a) | (7d) | (8a) | (9a) | (10a) |
| 422 | (Ia)-(Id) | (1d) | (2b) | (3c) | (4d) | (5b) | (6a) | (7d) | (8a) | (9a) | (10c) |
| 423 | (Ia)-(Id) | (1d) | (2b) | (3c) | (4d) | (5b) | (6a) | (7d) | (8a) | (9b) | (10a) |
| 424 | (Ia)-(Id) | (1d) | (2b) | (3c) | (4d) | (5b) | (6a) | (7d) | (8a) | (9b) | (10c) |
| 425 | (Ia)-(Id) | (1d) | (2b) | (3c) | (4d) | (5b) | (6k) | (7a), (7b) | (8a) | (9a) | (10a) |
| 426 | (Ia)-(Id) | (1d) | (2b) | (3c) | (4d) | (5b) | (6k) | (7a), (7b) | (8a) | (9a) | (10c) |
| 427 | (Ia)-(Id) | (1d) | (2b) | (3c) | (4d) | (5b) | (6k) | (7a), (7b) | (8a) | (9b) | (10a) |
| 428 | (Ia)-(Id) | (1d) | (2b) | (3c) | (4d) | (5b) | (6k) | (7a), (7b) | (8a) | (9b) | (10c) |
| 429 | (Ia)-(Id) | (1d) | (2b) | (3c) | (4d) | (5b) | (6k) | (7d) | (8a) | (9a) | (10a) |
| 430 | (Ia)-(Id) | (1d) | (2b) | (3c) | (4d) | (5b) | (6k) | (7d) | (8a) | (9a) | (10c) |
| 431 | (Ia)-(Id) | (1d) | (2b) | (3c) | (4d) | (5b) | (6k | (7d) | (8a) | (9b) | (10a) |
| 432 | (Ia)-(Id) | (1d) | (2b) | (3c) | (4d) | (5b) | (6k) | (7d) | (8a) | (9b) | (10c) |
| 433 | (Ia)-(Id) | (1d) | (2b) | (3c) | (4d) | (5a) | (6a) | (7a), (7b) | (8a) | (9a) | (10a) |
| 434 | (Ia)-(Id) | (1d) | (2b) | (3c) | (4d) | (5a) | (6a) | (7a), (7b) | (8a) | (9a) | (10c) |
| 435 | (Ia)-(Id) | (1d) | (2b) | (3c) | (4d) | (5a) | (6a) | (7a), (7b) | (8a) | (9b) | (10a) |
| 436 | (Ia)-(Id) | (1d) | (2b) | (3c) | (4d) | (5a) | (6a) | (7a), (7b) | (8a) | (9b) | (10c) |
| 437 | (Ia)-(Id) | (1d) | (2b) | (3c) | (4d) | (5a) | (6a) | (7d) | (8a) | (9a) | (10a) |
| 438 | (Ia)-(Id) | (1d) | (2b) | (3c) | (4d) | (5a) | (6a) | (7d) | (8a) | (9a) | (10c) |
| 439 | (Ia)-(Id) | (1d) | (2b) | (3c) | (4d) | (5a) | (6a) | (7d) | (8a) | (9b) | (10a) |
| 440 | (Ia)-(Id) | (1d) | (2b) | (3c) | (4d) | (5a) | (6a) | (7d) | (8a) | (9b) | (10c) |
| 441 | (Ia)-(Id) | (1d) | (2b) | (3c) | (4d) | (5a) | (6k) | (7a), (7b) | (8a) | (9a) | (10a) |
| 442 | (Ia)-(Id) | (1d) | (2b) | (3c) | (4d) | (5a) | (6k) | (7a), (7b) | (8a) | (9a) | (10c) |
| 443 | (Ia)-(Id) | (1d) | (2b) | (3c) | (4d) | (5a) | (6k) | (7a), (7b) | (8a) | (9b) | (10a) |
| 444 | (Ia)-(Id) | (1d) | (2b) | (3c) | (4d) | (5a) | (6k) | (7a), (7b) | (8a) | (9b) | (10c) |
| 445 | (Ia)-(Id) | (1d) | (2b) | (3c) | (4d) | (5a) | (6k) | (7d) | (8a) | (9a) | (10a) |
| 446 | (Ia)-(Id) | (1d) | (2b) | (3c) | (4d) | (5a) | (6k) | (7d) | (8a) | (9a) | (10c) |
| 447 | (Ia)-(Id) | (1d) | (2b) | (3c) | (4d) | (5a) | (6k) | (7d) | (8a) | (9b) | (10a) |
| 448 | (Ia)-(Id) | (1d) | (2b) | (3c) | (4d) | (5a) | (6k) | (7d) | (8a) | (9b) | (10c) |
| 449 | (Ia)-(Id) | (1d) | (2b) | (3b) | (4a) | (5b) | (6a) | (7a), (7b) | (8a) | (9a) | (10a) |
| 450 | (Ia)-(Id) | (1d) | (2b) | (3b) | (4a) | (5b) | (6a) | (7a), (7b) | (8a) | (9a) | (10c) |
| 451 | (Ia)-(Id) | (1d) | (2b) | (3b) | (4a) | (5b) | (6a) | (7a), (7b) | (8a) | (9b) | (10a) |
| 452 | (Ia)-(Id) | (1d) | (2b) | (3b) | (4a) | (5b) | (6a) | (7a), (7b) | (8a) | (9b) | (10c) |
| 453 | (Ia)-(Id) | (1d) | (2b) | (3b) | (4a) | (5b) | (6a) | (7d) | (8a) | (9a) | (10a) |
| 454 | (Ia)-(Id) | (1d) | (2b) | (3b) | (4a) | (5b) | (6a) | (7d) | (8a) | (9a) | (10c) |
| 455 | (Ia)-(Id) | (1d) | (2b) | (3b) | (4a) | (5b) | (6a) | (7d) | (8a) | (9b) | (10a) |
| 456 | (Ia)-(Id) | (1d) | (2b) | (3b) | (4a) | (5b) | (6a) | (7d) | (8a) | (9b) | (10c) |
| 457 | (Ia)-(Id) | (1d) | (2b) | (3b) | (4a) | (5b) | (6k) | (7a), (7b) | (8a) | (9a) | (10a) |
| 458 | (Ia)-(Id) | (1d) | (2b) | (3b) | (4a) | (5b) | (6k) | (7a), (7b) | (8a) | (9a) | (10c) |
| 459 | (Ia)-(Id) | (1d) | (2b) | (3b) | (4a) | (5b) | (6k) | (7a), (7b) | (8a) | (9b) | (10a) |
| 460 | (Ia)-(Id) | (1d) | (2b) | (3b) | (4a) | (5b) | (6k | (7a), (7b) | (8a) | (9b) | (10c) |
| 461 | (Ia)-(Id) | (1d) | (2b) | (3b) | (4a) | (5b) | (6k) | (7d) | (8a) | (9a) | (10a) |
| 462 | (Ia)-(Id) | (1d) | (2b) | (3b) | (4a) | (5b) | (6k) | (7d) | (8a) | (9a) | (10c) |
| 463 | (Ia)-(Id) | (1d) | (2b) | (3b) | (4a) | (5b) | (6k) | (7d) | (8a) | (9b) | (10a) |
| 464 | (Ia)-(Id) | (1d) | (2b) | (3b) | (4a) | (5b) | (6k) | (7d) | (8a) | (9b) | (10c) |
| 465 | (Ia)-(Id) | (1d) | (2b) | (3b) | (4a) | (5a) | (6a) | (7a), (7b) | (8a) | (9a) | (10a) |
| 466 | (Ia)-(Id) | (1d) | (2b) | (3b) | (4a) | (5a) | (6a) | (7a), (7b) | (8a) | (9a) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 467 | (Ia)-(Id) | (1d) | (2b) | (3b) | (4a) | (5a) | (6a) | (7a), (7b) | (8a) | (9b) | (10a) |
| 468 | (Ia)-(Id) | (1d) | (2b) | (3b) | (4a) | (5a) | (6a) | (7a), (7b) | (8a) | (9b) | (10c) |
| 469 | (Ia)-(Id) | (1d) | (2b) | (3b) | (4a) | (5a) | (6a) | (7d) | (8a) | (9a) | (10a) |
| 470 | (Ia)-(Id) | (1d) | (2b) | (3b) | (4a) | (5a) | (6a) | (7d) | (8a) | (9a) | (10c) |
| 471 | (Ia)-(Id) | (1d) | (2b) | (3b) | (4a) | (5a) | (6a) | (7d) | (8a) | (9b) | (10a) |
| 472 | (Ia)-(Id) | (1d) | (2b) | (3b) | (4a) | (5a) | (6a) | (7d) | (8a) | (9b) | (10c) |
| 473 | (Ia)-(Id) | (1d) | (2b) | (3b) | (4a) | (5a) | (6k) | (7a), (7b) | (8a) | (9a) | (10a) |
| 474 | (Ia)-(Id) | (1d) | (2b) | (3b) | (4a) | (5a) | (6k) | (7a), (7b) | (8a) | (9a) | (10c) |
| 475 | (Ia)-(Id) | (1d) | (2b) | (3b) | (4a) | (5a) | (6k) | (7a), (7b) | (8a) | (9b) | (10a) |
| 476 | (Ia)-(Id) | (1d) | (2b) | (3b) | (4a) | (5a) | (6k) | (7a), (7b) | (8a) | (9b) | (10c) |
| 477 | (Ia)-(Id) | (1d) | (2b) | (3b) | (4a) | (5a) | (6k) | (7d) | (8a) | (9a) | (10a) |
| 478 | (Ia)-(Id) | (1d) | (2b) | (3b) | (4a) | (5a) | (6k) | (7d) | (8a) | (9a) | (10c) |
| 479 | (Ia)-(Id) | (1d) | (2b) | (3b) | (4a) | (5a) | (6k) | (7d) | (8a) | (9b) | (10a) |
| 480 | (Ia)-(Id) | (1d) | (2b) | (3b) | (4a) | (5a) | (6k) | (7d) | (8a) | (9b) | (10c) |
| 481 | (Ia)-(Id) | (1d) | (2b) | (3b) | (4d) | (5b) | (6a) | (7a), (7b) | (8a) | (9a) | (10a) |
| 482 | (Ia)-(Id) | (1d) | (2b) | (3b) | (4d) | (5b) | (6a) | (7a), (7b) | (8a) | (9a) | (10c) |
| 483 | (Ia)-(Id) | (1d) | (2b) | (3b) | (4d) | (5b) | (6a) | (7a), (7b) | (8a) | (9b) | (10a) |
| 484 | (Ia)-(Id) | (1d) | (2b) | (3b) | (4d) | (5b) | (6a) | (7a), (7b) | (8a) | (9b) | (10c) |
| 485 | (Ia)-(Id) | (1d) | (2b) | (3b) | (4d) | (5b) | (6a) | (7d) | (8a) | (9a) | (10a) |
| 486 | (Ia)-(Id) | (1d) | (2b) | (3b) | (4d) | (5b) | (6a) | (7d) | (8a) | (9a) | (10c) |
| 487 | (Ia)-(Id) | (1d) | (2b) | (3b) | (4d) | (5b) | (6a) | (7d) | (8a) | (9b) | (10a) |
| 488 | (Ia)-(Id) | (1d) | (2b) | (3b) | (4d) | (5b) | (6a) | (7d) | (8a) | (9b) | (10c) |
| 489 | (Ia)-(Id) | (1d) | (2b) | (3b) | (4d) | (5b) | (6k) | (7a), (7b) | (8a) | (9a) | (10a) |
| 490 | (Ia)-(Id) | (1d) | (2b) | (3b) | (4d) | (5b) | (6k) | (7a), (7b) | (8a) | (9a) | (10c) |
| 491 | (Ia)-(Id) | (1d) | (2b) | (3b) | (4d) | (5b) | (6k) | (7a), (7b) | (8a) | (9b) | (10a) |
| 492 | (Ia)-(Id) | (1d) | (2b) | (3b) | (4d) | (5b) | (6k) | (7a), (7b) | (8a) | (9b) | (10c) |
| 493 | (Ia)-(Id) | (1d) | (2b) | (3b) | (4d) | (5b) | (6k) | (7d) | (8a) | (9a) | (10a) |
| 494 | (Ia)-(Id) | (1d) | (2b) | (3b) | (4d) | (5b) | (6k) | (7d) | (8a) | (9a) | (10c) |
| 495 | (Ia)-(Id) | (1d) | (2b) | (3b) | (4d) | (5b) | (6k) | (7d) | (8a) | (9b) | (10a) |
| 496 | (Ia)-(Id) | (1d) | (2b) | (3b) | (4d) | (5b) | (6k) | (7d) | (8a) | (9b) | (10c) |
| 497 | (Ia)-(Id) | (1d) | (2b) | (3b) | (4d) | (5a) | (6a) | (7a), (7b) | (8a) | (9a) | (10a) |
| 498 | (Ia)-(Id) | (1d) | (2b) | (3b) | (4d) | (5a) | (6a) | (7a), (7b) | (8a) | (9a) | (10c) |
| 499 | (Ia)-(Id) | (1d) | (2b) | (3b) | (4d) | (5a) | (6a) | (7a), (7b) | (8a) | (9b) | (10a) |
| 500 | (Ia)-(Id) | (1d) | (2b) | (3b) | (4d) | (5a) | (6a) | (7a), (7b) | (8a) | (9b) | (10c) |
| 501 | (Ia)-(Id) | (1d) | (2b) | (3b) | (4d) | (5a) | (6a) | (7d) | (8a) | (9a) | (10a) |
| 502 | (Ia)-(Id) | (1d) | (2b) | (3b) | (4d) | (5a) | (6a) | (7d) | (8a) | (9a) | (10c) |
| 503 | (Ia)-(Id) | (1d) | (2b) | (3b) | (4d) | (5a) | (6a) | (7d) | (8a) | (9b) | (10a) |
| 504 | (Ia)-(Id) | (1d) | (2b) | (3b) | (4d) | (5a) | (6a) | (7d) | (8a) | (9b) | (10c) |
| 505 | (Ia)-(Id) | (1d) | (2b) | (3b) | (4d) | (5a) | (6k) | (7a), (7b) | (8a) | (9a) | (10a) |
| 506 | (Ia)-(Id) | (1d) | (2b) | (3b) | (4d) | (5a) | (6k) | (7a), (7b) | (8a) | (9a) | (10c) |
| 507 | (Ia)-(Id) | (1d) | (2b) | (3b) | (4d) | (5a) | (6k) | (7a), (7b) | (8a) | (9b) | (10a) |
| 508 | (Ia)-(Id) | (1d) | (2b) | (3b) | (4d) | (5a) | (6k) | (7a), (7b) | (8a) | (9b) | (10c) |
| 509 | (Ia)-(Id) | (1d) | (2b) | (3b) | (4d) | (5a) | (6k) | (7d) | (8a) | (9a) | (10a) |
| 510 | (Ia)-(Id) | (1d) | (2b) | (3b) | (4d) | (5a) | (6k) | (7d) | (8a) | (9a) | (10c) |
| 511 | (Ia)-(Id) | (1d) | (2b) | (3b) | (4d) | (5a) | (6k) | (7d) | (8a) | (9b) | (10a) |
| 512 | (Ia)-(Id) | (1d) | (2b) | (3b) | (4d) | (5a) | (6k) | (7d) | (8a) | (9b) | (10c) |
| 513 | (Id) | (1a) | (2a) | (3c) | (4a) | (5b) | (6a) | (7a), (7b) | (8a) | (9a) | (10a) |
| 514 | (Id) | (1a) | (2a) | (3c) | (4a) | (5b) | (6a) | (7a), (7b) | (8a) | (9a) | (10c) |
| 515 | (Id) | (1a) | (2a) | (3c) | (4a) | (5b) | (6a) | (7a), (7b) | (8a) | (9b) | (10a) |
| 516 | (Id) | (1a) | (2a) | (3c) | (4a) | (5b) | (6a) | (7a), (7b) | (8a) | (9b) | (10c) |
| 517 | (Id) | (1a) | (2a) | (3c) | (4a) | (5b) | (6a) | (7d) | (8a) | (9a) | (10a) |
| 518 | (Id) | (1a) | (2a) | (3c) | (4a) | (5b) | (6a) | (7d) | (8a) | (9a) | (10c) |
| 519 | (Id) | (1a) | (2a) | (3c) | (4a) | (5b) | (6a) | (7d) | (8a) | (9b) | (10a) |
| 520 | (Id) | (1a) | (2a) | (3c) | (4a) | (5b) | (6a) | (7d) | (8a) | (9b) | (10c) |
| 521 | (Id) | (1a) | (2a) | (3c) | (4a) | (5b) | (6k) | (7a), (7b) | (8a) | (9a) | (10a) |
| 522 | (Id) | (1a) | (2a) | (3c) | (4a) | (5b) | (6k) | (7a), (7b) | (8a) | (9a) | (10c) |
| 523 | (Id) | (1a) | (2a) | (3c) | (4a) | (5b) | (6k) | (7a), (7b) | (8a) | (9b) | (10a) |
| 524 | (Id) | (1a) | (2a) | (3c) | (4a) | (5b) | (6k) | (7a), (7b) | (8a) | (9b) | (10c) |
| 525 | (Id) | (1a) | (2a) | (3c) | (4a) | (5b) | (6k) | (7d) | (8a) | (9a) | (10a) |
| 526 | (Id) | (1a) | (2a) | (3c) | (4a) | (5b) | (6k) | (7d) | (8a) | (9a) | (10c) |
| 527 | (Id) | (1a) | (2a) | (3c) | (4a) | (5b) | (6k) | (7d) | (8a) | (9b) | (10a) |
| 528 | (Id) | (1a) | (2a) | (3c) | (4a) | (5b) | (6k) | (7d) | (8a) | (9b) | (10c) |
| 529 | (Id) | (1a) | (2a) | (3c) | (4a) | (5a) | (6a) | (7a), (7b) | (8a) | (9a) | (10a) |
| 530 | (Id) | (1a) | (2a) | (3c) | (4a) | (5a) | (6a) | (7a), (7b) | (8a) | (9a) | (10c) |
| 531 | (Id) | (1a) | (2a) | (3c) | (4a) | (5a) | (6a) | (7a), (7b) | (8a) | (9b) | (10a) |
| 532 | (Id) | (1a) | (2a) | (3c) | (4a) | (5a) | (6a) | (7a), (7b) | (8a) | (9b) | (10c) |
| 533 | (Id) | (1a) | (2a) | (3c) | (4a) | (5a) | (6a) | (7d) | (8a) | (9a) | (10a) |
| 534 | (Id) | (1a) | (2a) | (3c) | (4a) | (5a) | (6a) | (7d) | (8a) | (9a) | (10c) |
| 535 | (Id) | (1a) | (2a) | (3c) | (4a) | (5a) | (6a) | (7d) | (8a) | (9b) | (10a) |
| 536 | (Id) | (1a) | (2a) | (3c) | (4a) | (5a) | (6a) | (7d) | (8a) | (9b) | (10c) |
| 537 | (Id) | (1a) | (2a) | (3c) | (4a) | (5a) | (6k) | (7a), (7b) | (8a) | (9a) | (10a) |
| 538 | (Id) | (1a) | (2a) | (3c) | (4a) | (5a) | (6k) | (7a), (7b) | (8a) | (9a) | (10c) |
| 539 | (Id) | (1a) | (2a) | (3c) | (4a) | (5a) | (6k) | (7a), (7b) | (8a) | (9b) | (10a) |
| 540 | (Id) | (1a) | (2a) | (3c) | (4a) | (5a) | (6k) | (7a), (7b) | (8a) | (9b) | (10c) |
| 541 | (Id) | (1a) | (2a) | (3c) | (4a) | (5a) | (6k) | (7d) | (8a) | (9a) | (10a) |
| 542 | (Id) | (1a) | (2a) | (3c) | (4a) | (5a) | (6k) | (7d) | (8a) | (9a) | (10c) |
| 543 | (Id) | (1a) | (2a) | (3c) | (4a) | (5a) | (6k) | (7d) | (8a) | (9b) | (10a) |

-continued

| | I | L[1] | R[1] | L[2] | Q | L[3] | R[3] | L[4] | R[4] | L[5] | R[5] |
|---|---|---|---|---|---|---|---|---|---|---|---|
| 544 | (Id) | (1a) | (2a) | (3c) | (4a) | (5a) | (6k) | (7d) | (8a) | (9b) | (10c) |
| 545 | (Id) | (1a) | (2a) | (3c) | (4d) | (5b) | (6a) | (7a), (7b) | (8a) | (9a) | (10a) |
| 546 | (Id) | (1a) | (2a) | (3c) | (4d) | (5b) | (6a) | (7a), (7b) | (8a) | (9a) | (10c) |
| 547 | (Id) | (1a) | (2a) | (3c) | (4d) | (5b) | (6a) | (7a), (7b) | (8a) | (9b) | (10a) |
| 548 | (Id) | (1a) | (2a) | (3c) | (4d) | (5b) | (6a) | (7a), (7b) | (8a) | (9b) | (10c) |
| 549 | (Id) | (1a) | (2a) | (3c) | (4d) | (5b) | (6a) | (7d) | (8a) | (9a) | (10a) |
| 550 | (Id) | (1a) | (2a) | (3c) | (4d) | (5b) | (6a) | (7d) | (8a) | (9a) | (10c) |
| 551 | (Id) | (1a) | (2a) | (3c) | (4d) | (5b) | (6a) | (7d) | (8a) | (9b) | (10a) |
| 552 | (Id) | (1a) | (2a) | (3c) | (4d) | (5b) | (6a) | (7d) | (8a) | (9b) | (10c) |
| 553 | (Id) | (1a) | (2a) | (3c) | (4d) | (5b) | (6k) | (7a), (7b) | (8a) | (9a) | (10a) |
| 554 | (Id) | (1a) | (2a) | (3c) | (4d) | (5b) | (6k) | (7a), (7b) | (8a) | (9a) | (10c) |
| 555 | (Id) | (1a) | (2a) | (3c) | (4d) | (5b) | (6k) | (7a), (7b) | (8a) | (9b) | (10a) |
| 556 | (Id) | (1a) | (2a) | (3c) | (4d) | (5b) | (6k) | (7a), (7b) | (8a) | (9b) | (10c) |
| 557 | (Id) | (1a) | (2a) | (3c) | (4d) | (5b) | (6k) | (7d) | (8a) | (9a) | (10a) |
| 558 | (Id) | (1a) | (2a) | (3c) | (4d) | (5b) | (6k) | (7d) | (8a) | (9a) | (10c) |
| 559 | (Id) | (1a) | (2a) | (3c) | (4d) | (5b) | (6k) | (7d) | (8a) | (9b) | (10a) |
| 560 | (Id) | (1a) | (2a) | (3c) | (4d) | (5b) | (6k) | (7d) | (8a) | (9b) | (10c) |
| 561 | (Id) | (1a) | (2a) | (3c) | (4d) | (5a) | (6a) | (7a), (7b) | (8a) | (9a) | (10a) |
| 562 | (Id) | (1a) | (2a) | (3c) | (4d) | (5a) | (6a) | (7a), (7b) | (8a) | (9a) | (10c) |
| 563 | (Id) | (1a) | (2a) | (3c) | (4d) | (5a) | (6a) | (7a), (7b) | (8a) | (9b) | (10a) |
| 564 | (Id) | (1a) | (2a) | (3c) | (4d) | (5a) | (6a) | (7a), (7b) | (8a) | (9b) | (10c) |
| 565 | (Id) | (1a) | (2a) | (3c) | (4d) | (5a) | (6a) | (7d) | (8a) | (9a) | (10a) |
| 566 | (Id) | (1a) | (2a) | (3c) | (4d) | (5a) | (6a) | (7d) | (8a) | (9a) | (10c) |
| 567 | (Id) | (1a) | (2a) | (3c) | (4d) | (5a) | (6a) | (7d) | (8a) | (9b) | (10a) |
| 568 | (Id) | (1a) | (2a) | (3c) | (4d) | (5a) | (6a) | (7d) | (8a) | (9b) | (10c) |
| 569 | (Id) | (1a) | (2a) | (3c) | (4d) | (5a) | (6k) | (7a), (7b) | (8a) | (9a) | (10a) |
| 570 | (Id) | (1a) | (2a) | (3c) | (4d) | (5a) | (6k) | (7a), (7b) | (8a) | (9a) | (10c) |
| 571 | (Id) | (1a) | (2a) | (3c) | (4d) | (5a) | (6k) | (7a), (7b) | (8a) | (9b) | (10a) |
| 572 | (Id) | (1a) | (2a) | (3c) | (4d) | (5a) | (6k) | (7a), (7b) | (8a) | (9b) | (10c) |
| 573 | (Id) | (1a) | (2a) | (3c) | (4d) | (5a) | (6k) | (7d) | (8a) | (9a) | (10a) |
| 574 | (Id) | (1a) | (2a) | (3c) | (4d) | (5a) | (6k) | (7d) | (8a) | (9a) | (10c) |
| 575 | (Id) | (1a) | (2a) | (3c) | (4d) | (5a) | (6k) | (7d) | (8a) | (9b) | (10a) |
| 576 | (Id) | (1a) | (2a) | (3c) | (4d) | (5a) | (6k) | (7d) | (8a) | (9b) | (10c) |
| 577 | (Id) | (1a) | (2a) | (3b) | (4a) | (5b) | (6a) | (7a), (7b) | (8a) | (9a) | (10a) |
| 578 | (Id) | (1a) | (2a) | (3b) | (4a) | (5b) | (6a) | (7a), (7b) | (8a) | (9a) | (10c) |
| 579 | (Id) | (1a) | (2a) | (3b) | (4a) | (5b) | (6a) | (7a), (7b) | (8a) | (9b) | (10a) |
| 580 | (Id) | (1a) | (2a) | (3b) | (4a) | (5b) | (6a) | (7a), (7b) | (8a) | (9b) | (10c) |
| 581 | (Id) | (1a) | (2a) | (3b) | (4a) | (5b) | (6a) | (7d) | (8a) | (9a) | (10a) |
| 582 | (Id) | (1a) | (2a) | (3b) | (4a) | (5b) | (6a) | (7d) | (8a) | (9a) | (10c) |
| 583 | (Id) | (1a) | (2a) | (3b) | (4a) | (5b) | (6a) | (7d) | (8a) | (9b) | (10a) |
| 584 | (Id) | (1a) | (2a) | (3b) | (4a) | (5b) | (6a) | (7d) | (8a) | (9b) | (10c) |
| 585 | (Id) | (1a) | (2a) | (3b) | (4a) | (5b) | (6k) | (7a), (7b) | (8a) | (9a) | (10a) |
| 586 | (Id) | (1a) | (2a) | (3b) | (4a) | (5b) | (6k) | (7a), (7b) | (8a) | (9a) | (10c) |
| 587 | (Id) | (1a) | (2a) | (3b) | (4a) | (5b) | (6k) | (7a), (7b) | (8a) | (9b) | (10a) |
| 588 | (Id) | (1a) | (2a) | (3b) | (4a) | (5b) | (6k) | (7a), (7b) | (8a) | (9b) | (10c) |
| 589 | (Id) | (1a) | (2a) | (3b) | (4a) | (5b) | (6k) | (7d) | (8a) | (9a) | (10a) |
| 590 | (Id) | (1a) | (2a) | (3b) | (4a) | (5b) | (6k) | (7d) | (8a) | (9a) | (10c) |
| 591 | (Id) | (1a) | (2a) | (3b) | (4a) | (5b) | (6k) | (7d) | (8a) | (9b) | (10a) |
| 592 | (Id) | (1a) | (2a) | (3b) | (4a) | (5b) | (6k) | (7d) | (8a) | (9b) | (10c) |
| 593 | (Id) | (1a) | (2a) | (3b) | (4a) | (5a) | (6a) | (7a), (7b) | (8a) | (9a) | (10a) |
| 594 | (Id) | (1a) | (2a) | (3b) | (4a) | (5a) | (6a) | (7a), (7b) | (8a) | (9a) | (10c) |
| 595 | (Id) | (1a) | (2a) | (3b) | (4a) | (5a) | (6a) | (7a), (7b) | (8a) | (9b) | (10a) |
| 596 | (Id) | (1a) | (2a) | (3b) | (4a) | (5a) | (6a) | (7a), (7b) | (8a) | (9b) | (10c) |
| 597 | (Id) | (1a) | (2a) | (3b) | (4a) | (5a) | (6a) | (7d) | (8a) | (9a) | (10a) |
| 598 | (Id) | (1a) | (2a) | (3b) | (4a) | (5a) | (6a) | (7d) | (8a) | (9a) | (10c) |
| 599 | (Id) | (1a) | (2a) | (3b) | (4a) | (5a) | (6a) | (7d) | (8a) | (9b) | (10a) |
| 600 | (Id) | (1a) | (2a) | (3b) | (4a) | (5a) | (6a) | (7d) | (8a) | (9b) | (10c) |
| 601 | (Id) | (1a) | (2a) | (3b) | (4a) | (5a) | (6k) | (7a), (7b) | (8a) | (9a) | (10a) |
| 602 | (Id) | (1a) | (2a) | (3b) | (4a) | (5a) | (6k) | (7a), (7b) | (8a) | (9a) | (10c) |
| 603 | (Id) | (1a) | (2a) | (3b) | (4a) | (5a) | (6k) | (7a), (7b) | (8a) | (9b) | (10a) |
| 604 | (Id) | (1a) | (2a) | (3b) | (4a) | (5a) | (6k) | (7a), (7b) | (8a) | (9b) | (10c) |
| 605 | (Id) | (1a) | (2a) | (3b) | (4a) | (5a) | (6k) | (7d) | (8a) | (9a) | (10a) |
| 606 | (Id) | (1a) | (2a) | (3b) | (4a) | (5a) | (6k) | (7d) | (8a) | (9a) | (10c) |
| 607 | (Id) | (1a) | (2a) | (3b) | (4a) | (5a) | (6k) | (7d) | (8a) | (9b) | (10a) |
| 608 | (Id) | (1a) | (2a) | (3b) | (4a) | (5a) | (6k) | (7d) | (8a) | (9b) | (10c) |
| 609 | (Id) | (1a) | (2a) | (3b) | (4d) | (5b) | (6a) | (7a), (7b) | (8a) | (9a) | (10a) |
| 610 | (Id) | (1a) | (2a) | (3b) | (4d) | (5b) | (6a) | (7a), (7b) | (8a) | (9a) | (10c) |
| 611 | (Id) | (1a) | (2a) | (3b) | (4d) | (5b) | (6a) | (7a), (7b) | (8a) | (9b) | (10a) |
| 612 | (Id) | (1a) | (2a) | (3b) | (4d) | (5b) | (6a) | (7a), (7b) | (8a) | (9b) | (10c) |
| 613 | (Id) | (1a) | (2a) | (3b) | (4d) | (5b) | (6a) | (7d) | (8a) | (9a) | (10a) |
| 614 | (Id) | (1a) | (2a) | (3b) | (4d) | (5b) | (6a) | (7d) | (8a) | (9a) | (10c) |
| 615 | (Id) | (1a) | (2a) | (3b) | (4d) | (5b) | (6a) | (7d) | (8a) | (9b) | (10a) |
| 616 | (Id) | (1a) | (2a) | (3b) | (4d) | (5b) | (6a) | (7d) | (8a) | (9b) | (10c) |
| 617 | (Id) | (1a) | (2a) | (3b) | (4d) | (5b) | (6k) | (7a), (7b) | (8a) | (9a) | (10a) |
| 618 | (Id) | (1a) | (2a) | (3b) | (4d) | (5b) | (6k) | (7a), (7b) | (8a) | (9a) | (10c) |
| 619 | (Id) | (1a) | (2a) | (3b) | (4d) | (5b) | (6k) | (7a), (7b) | (8a) | (9b) | (10a) |
| 620 | (Id) | (1a) | (2a) | (3b) | (4d) | (5b) | (6k) | (7a), (7b) | (8a) | (9b) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 621 | (Id) | (1a) | (2a) | (3b) | (4d) | (5b) | (6k) | (7d) | (8a) | (9a) | (10a) |
| 622 | (Id) | (1a) | (2a) | (3b) | (4d) | (5b) | (6k) | (7d) | (8a) | (9a) | (10c) |
| 623 | (Id) | (1a) | (2a) | (3b) | (4d) | (5b) | (6k) | (7d) | (8a) | (9b) | (10a) |
| 624 | (Id) | (1a) | (2a) | (3b) | (4d) | (5b) | (6k) | (7d) | (8a) | (9b) | (10c) |
| 625 | (Id) | (1a) | (2a) | (3b) | (4d) | (5a) | (6a) | (7a), (7b) | (8a) | (9a) | (10a) |
| 626 | (Id) | (1a) | (2a) | (3b) | (4d) | (5a) | (6a) | (7a), (7b) | (8a) | (9a) | (10c) |
| 627 | (Id) | (1a) | (2a) | (3b) | (4d) | (5a) | (6a) | (7a), (7b) | (8a) | (9b) | (10a) |
| 628 | (Id) | (1a) | (2a) | (3b) | (4d) | (5a) | (6a) | (7a), (7b) | (8a) | (9b) | (10c) |
| 629 | (Id) | (1a) | (2a) | (3b) | (4d) | (5a) | (6a) | (7d) | (8a) | (9a) | (10a) |
| 630 | (Id) | (1a) | (2a) | (3b) | (4d) | (5a) | (6a) | (7d) | (8a) | (9a) | (10c) |
| 631 | (Id) | (1a) | (2a) | (3b) | (4d) | (5a) | (6a) | (7d) | (8a) | (9b) | (10a) |
| 632 | (Id) | (1a) | (2a) | (3b) | (4d) | (5a) | (6a) | (7d) | (8a) | (9b) | (10c) |
| 633 | (Id) | (1a) | (2a) | (3b) | (4d) | (5a) | (6k) | (7a), (7b) | (8a) | (9a) | (10a) |
| 634 | (Id) | (1a) | (2a) | (3b) | (4d) | (5a) | (6k) | (7a), (7b) | (8a) | (9a) | (10c) |
| 635 | (Id) | (1a) | (2a) | (3b) | (4d) | (5a) | (6k) | (7a), (7b) | (8a) | (9b) | (10a) |
| 636 | (Id) | (1a) | (2a) | (3b) | (4d) | (5a) | (6k) | (7a), (7b) | (8a) | (9b) | (10c) |
| 637 | (Id) | (1a) | (2a) | (3b) | (4d) | (5a) | (6k) | (7d) | (8a) | (9a) | (10a) |
| 638 | (Id) | (1a) | (2a) | (3b) | (4d) | (5a) | (6k) | (7d) | (8a) | (9a) | (10c) |
| 639 | (Id) | (1a) | (2a) | (3b) | (4d) | (5a) | (6k) | (7d) | (8a) | (9b) | (10a) |
| 640 | (Id) | (1a) | (2a) | (3b) | (4d) | (5a) | (6k) | (7d) | (8a) | (9b) | (10c) |
| 641 | (Id) | (1a) | (2b) | (3c) | (4a) | (5b) | (6a) | (7a), (7b) | (8a) | (9a) | (10a) |
| 642 | (Id) | (1a) | (2b) | (3c) | (4a) | (5b) | (6a) | (7a), (7b) | (8a) | (9a) | (10c) |
| 643 | (Id) | (1a) | (2b) | (3c) | (4a) | (5b) | (6a) | (7a), (7b) | (8a) | (9b) | (10a) |
| 644 | (Id) | (1a) | (2b) | (3c) | (4a) | (5b) | (6a) | (7a), (7b) | (8a) | (9b) | (10c) |
| 645 | (Id) | (1a) | (2b) | (3c) | (4a) | (5b) | (6a) | (7d) | (8a) | (9a) | (10a) |
| 646 | (Id) | (1a) | (2b) | (3c) | (4a) | (5b) | (6a) | (7d) | (8a) | (9a) | (10c) |
| 647 | (Id) | (1a) | (2b) | (3c) | (4a) | (5b) | (6a) | (7d) | (8a) | (9b) | (10a) |
| 648 | (Id) | (1a) | (2b) | (3c) | (4a) | (5b) | (6a) | (7d) | (8a) | (9b) | (10c) |
| 649 | (Id) | (1a) | (2b) | (3c) | (4a) | (5b) | (6k) | (7a), (7b) | (8a) | (9a) | (10a) |
| 650 | (Id) | (1a) | (2b) | (3c) | (4a) | (5b) | (6k) | (7a), (7b) | (8a) | (9a) | (10c) |
| 651 | (Id) | (1a) | (2b) | (3c) | (4a) | (5b) | (6k) | (7a), (7b) | (8a) | (9b) | (10a) |
| 652 | (Id) | (1a) | (2b) | (3c) | (4a) | (5b) | (6k) | (7a), (7b) | (8a) | (9b) | (10c) |
| 653 | (Id) | (1a) | (2b) | (3c) | (4a) | (5b) | (6k) | (7d) | (8a) | (9a) | (10a) |
| 654 | (Id) | (1a) | (2b) | (3c) | (4a) | (5b) | (6k) | (7d) | (8a) | (9a) | (10c) |
| 655 | (Id) | (1a) | (2b) | (3c) | (4a) | (5b) | (6k) | (7d) | (8a) | (9b) | (10a) |
| 656 | (Id) | (1a) | (2b) | (3c) | (4a) | (5b) | (6k) | (7d) | (8a) | (9b) | (10c) |
| 657 | (Id) | (1a) | (2b) | (3c) | (4a) | (5a) | (6a) | (7a), (7b) | (8a) | (9a) | (10a) |
| 658 | (Id) | (1a) | (2b) | (3c) | (4a) | (5a) | (6a) | (7a), (7b) | (8a) | (9a) | (10c) |
| 659 | (Id) | (1a) | (2b) | (3c) | (4a) | (5a) | (6a) | (7a), (7b) | (8a) | (9b) | (10a) |
| 660 | (Id) | (1a) | (2b) | (3c) | (4a) | (5a) | (6a) | (7a), (7b) | (8a) | (9b) | (10c) |
| 661 | (Id) | (1a) | (2b) | (3c) | (4a) | (5a) | (6a) | (7d) | (8a) | (9a) | (10a) |
| 662 | (Id) | (1a) | (2b) | (3c) | (4a) | (5a) | (6a) | (7d) | (8a) | (9a) | (10c) |
| 663 | (Id) | (1a) | (2b) | (3c) | (4a) | (5a) | (6a) | (7d) | (8a) | (9b) | (10a) |
| 664 | (Id) | (1a) | (2b) | (3c) | (4a) | (5a) | (6a) | (7d) | (8a) | (9b) | (10c) |
| 665 | (Id) | (1a) | (2b) | (3c) | (4a) | (5a) | (6k) | (7a), (7b) | (8a) | (9a) | (10a) |
| 666 | (Id) | (1a) | (2b) | (3c) | (4a) | (5a) | (6k) | (7a), (7b) | (8a) | (9a) | (10c) |
| 667 | (Id) | (1a) | (2b) | (3c) | (4a) | (5a) | (6k) | (7a), (7b) | (8a) | (9b) | (10a) |
| 668 | (Id) | (1a) | (2b) | (3c) | (4a) | (5a) | (6k) | (7a), (7b) | (8a) | (9b) | (10c) |
| 669 | (Id) | (1a) | (2b) | (3c) | (4a) | (5a) | (6k) | (7d) | (8a) | (9a) | (10a) |
| 670 | (Id) | (1a) | (2b) | (3c) | (4a) | (5a) | (6k) | (7d) | (8a) | (9a) | (10c) |
| 671 | (Id) | (1a) | (2b) | (3c) | (4a) | (5a) | (6k) | (7d) | (8a) | (9b) | (10a) |
| 672 | (Id) | (1a) | (2b) | (3c) | (4a) | (5a) | (6k) | (7d) | (8a) | (9b) | (10c) |
| 673 | (Id) | (1a) | (2b) | (3c) | (4d) | (5b) | (6a) | (7a), (7b) | (8a) | (9a) | (10a) |
| 674 | (Id) | (1a) | (2b) | (3c) | (4d) | (5b) | (6a) | (7a), (7b) | (8a) | (9a) | (10c) |
| 675 | (Id) | (1a) | (2b) | (3c) | (4d) | (5b) | (6a) | (7a), (7b) | (8a) | (9b) | (10a) |
| 676 | (Id) | (1a) | (2b) | (3c) | (4d) | (5b) | (6a) | (7a), (7b) | (8a) | (9b) | (10c) |
| 677 | (Id) | (1a) | (2b) | (3c) | (4d) | (5b) | (6a) | (7d) | (8a) | (9a) | (10a) |
| 678 | (Id) | (1a) | (2b) | (3c) | (4d) | (5b) | (6a) | (7d) | (8a) | (9a) | (10c) |
| 679 | (Id) | (1a) | (2b) | (3c) | (4d) | (5b) | (6a) | (7d) | (8a) | (9b) | (10a) |
| 680 | (Id) | (1a) | (2b) | (3c) | (4d) | (5b) | (6a) | (7d) | (8a) | (9b) | (10c) |
| 681 | (Id) | (1a) | (2b) | (3c) | (4d) | (5b) | (6k) | (7a), (7b) | (8a) | (9a) | (10a) |
| 682 | (Id) | (1a) | (2b) | (3c) | (4d) | (5b) | (6k) | (7a), (7b) | (8a) | (9a) | (10c) |
| 683 | (Id) | (1a) | (2b) | (3c) | (4d) | (5b) | (6k) | (7a), (7b) | (8a) | (9b) | (10a) |
| 684 | (Id) | (1a) | (2b) | (3c) | (4d) | (5b) | (6k) | (7a), (7b) | (8a) | (9b) | (10c) |
| 685 | (Id) | (1a) | (2b) | (3c) | (4d) | (5b) | (6k) | (7d) | (8a) | (9a) | (10a) |
| 686 | (Id) | (1a) | (2b) | (3c) | (4d) | (5b) | (6k) | (7d) | (8a) | (9a) | (10c) |
| 687 | (Id) | (1a) | (2b) | (3c) | (4d) | (5b) | (6k) | (7d) | (8a) | (9b) | (10a) |
| 688 | (Id) | (1a) | (2b) | (3c) | (4d) | (5b) | (6k) | (7d) | (8a) | (9b) | (10c) |
| 689 | (Id) | (1a) | (2b) | (3c) | (4d) | (5a) | (6a) | (7a), (7b) | (8a) | (9a) | (10a) |
| 690 | (Id) | (1a) | (2b) | (3c) | (4d) | (5a) | (6a) | (7a), (7b) | (8a) | (9a) | (10c) |
| 691 | (Id) | (1a) | (2b) | (3c) | (4d) | (5a) | (6a) | (7a), (7b) | (8a) | (9b) | (10a) |
| 692 | (Id) | (1a) | (2b) | (3c) | (4d) | (5a) | (6a) | (7a), (7b) | (8a) | (9b) | (10c) |
| 693 | (Id) | (1a) | (2b) | (3c) | (4d) | (5a) | (6a) | (7d) | (8a) | (9a) | (10a) |
| 694 | (Id) | (1a) | (2b) | (3c) | (4d) | (5a) | (6a) | (7d) | (8a) | (9a) | (10c) |
| 695 | (Id) | (1a) | (2b) | (3c) | (4d) | (5a) | (6a) | (7d) | (8a) | (9b) | (10a) |
| 696 | (Id) | (1a) | (2b) | (3c) | (4d) | (5a) | (6a) | (7d) | (8a) | (9b) | (10c) |
| 697 | (Id) | (1a) | (2b) | (3c) | (4d) | (5a) | (6k) | (7a), (7b) | (8a) | (9a) | (10a) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 698 | (Id) | (1a) | (2b) | (3c) | (4d) | (5a) | (6k) | (7a), (7b) | (8a) | (9a) | (10c) |
| 699 | (Id) | (1a) | (2b) | (3c) | (4d) | (5a) | (6k) | (7a), (7b) | (8a) | (9b) | (10a) |
| 700 | (Id) | (1a) | (2b) | (3c) | (4d) | (5a) | (6k) | (7a), (7b) | (8a) | (9b) | (10c) |
| 701 | (Id) | (1a) | (2b) | (3c) | (4d) | (5a) | (6k) | (7d) | (8a) | (9a) | (10a) |
| 702 | (Id) | (1a) | (2b) | (3c) | (4d) | (5a) | (6k) | (7d) | (8a) | (9a) | (10c) |
| 703 | (Id) | (1a) | (2b) | (3c) | (4d) | (5a) | (6k) | (7d) | (8a) | (9b) | (10a) |
| 704 | (Id) | (1a) | (2b) | (3c) | (4d) | (5a) | (6k) | (7d) | (8a) | (9b) | (10c) |
| 705 | (Id) | (1a) | (2b) | (3b) | (4a) | (5b) | (6a) | (7a), (7b) | (8a) | (9a) | (10a) |
| 706 | (Id) | (1a) | (2b) | (3b) | (4a) | (5b) | (6a) | (7a), (7b) | (8a) | (9a) | (10c) |
| 707 | (Id) | (1a) | (2b) | (3b) | (4a) | (5b) | (6a) | (7a), (7b) | (8a) | (9b) | (10a) |
| 708 | (Id) | (1a) | (2b) | (3b) | (4a) | (5b) | (6a) | (7a), (7b) | (8a) | (9b) | (10c) |
| 709 | (Id) | (1a) | (2b) | (3b) | (4a) | (5b) | (6a) | (7d) | (8a) | (9a) | (10a) |
| 710 | (Id) | (1a) | (2b) | (3b) | (4a) | (5b) | (6a) | (7d) | (8a) | (9a) | (10c) |
| 711 | (Id) | (1a) | (2b) | (3b) | (4a) | (5b) | (6a) | (7d) | (8a) | (9b) | (10a) |
| 712 | (Id) | (1a) | (2b) | (3b) | (4a) | (5b) | (6a) | (7d) | (8a) | (9b) | (10c) |
| 713 | (Id) | (1a) | (2b) | (3b) | (4a) | (5b) | (6k) | (7a), (7b) | (8a) | (9a) | (10a) |
| 714 | (Id) | (1a) | (2b) | (3b) | (4a) | (5b) | (6k) | (7a), (7b) | (8a) | (9a) | (10c) |
| 715 | (Id) | (1a) | (2b) | (3b) | (4a) | (5b) | (6k) | (7a), (7b) | (8a) | (9b) | (10a) |
| 716 | (Id) | (1a) | (2b) | (3b) | (4a) | (5b) | (6k) | (7a), (7b) | (8a) | (9b) | (10c) |
| 717 | (Id) | (1a) | (2b) | (3b) | (4a) | (5b) | (6k) | (7d) | (8a) | (9a) | (10a) |
| 718 | (Id) | (1a) | (2b) | (3b) | (4a) | (5b) | (6k) | (7d) | (8a) | (9a) | (10c) |
| 719 | (Id) | (1a) | (2b) | (3b) | (4a) | (5b) | (6k) | (7d) | (8a) | (9b) | (10a) |
| 720 | (Id) | (1a) | (2b) | (3b) | (4a) | (5b) | (6k) | (7d) | (8a) | (9b) | (10c) |
| 721 | (Id) | (1a) | (2b) | (3b) | (4a) | (5a) | (6a) | (7a), (7b) | (8a) | (9a) | (10a) |
| 722 | (Id) | (1a) | (2b) | (3b) | (4a) | (5a) | (6a) | (7a), (7b) | (8a) | (9a) | (10c) |
| 723 | (Id) | (1a) | (2b) | (3b) | (4a) | (5a) | (6a) | (7a), (7b) | (8a) | (9b) | (10a) |
| 724 | (Id) | (1a) | (2b) | (3b) | (4a) | (5a) | (6a) | (7a), (7b) | (8a) | (9b) | (10c) |
| 725 | (Id) | (1a) | (2b) | (3b) | (4a) | (5a) | (6a) | (7d) | (8a) | (9a) | (10a) |
| 726 | (Id) | (1a) | (2b) | (3b) | (4a) | (5a) | (6a) | (7d) | (8a) | (9a) | (10c) |
| 727 | (Id) | (1a) | (2b) | (3b) | (4a) | (5a) | (6a) | (7d) | (8a) | (9b) | (10a) |
| 728 | (Id) | (1a) | (2b) | (3b) | (4a) | (5a) | (6a) | (7d) | (8a) | (9b) | (10c) |
| 729 | (Id) | (1a) | (2b) | (3b) | (4a) | (5a) | (6k) | (7a), (7b) | (8a) | (9a) | (10a) |
| 730 | (Id) | (1a) | (2b) | (3b) | (4a) | (5a) | (6k) | (7a), (7b) | (8a) | (9a) | (10c) |
| 731 | (Id) | (1a) | (2b) | (3b) | (4a) | (5a) | (6k) | (7a), (7b) | (8a) | (9b) | (10a) |
| 732 | (Id) | (1a) | (2b) | (3b) | (4a) | (5a) | (6k) | (7a), (7b) | (8a) | (9b) | (10c) |
| 733 | (Id) | (1a) | (2b) | (3b) | (4a) | (5a) | (6k) | (7d) | (8a) | (9a) | (10a) |
| 734 | (Id) | (1a) | (2b) | (3b) | (4a) | (5a) | (6k) | (7d) | (8a) | (9a) | (10c) |
| 735 | (Id) | (1a) | (2b) | (3b) | (4a) | (5a) | (6k) | (7d) | (8a) | (9b) | (10a) |
| 736 | (Id) | (1a) | (2b) | (3b) | (4a) | (5a) | (6k) | (7d) | (8a) | (9b) | (10c) |
| 737 | (Id) | (1a) | (2b) | (3b) | (4d) | (5b) | (6a) | (7a), (7b) | (8a) | (9a) | (10a) |
| 738 | (Id) | (1a) | (2b) | (3b) | (4d) | (5b) | (6a) | (7a), (7b) | (8a) | (9a) | (10c) |
| 739 | (Id) | (1a) | (2b) | (3b) | (4d) | (5b) | (6a) | (7a), (7b) | (8a) | (9b) | (10a) |
| 740 | (Id) | (1a) | (2b) | (3b) | (4d) | (5b) | (6a) | (7a), (7b) | (8a) | (9b) | (10c) |
| 741 | (Id) | (1a) | (2b) | (3b) | (4d) | (5b) | (6a) | (7d) | (8a) | (9a) | (10a) |
| 742 | (Id) | (1a) | (2b) | (3b) | (4d) | (5b) | (6a) | (7d) | (8a) | (9a) | (10c) |
| 743 | (Id) | (1a) | (2b) | (3b) | (4d) | (5b) | (6a) | (7d) | (8a) | (9b) | (10a) |
| 744 | (Id) | (1a) | (2b) | (3b) | (4d) | (5b) | (6a) | (7d) | (8a) | (9b) | (10c) |
| 745 | (Id) | (1a) | (2b) | (3b) | (4d) | (5b) | (6k) | (7a), (7b) | (8a) | (9a) | (10a) |
| 746 | (Id) | (1a) | (2b) | (3b) | (4d) | (5b) | (6k) | (7a), (7b) | (8a) | (9a) | (10c) |
| 747 | (Id) | (1a) | (2b) | (3b) | (4d) | (5b) | (6k) | (7a), (7b) | (8a) | (9b) | (10a) |
| 748 | (Id) | (1a) | (2b) | (3b) | (4d) | (5b) | (6k) | (7a), (7b) | (8a) | (9b) | (10c) |
| 749 | (Id) | (1a) | (2b) | (3b) | (4d) | (5b) | (6k) | (7d) | (8a) | (9a) | (10a) |
| 750 | (Id) | (1a) | (2b) | (3b) | (4d) | (5b) | (6k) | (7d) | (8a) | (9a) | (10c) |
| 751 | (Id) | (1a) | (2b) | (3b) | (4d) | (5b) | (6k) | (7d) | (8a) | (9b) | (10a) |
| 752 | (Id) | (1a) | (2b) | (3b) | (4d) | (5b) | (6k) | (7d) | (8a) | (9b) | (10c) |
| 753 | (Id) | (1a) | (2b) | (3b) | (4d) | (5a) | (6a) | (7a), (7b) | (8a) | (9a) | (10a) |
| 754 | (Id) | (1a) | (2b) | (3b) | (4d) | (5a) | (6a) | (7a), (7b) | (8a) | (9a) | (10c) |
| 755 | (Id) | (1a) | (2b) | (3b) | (4d) | (5a) | (6a) | (7a), (7b) | (8a) | (9b) | (10a) |
| 756 | (Id) | (1a) | (2b) | (3b) | (4d) | (5a) | (6a) | (7a), (7b) | (8a) | (9b) | (10c) |
| 757 | (Id) | (1a) | (2b) | (3b) | (4d) | (5a) | (6a) | (7d) | (8a) | (9a) | (10a) |
| 758 | (Id) | (1a) | (2b) | (3b) | (4d) | (5a) | (6a) | (7d) | (8a) | (9a) | (10c) |
| 759 | (Id) | (1a) | (2b) | (3b) | (4d) | (5a) | (6a) | (7d) | (8a) | (9b) | (10a) |
| 760 | (Id) | (1a) | (2b) | (3b) | (4d) | (5a) | (6a) | (7d) | (8a) | (9b) | (10c) |
| 761 | (Id) | (1a) | (2b) | (3b) | (4d) | (5a) | (6k) | (7a), (7b) | (8a) | (9a) | (10a) |
| 762 | (Id) | (1a) | (2b) | (3b) | (4d) | (5a) | (6k) | (7a), (7b) | (8a) | (9a) | (10c) |
| 763 | (Id) | (1a) | (2b) | (3b) | (4d) | (5a) | (6k) | (7a), (7b) | (8a) | (9b) | (10a) |
| 764 | (Id) | (1a) | (2b) | (3b) | (4d) | (5a) | (6k) | (7a), (7b) | (8a) | (9b) | (10c) |
| 765 | (Id) | (1a) | (2b) | (3b) | (4d) | (5a) | (6k) | (7d) | (8a) | (9a) | (10a) |
| 766 | (Id) | (1a) | (2b) | (3b) | (4d) | (5a) | (6k) | (7d) | (8a) | (9a) | (10c) |
| 767 | (Id) | (1a) | (2b) | (3b) | (4d) | (5a) | (6k) | (7d) | (8a) | (9b) | (10a) |
| 768 | (Id) | (1a) | (2b) | (3b) | (4d) | (5a) | (6k) | (7d) | (8a) | (9b) | (10c) |
| 769 | (Id) | (1d) | (2a) | (3c) | (4a) | (5b) | (6a) | (7a), (7b) | (8a) | (9a) | (10a) |
| 770 | (Id) | (1d) | (2a) | (3c) | (4a) | (5b) | (6a) | (7a), (7b) | (8a) | (9a) | (10c) |
| 771 | (Id) | (1d) | (2a) | (3c) | (4a) | (5b) | (6a) | (7a), (7b) | (8a) | (9b) | (10a) |
| 772 | (Id) | (1d) | (2a) | (3c) | (4a) | (5b) | (6a) | (7a), (7b) | (8a) | (9b) | (10c) |
| 773 | (Id) | (1d) | (2a) | (3c) | (4a) | (5b) | (6a) | (7d) | (8a) | (9a) | (10a) |
| 774 | (Id) | (1d) | (2a) | (3c) | (4a) | (5b) | (6a) | (7d) | (8a) | (9a) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 775 | (Id) | (1d) | (2a) | (3c) | (4a) | (5b) | (6a) | (7d) | (8a) | (9b) | (10a) |
| 776 | (Id) | (1d) | (2a) | (3c) | (4a) | (5b) | (6a) | (7d) | (8a) | (9b) | (10c) |
| 777 | (Id) | (1d) | (2a) | (3c) | (4a) | (5b) | (6k) | (7a), (7b) | (8a) | (9a) | (10a) |
| 778 | (Id) | (1d) | (2a) | (3c) | (4a) | (5b) | (6k) | (7a), (7b) | (8a) | (9a) | (10c) |
| 779 | (Id) | (1d) | (2a) | (3c) | (4a) | (5b) | (6k) | (7a), (7b) | (8a) | (9b) | (10a) |
| 780 | (Id) | (1d) | (2a) | (3c) | (4a) | (5b) | (6k) | (7a), (7b) | (8a) | (9b) | (10c) |
| 781 | (Id) | (1d) | (2a) | (3c) | (4a) | (5b) | (6k) | (7d) | (8a) | (9a) | (10a) |
| 782 | (Id) | (1d) | (2a) | (3c) | (4a) | (5b) | (6k) | (7d) | (8a) | (9a) | (10c) |
| 783 | (Id) | (1d) | (2a) | (3c) | (4a) | (5b) | (6k) | (7d) | (8a) | (9b) | (10a) |
| 784 | (Id) | (1d) | (2a) | (3c) | (4a) | (5b) | (6k) | (7d) | (8a) | (9b) | (10c) |
| 785 | (Id) | (1d) | (2a) | (3c) | (4a) | (5a) | (6a) | (7a), (7b) | (8a) | (9a) | (10a) |
| 786 | (Id) | (1d) | (2a) | (3c) | (4a) | (5a) | (6a) | (7a), (7b) | (8a) | (9a) | (10c) |
| 787 | (Id) | (1d) | (2a) | (3c) | (4a) | (5a) | (6a) | (7a), (7b) | (8a) | (9b) | (10a) |
| 788 | (Id) | (1d) | (2a) | (3c) | (4a) | (5a) | (6a) | (7a), (7b) | (8a) | (9b) | (10c) |
| 789 | (Id) | (1d) | (2a) | (3c) | (4a) | (5a) | (6a) | (7d) | (8a) | (9a) | (10a) |
| 790 | (Id) | (1d) | (2a) | (3c) | (4a) | (5a) | (6a) | (7d) | (8a) | (9a) | (10c) |
| 791 | (Id) | (1d) | (2a) | (3c) | (4a) | (5a) | (6a) | (7d) | (8a) | (9b) | (10a) |
| 792 | (Id) | (1d) | (2a) | (3c) | (4a) | (5a) | (6a) | (7d) | (8a) | (9b) | (10c) |
| 793 | (Id) | (1d) | (2a) | (3c) | (4a) | (5a) | (6k) | (7a), (7b) | (8a) | (9a) | (10a) |
| 794 | (Id) | (1d) | (2a) | (3c) | (4a) | (5a) | (6k) | (7a), (7b) | (8a) | (9a) | (10c) |
| 795 | (Id) | (1d) | (2a) | (3c) | (4a) | (5a) | (6k) | (7a), (7b) | (8a) | (9b) | (10a) |
| 796 | (Id) | (1d) | (2a) | (3c) | (4a) | (5a) | (6k) | (7a), (7b) | (8a) | (9b) | (10c) |
| 797 | (Id) | (1d) | (2a) | (3c) | (4a) | (5a) | (6k) | (7d) | (8a) | (9a) | (10a) |
| 798 | (Id) | (1d) | (2a) | (3c) | (4a) | (5a) | (6k) | (7d) | (8a) | (9a) | (10c) |
| 799 | (Id) | (1d) | (2a) | (3c) | (4a) | (5a) | (6k) | (7d) | (8a) | (9b) | (10a) |
| 800 | (Id) | (1d) | (2a) | (3c) | (4a) | (5a) | (6k) | (7d) | (8a) | (9b) | (10c) |
| 801 | (Id) | (1d) | (2a) | (3c) | (4d) | (5b) | (6a) | (7a), (7b) | (8a) | (9a) | (10a) |
| 802 | (Id) | (1d) | (2a) | (3c) | (4d) | (5b) | (6a) | (7a), (7b) | (8a) | (9a) | (10c) |
| 803 | (Id) | (1d) | (2a) | (3c) | (4d) | (5b) | (6a) | (7a), (7b) | (8a) | (9b) | (10a) |
| 804 | (Id) | (1d) | (2a) | (3c) | (4d) | (5b) | (6a) | (7a), (7b) | (8a) | (9b) | (10c) |
| 805 | (Id) | (1d) | (2a) | (3c) | (4d) | (5b) | (6a) | (7d) | (8a) | (9a) | (10a) |
| 806 | (Id) | (1d) | (2a) | (3c) | (4d) | (5b) | (6a) | (7d) | (8a) | (9a) | (10c) |
| 807 | (Id) | (1d) | (2a) | (3c) | (4d) | (5b) | (6a) | (7d) | (8a) | (9b) | (10a) |
| 808 | (Id) | (1d) | (2a) | (3c) | (4d) | (5b) | (6a) | (7d) | (8a) | (9b) | (10c) |
| 809 | (Id) | (1d) | (2a) | (3c) | (4d) | (5b) | (6k) | (7a), (7b) | (8a) | (9a) | (10a) |
| 810 | (Id) | (1d) | (2a) | (3c) | (4d) | (5b) | (6k) | (7a), (7b) | (8a) | (9a) | (10c) |
| 811 | (Id) | (1d) | (2a) | (3c) | (4d) | (5b) | (6k) | (7a), (7b) | (8a) | (9b) | (10a) |
| 812 | (Id) | (1d) | (2a) | (3c) | (4d) | (5b) | (6k) | (7a), (7b) | (8a) | (9b) | (10c) |
| 813 | (Id) | (1d) | (2a) | (3c) | (4d) | (5b) | (6k) | (7d) | (8a) | (9a) | (10a) |
| 814 | (Id) | (1d) | (2a) | (3c) | (4d) | (5b) | (6k) | (7d) | (8a) | (9a) | (10c) |
| 815 | (Id) | (1d) | (2a) | (3c) | (4d) | (5b) | (6k) | (7d) | (8a) | (9b) | (10a) |
| 816 | (Id) | (1d) | (2a) | (3c) | (4d) | (5b) | (6k) | (7d) | (8a) | (9b) | (10c) |
| 817 | (Id) | (1d) | (2a) | (3c) | (4d) | (5a) | (6a) | (7a), (7b) | (8a) | (9a) | (10a) |
| 818 | (Id) | (1d) | (2a) | (3c) | (4d) | (5a) | (6a) | (7a), (7b) | (8a) | (9a) | (10c) |
| 819 | (Id) | (1d) | (2a) | (3c) | (4d) | (5a) | (6a) | (7a), (7b) | (8a) | (9b) | (10a) |
| 820 | (Id) | (1d) | (2a) | (3c) | (4d) | (5a) | (6a) | (7a), (7b) | (8a) | (9b) | (10c) |
| 821 | (Id) | (1d) | (2a) | (3c) | (4d) | (5a) | (6a) | (7d) | (8a) | (9a) | (10a) |
| 822 | (Id) | (1d) | (2a) | (3c) | (4d) | (5a) | (6a) | (7d) | (8a) | (9a) | (10c) |
| 823 | (Id) | (1d) | (2a) | (3c) | (4d) | (5a) | (6a) | (7d) | (8a) | (9b) | (10a) |
| 824 | (Id) | (1d) | (2a) | (3c) | (4d) | (5a) | (6a) | (7d) | (8a) | (9b) | (10c) |
| 825 | (Id) | (1d) | (2a) | (3c) | (4d) | (5a) | (6k) | (7a), (7b) | (8a) | (9a) | (10a) |
| 826 | (Id) | (1d) | (2a) | (3c) | (4d) | (5a) | (6k) | (7a), (7b) | (8a) | (9a) | (10c) |
| 827 | (Id) | (1d) | (2a) | (3c) | (4d) | (5a) | (6k) | (7a), (7b) | (8a) | (9b) | (10a) |
| 828 | (Id) | (1d) | (2a) | (3c) | (4d) | (5a) | (6k) | (7a), (7b) | (8a) | (9b) | (10c) |
| 829 | (Id) | (1d) | (2a) | (3c) | (4d) | (5a) | (6k) | (7d) | (8a) | (9a) | (10a) |
| 830 | (Id) | (1d) | (2a) | (3c) | (4d) | (5a) | (6k) | (7d) | (8a) | (9a) | (10c) |
| 831 | (Id) | (1d) | (2a) | (3c) | (4d) | (5a) | (6k) | (7d) | (8a) | (9b) | (10a) |
| 832 | (Id) | (1d) | (2a) | (3c) | (4d) | (5a) | (6k) | (7d) | (8a) | (9b) | (10c) |
| 833 | (Id) | (1d) | (2a) | (3b) | (4a) | (5b) | (6a) | (7a), (7b) | (8a) | (9a) | (10a) |
| 834 | (Id) | (1d) | (2a) | (3b) | (4a) | (5b) | (6a) | (7a), (7b) | (8a) | (9a) | (10c) |
| 835 | (Id) | (1d) | (2a) | (3b) | (4a) | (5b) | (6a) | (7a), (7b) | (8a) | (9b) | (10a) |
| 836 | (Id) | (1d) | (2a) | (3b) | (4a) | (5b) | (6a) | (7a), (7b) | (8a) | (9b) | (10c) |
| 837 | (Id) | (1d) | (2a) | (3b) | (4a) | (5b) | (6a) | (7d) | (8a) | (9a) | (10a) |
| 838 | (Id) | (1d) | (2a) | (3b) | (4a) | (5b) | (6a) | (7d) | (8a) | (9a) | (10c) |
| 839 | (Id) | (1d) | (2a) | (3b) | (4a) | (5b) | (6a) | (7d) | (8a) | (9b) | (10a) |
| 840 | (Id) | (1d) | (2a) | (3b) | (4a) | (5b) | (6a) | (7d) | (8a) | (9b) | (10c) |
| 841 | (Id) | (1d) | (2a) | (3b) | (4a) | (5b) | (6k) | (7a), (7b) | (8a) | (9a) | (10a) |
| 842 | (Id) | (1d) | (2a) | (3b) | (4a) | (5b) | (6k) | (7a), (7b) | (8a) | (9a) | (10c) |
| 843 | (Id) | (1d) | (2a) | (3b) | (4a) | (5b) | (6k) | (7a), (7b) | (8a) | (9b) | (10a) |
| 844 | (Id) | (1d) | (2a) | (3b) | (4a) | (5b) | (6k) | (7a), (7b) | (8a) | (9b) | (10c) |
| 845 | (Id) | (1d) | (2a) | (3b) | (4a) | (5b) | (6k) | (7d) | (8a) | (9a) | (10a) |
| 846 | (Id) | (1d) | (2a) | (3b) | (4a) | (5b) | (6k) | (7d) | (8a) | (9a) | (10c) |
| 847 | (Id) | (1d) | (2a) | (3b) | (4a) | (5b) | (6k) | (7d) | (8a) | (9b) | (10a) |
| 848 | (Id) | (1d) | (2a) | (3b) | (4a) | (5b) | (6k) | (7d) | (8a) | (9b) | (10c) |
| 849 | (Id) | (1d) | (2a) | (3b) | (4a) | (5a) | (6a) | (7a), (7b) | (8a) | (9a) | (10a) |
| 850 | (Id) | (1d) | (2a) | (3b) | (4a) | (5a) | (6a) | (7a), (7b) | (8a) | (9a) | (10c) |
| 851 | (Id) | (1d) | (2a) | (3b) | (4a) | (5a) | (6a) | (7a), (7b) | (8a) | (9b) | (10a) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 852 | (Id) | (1d) | (2a) | (3b) | (4a) | (5a) | (6a) | (7a), (7b) | (8a) | (9b) | (10c) |
| 853 | (Id) | (1d) | (2a) | (3b) | (4a) | (5a) | (6a) | (7d) | (8a) | (9a) | (10a) |
| 854 | (Id) | (1d) | (2a) | (3b) | (4a) | (5a) | (6a) | (7d) | (8a) | (9a) | (10c) |
| 855 | (Id) | (1d) | (2a) | (3b) | (4a) | (5a) | (6a) | (7d) | (8a) | (9b) | (10a) |
| 856 | (Id) | (1d) | (2a) | (3b) | (4a) | (5a) | (6a) | (7d) | (8a) | (9b) | (10c) |
| 857 | (Id) | (1d) | (2a) | (3b) | (4a) | (5a) | (6k) | (7a), (7b) | (8a) | (9a) | (10a) |
| 858 | (Id) | (1d) | (2a) | (3b) | (4a) | (5a) | (6k) | (7a), (7b) | (8a) | (9a) | (10c) |
| 859 | (Id) | (1d) | (2a) | (3b) | (4a) | (5a) | (6k) | (7a), (7b) | (8a) | (9b) | (10a) |
| 860 | (Id) | (1d) | (2a) | (3b) | (4a) | (5a) | (6k) | (7a), (7b) | (8a) | (9b) | (10c) |
| 861 | (Id) | (1d) | (2a) | (3b) | (4a) | (5a) | (6k) | (7d) | (8a) | (9a) | (10a) |
| 862 | (Id) | (1d) | (2a) | (3b) | (4a) | (5a) | (6k) | (7d) | (8a) | (9a) | (10c) |
| 863 | (Id) | (1d) | (2a) | (3b) | (4a) | (5a) | (6k) | (7d) | (8a) | (9b) | (10a) |
| 864 | (Id) | (1d) | (2a) | (3b) | (4a) | (5a) | (6k) | (7d) | (8a) | (9b) | (10c) |
| 865 | (Id) | (1d) | (2a) | (3b) | (4d) | (5b) | (6a) | (7a), (7b) | (8a) | (9a) | (10a) |
| 866 | (Id) | (1d) | (2a) | (3b) | (4d) | (5b) | (6a) | (7a), (7b) | (8a) | (9a) | (10c) |
| 867 | (Id) | (1d) | (2a) | (3b) | (4d) | (5b) | (6a) | (7a), (7b) | (8a) | (9b) | (10a) |
| 868 | (Id) | (1d) | (2a) | (3b) | (4d) | (5b) | (6a) | (7a), (7b) | (8a) | (9b) | (10c) |
| 869 | (Id) | (1d) | (2a) | (3b) | (4d) | (5b) | (6a) | (7d) | (8a) | (9a) | (10a) |
| 870 | (Id) | (1d) | (2a) | (3b) | (4d) | (5b) | (6a) | (7d) | (8a) | (9a) | (10c) |
| 871 | (Id) | (1d) | (2a) | (3b) | (4d) | (5b) | (6a) | (7d) | (8a) | (9b) | (10a) |
| 872 | (Id) | (1d) | (2a) | (3b) | (4d) | (5b) | (6a) | (7d) | (8a) | (9b) | (10c) |
| 873 | (Id) | (1d) | (2a) | (3b) | (4d) | (5b) | (6k) | (7a), (7b) | (8a) | (9a) | (10a) |
| 874 | (Id) | (1d) | (2a) | (3b) | (4d) | (5b) | (6k) | (7a), (7b) | (8a) | (9a) | (10c) |
| 875 | (Id) | (1d) | (2a) | (3b) | (4d) | (5b) | (6k) | (7a), (7b) | (8a) | (9b) | (10a) |
| 876 | (Id) | (1d) | (2a) | (3b) | (4d) | (5b) | (6k) | (7a), (7b) | (8a) | (9b) | (10c) |
| 877 | (Id) | (1d) | (2a) | (3b) | (4d) | (5b) | (6k) | (7d) | (8a) | (9a) | (10a) |
| 878 | (Id) | (1d) | (2a) | (3b) | (4d) | (5b) | (6k) | (7d) | (8a) | (9a) | (10c) |
| 879 | (Id) | (1d) | (2a) | (3b) | (4d) | (5b) | (6k) | (7d) | (8a) | (9b) | (10a) |
| 880 | (Id) | (1d) | (2a) | (3b) | (4d) | (5b) | (6k) | (7d) | (8a) | (9b) | (10c) |
| 881 | (Id) | (1d) | (2a) | (3b) | (4d) | (5a) | (6a) | (7a), (7b) | (8a) | (9a) | (10a) |
| 882 | (Id) | (1d) | (2a) | (3b) | (4d) | (5a) | (6a) | (7a), (7b) | (8a) | (9a) | (10c) |
| 883 | (Id) | (1d) | (2a) | (3b) | (4d) | (5a) | (6a) | (7a), (7b) | (8a) | (9b) | (10a) |
| 884 | (Id) | (1d) | (2a) | (3b) | (4d) | (5a) | (6a) | (7a), (7b) | (8a) | (9b) | (10c) |
| 885 | (Id) | (1d) | (2a) | (3b) | (4d) | (5a) | (6a) | (7d) | (8a) | (9a) | (10a) |
| 886 | (Id) | (1d) | (2a) | (3b) | (4d) | (5a) | (6a) | (7d) | (8a) | (9a) | (10c) |
| 887 | (Id) | (1d) | (2a) | (3b) | (4d) | (5a) | (6a) | (7d) | (8a) | (9b) | (10a) |
| 888 | (Id) | (1d) | (2a) | (3b) | (4d) | (5a) | (6a) | (7d) | (8a) | (9b) | (10c) |
| 889 | (Id) | (1d) | (2a) | (3b) | (4d) | (5a) | (6k) | (7a), (7b) | (8a) | (9a) | (10a) |
| 890 | (Id) | (1d) | (2a) | (3b) | (4d) | (5a) | (6k) | (7a), (7b) | (8a) | (9a) | (10c) |
| 891 | (Id) | (1d) | (2a) | (3b) | (4d) | (5a) | (6k) | (7a), (7b) | (8a) | (9b) | (10a) |
| 892 | (Id) | (1d) | (2a) | (3b) | (4d) | (5a) | (6k) | (7a), (7b) | (8a) | (9b) | (10c) |
| 893 | (Id) | (1d) | (2a) | (3b) | (4d) | (5a) | (6k) | (7d) | (8a) | (9a) | (10a) |
| 894 | (Id) | (1d) | (2a) | (3b) | (4d) | (5a) | (6k) | (7d) | (8a) | (9a) | (10c) |
| 895 | (Id) | (1d) | (2a) | (3b) | (4d) | (5a) | (6k) | (7d) | (8a) | (9b) | (10a) |
| 896 | (Id) | (1d) | (2a) | (3b) | (4d) | (5a) | (6k) | (7d) | (8a) | (9b) | (10c) |
| 897 | (Id) | (1d) | (2b) | (3c) | (4a) | (5b) | (6a) | (7a), (7b) | (8a) | (9a) | (10a) |
| 898 | (Id) | (1d) | (2b) | (3c) | (4a) | (5b) | (6a) | (7a), (7b) | (8a) | (9a) | (10c) |
| 899 | (Id) | (1d) | (2b) | (3c) | (4a) | (5b) | (6a) | (7a), (7b) | (8a) | (9b) | (10a) |
| 900 | (Id) | (1d) | (2b) | (3c) | (4a) | (5b) | (6a) | (7a), (7b) | (8a) | (9b) | (10c) |
| 901 | (Id) | (1d) | (2b) | (3c) | (4a) | (5b) | (6a) | (7d) | (8a) | (9a) | (10a) |
| 902 | (Id) | (1d) | (2b) | (3c) | (4a) | (5b) | (6a) | (7d) | (8a) | (9a) | (10c) |
| 903 | (Id) | (1d) | (2b) | (3c) | (4a) | (5b) | (6a) | (7d) | (8a) | (9b) | (10a) |
| 904 | (Id) | (1d) | (2b) | (3c) | (4a) | (5b) | (6a) | (7d) | (8a) | (9b) | (10c) |
| 905 | (Id) | (1d) | (2b) | (3c) | (4a) | (5b) | (6k) | (7a), (7b) | (8a) | (9a) | (10a) |
| 906 | (Id) | (1d) | (2b) | (3c) | (4a) | (5b) | (6k) | (7a), (7b) | (8a) | (9a) | (10c) |
| 907 | (Id) | (1d) | (2b) | (3c) | (4a) | (5b) | (6k) | (7a), (7b) | (8a) | (9b) | (10a) |
| 908 | (Id) | (1d) | (2b) | (3c) | (4a) | (5b) | (6k) | (7a), (7b) | (8a) | (9b) | (10c) |
| 909 | (Id) | (1d) | (2b) | (3c) | (4a) | (5b) | (6k) | (7d) | (8a) | (9a) | (10a) |
| 910 | (Id) | (1d) | (2b) | (3c) | (4a) | (5b) | (6k) | (7d) | (8a) | (9a) | (10c) |
| 911 | (Id) | (1d) | (2b) | (3c) | (4a) | (5b) | (6k) | (7d) | (8a) | (9b) | (10a) |
| 912 | (Id) | (1d) | (2b) | (3c) | (4a) | (5b) | (6k) | (7d) | (8a) | (9b) | (10c) |
| 913 | (Id) | (1d) | (2b) | (3c) | (4a) | (5a) | (6a) | (7a), (7b) | (8a) | (9a) | (10a) |
| 914 | (Id) | (1d) | (2b) | (3c) | (4a) | (5a) | (6a) | (7a), (7b) | (8a) | (9a) | (10c) |
| 915 | (Id) | (1d) | (2b) | (3c) | (4a) | (5a) | (6a) | (7a), (7b) | (8a) | (9b) | (10a) |
| 916 | (Id) | (1d) | (2b) | (3c) | (4a) | (5a) | (6a) | (7a), (7b) | (8a) | (9b) | (10c) |
| 917 | (Id) | (1d) | (2b) | (3c) | (4a) | (5a) | (6a) | (7d) | (8a) | (9a) | (10a) |
| 918 | (Id) | (1d) | (2b) | (3c) | (4a) | (5a) | (6a) | (7d) | (8a) | (9a) | (10c) |
| 919 | (Id) | (1d) | (2b) | (3c) | (4a) | (5a) | (6a) | (7d) | (8a) | (9b) | (10a) |
| 920 | (Id) | (1d) | (2b) | (3c) | (4a) | (5a) | (6a) | (7d) | (8a) | (9b) | (10c) |
| 921 | (Id) | (1d) | (2b) | (3c) | (4a) | (5a) | (6k) | (7a), (7b) | (8a) | (9a) | (10a) |
| 922 | (Id) | (1d) | (2b) | (3c) | (4a) | (5a) | (6k) | (7a), (7b) | (8a) | (9a) | (10c) |
| 923 | (Id) | (1d) | (2b) | (3c) | (4a) | (5a) | (6k) | (7a), (7b) | (8a) | (9b) | (10a) |
| 924 | (Id) | (1d) | (2b) | (3c) | (4a) | (5a) | (6k) | (7a), (7b) | (8a) | (9b) | (10c) |
| 925 | (Id) | (1d) | (2b) | (3c) | (4a) | (5a) | (6k) | (7d) | (8a) | (9a) | (10a) |
| 926 | (Id) | (1d) | (2b) | (3c) | (4a) | (5a) | (6k) | (7d) | (8a) | (9a) | (10c) |
| 927 | (Id) | (1d) | (2b) | (3c) | (4a) | (5a) | (6k) | (7d) | (8a) | (9b) | (10a) |
| 928 | (Id) | (1d) | (2b) | (3c) | (4a) | (5a) | (6k) | (7d) | (8a) | (9b) | (10c) |

-continued

| | I | $L^1$ | $R^1$ | $L^2$ | Q | $L^3$ | $R^3$ | $L^4$ | $R^4$ | $L^5$ | $R^5$ |
|---|---|---|---|---|---|---|---|---|---|---|---|
| 929 | (Id) | (1d) | (2b) | (3c) | (4d) | (5b) | (6a) | (7a), (7b) | (8a) | (9a) | (10a) |
| 930 | (Id) | (1d) | (2b) | (3c) | (4d) | (5b) | (6a) | (7a), (7b) | (8a) | (9a) | (10c) |
| 931 | (Id) | (1d) | (2b) | (3c) | (4d) | (5b) | (6a) | (7a), (7b) | (8a) | (9b) | (10a) |
| 932 | (Id) | (1d) | (2b) | (3c) | (4d) | (5b) | (6a) | (7a), (7b) | (8a) | (9b) | (10c) |
| 933 | (Id) | (1d) | (2b) | (3c) | (4d) | (5b) | (6a) | (7d) | (8a) | (9a) | (10a) |
| 934 | (Id) | (1d) | (2b) | (3c) | (4d) | (5b) | (6a) | (7d) | (8a) | (9a) | (10c) |
| 935 | (Id) | (1d) | (2b) | (3c) | (4d) | (5b) | (6a) | (7d) | (8a) | (9b) | (10a) |
| 936 | (Id) | (1d) | (2b) | (3c) | (4d) | (5b) | (6a) | (7d) | (8a) | (9b) | (10c) |
| 937 | (Id) | (1d) | (2b) | (3c) | (4d) | (5b) | (6k) | (7a), (7b) | (8a) | (9a) | (10a) |
| 938 | (Id) | (1d) | (2b) | (3c) | (4d) | (5b) | (6k) | (7a), (7b) | (8a) | (9a) | (10c) |
| 939 | (Id) | (1d) | (2b) | (3c) | (4d) | (5b) | (6k) | (7a), (7b) | (8a) | (9b) | (10a) |
| 940 | (Id) | (1d) | (2b) | (3c) | (4d) | (5b) | (6k) | (7a), (7b) | (8a) | (9b) | (10c) |
| 941 | (Id) | (1d) | (2b) | (3c) | (4d) | (5b) | (6k) | (7d) | (8a) | (9a) | (10a) |
| 942 | (Id) | (1d) | (2b) | (3c) | (4d) | (5b) | (6k) | (7d) | (8a) | (9a) | (10c) |
| 943 | (Id) | (1d) | (2b) | (3c) | (4d) | (5b) | (6k) | (7d) | (8a) | (9b) | (10a) |
| 944 | (Id) | (1d) | (2b) | (3c) | (4d) | (5b) | (6k) | (7d) | (8a) | (9b) | (10c) |
| 945 | (Id) | (1d) | (2b) | (3c) | (4d) | (5a) | (6a) | (7a), (7b) | (8a) | (9a) | (10a) |
| 946 | (Id) | (1d) | (2b) | (3c) | (4d) | (5a) | (6a) | (7a), (7b) | (8a) | (9a) | (10c) |
| 947 | (Id) | (1d) | (2b) | (3c) | (4d) | (5a) | (6a) | (7a), (7b) | (8a) | (9b) | (10a) |
| 948 | (Id) | (1d) | (2b) | (3c) | (4d) | (5a) | (6a) | (7a), (7b) | (8a) | (9b) | (10c) |
| 949 | (Id) | (1d) | (2b) | (3c) | (4d) | (5a) | (6a) | (7d) | (8a) | (9a) | (10a) |
| 950 | (Id) | (1d) | (2b) | (3c) | (4d) | (5a) | (6a) | (7d) | (8a) | (9a) | (10c) |
| 951 | (Id) | (1d) | (2b) | (3c) | (4d) | (5a) | (6a) | (7d) | (8a) | (9b) | (10a) |
| 952 | (Id) | (1d) | (2b) | (3c) | (4d) | (5a) | (6a) | (7d) | (8a) | (9b) | (10c) |
| 953 | (Id) | (1d) | (2b) | (3c) | (4d) | (5a) | (6k) | (7a), (7b) | (8a) | (9a) | (10a) |
| 954 | (Id) | (1d) | (2b) | (3c) | (4d) | (5a) | (6k) | (7a), (7b) | (8a) | (9a) | (10c) |
| 955 | (Id) | (1d) | (2b) | (3c) | (4d) | (5a) | (6k) | (7a), (7b) | (8a) | (9b) | (10a) |
| 956 | (Id) | (1d) | (2b) | (3c) | (4d) | (5a) | (6k) | (7a), (7b) | (8a) | (9b) | (10c) |
| 957 | (Id) | (1d) | (2b) | (3c) | (4d) | (5a) | (6k) | (7d) | (8a) | (9a) | (10a) |
| 958 | (Id) | (1d) | (2b) | (3c) | (4d) | (5a) | (6k) | (7d) | (8a) | (9a) | (10c) |
| 959 | (Id) | (1d) | (2b) | (3c) | (4d) | (5a) | (6k) | (7d) | (8a) | (9b) | (10a) |
| 960 | (Id) | (1d) | (2b) | (3c) | (4d) | (5a) | (6k) | (7d) | (8a) | (9b) | (10c) |
| 961 | (Id) | (1d) | (2b) | (3b) | (4a) | (5b) | (6a) | (7a), (7b) | (8a) | (9a) | (10a) |
| 962 | (Id) | (1d) | (2b) | (3b) | (4a) | (5b) | (6a) | (7a), (7b) | (8a) | (9a) | (10c) |
| 963 | (Id) | (1d) | (2b) | (3b) | (4a) | (5b) | (6a) | (7a), (7b) | (8a) | (9b) | (10a) |
| 964 | (Id) | (1d) | (2b) | (3b) | (4a) | (5b) | (6a) | (7a), (7b) | (8a) | (9b) | (10c) |
| 965 | (Id) | (1d) | (2b) | (3b) | (4a) | (5b) | (6a) | (7d) | (8a) | (9a) | (10a) |
| 966 | (Id) | (1d) | (2b) | (3b) | (4a) | (5b) | (6a) | (7d) | (8a) | (9a) | (10c) |
| 967 | (Id) | (1d) | (2b) | (3b) | (4a) | (5b) | (6a) | (7d) | (8a) | (9b) | (10a) |
| 968 | (Id) | (1d) | (2b) | (3b) | (4a) | (5b) | (6a) | (7d) | (8a) | (9b) | (10c) |
| 969 | (Id) | (1d) | (2b) | (3b) | (4a) | (5b) | (6k) | (7a), (7b) | (8a) | (9a) | (10a) |
| 970 | (Id) | (1d) | (2b) | (3b) | (4a) | (5b) | (6k) | (7a), (7b) | (8a) | (9a) | (10c) |
| 971 | (Id) | (1d) | (2b) | (3b) | (4a) | (5b) | (6k) | (7a), (7b) | (8a) | (9b) | (10a) |
| 972 | (Id) | (1d) | (2b) | (3b) | (4a) | (5b) | (6k) | (7a), (7b) | (8a) | (9b) | (10c) |
| 973 | (Id) | (1d) | (2b) | (3b) | (4a) | (5b) | (6k) | (7d) | (8a) | (9a) | (10a) |
| 974 | (Id) | (1d) | (2b) | (3b) | (4a) | (5b) | (6k) | (7d) | (8a) | (9a) | (10c) |
| 975 | (Id) | (1d) | (2b) | (3b) | (4a) | (5b) | (6k) | (7d) | (8a) | (9b) | (10a) |
| 976 | (Id) | (1d) | (2b) | (3b) | (4a) | (5b) | (6k) | (7d) | (8a) | (9b) | (10c) |
| 977 | (Id) | (1d) | (2b) | (3b) | (4a) | (5a) | (6a) | (7a), (7b) | (8a) | (9a) | (10a) |
| 978 | (Id) | (1d) | (2b) | (3b) | (4a) | (5a) | (6a) | (7a), (7b) | (8a) | (9a) | (10c) |
| 979 | (Id) | (1d) | (2b) | (3b) | (4a) | (5a) | (6a) | (7a), (7b) | (8a) | (9b) | (10a) |
| 980 | (Id) | (1d) | (2b) | (3b) | (4a) | (5a) | (6a) | (7a), (7b) | (8a) | (9b) | (10c) |
| 981 | (Id) | (1d) | (2b) | (3b) | (4a) | (5a) | (6a) | (7d) | (8a) | (9a) | (10a) |
| 982 | (Id) | (1d) | (2b) | (3b) | (4a) | (5a) | (6a) | (7d) | (8a) | (9a) | (10c) |
| 983 | (Id) | (1d) | (2b) | (3b) | (4a) | (5a) | (6a) | (7d) | (8a) | (9b) | (10a) |
| 984 | (Id) | (1d) | (2b) | (3b) | (4a) | (5a) | (6a) | (7d) | (8a) | (9b) | (10c) |
| 985 | (Id) | (1d) | (2b) | (3b) | (4a) | (5a) | (6k) | (7a), (7b) | (8a) | (9a) | (10a) |
| 986 | (Id) | (1d) | (2b) | (3b) | (4a) | (5a) | (6k) | (7a), (7b) | (8a) | (9a) | (10c) |
| 987 | (Id) | (1d) | (2b) | (3b) | (4a) | (5a) | (6k) | (7a), (7b) | (8a) | (9b) | (10a) |
| 988 | (Id) | (1d) | (2b) | (3b) | (4a) | (5a) | (6k) | (7a), (7b) | (8a) | (9b) | (10c) |
| 989 | (Id) | (1d) | (2b) | (3b) | (4a) | (5a) | (6k) | (7d) | (8a) | (9a) | (10a) |
| 990 | (Id) | (1d) | (2b) | (3b) | (4a) | (5a) | (6k) | (7d) | (8a) | (9a) | (10c) |
| 991 | (Id) | (1d) | (2b) | (3b) | (4a) | (5a) | (6k) | (7d) | (8a) | (9b) | (10a) |
| 992 | (Id) | (1d) | (2b) | (3b) | (4a) | (5a) | (6k) | (7d) | (8a) | (9b) | (10c) |
| 993 | (Id) | (1d) | (2b) | (3b) | (4d) | (5b) | (6a) | (7a), (7b) | (8a) | (9a) | (10a) |
| 994 | (Id) | (1d) | (2b) | (3b) | (4d) | (5b) | (6a) | (7a), (7b) | (8a) | (9a) | (10c) |
| 995 | (Id) | (1d) | (2b) | (3b) | (4d) | (5b) | (6a) | (7a), (7b) | (8a) | (9b) | (10a) |
| 996 | (Id) | (1d) | (2b) | (3b) | (4d) | (5b) | (6a) | (7a), (7b) | (8a) | (9b) | (10c) |
| 997 | (Id) | (1d) | (2b) | (3b) | (4d) | (5b) | (6a) | (7d) | (8a) | (9a) | (10a) |
| 998 | (Id) | (1d) | (2b) | (3b) | (4d) | (5b) | (6a) | (7d) | (8a) | (9a) | (10c) |
| 999 | (Id) | (1d) | (2b) | (3b) | (4d) | (5b) | (6a) | (7d) | (8a) | (9b) | (10a) |
| 1000 | (Id) | (1d) | (2b) | (3b) | (4d) | (5b) | (6a) | (7d) | (8a) | (9b) | (10c) |
| 1001 | (Id) | (1d) | (2b) | (3b) | (4d) | (5b) | (6k) | (7a), (7b) | (8a) | (9a) | (10a) |
| 1002 | (Id) | (1d) | (2b) | (3b) | (4d) | (5b) | (6k) | (7a), (7b) | (8a) | (9a) | (10c) |
| 1003 | (Id) | (1d) | (2b) | (3b) | (4d) | (5b) | (6k) | (7a), (7b) | (8a) | (9b) | (10a) |
| 1004 | (Id) | (1d) | (2b) | (3b) | (4d) | (5b) | (6k) | (7a), (7b) | (8a) | (9b) | (10c) |
| 1005 | (Id) | (1d) | (2b) | (3b) | (4d) | (5b) | (6k) | (7d) | (8a) | (9a) | (10a) |

-continued

| I | L1 | R1 | L2 | Q | L3 | R3 | L4 | R4 | L5 | R5 |
|---|---|---|---|---|---|---|---|---|---|---|
| 1006 (Id) | (1d) | (2b) | (3b) | (4d) | (5b) | (6k) | (7d) | (8a) | (9a) | (10c) |
| 1007 (Id) | (1d) | (2b) | (3b) | (4d) | (5b) | (6k) | (7d) | (8a) | (9b) | (10a) |
| 1008 (Id) | (1d) | (2b) | (3b) | (4d) | (5b) | (6k) | (7d) | (8a) | (9b) | (10c) |
| 1009 (Id) | (1d) | (2b) | (3b) | (4d) | (5a) | (6a) | (7a), (7b) | (8a) | (9a) | (10a) |
| 1010 (Id) | (1d) | (2b) | (3b) | (4d) | (5a) | (6a) | (7a), (7b) | (8a) | (9a) | (10c) |
| 1011 (Id) | (1d) | (2b) | (3b) | (4d) | (5a) | (6a) | (7a), (7b) | (8a) | (9b) | (10a) |
| 1012 (Id) | (1d) | (2b) | (3b) | (4d) | (5a) | (6a) | (7a), (7b) | (8a) | (9b) | (10c) |
| 1013 (Id) | (1d) | (2b) | (3b) | (4d) | (5a) | (6a) | (7d) | (8a) | (9a) | (10a) |
| 1014 (Id) | (1d) | (2b) | (3b) | (4d) | (5a) | (6a) | (7d) | (8a) | (9a) | (10c) |
| 1015 (Id) | (1d) | (2b) | (3b) | (4d) | (5a) | (6a) | (7d) | (8a) | (9b) | (10a) |
| 1016 (Id) | (1d) | (2b) | (3b) | (4d) | (5a) | (6a) | (7d) | (8a) | (9b) | (10c) |
| 1017 (Id) | (1d) | (2b) | (3b) | (4d) | (5a) | (6k) | (7a), (7b) | (8a) | (9a) | (10a) |
| 1018 (Id) | (1d) | (2b) | (3b) | (4d) | (5a) | (6k) | (7a), (7b) | (8a) | (9a) | (10c) |
| 1019 (Id) | (1d) | (2b) | (3b) | (4d) | (5a) | (6k) | (7a), (7b) | (8a) | (9b) | (10a) |
| 1020 (Id) | (1d) | (2b) | (3b) | (4d) | (5a) | (6k) | (7a), (7b) | (8a) | (9b) | (10c) |
| 1021 (Id) | (1d) | (2b) | (3b) | (4d) | (5a) | (6k) | (7d) | (8a) | (9a) | (10a) |
| 1022 (Id) | (1d) | (2b) | (3b) | (4d) | (5a) | (6k) | (7d) | (8a) | (9a) | (10c) |
| 1023 (Id) | (1d) | (2b) | (3b) | (4d) | (5a) | (6k) | (7d) | (8a) | (9b) | (10a) |
| 1024 (Id) | (1d) | (2b) | (3b) | (4d) | (5a) | (6k) | (7d) | (8a) | (9b) | (10c) |

Certain particular embodiments of the compounds of the disclosure are compounds of embodiments 1-512 of the table above, in which the structural formula is (Ia).

For example, certain embodiments of the compounds as otherwise described herein have any of the structural formulae (Ia)-(Ie) above, for example, structural formula (Ia) or (Ie), in which the variables are as otherwise described in any embodiment herein (e.g., with respect to any of the alternative definitions of the variables $L^1$, $L^2$, Q, $L^3$, $R^3$, $L^4$, $R^4$, $L^5$ and $R^5$ as described herein, and with respect to any of embodiments 1-1024 of the table above as applicable), and in which $R^1$ is unsubstituted or fluorinated $C_1$-$C_8$ alkenyl. In certain such embodiments, $L^1$ is a bond.

For example, certain embodiments of the compounds as otherwise described herein have any of the structural formulae (Ia)-(Ie) above, for example, structural formula (Ia) or (Ie), in which the variables are as otherwise described in any embodiment herein (e.g., with respect to any of the alternative definitions of the variables $L^1$, $L^2$, Q, $L^3$, $R^3$, $L^4$, $R^4$, $L^5$ and $R^5$ as described herein, and with respect to any of embodiments 1-1024 of the table above as applicable), and in which $R^1$ is phenyl optionally substituted with 1-5 $R^E$. In certain such embodiments, $L^1$ is a bond.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $L^2$, Q, $L^3$, $R^3$, $L^4$, $R^4$, $L^5$ and $R^5$ as described herein, and with respect to any of embodiments 1-1024 of the table above as applicable), and in which $R^1$ is phenyl substituted with one, two or three substituents each independently selected from fluoro, chloro, nitro, methyl, methoxy, ethyl, ethoxy, trifluoromethyl, difluoromethyl, fluoromethyl, trifluoromethoxy, pentafluoroethyl and 2,2,2-trifluoroethoxy. In certain such embodiments, $L^1$ is a bond.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $L^2$, Q, $L^3$, $R^3$, $L^4$, $R^4$, $L^5$ and $R^5$ as described herein, and with respect to any of embodiments 1-1024 of the table above as applicable), and in which $R^1$ is trifluoromethyl-substituted phenyl, methoxymethyl, hydroxymethyl, methoxy-substituted phenyl or fluoro-substituted phenyl. In certain such embodiments, $L^1$ is a bond.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $L^2$, Q, $L^3$, $R^3$, $L^4$, $R^4$, $L^5$ and $R^5$ as described herein, and with respect to any of embodiments 1-1024 of the table above as applicable), and in which $R^1$ is -phenyl substituted with —$(OCH_2CH_2O)_n$—$R^{1G}$ in which n is 1-4, —$N(R^{1G})C(O)CH_2$—O—$(CH_2CH_2O)_nR^{1G}$ in which n is 0-3, or —$C(O)NR^{1G}(CH_2CH_2O)_nR^{1G}$. In certain such embodiments, $L^1$ is a bond.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $L^2$, Q, $L^3$, $R^3$, $L^4$, $R^4$, $L^5$ and $R^5$ as described herein, and with respect to any of embodiments 1-1024 of the table above as applicable), and in which $R^1$ is hydroxymethyl, methoxymethyl, hydroxyethyl or methoxyethyl. In certain such embodiments, $L^1$ is a bond.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^5$ and $R^5$ as described herein, and with respect to any of embodiments 1-1024 of the table above as applicable), and in which -$L^4$-$R^4$ is —OH or —O-(unsubstituted or fluorinated $C_1$-$C_8$ alkyl), e.g., methoxy.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which -$L^5$-$R^5$ is phenyl substituted with a single substituent selected from -$L^{5C}$-(phenyl optionally substituted with 1-5 $R^{5D}$), -$L^{5C}$-(monocyclic heteroaryl optionally substituted with 1-5 $R^{5D}$), and $-L^{5C}$-(monocyclic cycloalkyl optionally substituted with 1-5 $R^{5E}$) $-L^{5C}$-(monocyclic heterocycloalkyl optionally substituted with 1-5 $R^{5E}$) and (ii) optionally substituted with 1-5 $R^{5E}$.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which $-L^5-R^5$ is $R^5$ is phenyl substituted with a single $-L^{5C}$-(monocyclic heteroaryl optionally substituted with 1-5 $R^{5D}$) substituent and (ii) optionally substituted with 1-5 $R^{5E}$. The monocyclic heteroaryl can be, for example, an oxadiazole.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which $-L^5-R^5$ is $R^5$ is phenyl substituted with a single $-L^{5C}$-(monocyclic heterocycloalkyl optionally substituted with 1-5 $R^{5E}$) substituent and (ii) optionally substituted with 1-5 $R^{5E}$. The monocyclic heterocycloalkyl can be, for example, an morpholinyl, e.g., a morpholin-1-yl, or a oxetanyl, e.g., an oxetan-3-yl.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which $-L^5-R^5$ is heterocycloalkyl optionally substituted with 1-5 $R^{5E}$. The heterocycloalkyl can be, for example, a nitrogen-containing heterocycloalkyl, attached to the $-L^5-$ through a nitrogen atom. In certain such embodiments, the heterocycloalkyl is moncyclic. In other such embodiments, the heterocycloalkyl is bicyclic. In certain such embodiments, the heterocycloalkyl is saturated. In various embodiments as otherwise described herein, the heterocycloalkyl is a morpholinyl (e.g., a morpholin-1-yl), a 1,4-dioxaspiro[4,5]dec-enyl (e.g., 1,4-dioxaspiro[4,5]dec-en-8-yl), a piperidinyl (e.g., a piperidin-1-yl), an azabicyclo[3.2.1]octanyl (e.g., an azabicyclo[3.2.1]octan-8-yl), a piperazinyl (e.g., a piperazin-1-yl), a pyrrolidinyl (e.g., a pyrrolidin-1-yl), or an azaspiro[2.5]octanyl (e.g., an azaspiro[2.5]octan-6-yl).

Other embodiments of the compounds of otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which $-L^5-R^5$ is heterocycloalkyl substituted with a single $-L^{5C}$-(monocyclic cycloalkyl optionally substituted with 1-5 $R^{5E}$) substituent and (ii) optionally substituted with 1-5 $R^{5E}$. The heterocycloalkyl can be, for example, a nitrogen-containing heterocycloalkyl, attached to the $-L^5-$ through a nitrogen atom. In certain such embodiments, the heterocycloalkyl is moncyclic. In other such embodiments, the heterocycloalkyl is bicyclic. In certain such embodiments, the heterocycloalkyl is saturated. In various embodiments as otherwise described herein, the heterocycloalkyl is a morpholinyl (e.g., a morpholin-1-yl), a 1,4-dioxaspiro[4,5]dec-enyl (e.g., 1,4-dioxaspiro[4,5]dec-en-8-yl), a piperidinyl (e.g., a piperidin-1-yl), an azabicyclo[3.2.1]octanyl (e.g., an azabicyclo[3.2.1]octan-8-yl), a piperazinyl (e.g., a piperazin-1-yl), a pyrrolidinyl (e.g., a pyrrolidin-1-yl), or an azaspiro[2.5]octanyl (e.g., an azaspiro[2.5]octan-6-yl). The cycloalkyl can be, for example, a saturated cycloalkyl, such as a saturated $C_3$-$C_5$ cycloalkyl, e.g., cyclopropyl.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which $-L^5-R^5$ is cycloalkyl optionally substituted with 1-5 $R^{5E}$. In certain such embodiments, the cycloalkyl is moncyclic. In other such embodiments, the cycloalkyl is bicyclic. In certain such embodiments, the cycloalkyl is saturated. In various embodiments as otherwise described herein, the cycloalkyl is a cyclohexenyl (e.g., a cyclohexen-1-yl, for example, 4-trifluoromethylcyclohexen-1-yl), or a cyclohexyl.

Other embodiments of the compounds as otherwise described herein have any of the structural formulae (Ia)-(Ie) above, for example, structural formula (Ia), in which the variables are as otherwise described in any embodiment herein (e.g., with respect to any of the alternative definitions of the variables $L^1$, $R^1$, $L^2$, Q, $L^3$, $R^3$, $L^4$ and $R^4$ as described herein, and with respect to any of embodiments 1-1024 of the table above as applicable), and in which $-L^5-R^5$ is phenyl substituted with one, two or three substituents each independently selected from fluoro, chloro, nitro, methyl, methoxy, ethyl, ethoxy, trifluoromethyl, difluoromethyl, fluoromethyl, trifluoromethoxy, pentafluoroethyl and 2,2,2-trifluoroethoxy. In certain such embodiments, $L^5$ is a bond.

In certain additional embodiments, including any of the embodiments described with reference to formulae (I) and (Ia)-(If) and embodiments 1-1024 above, each optionally substituted alkylene, alkenylene, and alkynylene recited in any one of the preceding embodiments is unsubstituted. In alternative additional embodiments, including any of the embodiments described with reference to formulae (I)-(Io) and embodiments 1-1024 above, each optionally substituted alkylene, alkenylene, and alkynylene recited in any one of the preceding embodiments is unsubstituted or fluorinated.

In certain additional embodiments, including any of the embodiments described with reference to formulae (I) and (Ia)-(If) and embodiments 1-1024 above and any embodiment described in the paragraph immediately above, each optionally substituted alkyl, alkenyl, and alkynyl recited in any one of preceding embodiments is unsubstituted. In alternative additional embodiments, including any of the embodiments described with reference to formulae (I)-(Io) and embodiments 1-1024 above and any embodiment described in the paragraph immediately above, each optionally substituted alkyl, alkenyl, and alkynyl recited in any one of preceding embodiments is unsubstituted.

In certain additional embodiments, including any of the embodiments described with reference to formulae (I) and (Ia)-(If) and embodiments 1-1024 above and any embodiment described in the two paragraphs immediately above, each cycloalkyl recited in any one of the preceding embodiments is a 3-7 membered monocyclic cycloalkyl. For example, in certain particular embodiments, including any of the embodiments described with reference to formulae (I) and (Ia)-(If) and embodiments 1-1024 above and any embodiment described in the two paragraphs immediately above, each cycloalkyl recited in any one of the preceding embodiments is a cyclopropyl, a cyclobutyl, a cyclopentyl, a cyclopentenyl, a cyclohexyl or a cyclohexenyl.

In certain additional embodiments, including any of the embodiments described with reference to formulae (I) and (Ia)-(If) and embodiments 1-1024 above and any embodiment described in the three paragraphs immediately above, each heterocycloalkyl recited in any one of the preceding embodiments is a 4-7 membered monocyclic heterocycloalkyl having 1-2 heteroatoms selected from O, S and N. For example, in certain particular embodiments, including any of the embodiments described with reference to formulae (I) and (Ia)-(If) and embodiments 1-1024 above and any embodiment described in the three paragraphs immediately above, each heterocycloalkyl recited in any one of the preceding embodiments is a pyrrolidinyl, a tetrahydrofuranyl, a tetrahydrothienyl, a piperidinyl, a piperazinyl, a morpholinyl, a thiomorpholinyl, a tetrahydro-2H-pyranyl, or a tetrahydro-2H-thiopyranyl.

In certain additional embodiments, including any of the embodiments described with reference to formulae (I) and (Ia)-(If) and embodiments 1-1024 above and any embodiment described in the four paragraphs immediately above, each heteroaryl is a 5-6 membered monocyclic heteroaryl having 1-3 heteroatoms selected from O, S and N. For example, in certain particular embodiments, including any of the embodiments described with reference to formulae (I) and (Ia)-(If) and embodiments 1-1024 above and any embodiment described in the four paragraphs immediately above, each heteroaryl is a furanyl, a thienyl, a pyrrolyl, a pyrazolyl, an imidazolyl, an oxazolyl or a thiazolyl.

In certain additional embodiments, including any of the embodiments described with reference to formulae (I) and (Ia)-(If) and embodiments 1-1024 above and any embodiment described in the four paragraphs immediately above, each aryl is phenyl.

In certain additional embodiments as described above, including any of the embodiments described with reference to formulae (I) and (Ia)-(If) and embodiments 1-1024 above and any embodiment described in the five paragraphs immediately above, $R^5$ is substituted with 1, 2 or 3 substituents selected from halogen (e.g., chloro- or fluoro-) and fluorinated $C_1$-$C_3$ alkyl (e.g., trifluoromethyl, difluoromethyl, fluoromethyl, pentafluoroethyl, trifluoroethyl). For example, in certain embodiment as described above, $R^5$ is phenyl substituted (e.g., 3-substituted, 4-substituted, 3,4-disubstituted, 2,4-disubstituted, or 2,5-disubstituted) with one or two substitutents selected from trifluoromethyl, fluorine and chlorine. For example, in particular embodiments, $R^5$ can be dichlorophenyl, e.g., 3,4-dichlorophenyl, or trifluoromethylphenyl, e.g., 4-trifluoromethylphenyl.

In certain embodiments, the compound is one of the compounds of the compound table below, optionally provided as a pharmaceutically-acceptable salt or N-oxide, and/or a solvate or hydrate. BJAB cell proliferation data is presented in the table; "A" indicates a measured $EC_{50}$ less than or equal to 1 μM; "B" indicates a measured $EC_{50}$ greater than 1 μM and less than or equal to 5 μM; "C" indicates a measured $EC_{50}$ greater than 5 μM and less than or equal to 10 μM; "D" indicates a measured $EC_{50}$ greater than 10 μM and less than or equal to 25 μM; "E" indicates a measured $EC_{50}$ greater than 25 μM and less than or equal to 50 μM; "F" indicates a measured $EC_{50}$ greater than 50 μM and less than or equal to 100 μM; "G" indicates that in the experiments performed there was no measured $EC_{50}$ less than or equal to 80 μM; "H" indicates that in the experiments performed there was no measured $EC_{50}$ less than or equal to 50 μM; "I" indicates that in the experiments performed there was no measured $EC_{50}$ less than or equal to 40 μM; "J" indicates that in the experiments performed there was no measured $EC_{50}$ less than or equal to 25 μM; "K" indicates that in the experiments performed there was no measured $EC_{50}$ less than or equal to 20 μM; and "L" indicates that in the experiments performed there was no measured $EC_{50}$ less than or equal to 5 μM.

| Cpd | Structure | Name | BJAB |
|---|---|---|---|
| 1 | 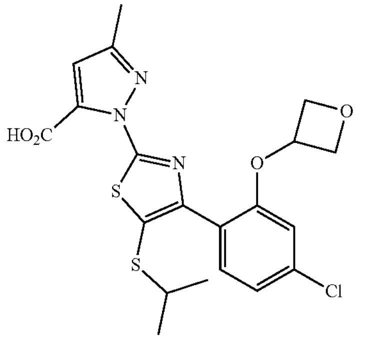 [SMILES: Cc1cc(C(=O)O)n(-c2nc(-c3ccc(Cl)cc3OC3COC3)c(SC(C)C)s2)n1] | 1-(4-(4-chloro-2-(oxetan-3-yloxy)phenyl)-5-(isopropylthio)thiazol-2-yl)-3-methyl-1H-pyrazole-5-carboxylic acid | I |

-continued

| Cpd | Structure | Name | BJAB |
|---|---|---|---|
| 2 | 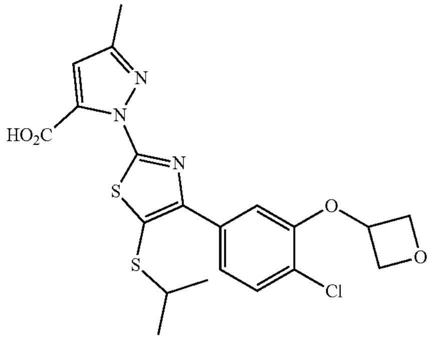 [SMILES: Cc1cc(C(=O)O)n(-c2nc(-c3ccc(Cl)c(OC4COC4)c3)c(SC(C)C)s2)n1] | 1-(4-(4-chloro-3-(oxetan-3-yloxy)phenyl)-5-(isopropylthio)thiazol-2-yl)-3-methyl-1H-pyrazole-5-carboxylic acid | I |
| 3 | 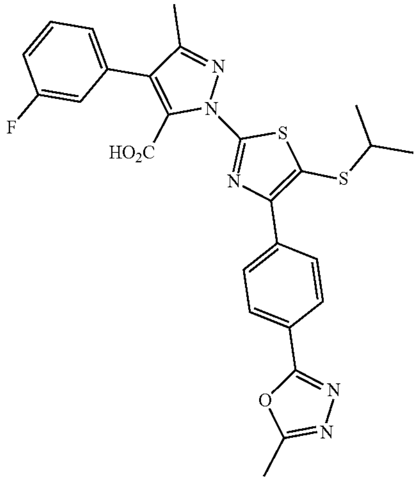 [SMILES: Cc1nnc(-c2ccc(-c3nc(-n4nc(C)c(-c5cccc(F)c5)c4C(=O)O)sc3SC(C)C)cc2)o1] | 4-(3-fluorophenyl)-1-(5-(isopropylthio)-4-(4-(5-methyl-1,3,4-oxadiazol-2-yl)phenyl)thiazol-2-yl)-3-methyl-1H-pyrazole-5-carboxylic acid | E |
| 4 | 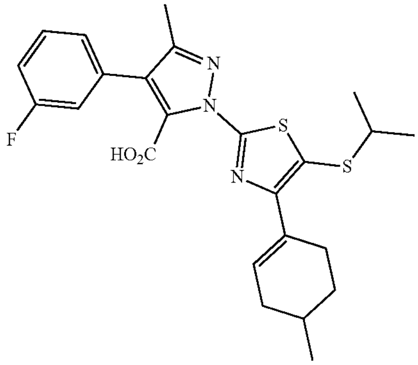 [SMILES: Cc1nn(-c2nc(C3=CCC(C)CC3)c(SC(C)C)s2)c(C(=O)O)c1-c1cccc(F)c1] | 4-(3-fluorophenyl)-1-(5-(isopropylthio)-4-(4-methylcyclohex-1-en-1-yl)thiazol-2-yl)-3-methyl-1H-pyrazole-5-carboxylic acid | B |
| 5 | 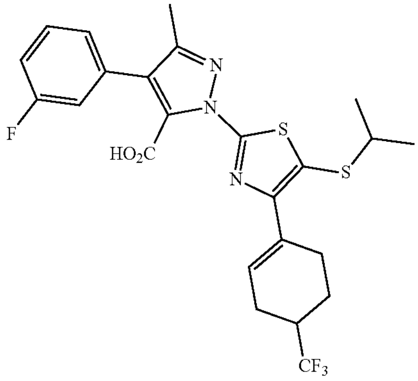 [SMILES: Cc1nn(-c2nc(C3=CCC(C(F)(F)F)CC3)c(SC(C)C)s2)c(C(=O)O)c1-c1cccc(F)c1] | 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid | A |

-continued

| Cpd | Structure | Name | BJAB |
|---|---|---|---|
| 6 | 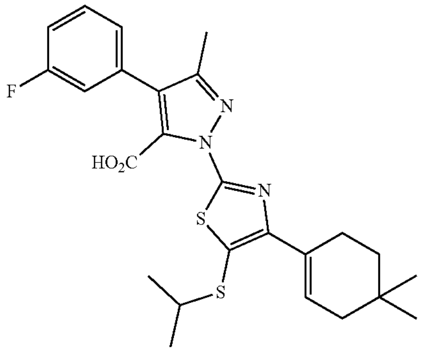 [SMILES: Cc1nn(-c2nc(C3=CCC(C)(C)CC3)c(SC(C)C)s2)c(C(=O)O)c1-c1cccc(F)c1] | 1-(4-(4,4-dimethylcyclohex-1-en-1-yl)-5-(isopropylthio)thiazol-2-yl)-4-(3-fluorophenyl)-3-methyl-1H-pyrazole-5-carboxylic acid | A |
| 7 | 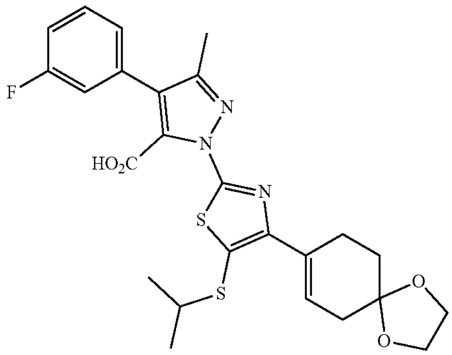 [SMILES: Cc1nn(-c2nc(C3=CCC4(CC3)OCCO4)c(SC(C)C)s2)c(C(=O)O)c1-c1cccc(F)c1] | 4-(3-fluorophenyl)-1-(5-(isopropylthio)-4-(1,4-dioxaspiro[4.5]dec-7-en-8-yl)thiazol-2-yl)-3-methyl-1H-pyrazole-5-carboxylic acid | E |
| 8 | 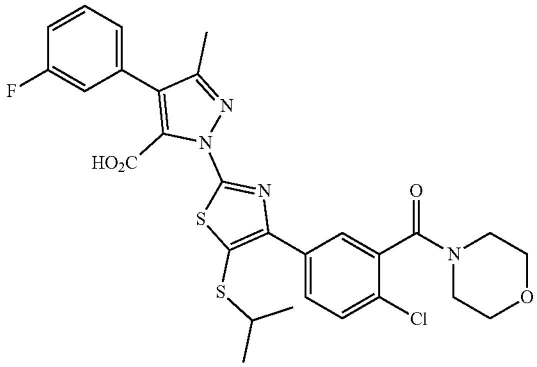 [SMILES: Cc1nn(-c2nc(-c3ccc(Cl)c(C(=O)N4CCOCC4)c3)c(SC(C)C)s2)c(C(=O)O)c1-c1cccc(F)c1] | 1-(4-(4-chloro-3-(morpholine-4-carbonyl)phenyl)-5-(isopropylthio)thiazol-2-yl)-4-(3-fluorophenyl)-3-methyl-1H-pyrazole-5-carboxylic acid | I |
| 9 | 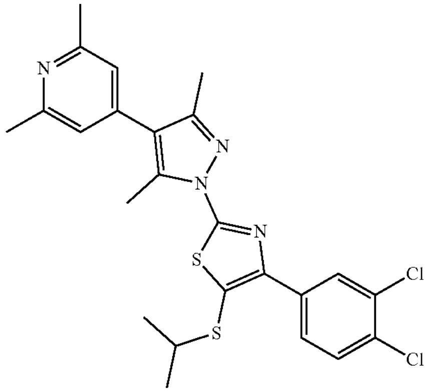 [SMILES: Cc1cc(-c2c(C)nn(-c3nc(-c4ccc(Cl)c(Cl)c4)c(SC(C)C)s3)c2C)cc(C)n1] | 4-(3,4-dichlorophenyl)-2-(4-(2,6-dimethylpyridin-4-yl)-3-methyl-1H-pyrazol-1-yl)-5-(isopropylthio)thiazole | A, C, L |

-continued

| Cpd | Structure | Name | BJAB |
|---|---|---|---|
| 10 | 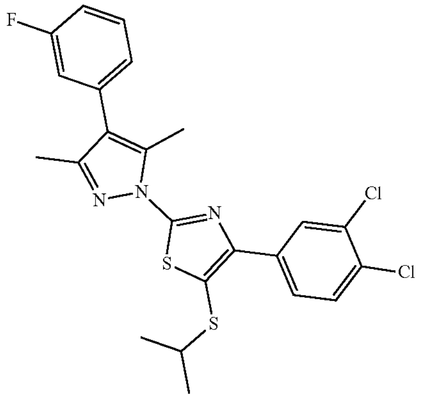 [SMILES: Cc1nn(-c2nc(-c3ccc(Cl)c(Cl)c3)c(SC(C)C)s2)c(C)c1-c1cccc(F)c1] | 2-(4-(3-fluorophenyl)-3,5-dimethyl-1H-pyrazol-1-yl)-5-(isopropylthio)-4-(4-(trifluoromethyl)phenyl)thiazole | I |
| 11 | 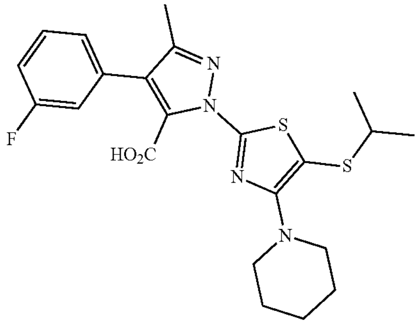 [SMILES: Cc1nn(-c2nc(N3CCCCC3)c(SC(C)C)s2)c(C(=O)O)c1-c1cccc(F)c1] | 4-(3-fluorophenyl)-1-(5-(isopropylthio)-4-(piperidin-1-yl)thiazol-2-yl)-3-methyl-1H-pyrazole-5-carboxylic acid | D |
| 12 | 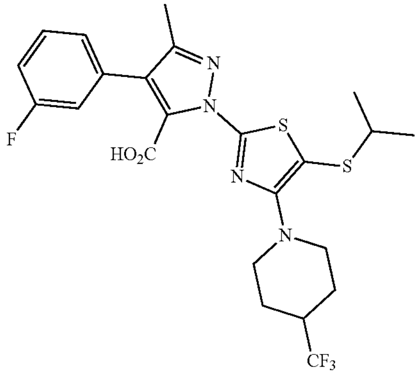 [SMILES: Cc1nn(-c2nc(N3CCC(C(F)(F)F)CC3)c(SC(C)C)s2)c(C(=O)O)c1-c1cccc(F)c1] | 4-(3-fluorophenyl)-1-(5-(isopropylthio)-4-(4-(trifluoromethyl)piperidin-1-yl)thiazol-2-yl)-3-methyl-1H-pyrazole-5-carboxylic acid | A |
| 13 | 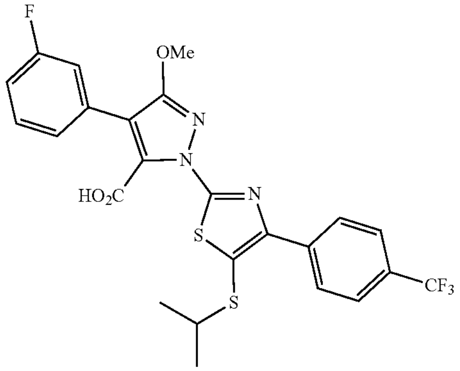 [SMILES: COc1nn(-c2nc(-c3ccc(C(F)(F)F)cc3)c(SC(C)C)s2)c(C(=O)O)c1-c1cccc(F)c1] | 4-(3-fluorophenyl)-1-(5-(isopropylthio)-4-(4-(trifluoromethyl)phenyl)thiazol-2-yl)-3-methoxy-1H-pyrazole-5-carboxylic acid | B |

-continued

| Cpd | Structure | Name | BJAB |
|---|---|---|---|
| 14 | 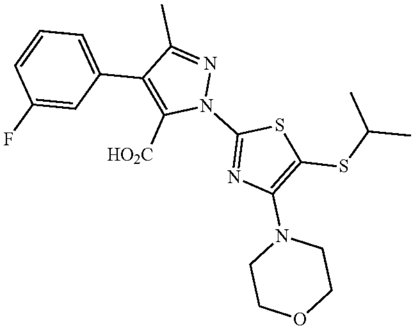 [SMILES: Cc1nn(-c2nc(N3CCOCC3)c(SC(C)C)s2)c(C(=O)O)c1-c1cccc(F)c1] | 4-(3-fluorophenyl)-1-(5-(isopropylthio)-4-morpholinothiazol-2-yl)-3-methyl-1H-pyrazole-5-carboxylic acid | I |
| 15 | 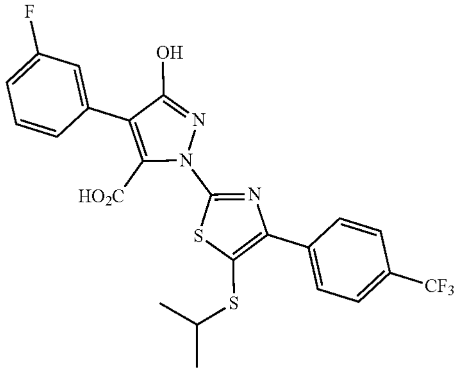 [SMILES: CC(C)Sc1sc(-n2nc(O)c(-c3cccc(F)c3)c2C(=O)O)nc1-c1ccc(C(F)(F)F)cc1] | 4-(3-fluorophenyl)-3-hydroxy-1-(5-(isopropylthio)-4-(4-(trifluoromethyl)phenyl)thiazol-2-yl)-1H-pyrazole-5-carboxylic acid | K |
| 16 | 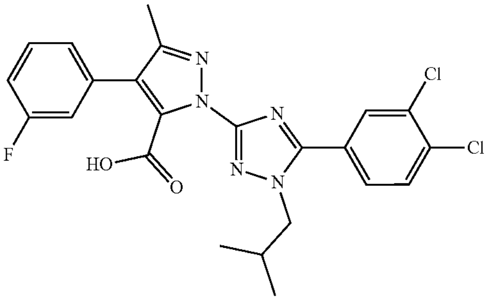 [SMILES: Cc1nn(-c2nc(-c3ccc(Cl)c(Cl)c3)n(CC(C)C)n2)c(C(=O)O)c1-c1cccc(F)c1] | 1-(5-(3,4-dichlorophenyl)-1-isobutyl-1H-1,2,4-triazol-3-yl)-4-(3-fluorophenyl)-3-methyl-1H-pyrazole-5-carboxylic acid | K |
| 17 | 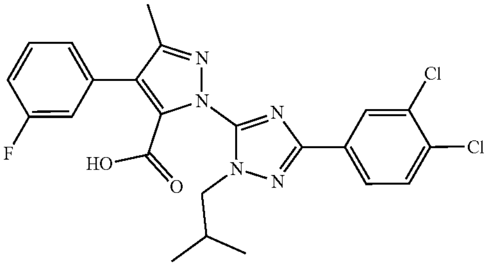 [SMILES: Cc1nn(-c2nc(-c3ccc(Cl)c(Cl)c3)nn2CC(C)C)c(C(=O)O)c1-c1cccc(F)c1] | 1-(3-(3,4-dichlorophenyl)-1-isobutyl-1H-1,2,4-triazol-5-yl)-4-(3-fluorophenyl)-3-methyl-1H-pyrazole-5-carboxylic acid | K |

-continued

| Cpd | Structure | Name | BJAB |
|---|---|---|---|
| 18 | 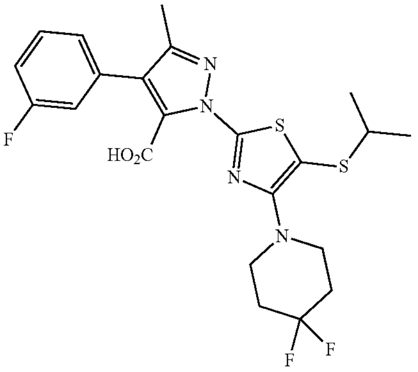 [SMILES: Cc1nn(-c2nc(N3CCC(F)(F)CC3)c(SC(C)C)s2)c(C(=O)O)c1-c1cccc(F)c1] | 1-(4-(4,4-difluoropiperidin-1-yl)-5-(isopropylthio)thiazol-2-yl)-4-(3-fluorophenyl)-3-methyl-1H-pyrazole-5-carboxylic acid | B |
| 19 | 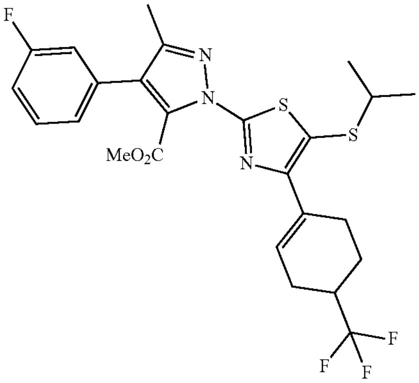 [SMILES: COC(=O)c1c(-c2cccc(F)c2)c(C)nn1-c1nc(C2=CCC(C(F)(F)F)CC2)c(SC(C)C)s1] | methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (enantiopure - unknown stereochemistry) | A |
| 20 | 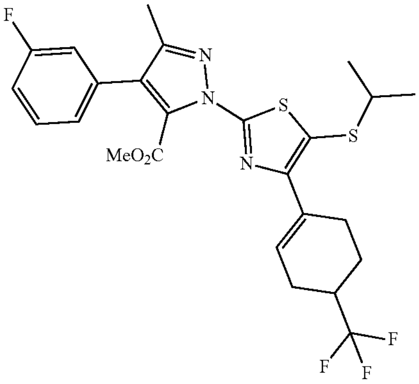 [SMILES: COC(=O)c1c(-c2cccc(F)c2)c(C)nn1-c1nc(C2=CCC(C(F)(F)F)CC2)c(SC(C)C)s1] | methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (enantiopure - unknown stereochemistry) | A |
| 21 | 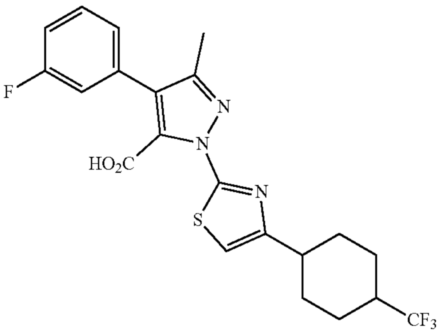 [SMILES: Cc1nn(-c2nc(C3CCC(C(F)(F)F)CC3)cs2)c(C(=O)O)c1-c1cccc(F)c1] | 4-(3-fluorophenyl)-3-methyl-1-(4-(4-(trifluoromethyl)cyclohexyl)thiazol-2-yl)-1H-pyrazole-5-carboxylic acid | K |

-continued

| Cpd | Structure | Name | BJAB |
|---|---|---|---|
| 22 | 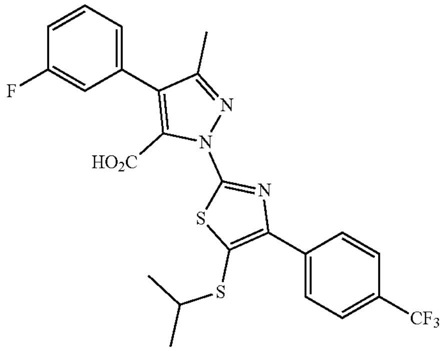 [SMILES: Cc1nn(-c2nc(-c3ccc(C(F)(F)F)cc3)c(SC(C)C)s2)c(C(=O)O)c1-c1cccc(F)c1] | 4-(3-fluorophenyl)-1-(5-isobutyl-4-(4-(trifluoromethyl)phenyl)thiazol-2-yl)-3-methyl-1H-pyrazole-5-carboxylic acid | A |
| 23 | 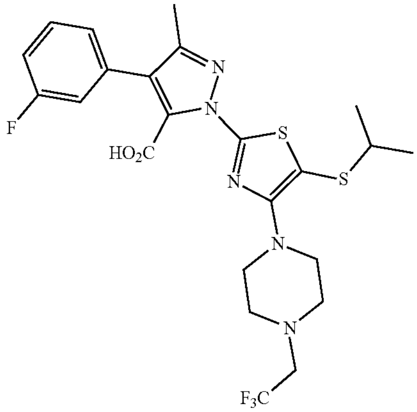 [SMILES: Cc1nn(-c2nc(N3CCN(CC(F)(F)F)CC3)c(SC(C)C)s2)c(C(=O)O)c1-c1cccc(F)c1] | 4-(3-fluorophenyl)-1-(5-(isopropylthio)-4-(4-(2,2,2-trifluoroethyl)piperazin-1-yl)thiazol-2-yl)-3-methyl-1H-pyrazole-5-carboxylic acid | C |
| 24 | 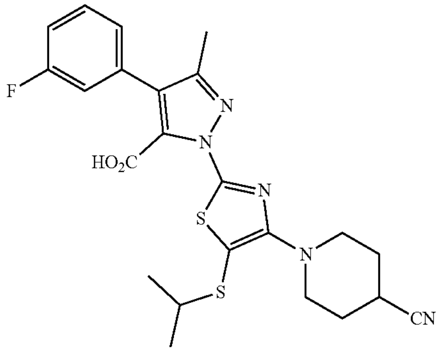 [SMILES: Cc1nn(-c2nc(N3CCC(C#N)CC3)c(SC(C)C)s2)c(C(=O)O)c1-c1cccc(F)c1] | 1-(4-(4-cyanopiperidin-1-yl)-5-(isopropylthio)thiazol-2-yl)-4-(3-fluorophenyl)-3-methyl-1H-pyrazole-5-carboxylic acid | D |
| 25 | 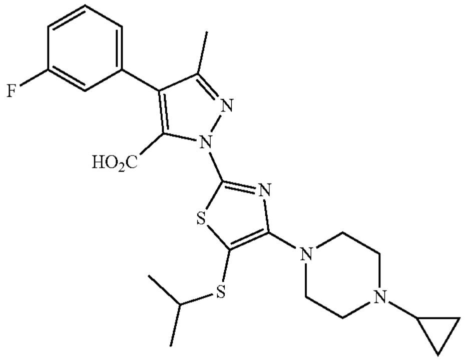 [SMILES: Cc1nn(-c2nc(N3CCN(C4CC4)CC3)c(SC(C)C)s2)c(C(=O)O)c1-c1cccc(F)c1] | 1-(4-(4-cyclopropylpiperazin-1-yl)-5-(isopropylthio)thiazol-2-yl)-4-(3-fluorophenyl)-3-methyl-1H-pyrazole-5-carboxylic acid | C |

-continued

| Cpd | Structure | Name | BJAB |
|---|---|---|---|
| 26 | 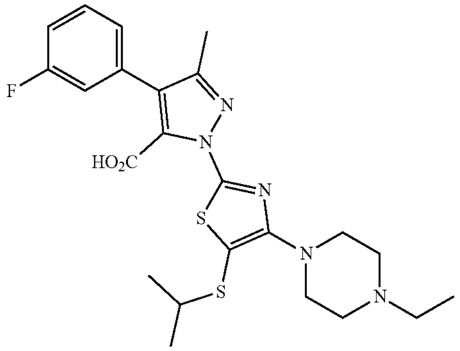 [SMILES: CCN1CCN(c2nc(-n3nc(C)c(-c4cccc(F)c4)c3C(=O)O)sc2SC(C)C)CC1] | 1-(4-(4-ethylpiperazin-1-yl)-5-(isopropylthio)thiazol-2-yl)-4-(3-fluorophenyl)-3-methyl-1H-pyrazole-5-carboxylic acid | K |
| 27 | 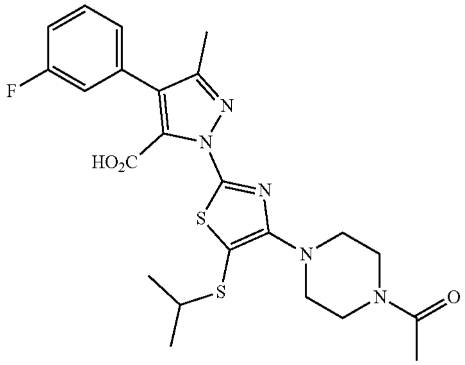 [SMILES: CC(=O)N1CCN(c2nc(-n3nc(C)c(-c4cccc(F)c4)c3C(=O)O)sc2SC(C)C)CC1] | 1-(4-(4-acetylpiperazin-1-yl)-5-(isopropylthio)thiazol-2-yl)-4-(3-fluorophenyl)-3-methyl-1H-pyrazole-5-carboxylic acid | K |
| 28 | 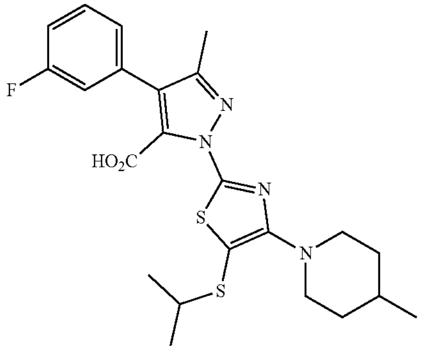 [SMILES: Cc1nn(-c2nc(N3CCC(C)CC3)c(SC(C)C)s2)c(C(=O)O)c1-c1cccc(F)c1] | 4-(3-fluorophenyl)-1-(5-(isopropylthio)-4-(4-methylpiperidin-1-yl)thiazol-2-yl)-3-methyl-1H-pyrazole-5-carboxylic acid | B |
| 29 | 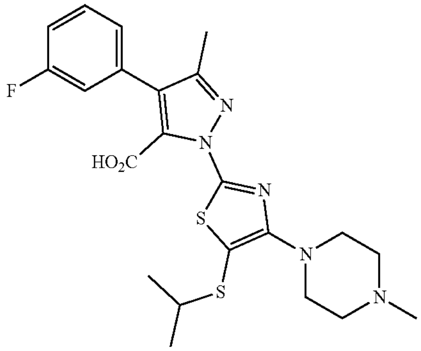 [SMILES: Cc1nn(-c2nc(N3CCN(C)CC3)c(SC(C)C)s2)c(C(=O)O)c1-c1cccc(F)c1] | 4-(3-fluorophenyl)-1-(5-(isopropylthio)-4-(4-methylpiperazin-1-yl)thiazol-2-yl)-3-methyl-1H-pyrazole-5-carboxylic acid | |

-continued

| Cpd | Structure | Name | BJAB |
|---|---|---|---|
| 30 | 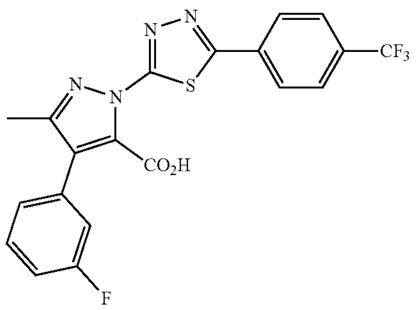 [SMILES: Cc1nn(-c2nnc(-c3ccc(C(F)(F)F)cc3)s2)c(C(=O)O)c1-c1cccc(F)c1] | 4-(3-fluorophenyl)-3-methyl-1-(5-(4-(trifluoromethyl)phenyl)-1,3,4-thiadiazol-2-yl)-1H-pyrazole-5-carboxylic acid | K |
| 31 | 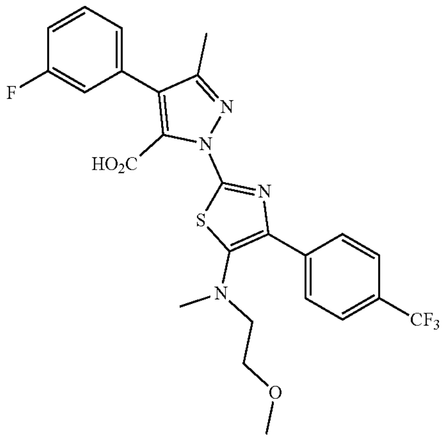 [SMILES: COCCN(C)c1sc(-n2nc(C)c(-c3cccc(F)c3)c2C(=O)O)nc1-c1ccc(C(F)(F)F)cc1] | 4-(3-fluorophenyl)-1-(5-((2-methoxyethyl)(methyl)amino)-4-(4-(trifluoromethyl)phenyl)thiazol-2-yl)-3-methyl-1H-pyrazole-5-carboxylic acid | B |
| 32 | 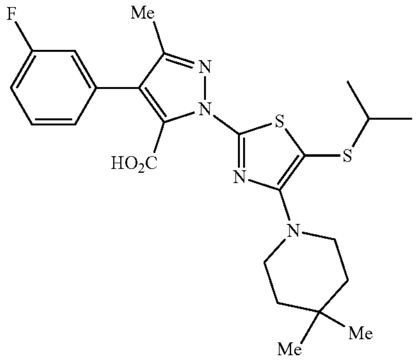 [SMILES: Cc1nn(-c2nc(N3CCC(C)(C)CC3)c(SC(C)C)s2)c(C(=O)O)c1-c1cccc(F)c1] | 1-(4-(4,4-dimethylpiperidin-1-yl)-5-(isopropylthio)thiazol-2-yl)-4-(3-fluorophenyl)-3-methyl-1H-pyrazole-5-carboxylic acid | A |
| 33 | 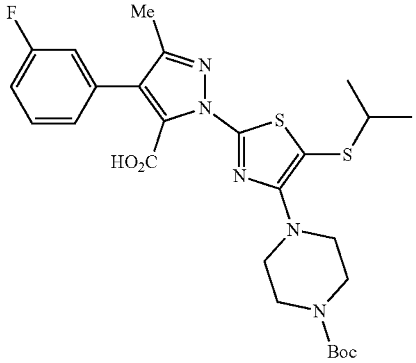 [SMILES: Cc1nn(-c2nc(N3CCN(C(=O)OC(C)(C)C)CC3)c(SC(C)C)s2)c(C(=O)O)c1-c1cccc(F)c1] | 1-(4-(4-(tert-butoxycarbonyl)piperazin-1-yl)-5-(isopropylthio)thiazol-2-yl)-4-(3-fluorophenyl)-3-methyl-1H-pyrazole-5-carboxylic acid | K |

-continued

| Cpd | Structure | Name | BJAB |
|---|---|---|---|
| 34 | 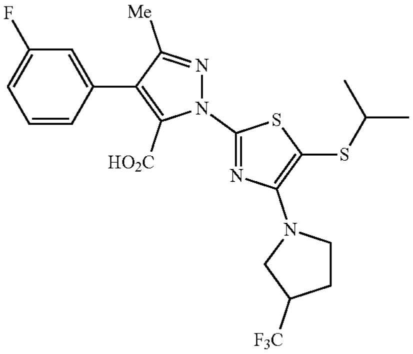 [SMILES: Cc1nn(-c2nc(N3CCC(C(F)(F)F)C3)c(SC(C)C)s2)c(C(=O)O)c1-c1cccc(F)c1] | 4-(3-fluorophenyl)-1-(5-(isopropylthio)-4-(3-(trifluoromethyl)pyrrolidin-1-yl)thiazol-2-yl)-3-methyl-1H-pyrazole-5-carboxylic acid | B |
| 35 | 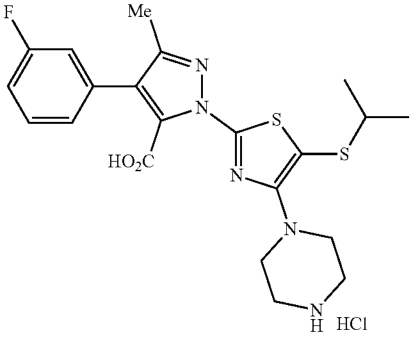 [SMILES: Cc1nn(-c2nc(N3CCNCC3)c(SC(C)C)s2)c(C(=O)O)c1-c1cccc(F)c1 ; Cl] | 4-(3-fluorophenyl)-1-(5-(isopropylthio)-4-(piperazin-1-yl)thiazol-2-yl)-3-methyl-1H-pyrazole-5-carboxylic acid hydrochloric acid salt | K |
| 36 | 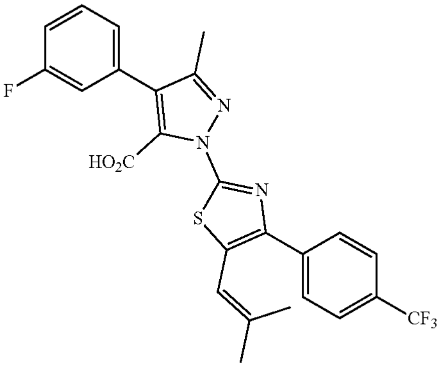 [SMILES: CC(C)=Cc1sc(-n2nc(C)c(-c3cccc(F)c3)c2C(=O)O)nc1-c1ccc(C(F)(F)F)cc1] | 4-(3-fluorophenyl)-3-methyl-1-(5-(2-methylprop-1-en-1-yl)-4-(4-(trifluoromethyl)phenyl)thiazol-2-yl)-1H-pyrazole-5-carboxylic acid | A |
| 37 | 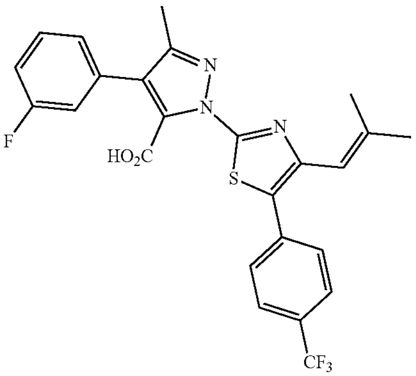 [SMILES: CC(C)=Cc1nc(-n2nc(C)c(-c3cccc(F)c3)c2C(=O)O)sc1-c1ccc(C(F)(F)F)cc1] | 4-(3-fluorophenyl)-3-methyl-1-(4-(2-methylprop-1-en-1-yl)-5-(4-(trifluoromethyl)phenyl)thiazol-2-yl)-1H-pyrazole-5-carboxylic acid | D |

-continued
| Cpd | Structure | Name | BJAB |
| --- | --- | --- | --- |
| 38 | 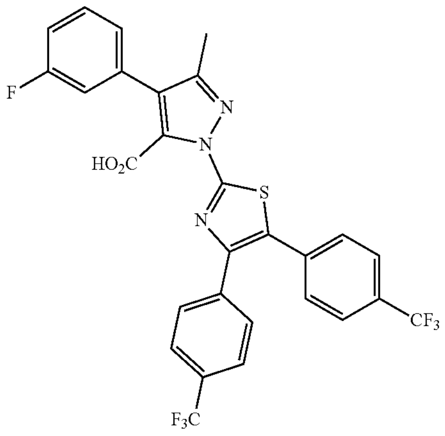 [SMILES: Cc1nn(-c2nc(-c3ccc(C(F)(F)F)cc3)c(-c3ccc(C(F)(F)F)cc3)s2)c(C(=O)O)c1-c1cccc(F)c1] | 1-(4,5-bis(4-(trifluoromethyl)phenyl)thiazol-2-yl)-4-(3-fluorophenyl)-3-methyl-1H-pyrazole-5-carboxylic acid | A |
| 39 | 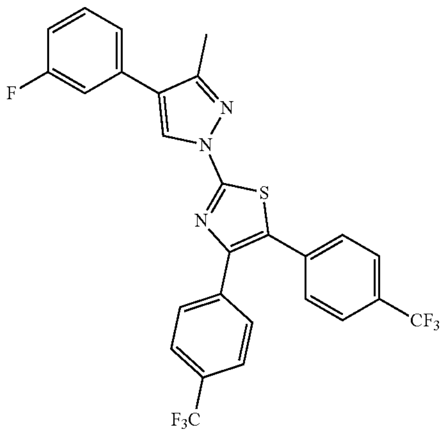 [SMILES: Cc1nn(-c2nc(-c3ccc(C(F)(F)F)cc3)c(-c3ccc(C(F)(F)F)cc3)s2)cc1-c1cccc(F)c1] | 2-(4-(3-fluorophenyl)-3-methyl-1H-pyrazol-1-yl)-4,5-bis(4-(trifluoromethyl)phenyl)thiazole | K |
| 40 | 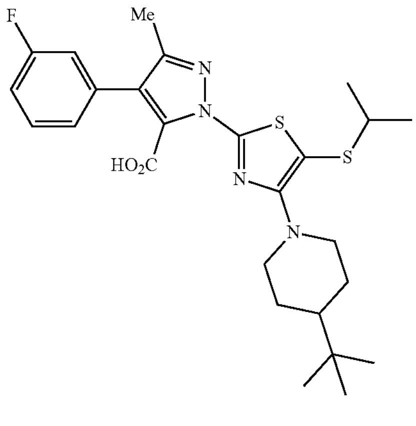 [SMILES: Cc1nn(-c2nc(N3CCC(C(C)(C)C)CC3)c(SC(C)C)s2)c(C(=O)O)c1-c1cccc(F)c1] | 1-(4-(4-(tert-butyl)piperidin-1-yl)-5-(isopropylthio)thiazol-2-yl)-4-(3-fluorophenyl)-3-methyl-1H-pyrazole-5-carboxylic acid | A |

-continued

| Cpd | Structure | Name | BJAB |
|---|---|---|---|
| 41 | 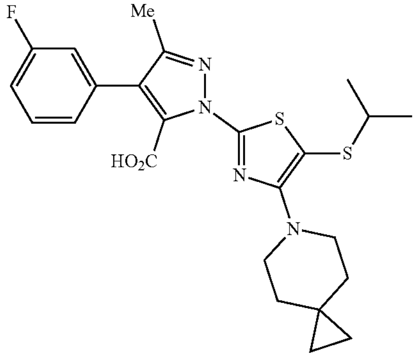 [SMILES: Cc1nn(-c2nc(N3CCC4(CC3)CC4)c(SC(C)C)s2)c(C(=O)O)c1-c1cccc(F)c1] | 4-(3-fluorophenyl)-1-(5-(isopropylthio)-4-(6-azaspiro[2.5]octan-6-yl)thiazol-2-yl)-3-methyl-1H-pyrazole-5-carboxylic acid | B |
| 42 | 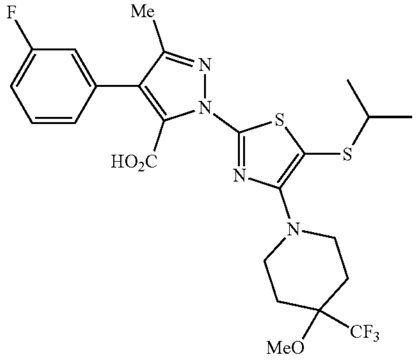 [SMILES: COC1(C(F)(F)F)CCN(c2nc(-n3nc(C)c(-c4cccc(F)c4)c3C(=O)O)sc2SC(C)C)CC1] | 4-(3-fluorophenyl)-1-(5-(isopropylthio)-4-(4-methoxy-4-(trifluoromethyl)piperidin-1-yl)thiazol-2-yl)-3-methyl-1H-pyrazole-5-carboxylic acid | A |
| 43 | 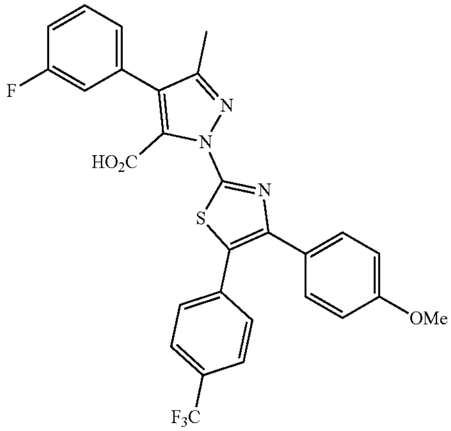 [SMILES: COc1ccc(-c2nc(-n3nc(C)c(-c4cccc(F)c4)c3C(=O)O)sc2-c2ccc(C(F)(F)F)cc2)cc1] | 4-(3-fluorophenyl)-1-(4-(4-methoxyphenyl)-5-(4-(trifluoromethyl)phenyl)thiazol-2-yl)-3-methyl-1H-pyrazole-5-carboxylic acid | B |
| 44 | 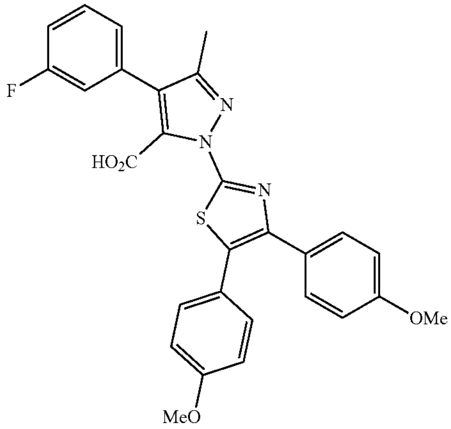 [SMILES: COc1ccc(-c2nc(-n3nc(C)c(-c4cccc(F)c4)c3C(=O)O)sc2-c2ccc(OC)cc2)cc1] | 1-(4,5-bis(4-methoxyphenyl)thiazol-2-yl)-4-(3-fluorophenyl)-3-methyl-1H-pyrazole-5-carboxylic acid | D |

-continued
| Cpd | Structure | Name | BJAB |
|---|---|---|---|
| 45 | 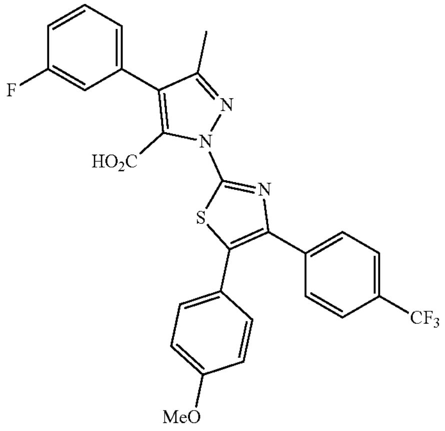 [SMILES: COc1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-methoxyphenyl)-4-(4-(trifluoromethyl)phenyl)thiazol-2-yl)-3-methyl-1H-pyrazole-5-carboxylic acid | A |
| 46 | 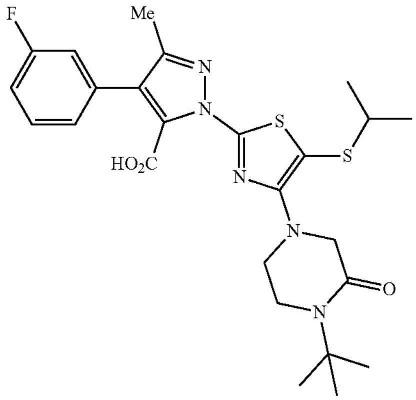 [SMILES: Cc1nn(-c2nc(N3CCN(C(C)(C)C)C(=O)C3)c(SC(C)C)s2)c(C(=O)O)c1-c1cccc(F)c1] | 1-(4-(4-(tert-butyl)-3-oxopiperazin-1-yl)-5-(isopropylthio)thiazol-2-yl)-4-(3-fluorophenyl)-3-methyl-1H-pyrazole-5-carboxylic acid | K |
| 47 | 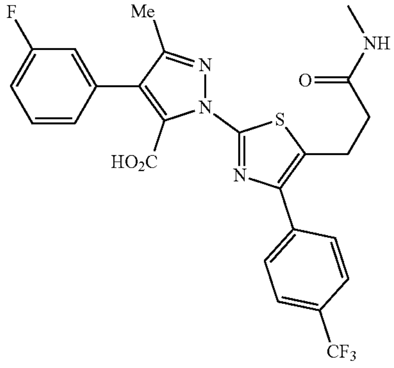 [SMILES: CNC(=O)CCc1sc(-n2nc(C)c(-c3cccc(F)c3)c2C(=O)O)nc1-c1ccc(C(F)(F)F)cc1] | 4-(3-fluorophenyl)-3-methyl-1-(5-(3-(methylamino)-3-oxopropyl)-4-(4-(trifluoromethyl)phenyl)thiazol-2-yl)-1H-pyrazole-5-carboxylic acid | K |

-continued

| Cpd | Structure | Name | BJAB |
|---|---|---|---|
| 48 | 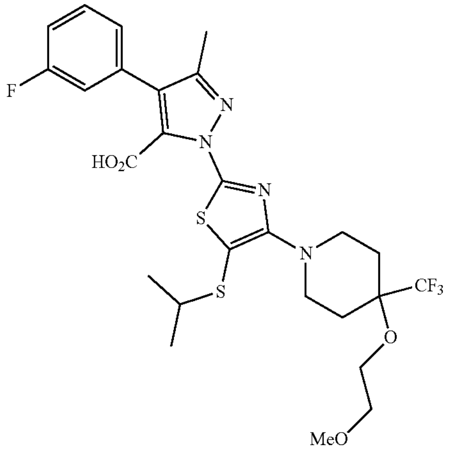 [SMILES: COCCOC1(C(F)(F)F)CCN(c2nc(-n3nc(C)c(-c4cccc(F)c4)c3C(=O)O)sc2SC(C)C)CC1] | 4-(3-fluorophenyl)-1-(5-(isopropylthio)-4-(4-(2-methoxyethoxy)-4-(trifluoromethyl)piperidin-1-yl)thiazol-2-yl)-3-methyl-1H-pyrazole-5-carboxylic acid | B |
| 49 | 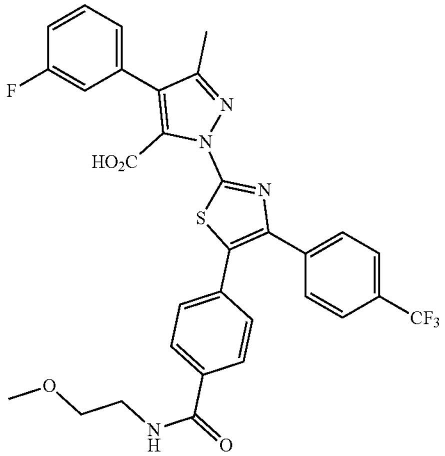 [SMILES: COCCNC(=O)c1ccc(-c2sc(-n3nc(C)c(-c4cccc(F)c4)c3C(=O)O)nc2-c2ccc(C(F)(F)F)cc2)cc1] | 4-(3-fluorophenyl)- 1-(5-(4-((2-methoxyethyl)carbamoyl)phenyl)-4-(4-(trifluoromethyl)phenyl)thiazol-2-yl)-3-methyl-1H-pyrazole-5-carboxylic acid | K |
| 50 | 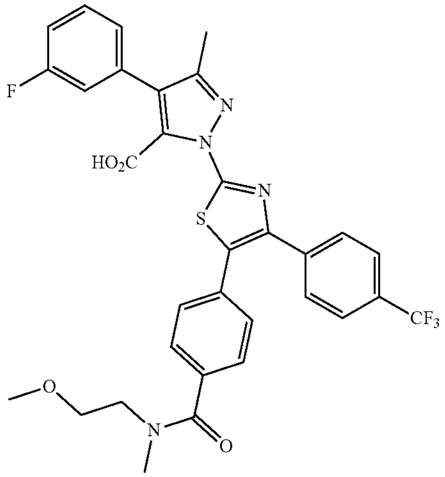 [SMILES: COCCN(C)C(=O)c1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-((2-methoxyethyl)(methyl)carbamoyl)phenyl)-4-(4-(trifluoromethyl)phenyl)thiazol-2-yl)-3-methyl-1H-pyrazole-5-carboxylic acid | K |

-continued

| Cpd | Structure | Name | BJAB |
|---|---|---|---|
| 51 | 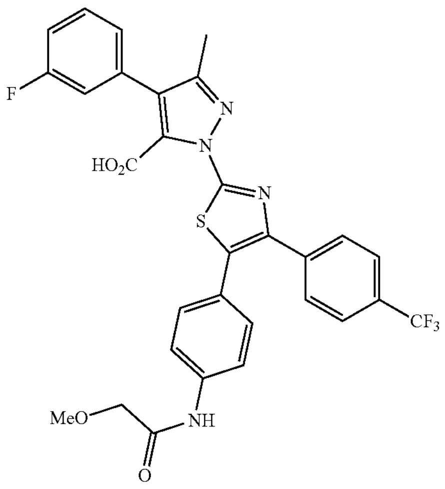 [SMILES: COCC(=O)Nc1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-(2-methoxyacetamido)phenyl)-4-(4-(trifluoromethyl)phenyl)thiazol-2-yl)-3-methyl-1H-pyrazole-5-carboxylic acid | D |
| 52 | 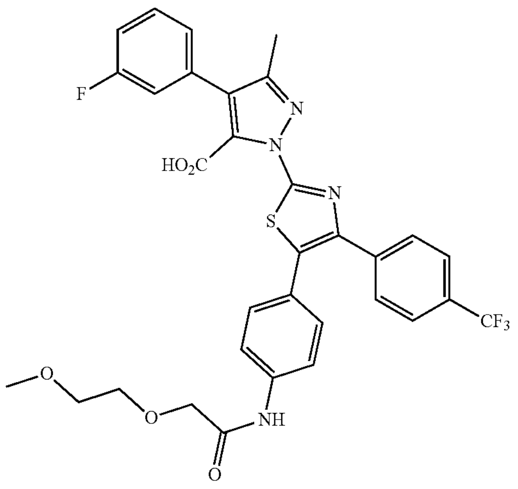 [SMILES: COCCOCC(=O)Nc1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-(2-(2-methoxyethoxy)acetamido)phenyl)-4-(4-(trifluoromethyl)phenyl)thiazol-2-yl)-3-methyl-1H-pyrazole-5-carboxylic acid | D |
| 53 | 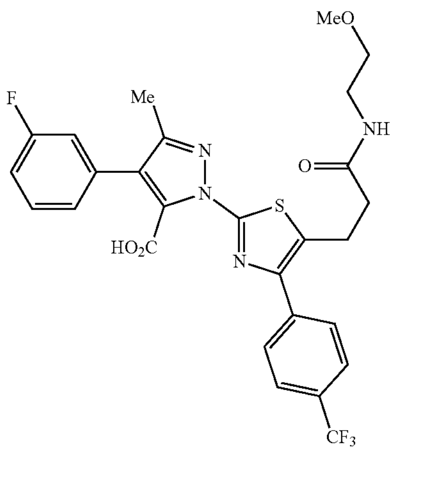 [SMILES: COCCNC(=O)CCc1sc(-n2nc(C)c(-c3cccc(F)c3)c2C(=O)O)nc1-c1ccc(C(F)(F)F)cc1] | 4-(3-fluorophenyl)-1-(5-(3-((2-methoxyethyl)amino)-3-oxopropyl)-4-(4-(trifluoromethyl)phenyl)thiazol-2-yl)-3-methyl-1H-pyrazole-5-carboxylic acid | K |

-continued

| Cpd | Structure | Name | BJAB |
|---|---|---|---|
| 54 | 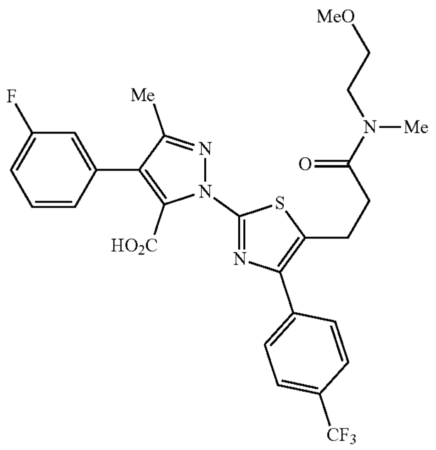 [SMILES: COCCN(C)C(=O)CCc1sc(-n2nc(C)c(-c3cccc(F)c3)c2C(=O)O)nc1-c1ccc(C(F)(F)F)cc1] | 4-(3-fluorophenyl)-1-(5-(3-((2-methoxyethyl)(methyl)amino)-3-oxopropyl)-4-(4-(trifluoromethyl)phenyl)thiazol-2-yl)-3-methyl-1H-pyrazole-5-carboxylic acid | K |
| 55 | 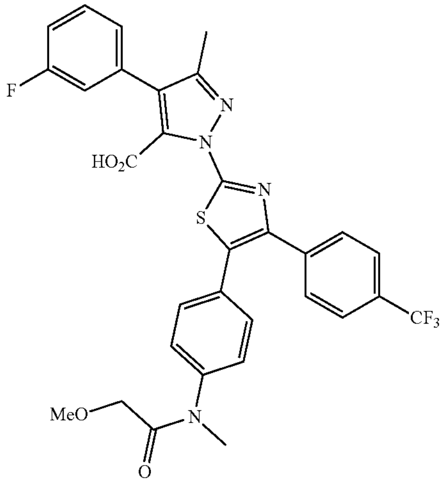 [SMILES: COCC(=O)N(C)c1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-(2-methoxy-N-methylacetamido)phenyl)-4-(4-(trifluoromethyl)phenyl)thiazol-2-yl)-3-methyl-1H-pyrazole-5-carboxylic acid | K |
| 56 | 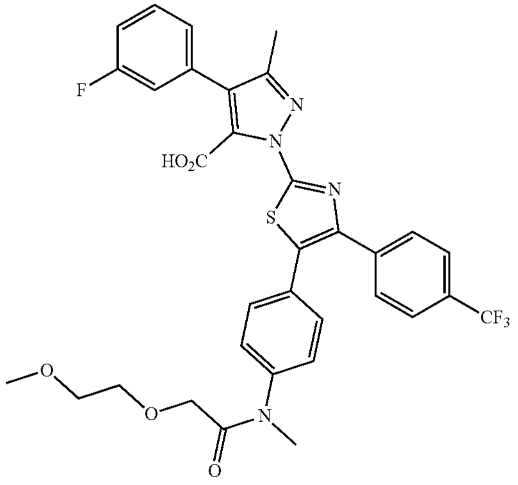 [SMILES: COCCOCC(=O)N(C)c1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-(2-(2-methoxyethoxy)-N-methylacetamido)phenyl)-4-(4-(trifluoromethyl)phenyl)thiazol-2-yl)-3-methyl-1H-pyrazole-5-carboxylic acid | K |

-continued

| Cpd | Structure | Name | BJAB |
| --- | --- | --- | --- |
| 57 | 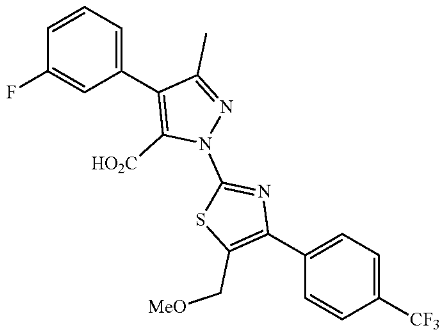 [SMILES: COCc1sc(-n2nc(C)c(-c3cccc(F)c3)c2C(=O)O)nc1-c1ccc(C(F)(F)F)cc1] | 4-(3-fluorophenyl)-1-(5-(methoxymethyl)-4-(4-(trifluoromethyl)phenyl)thiazol-2-yl)-3-methyl-1H-pyrazole-5-carboxylic acid | C |
| 58 | 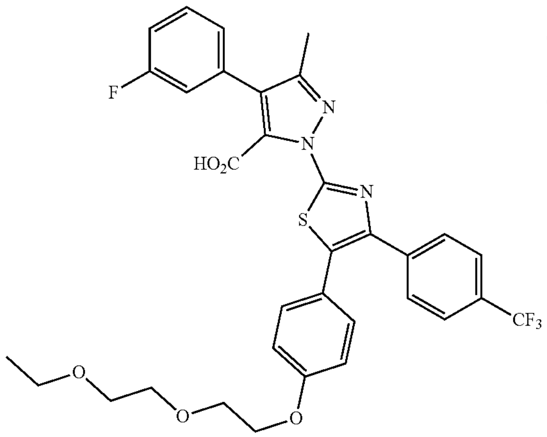 [SMILES: CCOCCOCCOc1ccc(-c2sc(-n3nc(C)c(-c4cccc(F)c4)c3C(=O)O)nc2-c2ccc(C(F)(F)F)cc2)cc1] | 1-(5-(4-(2-(2-ethoxyethoxy)ethoxy)phenyl)-4-(4-(trifluoromethyl)phenyl)thiazol-2-yl)-4-(3-fluorophenyl)-3-methyl-1H-pyrazole-5-carboxylic acid | B |
| 59 | 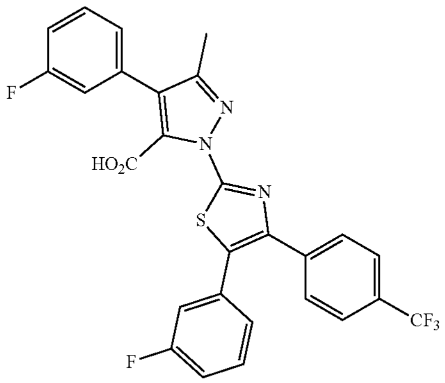 [SMILES: Cc1nn(-c2nc(-c3ccc(C(F)(F)F)cc3)c(-c3cccc(F)c3)s2)c(C(=O)O)c1-c1cccc(F)c1] | 4-(3-fluorophenyl)-1-(5-(3-fluorophenyl)-4-(4-(trifluoromethyl)phenyl)thiazol-2-yl)-3-methyl-1H-pyrazole-5-carboxylic acid | A |
| 60 | 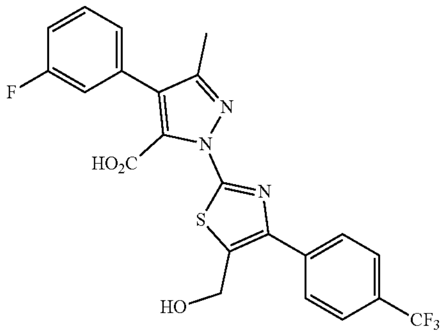 [SMILES: Cc1nn(-c2nc(-c3ccc(C(F)(F)F)cc3)c(CO)s2)c(C(=O)O)c1-c1cccc(F)c1] | 4-(3-fluorophenyl)-1-(5-(hydroxymethyl)-4-(4-(trifluoromethyl)phenyl)thiazol-2-yl)-3-methyl-1H-pyrazole-5-carboxylic acid | K |

-continued

| Cpd | Structure | Name | BJAB |
|---|---|---|---|
| 61 | 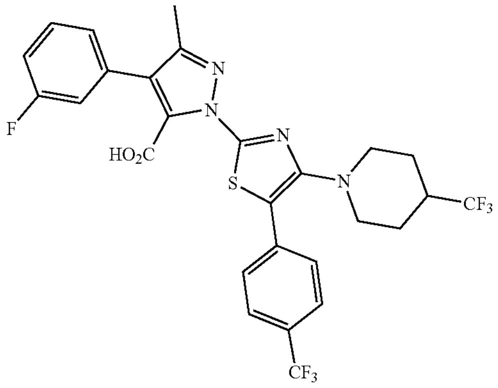 [SMILES: Cc1nn(-c2nc(N3CCC(C(F)(F)F)CC3)c(-c3ccc(C(F)(F)F)cc3)s2)c(C(=O)O)c1-c1cccc(F)c1] | 4-(3-fluorophenyl)-3-methyl-1-(5-(4-(trifluoromethyl)phenyl)-4-(4-(trifluoromethyl)piperidin-1-yl)thiazol-2-yl)-1H-pyrazole-5-carboxylic acid | A |
| 62 | 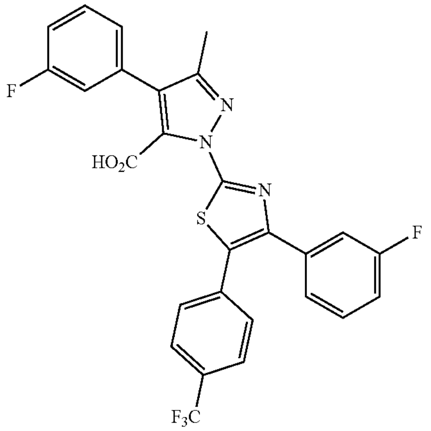 [SMILES: Cc1nn(-c2nc(-c3cccc(F)c3)c(-c3ccc(C(F)(F)F)cc3)s2)c(C(=O)O)c1-c1cccc(F)c1] | 4-(3-fluorophenyl)-1-(4-(3-fluorophenyl)-5-(4-(trifluoromethyl)phenyl)thiazol-2-yl)-3-methyl-1H-pyrazole-5-carboxylic acid | C |
| 63 | 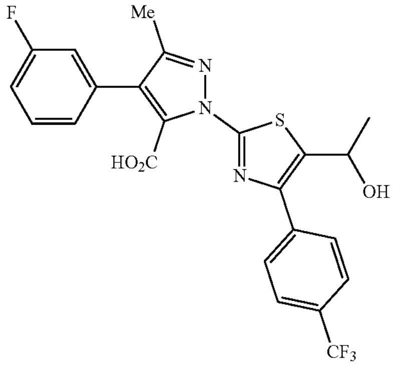 [SMILES: Cc1nn(-c2nc(-c3ccc(C(F)(F)F)cc3)c(C(C)O)s2)c(C(=O)O)c1-c1cccc(F)c1] | 4-(3-fluorophenyl)-1-(5-(1-hydroxyethyl)-4-(4-(trifluoromethyl)phenyl)thiazol-2-yl)-3-methyl-1H-pyrazole-5-carboxylic acid | K |
| 64 | 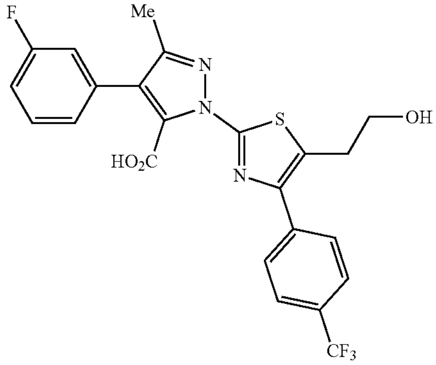 [SMILES: Cc1nn(-c2nc(-c3ccc(C(F)(F)F)cc3)c(CCO)s2)c(C(=O)O)c1-c1cccc(F)c1] | 4-(3-fluorophenyl)-1-(5-(2-hydroxyethyl)-4-(4-(trifluoromethyl)phenyl)thiazol-2-yl)-3-methyl-1H-pyrazole-5-carboxylic acid | K |

-continued

| Cpd | Structure | Name | BJAB |
|---|---|---|---|
| 65 | 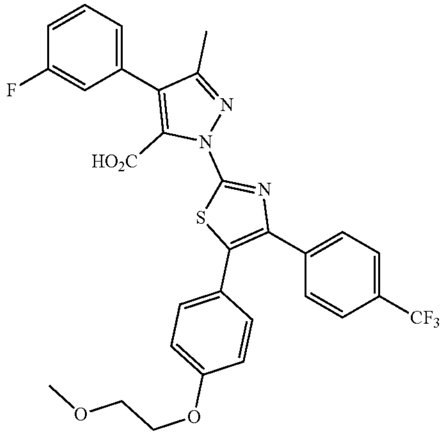 [SMILES: COCCOc1ccc(-c2sc(-n3nc(C)c(-c4cccc(F)c4)c3C(=O)O)nc2-c2ccc(C(F)(F)F)cc2)cc1] | 4-(3-fluorophenyl)-1-(5-(4-(2-methoxyethoxy)phenyl)-4-(4-(trifluoromethyl)phenyl)thiazol-2-yl)-3-methyl-1H-pyrazole-5-carboxylic acid | B |
| 66 | 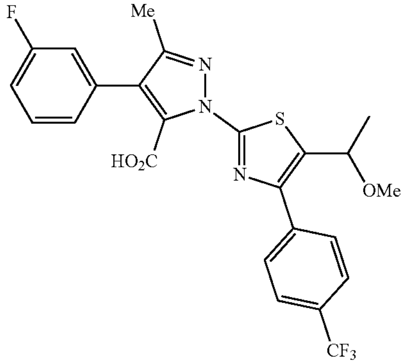 [SMILES: COC(C)c1sc(-n2nc(C)c(-c3cccc(F)c3)c2C(=O)O)nc1-c1ccc(C(F)(F)F)cc1] | 4-(3-fluorophenyl)-1-(5-(1-methoxyethyl)-4-(4-(trifluoromethyl)phenyl)thiazol-2-yl)-3-methyl-1H-pyrazole-5-carboxylic acid | C |
| 67 | 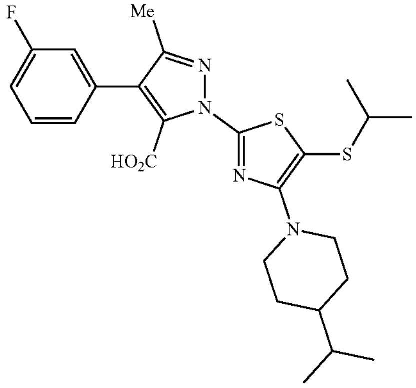 [SMILES: Cc1nn(-c2nc(N3CCC(C(C)C)CC3)c(SC(C)C)s2)c(C(=O)O)c1-c1cccc(F)c1] | 4-(3-fluorophenyl)-1-(4-(4-isopropylpiperidin-1-yl)-5-(isopropylthio)thiazol-2-yl)-3-methyl-1H-pyrazole-5-carboxylic acid | B |
| 68 | 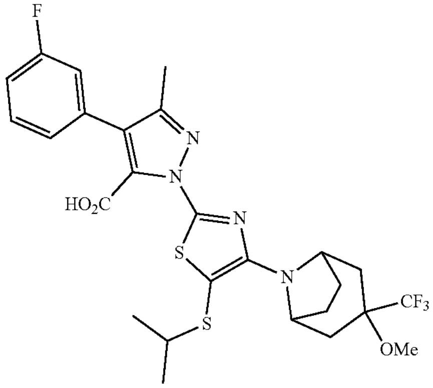 [SMILES: COC1(C(F)(F)F)CC2CCC(C1)N2c1nc(-n2nc(C)c(-c3cccc(F)c3)c2C(=O)O)sc1SC(C)C] | 4-(3-fluorophenyl)-1-(5-(isopropylthio)-4-(3-methoxy-3-(trifluoromethyl)-8-azabicyclo[3.2.1]octan-8-yl)thiazol-2-yl)-3-methyl-1H-pyrazole-5-carboxylic acid | — |

The compounds described herein may in certain embodiments contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral hPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E- configurations. Likewise, all tautomeric forms are also intended to be included.

In certain embodiments of the methods, compounds and uses as otherwise described herein, the compound is not one of compounds listed below:

methyl 1-(4-(3,4-dichlorophenyl)thiazol-2-yl)-3-methyl-4-(2-nitrobenzyl)-1H-pyrazole-5-carboxylate;

1-(4-(3,4-dichlorophenyl)thiazol-2-yl)-3-methyl-4-(2-nitrobenzyl)-1H-pyrazole-5-carboxylic acid;

methyl 1-(4-(3,4-dichlorophenyl)-5-(ethylthio)thiazol-2-yl)-3-methyl-4-(2-nitrobenzyl)-1H-pyrazole-5-carboxylate;

1-(4-(3,4-dichlorophenyl)-5-(ethylthio)thiazol-2-yl)-3-methyl-4-(2-nitrobenzyl)-1H-pyrazole-5-carboxylic acid;

methyl 1-(4-(3,4-dichlorophenyl)-5-(isopropylthio)thiazol-2-yl)-3-methyl-4-(2-nitrobenzyl)-1H-pyrazole-5-carboxylate;

1-(4-(3,4-dichlorophenyl)-5-(isopropylthio)thiazol-2-yl)-3-methyl-4-(2-nitrobenzyl)-1H-pyrazole-5-carboxylic acid;

methyl 1-(4-(3,4-dichlorophenyl)thiazol-2-yl)-3-methyl-4-(2-(methylsulfonamido)benzyl)-1H-pyrazole-5-carboxylate;

1-(4-(3,4-dichlorophenyl)thiazol-2-yl)-3-methyl-4-(2-(methylsulfonamido)benzyl)-1H-pyrazole-5-carboxylic acid;

methyl 1-(4-(3,4-dichlorophenyl)-5-(propylthio)thiazol-2-yl)-3-methyl-4-(2-nitrobenzyl)-1H-pyrazole-5-carboxylate;

1-(4-(3,4-dichlorophenyl)-5-(propylthio)thiazol-2-yl)-3-methyl-4-(2-nitrobenzyl)-1H-pyrazole-5-carboxylic acid;

methyl 1-(5-(butylthio)-4-(3,4-dichlorophenyl)thiazol-2-yl)-3-methyl-4-(2-nitrobenzyl)-1H-pyrazole-5-carboxylate;

1-(5-(butylthio)-4-(3,4-dichlorophenyl)thiazol-2-yl)-3-methyl-4-(2-nitrobenzyl)-1H-pyrazole-5-carboxylic acid;

1-(4-(3,4-dichlorophenyl)-5-(propylthio)thiazol-2-yl)-3-methyl-4-(2-(methylsulfonamido)benzyl)-1H-pyrazole-5-carboxylic acid;

N-(2-((5-(4-(aminomethyl)piperidine-1-carbonyl)-1-(4-(3,4-dichlorophenyl)-5-(propylthio)thiazol-2-yl)-3-methyl-1H-pyrazol-4-yl)methyl)phenyl)methanesulfonamide;

4-bromo-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(imidazo[1,2-a]pyridin-6-yl)-3-methyl-1H-pyrazole-5-carboxylic acid;

1-(4-(3,4-dichlorophenyl)-5-(isopropylthio)thiazol-2-yl)-3-methyl-4-phenyl-1H-pyrazole-5-carboxylic acid;

1-(5-(cyclohexylthio)-4-(3,4-dichlorophenyl)thiazol-2-yl)-3-methyl-4-(2-nitrobenzyl)-1H-pyrazole-5-carboxylic acid;

4-(benzofuran-2-yl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(2-fluoropyridin-4-yl)-3-methyl-1H-pyrazole-5-carboxylic acid;

2-(4-(3,4-dichlorophenyl)-5-(isopropylthio)thiazol-2-yl)-2',5,5'-trimethyl-4,4'-bi(2H-pyrazole)-3-carboxylic acid;

1-(4-(3,4-dichlorophenyl)-5-(isopropylthio)thiazol-2-yl)-4-(2,6-dimethylpyridin-4-yl)-3-methyl-1H-pyrazole-5-carboxylic acid;

1-(4-(3,4-dichlorophenyl)-5-(isopropylthio)thiazol-2-yl)-4-(3,5-difluorophenyl)-3-methyl-1H-pyrazole-5-carboxylic acid;

1-(4-(5-chloro-2-fluorophenyl)-5-(isopropylthio)thiazol-2-yl)-4-(3,5-dichlorophenyl)-3-methyl-1H-pyrazole-5-carboxylic acid;

1-(4-(5-chloro-2-fluorophenyl)-5-(isopropylthio)thiazol-2-yl)-4-(2,6-dimethylpyridin-4-yl)-3-methyl-1H-pyrazole-5-carboxylic acid;

4-(3,5-dichlorophenyl)-1-(4-(3,5-dimethylisoxazol-4-yl)-5-(isopropylthio)thiazol-2-yl)-3-methyl-1H-pyrazole-5-carboxylic acid;

4-(3,5-dichlorophenyl)-1-(5-(isopropylthio)-4-(1-methyl-1H-pyrazol-4-yl)thiazol-2-yl)-3-methyl-1H-pyrazole-5-carboxylic acid;

4-(3,5-dichlorophenyl)-1-(5-(isopropylthio)-4-(pyridin-4-yl)thiazol-2-yl)-3-methyl-1H-pyrazole-5-carboxylic acid;

4-(3,5-dichlorophenyl)-1-(5-(isopropylthio)-4-(pyridin-3-yl)thiazol-2-yl)-3-methyl-1H-pyrazole-5-carboxylic acid;

4-(3,5-dichlorophenyl)-1-(4-(imidazo[1,2-a]pyridin-6-yl)-5-(isopropylthio)thiazol-2-yl)-3-methyl-1H-pyrazole-5-carboxylic acid;

methyl 1-(5-(sec-butylthio)-4-(3,4-dichlorophenyl)thiazol-2-yl)-4-(3,5-dichlorophenyl)-3-methyl-1H-pyrazole-5-carboxylate;

1-(5-(sec-butylthio)-4-(3,4-dichlorophenyl)thiazol-2-yl)-4-(3,5-dichlorophenyl)-3-methyl-1H-pyrazole-5-carboxylic acid;

methyl 1-(5-(sec-butylthio)-4-(3,4-dichlorophenyl)thiazol-2-yl)-4-(2,6-dimethylpyridin-4-yl)-3-methyl-1H-pyrazole-5-carboxylate;

1-(5-(sec-butylthio)-4-(3,4-dichlorophenyl)thiazol-2-yl)-4-(2,6-dimethylpyridin-4-yl)-3-methyl-1H-pyrazole-5-carboxylic acid;

4-(2,6-dimethylpyridin-4-yl)-1-(5-(isopropylthio)-4-(2-methoxyphenyl)thiazol-2-yl)-3-methyl-1H-pyrazole-5-carboxylic acid;

4-(2,6-dimethylpyridin-4-yl)-1-(5-(isopropylthio)-4-(3-methoxyphenyl)thiazol-2-yl)-3-methyl-1H-pyrazole-5-carboxylic acid;

4-(2,6-dimethylpyridin-4-yl)-1-(5-(isopropylthio)-4-(4-methoxyphenyl)thiazol-2-yl)-3-methyl-1H-pyrazole-5-carboxylic acid;

4-(2,6-dimethylpyridin-4-yl)-1-(5-(isopropylthio)-4-phenylthiazol-2-yl)-3-methyl-1H-pyrazole-5-carboxylic acid;

1-(4-(3,4-dichlorophenyl)-5-(isopropylthio)thiazol-2-yl)-4-(3-(hydroxymethyl)-5-methylisoxazol-4-yl)-3-methyl-1H-pyrazole-5-carboxylic acid;

1-(4-(3,4-dichlorophenyl)-5-(isopropylthio)thiazol-2-yl)-4-(3-(methoxymethyl)-5-methylisoxazol-4-yl)-3-methyl-1H-pyrazole-5-carboxylic acid;

4-(2,6-dimethylpyridin-4-yl)-1-(5-(isopropylthio)-4-p-tolylthiazol-2-yl)-3-methyl-1H-pyrazole-5-carboxylic acid;

4-(2,6-dimethylpyridin-4-yl)-1-(5-(isopropylthio)-4-m-tolylthiazol-2-yl)-3-methyl-1H-pyrazole-5-carboxylic acid;

4-(2,6-dimethylpyridin-4-yl)-1-(5-(isopropylthio)-4-o-tolylthiazol-2-yl)-3-methyl-1H-pyrazole-5-carboxylic acid;

4-(2,6-dimethylpyridin-4-yl)-1-(5-(isopropylthio)-4-(phenylethynyl)thiazol-2-yl)-3-methyl-1H-pyrazole-5-carboxylic acid;

1-(4-(3,4-dichlorophenyl)-5-(isopropylthio)thiazol-2-yl)-3-methyl-4-(pyridin-3-yl)-1H-pyrazole-5-carboxylic acid;

1-(4-(3,4-dichlorophenyl)-5-(methylthio)thiazol-2-yl)-3-methyl-4-(2-nitrobenzyl)-1H-pyrazole-5-carboxylic acid;

1-(4-(3,4-dichlorophenyl)-5-(isopropylthio)thiazol-2-yl)-4-(3-(hydroxymethyl)phenyl)-3-methyl-1H-pyrazole-5-carboxylic acid;

1-(4-(3,4-dichlorophenyl)-5-(isopropylthio)thiazol-2-yl)-3-methyl-4-(pyridin-4-yl)-1H-pyrazole-5-carboxylic acid;

4-(3-(aminomethyl)phenyl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(4-(hydroxymethyl)phenyl)-3-methyl-1H-pyrazole-5-carboxylic acid;

1-(4-(3,4-dichlorophenyl)-5-(isopropylthio)thiazol-2-yl)-3-methyl-4-(2-(trifluoromethyl)phenyl)-1H-pyrazole-5-carboxylic acid;

1-(4-(3,4-dichlorophenyl)-5-(isopropylthio)thiazol-2-yl)-3-methyl-4-(3-(trifluoromethyl)phenyl)-1H-pyrazole-5-carboxylic acid;

1-(4-(3,4-dichlorophenyl)-5-(isopropylthio)thiazol-2-yl)-3-methyl-4-(4-(trifluoromethyl)phenyl)-1H-pyrazole-5-carboxylic acid;

1-(4-(3,4-dichlorophenyl)-5-(isopropylthio)thiazol-2-yl)-4-(hydroxy(phenyl)methyl)-3-methyl-1H-pyrazole-5-carboxylic acid;

1-(4-(3,4-dichlorophenyl)-5-(isopropylsulfinyl)thiazol-2-yl)-3-methyl-4-(2-nitrobenzyl)-1H-pyrazole-5-carboxylic acid;

1-(4-(3,4-dichlorophenyl)-5-(isopropylsulfonyl)thiazol-2-yl)-3-methyl-4-(2-nitrobenzyl)-1H-pyrazole-5-carboxylic acid;

4-([1,2,4]triazolo[4,3-a]pyridin-3-yl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(3,5-dimethylisoxazol-4-yl)-3-methyl-1H-pyrazole-5-carboxylic acid;

4-(1H-benzo[d]imidazol-2-yl)-1-(4-(3,4-dichlorophenyl)-5-(isopropylthio)thiazol-2-yl)-3-methyl-1H-pyrazole-5-carboxylic acid;

4-(3-chloro-2-methylphenyl)-1-(4-(3,4-dichlorophenyl)-5-(isopropylthio)thiazol-2-yl)-3-methyl-1H-pyrazole-5-carboxylic acid;

4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(3-isopropylphenyl)-3-methyl-1H-pyrazole-5-carboxylic acid;

1-(4-(3,4-dichlorophenyl)-5-(isopropylthio)thiazol-2-yl)-4-(2-methoxy-5-methylphenyl)-3-methyl-1H-pyrazole-5-carboxylic acid;

1-(4-(3,4-dichlorophenyl)-5-(isopropylthio)thiazol-2-yl)-4-(1H-imidazol-2-yl)-3-methyl-1H-pyrazole-5-carboxylic acid;

1-(4-(3,4-dichlorophenyl)-5-(isopropylthio)thiazol-2-yl)-3-methyl-4-(pyrazolo[1,5-a]pyridin-3-yl)-1H-pyrazole-5-carboxylic acid;

1-(4-(3,4-dichlorophenyl)-5-(isopropylthio)thiazol-2-yl)-3-methyl-4-(pyrazolo[1,5-a]pyrimidin-3-yl)-1H-pyrazole-5-carboxylic acid;

2-(4-(3,4-dichlorophenyl)-5-(isopropylthio)thiazol-2-yl)-2',5-dimethyl-4,4'-bi(2H-pyrazole)-3-carboxylic acid;

2-(4-(3,4-dichlorophenyl)-5-(isopropylsulfonyl)thiazol-2-yl)-2',5-dimethyl-4,4'-bi(2H-pyrazole)-3-carboxylic acid;

1-(4-(3,4-dichlorophenyl)-5-(isopropylthio)thiazol-2-yl)-3-methyl-4-(1-methyl-1H-benzo[d]imidazol-2-yl)-1H-pyrazole-5-carboxylic acid;

4-(5-cyanopyridin-3-yl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(2-ethoxypyridin-3-yl)-3-methyl-1H-pyrazole-5-carboxylic acid;

2'-(4-(3,4-dichlorophenyl)-5-(isopropylthio)thiazol-2-yl)-2,5,5'-trimethyl-3,4'-bi(2H-pyrazole)-3'-carboxylic acid;

1-(4-(3,4-dichlorophenyl)-5-(isopropylthio)thiazol-2-yl)-3-methyl-4-(pyrimidin-5-yl)-1H-pyrazole-5-carboxylic acid;

4-(3,5-bis(trifluoromethyl)phenyl)-1-(4-(3,4-dichlorophenyl)-5-(isopropylthio)thiazol-2-yl)-3-methyl-1H-pyrazole-5-carboxamide;

1-(4-(3,4-dichlorophenyl)-5-(isopropylthio)thiazol-2-yl)-4-(4,6-dimethylpyrimidin-2-yl)-3-methyl-1H-pyrazole-5-carboxylic acid;

4-(3,5-bis(trifluoromethyl)phenyl)-1-(4-(3,4-dichlorophenyl)-5-(isopropylthio)thiazol-2-yl)-3-methyl-N-(pyridin-2-ylmethyl)-1H-pyrazole-5-carboxamide;

4-(3,5-bis(trifluoromethyl)phenyl)-1-(4-(3,4-dichlorophenyl)-5-(isopropylthio)thiazol-2-yl)-N-(2-hydroxyethyl)-N,3-dimethyl-1H-pyrazole-5-carboxamide;

4-(3,5-bis(trifluoromethyl)phenyl)-1-(4-(3,4-dichlorophenyl)-5-(isopropylthio)thiazol-2-yl)-N,3-dimethyl-N-(5-(trifluoromethyl)-1,3,4-thiadiazol-2-yl)-1H-pyrazole-5-carboxamide;

(4-(3,5-bis(trifluoromethyl)phenyl)-1-(4-(3,4-dichlorophenyl)-5-(isopropylthio)thiazol-2-yl)-3-methyl-1H-pyrazol-5-yl)(3-(diethylamino)pyrrolidin-1-yl)methanone;

1-(4-(3,4-dichlorophenyl)-5-(isopropylthio)thiazol-2-yl)-3-methyl-4-(pyrazin-2-yl)-1H-pyrazole-5-carboxylic acid;

4-(3-cyano-5-methylphenyl)-1-(4-(3,4-dichlorophenyl)-5-(isopropylthio)thiazol-2-yl)-3-methyl-1H-pyrazole-5-carboxylic acid;

4-(3,5-bis(trifluoromethyl)phenyl)-1-(4-(3,4-dichlorophenyl)-5-(isopropylthio)thiazol-2-yl)-3-methyl-N-(1H-tetrazol-5-yl)-1H-pyrazole-5-carboxamide;

1-(4-(3,4-dichlorophenyl)-5-(isopropylthio)thiazol-2-yl)-3-methyl-4-(5-methyl-1,3,4-thiadiazol-2-yl)-1H-pyrazole-5-carboxylic acid;

4-(3-cyano-5-methoxyphenyl)-1-(4-(3,4-dichlorophenyl)-5-(isopropylthio)thiazol-2-yl)-3-methyl-1H-pyrazole-5-carboxylic acid;

4-(3-cyano-5-(trifluoromethyl)phenyl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(3-(methoxymethyl)phenyl)-3-methyl-1H-pyrazole-5-carboxylic acid;

4-(3-benzyl-5-methylisoxazol-4-yl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(3-((dimethylamino)methyl)phenyl)-3-methyl-1H-pyrazole-5-carboxylic acid;

(1-(4-(3,4-dichlorophenyl)-5-(isopropylthio)thiazol-2-yl)-3-methyl-4-phenyl-1H-pyrazol-5-yl)MeOH;

4-(benzo[d][1,3]dioxol-5-yl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(4-methoxypyrimidin-2-yl)-3-methyl-1H-pyrazole-5-carboxylic acid;

1-(4-(3,4-dichlorophenyl)-5-(isopropylthio)thiazol-2-yl)-4-(isothiazol-4-yl)-3-methyl-1H-pyrazole-5-carboxylic acid;

1-(4-(3,4-dichlorophenyl)-5-(isopropylthio)thiazol-2-yl)-3-methyl-4-(3-methylisothiazol-5-yl)-1H-pyrazole-5-carboxylic acid;

1-(4-(3,4-dichlorophenyl)-5-(isopropylthio)thiazol-2-yl)-3-methyl-4-(1-methyl-2-oxo-1,2-dihydropyridin-4-yl)-1H-pyrazole-5-carboxylic acid;

1-(4-(3,4-dichlorophenyl)-5-(isopropylthio)thiazol-2-yl)-4-(1,5-dimethyl-6-oxo-1,6-dihydropyridin-3-yl)-3-methyl-1H-pyrazole-5-carboxylic acid;

1-(4-(3,4-dichlorophenyl)-5-(isopropylthio)thiazol-2-yl)-4-(3-fluoro-5-methylphenyl)-3-methyl-1H-pyrazole-5-carboxylic acid;

1-(4-(3,4-dichlorophenyl)-5-(isopropylthio)thiazol-2-yl)-4-(3-hydroxy-5-methylphenyl)-3-methyl-1H-pyrazole-5-carboxylic acid;

1-(4-(3,4-dichlorophenyl)-5-(isopropylthio)thiazol-2-yl)-4-(3-isopropoxy-5-methylphenyl)-3-methyl-1H-pyrazole-5-carboxylic acid;

1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic acid;

1-(4-(3,4-dichlorophenyl)-5-(isopropylthio)thiazol-2-yl)-4-(3-(dimethylamino)-5-methylphenyl)-3-methyl-1H-pyrazole-5-carboxylic acid;

4-(3-(1H-imidazol-1-yl)-5-methylphenyl)-1-(4-(3,4-dichlorophenyl)-5-(isopropylthio)thiazol-2-yl)-3-methyl-1H-pyrazole-5-carboxylic acid;

4-(2-(azetidin-1-yl)-6-methylpyridin-4-yl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-3-methyl-4-(2-methyl-6-morpholinopyridin-4-yl)-1H-pyrazole-5-carboxylic acid;

1-(5-(isopropylthio)-4-(3-methoxyphenyl)thiazol-2-yl)-3-methyl-4-(2-nitrobenzyl)-1H-pyrazole-5-carboxylic acid;

1-(4-(3,4-dichlorophenyl)-5-(isopentylthio)thiazol-2-yl)-3-methyl-4-(2-nitrobenzyl)-1H-pyrazole-5-carboxylic acid;

1-(5-(isopropylthio)-4-(3-methoxyphenyl)thiazol-2-yl)-3-methyl-4-(2-(methylsulfonamido)benzyl)-1H-pyrazole-5-carboxylic acid;

1-(5-(sec-butylthio)-4-(3,4-dichlorophenyl)thiazol-2-yl)-3-methyl-4-(2-nitrobenzyl)-1H-pyrazole-5-carboxylic acid;

1-(4-(3,4-dichlorophenyl)-5-(isopropylthio)thiazol-2-yl)-4-(1H-indol-6-yl)-3-methyl-1H-pyrazole-5-carboxylic acid;

1-(4-(3,4-dichlorophenyl)-5-(isopropylthio)thiazol-2-yl)-3-methyl-4-(3-nitrophenyl)-1H-pyrazole-5-carboxylic acid;

2-(4-(3,4-dichlorophenyl)-5-(isopropylthio)thiazol-2-yl)-5-methyl-4,4'-bi(2H-pyrazole)-3-carboxylic acid;

1-(4-(3,4-dichlorophenyl)-5-(isopropylthio)thiazol-2-yl)-4-(1H-indol-3-yl)-3-methyl-1H-pyrazole-5-carboxylic acid;

4-(2-chlorophenyl)-1-(4-(3,4-dichlorophenyl)-5-(isopropylthio)thiazol-2-yl)-3-methyl-1H-pyrazole-5-carboxylic acid;

4-(3-chlorophenyl)-1-(4-(3,4-dichlorophenyl)-5-(isopropylthio)thiazol-2-yl)-3-methyl-1H-pyrazole-5-carboxylic acid;

4-(4-chlorophenyl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-4-(2-methoxyphenyl)-3-methyl-1H-pyrazole-5-carboxylic acid;

1-(4-(3,4-dichlorophenyl)-5-(isopropylthio)thiazol-2-yl)-4-(3-methoxyphenyl)-3-methyl-1H-pyrazole-5-carboxylic acid;

1-(4-(3,4-dichlorophenyl)-5-(isopropylthio)thiazol-2-yl)-4-(4-methoxyphenyl)-3-methyl-1H-pyrazole-5-carboxylic acid;

1-(4-(3,4-dichlorophenyl)-5-(isopropylthio)thiazol-2-yl)-3-methyl-4-o-tolyl-1H-pyrazole-5-carboxylic acid;

1-(4-(3,4-dichlorophenyl)-5-(isopropylthio)thiazol-2-yl)-3-methyl-4-m-tolyl-1H-pyrazole-5-carboxylic acid;

1-(4-(3,4-dichlorophenyl)-5-(isopropylthio)thiazol-2-yl)-3-methyl-4-p-tolyl-1H-pyrazole-5-carboxylic acid;

4-(4-acetamidophenyl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-3-methyl-4-(2-(methylsulfonamido)benzyl)-1H-pyrazole-5-carboxylic acid;

1-(4-(3,4-dichlorophenyl)-5-(isopropylthio)thiazol-2-yl)-4-(2-(N,N-dimethylsulfamoylamino)benzyl)-3-methyl-1H-pyrazole-5-carboxylic acid;

4-(4-aminophenyl)-1-(4-(3,4-dichlorophenyl)-5-(isopropylthio)thiazol-2-yl)-3-methyl-1H-pyrazole-5-carboxylic acid;

1-(4-(3,4-dichlorophenyl)-5-(isopropylthio)thiazol-2-yl)-3-methyl-4-(4-(methylsulfonamido)phenyl)-1H-pyrazole-5-carboxylic acid;

1-(4-(3,4-dichlorophenyl)-5-(isopropylthio)thiazol-2-yl)-3-methyl-4-(3-(methylsulfonamido)phenyl)-1H-pyrazole-5-carboxylic acid;

2-(4-(3,4-dichlorophenyl)-5-(isopropylthio)thiazol-2-yl)-2'-(2-methoxyethyl)-5-methyl-4,4'-bi(2H-pyrazole)-3-carboxylic acid;

1-(4-(3,4-dichlorophenyl)-5-(isopropylthio)thiazol-2-yl)-4-(1H-indol-7-yl)-3-methyl-1H-pyrazole-5-carboxylic acid;

2-(4-(1H-indol-7-yl)-3-methyl-1H-pyrazol-1-yl)-4-(3,4-dichlorophenyl)-5-(isopropylthio)thiazole;

2-(4-(3,4-dichlorophenyl)-5-(isopropylthio)thiazol-2-yl)-2'-ethyl-5-methyl-4,4'-bi(2H-pyrazole)-3-carboxylic acid;

1-(4-(3,4-dichlorophenyl)-5-(isopropylthio)thiazol-2-yl)-N-(2-methoxyethyl)-3-methyl-4-m-tolyl-1H-pyrazole-5-carboxamide;

(4-(aminomethyl)piperidin-1-yl)(1-(4-(3,4-dichlorophenyl)-5-(isopropylthio)thiazol-2-yl)-3-methyl-4-o-tolyl-1H-pyrazol-5-yl)methanone;

1-(4-(3,4-dichlorophenyl)-5-(isopropylthio)thiazol-2-yl)-4-(5-methoxypyridin-3-yl)-3-methyl-1H-pyrazole-5-carboxylic acid;

2-(4-(3,4-dichlorophenyl)-5-(isopropylthio)thiazol-2-yl)-2'-isobutyl-5-methyl-4,4'-bi(2H-pyrazole)-3-carboxylic acid;
1-(4-(3,4-dichlorophenyl)-5-(isopropylthio)thiazol-2-yl)-3-methyl-4-(2-(methylamino)pyridin-4-yl)-1H-pyrazole-5-carboxylic acid;
1-(4-(3,4-dichlorophenyl)-5-(isopropylthio)thiazol-2-yl)-1'-(dimethylcarbamoyl)-3-methyl-1H,1'H-[4,4'-bipyrazole]-5-carboxylic acid;
(4-(aminomethyl)piperidin-1-yl)(4-(3,5-bis(trifluoromethyl)phenyl)-1-(4-(3,4-dichlorophenyl)-5-(isopropylthio)thiazol-2-yl)-3-methyl-1H-pyrazol-5-yl)methanone;
N-(2-aminoethyl)-4-(3,5-bis(trifluoromethyl)phenyl)-1-(4-(3,4-dichlorophenyl)-5-(isopropylthio)thiazol-2-yl)-N,3-dimethyl-1H-pyrazole-5-carboxamide;
(3-aminoazetidin-1-yl)(4-(3,5-bis(trifluoromethyl)phenyl)-1-(4-(3,4-dichlorophenyl)-5-(isopropylthio)thiazol-2-yl)-3-methyl-1H-pyrazol-5-yl)methanone;
(4-(3,5-bis(trifluoromethyl)phenyl)-1-(4-(3,4-dichlorophenyl)-5-(isopropylthio)thiazol-2-yl)-3-methyl-1H-pyrazol-5-yl)(morpholino)methanone;
4-(3,5-bis(trifluoromethyl)phenyl)-1-(4-(3,4-dichlorophenyl)-5-(isopropylthio)thiazol-2-yl)-N,N,3-trimethyl-1H-pyrazole-5-carboxamide;
(4-(3,5-bis(trifluoromethyl)phenyl)-1-(4-(3,4-dichlorophenyl)-5-(isopropylthio)thiazol-2-yl)-3-methyl-1H-pyrazol-5-yl)(4-(hydroxymethyl)piperidin-1-yl)methanone;
1-(4-(3,4-dichlorophenyl)-5-isobutylthiazol-2-yl)-1',3-dimethyl-1H,1'H-[4,4'-bipyrazole]-5-carboxylic acid;
1-(4-(3,4-dichlorophenyl)-5-(isopropylthio)thiazol-2-yl)-4-(3,5-dimethylphenyl)-3-methyl-1H-pyrazole-5-carboxylic acid;
4-(3,5-dichlorophenyl)-1-(4-(3,4-dichlorophenyl)-5-(isopropylthio)thiazol-2-yl)-3-methyl-1H-pyrazole-5-carboxylic acid;
4-(3-chloro-5-methoxyphenyl)-1-(4-(3,4-dichlorophenyl)-5-(isopropylthio)thiazol-2-yl)-3-methyl-1H-pyrazole-5-carboxylic acid;
1-(4-(3,4-dichlorophenyl)-5-(isopropylthio)thiazol-2-yl)-4-(3-methoxy-5-(trifluoromethyl)phenyl)-3-methyl-1H-pyrazole-5-carboxylic acid;
4-(3-chloro-5-methylphenyl)-1-(4-(3,4-dichlorophenyl)-5-(isopropylthio)thiazol-2-yl)-3-methyl-1H-pyrazole-5-carboxylic acid;
4-(3,5-bis(trifluoromethyl)phenyl)-1-(4-(3,4-dichlorophenyl)-5-(isopropylthio)thiazol-2-yl)-3-methyl-N-(methylsulfonyl)-1H-pyrazole-5-carboxamide;
1-(4-(3,4-dichlorophenyl)-5-(isopropylthio)thiazol-2-yl)-4-(imidazo[1,2-a]pyridin-3-yl)-3-methyl-1H-pyrazole-5-carboxylic acid;
4-(3,5-dichlorophenyl)-1-(4-(3,5-dichlorophenyl)-5-(isopropylthio)thiazol-2-yl)-3-methyl-1H-pyrazole-5-carboxylic acid;
1-(4-(3,4-dichlorophenyl)-5-(isopropylthio)thiazol-2-yl)-4-(3-fluorophenyl)-3-methyl-1H-pyrazole-5-carboxylic acid;
1-(4-(3,4-dichlorophenyl)-5-(isopropylthio)thiazol-2-yl)-4-(3-fluoro-5-hydroxyphenyl)-3-methyl-1H-pyrazole-5-carboxylic acid;
4-(3-amino-5-methylphenyl)-1-(4-(3,4-dichlorophenyl)-5-(isopropylthio)thiazol-2-yl)-3-methyl-1H-pyrazole-5-carboxylic acid;
4-(3-chloro-5-hydroxyphenyl)-1-(4-(3,4-dichlorophenyl)-5-(isopropylthio)thiazol-2-yl)-3-methyl-1H-pyrazole-5-carboxylic acid;
1-(4-(3,4-dichlorophenyl)-5-(isopropylthio)thiazol-2-yl)-3-methyl-4-(1-methyl-1H-indol-7-yl)-1H-pyrazole-5-carboxylic acid;
4-(3,4-dichlorophenyl)-5-(isopropylthio)-2-(1H-pyrazol-1-yl)thiazole;
1-(4-(2-chlorophenyl)-5-(isopropylthio)thiazol-2-yl)-4-(2,6-dimethylpyridin-4-yl)-3-methyl-1H-pyrazole-5-carboxylic acid;
1-(4-(3-chlorophenyl)-5-(isopropylthio)thiazol-2-yl)-4-(2,6-dimethylpyridin-4-yl)-3-methyl-1H-pyrazole-5-carboxylic acid;
1-(4-(4-chlorophenyl)-5-(isopropylthio)thiazol-2-yl)-4-(2,6-dimethylpyridin-4-yl)-3-methyl-1H-pyrazole-5-carboxylic acid;
1-(4-(2,4-dichlorophenyl)-5-(isopropylthio)thiazol-2-yl)-4-(2,6-dimethylpyridin-4-yl)-3-methyl-1H-pyrazole-5-carboxylic acid;
1-(4-(2,5-dichlorophenyl)-5-(isopropylthio)thiazol-2-yl)-4-(2,6-dimethylpyridin-4-yl)-3-methyl-1H-pyrazole-5-carboxylic acid;
4-(2,6-dimethylpyridin-4-yl)-1-(5-(isopropylthio)-4-(phenylethynyl)thiazol-2-yl)-3-methyl-1H-pyrazole-5-carboxylic acid;
1-(4-benzyl-5-(isopropylthio)thiazol-2-yl)-4-(2,6-dimethylpyridin-4-yl)-3-methyl-1H-pyrazole-5-carboxylic acid;
1-(4-(3,4-dichlorophenyl)-5-(isopropylthio)thiazol-2-yl)-4-(3-fluoro-5-methoxyphenyl)-3-methyl-1H-pyrazole-5-carboxylic acid;
1-(4-(3,4-dichlorophenyl)-5-(isopropylthio)thiazol-2-yl)-4-(3-methoxy-5-methylphenyl)-3-methyl-1H-pyrazole-5-carboxylic acid;
1-(4-(3,4-dichlorophenyl)-5-(isopropylthio)thiazol-2-yl)-4-(2-methoxypyridin-4-yl)-3-methyl-1H-pyrazole-5-carboxylic acid;
1-(4-(3,4-dichlorophenyl)-5-(isopropylthio)thiazol-2-yl)-3-methyl-4-(2-methylpyridin-4-yl)-1H-pyrazole-5-carboxylic acid;
1-(4-(1H-indol-4-yl)-5-(isopropylthio)thiazol-2-yl)-4-(3-fluorophenyl)-3-methyl-1H-pyrazole-5-carboxylic acid;
1-(4-(3-fluorophenyl)-5-(isopropylthio)thiazol-2-yl)-4-(1H-indol-4-yl)-3-methyl-1H-pyrazole-5-carboxylic acid;
1-(4-(1H-indol-5-yl)-5-(isopropylthio)thiazol-2-yl)-4-(3-fluorophenyl)-3-methyl-1H-pyrazole-5-carboxylic acid;
1-(4-(cyclopropylethynyl)-5-(isopropylthio)thiazol-2-yl)-4-(3-fluorophenyl)-3-methyl-1H-pyrazole-5-carboxylic acid;
4-cyclopropyl-1-(4-cyclopropyl-5-(isopropylthio)thiazol-2-yl)-3-methyl-1H-pyrazole-5-carboxylic acid;
4-cyclopropyl-1-(4-(3,4-dichlorophenyl)-5-(isopropylthio)thiazol-2-yl)-3-methyl-1H-pyrazole-5-carboxylic acid;
4-(3-chloro-5-isopropoxyphenyl)-1-(4-(3,4-dichlorophenyl)-5-(isopropylthio)thiazol-2-yl)-3-methyl-1H-pyrazole-5-carboxylic acid;
4-(3-chloro-5-(2-methoxyethoxy)phenyl)-1-(4-(3,4-dichlorophenyl)-5-(isopropylthio)thiazol-2-yl)-3-methyl-1H-pyrazole-5-carboxylic acid;
1-(4-(3-chlorophenyl)-5-(isopropylthio)thiazol-2-yl)-4-(3-fluorophenyl)-3-methyl-1H-pyrazole-5-carboxylic acid;
1-(4-(4-chlorophenyl)-5-(isopropylthio)thiazol-2-yl)-4-(3-fluorophenyl)-3-methyl-1H-pyrazole-5-carboxylic acid;
1-(4-(2,4-dichlorophenyl)-5-(isopropylthio)thiazol-2-yl)-4-(3-fluorophenyl)-3-methyl-1H-pyrazole-5-carboxylic acid;
4-bromo-1-(4-(6-(3-fluorophenyl)pyridin-3-yl)-5-(isopropylthio)thiazol-2-yl)-3-methyl-1H-pyrazole-5-carboxylic acid;

(R)-1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylic acid;

1-(4-(3,4-dichlorophenyl)-5-(isopropylthio)thiazol-2-yl)-4-(2-(2-methoxyethoxy)-6-methylpyridin-4-yl)-3-methyl-1H-pyrazole-5-carboxylic acid;

(S)-1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylic acid;

1-(4-(cyclohex-1-en-1-yl)-5-(isopropylthio)thiazol-2-yl)-4-(3-fluorophenyl)-3-methyl-1H-pyrazole-5-carboxylic acid;

1-(4-(cyclopent-1-en-1-yl)-5-(isopropylthio)thiazol-2-yl)-4-(3-fluorophenyl)-3-methyl-1H-pyrazole-5-carboxylic acid;

4-(3-chloro-5-methoxyphenyl)-1-(5-(isopropylthio)-4-phenylthiazol-2-yl)-3-methyl-1H-pyrazole-5-carboxylic acid;

4-(3-fluorophenyl)-1-(4-(4-fluorophenyl)-5-(isopropylthio)thiazol-2-yl)-3-methyl-1H-pyrazole-5-carboxylic acid;

4-(3-fluorophenyl)-1-(5-(isopropylthio)-4-(4-methoxyphenyl)thiazol-2-yl)-3-methyl-1H-pyrazole-5-carboxylic acid;

4-(3-fluorophenyl)-1-(5-(isopropylthio)-4-(4-(methylsulfonyl)phenyl)thiazol-2-yl)-3-methyl-1H-pyrazole-5-carboxylic acid;

1-(4-(4-fluoro-3-methoxyphenyl)-5-(isopropylthio)thiazol-2-yl)-4-(3-fluorophenyl)-3-methyl-1H-pyrazole-5-carboxylic acid;

1-(4-(4-chloro-3-methylphenyl)-5-(isopropylthio)thiazol-2-yl)-4-(2,6-dimethylpyridin-4-yl)-3-methyl-1H-pyrazole-5-carboxylic acid;

1-(4-(4-chloro-3-methylphenyl)-5-(isopropylthio)thiazol-2-yl)-4-(3-fluorophenyl)-3-methyl-1H-pyrazole-5-carboxylic acid;

1-(4-(4-chloro-3,5-difluorophenyl)-5-(isopropylthio)thiazol-2-yl)-4-(2,6-dimethylpyridin-4-yl)-3-methyl-1H-pyrazole-5-carboxylic acid;

1-(4-(4-chloro-3,5-difluorophenyl)-5-(isopropylthio)thiazol-2-yl)-4-(3-fluorophenyl)-3-methyl-1H-pyrazole-5-carboxylic acid;

1-(4-(4-chloro-3-methoxyphenyl)-5-(isopropylthio)thiazol-2-yl)-4-(2,6-dimethylpyridin-4-yl)-3-methyl-1H-pyrazole-5-carboxylic acid;

1-(4-(4-chloro-3-methoxyphenyl)-5-(isopropylthio)thiazol-2-yl)-4-(3-fluorophenyl)-3-methyl-1H-pyrazole-5-carboxylic acid;

4-(2,6-dimethylpyridin-4-yl)-1-(5-(isopropylthio)-4-(4-(trifluoromethyl)phenyl)thiazol-2-yl)-3-methyl-1H-pyrazole-5-carboxylic acid;

4-(3-fluorophenyl)-1-(5-(isopropylthio)-4-(4-(trifluoromethyl)phenyl)thiazol-2-yl)-3-methyl-1H-pyrazole-5-carboxylic acid;

1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic acid;

1-(4-(3,4-dichlorophenyl)-5-(isopropylthio)thiazol-2-yl)-4-(2-methoxy-6-methylpyridin-4-yl)-3-methyl-1H-pyrazole-5-carboxylic acid;

1-(4-(3,4-dichlorophenyl)-5-(isopropylthio)thiazol-2-yl)-4-(3-fluoro-5-(oxetan-3-yloxy)phenyl)-3-methyl-1H-pyrazole-5-carboxylic acid;

4-(3-fluorophenyl)-1-(4-(3-fluorophenyl)-5-(isopropylthio)thiazol-2-yl)-3-methyl-1H-pyrazole-5-carboxylic acid;

1-(4-(benzofuran-2-yl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-phenylthiazol-2-yl)-3-methyl-1H-pyrazole-5-carboxylic acid;

1-(5-(isopropylthio)-4-phenylthiazol-2-yl)-1',3-dimethyl-1H,1'H-[4,4'-bipyrazole]-5-carboxylic acid;

4-(2,6-dimethylpyridin-4-yl)-1-(4-(4-fluorophenyl)-5-(isopropylthio)thiazol-2-yl)-3-methyl-1H-pyrazole-5-carboxylic acid;

1-(4-(4-chloro-2-methoxyphenyl)-5-(isopropylthio)thiazol-2-yl)-4-(3-fluorophenyl)-3-methyl-1H-pyrazole-5-carboxylic acid;

1-(4-(4-chloro-2-methoxyphenyl)-5-(isopropylthio)thiazol-2-yl)-4-(2,6-dimethylpyridin-4-yl)-3-methyl-1H-pyrazole-5-carboxylic acid;

1-(4-(3-chloro-4-methylphenyl)-5-(isopropylthio)thiazol-2-yl)-4-(3-fluorophenyl)-3-methyl-1H-pyrazole-5-carboxylic acid;

1-(4-(1,5-dimethyl-6-oxo-1,6-dihydropyridin-3-yl)-5-(isopropylthio)thiazol-2-yl)-4-(3-fluorophenyl)-3-methyl-1H-pyrazole-5-carboxylic acid;

1-(4-(2-chloro-5-(trifluoromethoxy)phenyl)-5-(isopropylthio)thiazol-2-yl)-4-(3-fluorophenyl)-3-methyl-1H-pyrazole-5-carboxylic acid;

1-(4-(5-cyanopyridin-3-yl)-5-(isopropylthio)thiazol-2-yl)-4-(3-fluorophenyl)-3-methyl-1H-pyrazole-5-carboxylic acid;

1-(4-(1,3-dimethyl-1H-pyrazol-5-yl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-(pyrimidin-5-yl)thiazol-2-yl)-3-methyl-1H-pyrazole-5-carboxylic acid;

1-(4-(4-cyanophenyl)-5-(isopropylthio)thiazol-2-yl)-4-(3-fluorophenyl)-3-methyl-1H-pyrazole-5-carboxylic acid;

1-(4-(3-fluoro-4-methylphenyl)-5-(isopropylthio)thiazol-2-yl)-4-(3-fluorophenyl)-3-methyl-1H-pyrazole-5-carboxylic acid;

1-(4-(2-cyanophenyl)-5-(isopropylthio)thiazol-2-yl)-4-(3-fluorophenyl)-3-methyl-1H-pyrazole-5-carboxylic acid;

1-(4-(4-chloro-2-methylphenyl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-(2-methyl-4-(trifluoromethyl)phenyl)thiazol-2-yl)-3-methyl-1H-pyrazole-5-carboxylic acid;

1-(4-(4-chloro-3-cyanophenyl)-5-(isopropylthio)thiazol-2-yl)-4-(3-fluorophenyl)-3-methyl-1H-pyrazole-5-carboxylic acid;

4-(3,5-dichlorophenyl)-1-(5-(isopropylthio)-4-(4-(trifluoromethyl)phenyl)thiazol-2-yl)-3-methyl-1H-pyrazole-5-carboxylic acid;

4-(3-fluorophenyl)-1-(5-(isopropylthio)-4-(4-((2-methoxyethyl)carbamoyl)phenyl)thiazol-2-yl)-3-methyl-1H-pyrazole-5-carboxylic acid;

1-(4-(4-(dimethylcarbamoyl)phenyl)-5-(isopropylthio)thiazol-2-yl)-4-(3-fluorophenyl)-3-methyl-1H-pyrazole-5-carboxylic acid;

4-(3-chloro-5-methoxyphenyl)-1-(5-(isopropylthio)-4-(4-(trifluoromethyl)phenyl)thiazol-2-yl)-3-methyl-1H-pyrazole-5-carboxylic acid;

4-(3-fluorophenyl)-1-(5-(isopropylthio)-4-(4-(trifluoromethoxy)phenyl)thiazol-2-yl)-3-methyl-1H-pyrazole-5-carboxylic acid;

4-(3-fluorophenyl)-1-(5-(isopropylthio)-4-(2-methyl-4-(trifluoromethoxy)phenyl)thiazol-2-yl)-3-methyl-1H-pyrazole-5-carboxylic acid;

4-(3-chloro-5-fluorophenyl)-1-(4-(3,4-dichlorophenyl)-5-(isopropylthio)thiazol-2-yl)-3-methyl-1H-pyrazole-5-carboxylic acid;

1-(4-(4-cyano-3-methylphenyl)-5-(isopropylthio)thiazol-2-yl)-4-(3-fluorophenyl)-3-methyl-1H-pyrazole-5-carboxylic acid;

1-(4-(3,4-dichlorophenyl)-5-fluorothiazol-2-yl)-4-(3-fluorophenyl)-3-methyl-1H-pyrazole-5-carboxylic acid;

1-(4-(3,4-dichlorophenyl)-5-(isopropylthio)thiazol-2-yl)-4-(3-fluorophenyl)-3-isopropyl-1H-pyrazole-5-carboxylic acid;

1-(4-(4-(difluoromethyl)phenyl)-5-(isopropylthio)thiazol-2-yl)-4-(3-fluorophenyl)-3-methyl-1H-pyrazole-5-carboxylic acid;

1-(4-(3,4-dichlorophenyl)-5-isopropoxythiazol-2-yl)-4-(3-fluorophenyl)-3-methyl-1H-pyrazole-5-carboxylic acid;

1-(4-(4-ethylphenyl)-5-(isopropylthio)thiazol-2-yl)-4-(3-fluorophenyl)-3-methyl-1H-pyrazole-5-carboxylic acid;

2-(4-(2,6-dimethylpyridin-4-yl)-3,5-dimethyl-1H-pyrazol-1-yl)-5-(isopropylthio)-4-(4-(trifluoromethyl)phenyl)thiazole;

4-(3-fluorophenyl)-1-(4-(5-fluoropyridin-3-yl)-5-(isopropylthio)thiazol-2-yl)-3-methyl-1H-pyrazole-5-carboxylic acid;

1-(4-(benzofuran-3-yl)-5-(isopropylthio)thiazol-2-yl)-4-(3-fluorophenyl)-3-methyl-1H-pyrazole-5-carboxylic acid;

4-(3,4-difluorophenyl)-1-(5-(isopropylthio)-4-(4-(trifluoromethyl)phenyl)thiazol-2-yl)-3-methyl-1H-pyrazole-5-carboxylic acid;

4-(4-fluoro-3-methylphenyl)-1-(5-(isopropylthio)-4-(4-(trifluoromethyl)phenyl)thiazol-2-yl)-3-methyl-1H-pyrazole-5-carboxylic acid;

4-(4-fluorophenyl)-1-(5-(isopropylthio)-4-(4-(trifluoromethyl)phenyl)thiazol-2-yl)-3-methyl-1H-pyrazole-5-carboxylic acid;

4-(4-fluoro-3-methoxyphenyl)-1-(5-(isopropylthio)-4-(4-(trifluoromethyl)phenyl)thiazol-2-yl)-3-methyl-1H-pyrazole-5-carboxylic acid;

1-(4-(4-chloro-2,6-dimethylphenyl)-5-(isopropylthio)thiazol-2-yl)-4-(3-fluorophenyl)-3-methyl-1H-pyrazole-5-carboxylic acid;

1-(4-(4-(1,1-difluoroethyl)phenyl)-5-(isopropylthio)thiazol-2-yl)-4-(3-fluorophenyl)-3-methyl-1H-pyrazole-5-carboxylic acid;

4-(4-fluoro-3,5-dimethylphenyl)-1-(5-(isopropylthio)-4-(4-(trifluoromethyl)phenyl)thiazol-2-yl)-3-methyl-1H-pyrazole-5-carboxylic acid;

4-(3-fluorophenyl)-1-(5-(isopropylthio)-4-(2-(trifluoromethyl)pyrimidin-5-yl)thiazol-2-yl)-3-methyl-1H-pyrazole-5-carboxylic acid;

1-(4-(4-chloro-3-(ethylcarbamoyl)phenyl)-5-(isopropylthio)thiazol-2-yl)-4-(3-fluorophenyl)-3-methyl-1H-pyrazole-5-carboxylic acid;

1-(4-(2-amino-4-(trifluoromethyl)phenyl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-((4-(trifluoromethyl)phenyl)ethynyl)thiazol-2-yl)-3-methyl-1H-pyrazole-5-carboxylic acid;

4-(3-fluorophenyl)-1-(5-(isopropylthio)-4-(5-(trifluoromethyl)pyrimidin-2-yl)thiazol-2-yl)-3-methyl-1H-pyrazole-5-carboxylic acid;

4-(3-fluorophenyl)-3-methyl-1-(4-(4-(trifluoromethyl)phenyl)thiazol-2-yl)-1H-pyrazole-5-carboxylic acid;

4-(3-fluorophenyl)-1-(5-(isopropylthio)-4-(4-(trifluoromethyl)phenyl)thiazol-2-yl)-N-(2-methoxyethyl)-N,3-dimethyl-1H-pyrazole-5-carboxamide;

N-(2-(2-(2-(2-azidoethoxy)ethoxy)ethoxy)ethyl)-4-(3-fluorophenyl)-1-(5-(isopropylthio)-4-(4-(trifluoromethyl)phenyl)thiazol-2-yl)-3-methyl-1H-pyrazole-5-carboxamide;

4-(3-fluorophenyl)-1-(5-(isopropylthio)-4-(4-(trifluoromethyl)phenyl)thiazol-2-yl)-N-(2-methoxyethyl)-3-methyl-1H-pyrazole-5-carboxamide;

4-(3-fluorophenyl)-1-(5-(isopropylthio)-4-(4-(trifluoromethyl)phenyl)thiazol-2-yl)-3-methyl-N-(propylsulfonyl)-1H-pyrazole-5-carboxamide;

4-(3-fluorophenyl)-1-(5-(isopropylthio)-4-(2-(trifluoromethyl)phenyl)thiazol-2-yl)-3-methyl-1H-pyrazole-5-carboxylic acid;

4-(3-fluorophenyl)-1-(5-(isopropylthio)-4-(3-(trifluoromethyl)phenyl)thiazol-2-yl)-3-methyl-1H-pyrazole-5-carboxylic acid;

4-(3-fluorophenyl)-1-(5-(isopropylamino)-4-(4-(trifluoromethyl)phenyl)thiazol-2-yl)-3-methyl-1H-pyrazole-5-carboxylic acid;

4-(3-fluorophenyl)-1-(5-(isopropylthio)-4-(4-(pentafluoro-$\lambda^6$-sulfaneyl)phenyl)thiazol-2-yl)-3-methyl-1H-pyrazole-5-carboxylic acid;

4-(3-fluorophenyl)-1-(5-(isopropylthio)-4-(4-(trifluoromethyl)phenyl)thiazol-2-yl)-N-methoxy-3-methyl-1H-pyrazole-5-carboxamide;

4-(3-fluorophenyl)-1-(5-(isopropylthio)-4-(4-(2,2,2-trifluoroethyl)phenyl)thiazol-2-yl)-3-methyl-1H-pyrazole-5-carboxylic acid;

4-(3-fluorophenyl)-1-(5-(isopropylthio)-4-(6-(trifluoromethyl)pyridin-3-yl)thiazol-2-yl)-3-methyl-1H-pyrazole-5-carboxylic acid; and 4-(3-fluorophenyl)-1-(5-(isopropylthio)-4-(1-(2,2,2-trifluoroethyl)-1H-pyrazol-4-yl)thiazol-2-yl)-3-methyl-1H-pyrazole-5-carboxylic acid.

In certain embodiments of the compounds as otherwise described herein, the compound is in the form of an N-oxide. But in certain embodiments as described above, the compound is not in the form of an N-oxide.

In certain embodiments of the compounds as otherwise described herein, the compound is in the form of a pharmaceutically-acceptable salt of a compound or N-oxide as described herein. The person of ordinary skill in the art will appreciate that a variety of pharmaceutically-acceptable salts may be provided, as described in additional detail below. The person of ordinary skill in the art will appreciate that the phrase "optionally in the form of a pharmaceutically acceptable salt or N-oxide, or a solvate or hydrate" includes compounds in the form of a pharmaceutically acceptable salt of an N-oxide. But in certain embodiments as described above, the compound is not in the form of a pharmaceutically acceptable salt.

In certain embodiments of the compounds as otherwise described herein, a compound is in the form of a solvate (e.g., a hydrate) of a compound, N-oxide or salt as described herein. The person of ordinary skill in the art will appreciate that a variety of solvates and/or hydrates may be formed. The person of ordinary skill in the art will appreciate that the phrase "optionally in the form of a pharmaceutically acceptable salt or N-oxide, or a solvate or hydrate" includes compounds in the form of solvates and hydrates of base compounds, pharmaceutically acceptable salts and N-oxides as described above. But in certain embodiments as described above, the compound is not in the form of a solvate or hydrate.

A compound as described herein can usefully be provided in the form of a pharmaceutical composition comprising a compound, N-oxide, salt, solvate or hydrate according to any one of the preceding aspects or embodiments described herein, together with a pharmaceutically acceptable excipient, diluent, or carrier. The pharmaceutical composition can be, for example, in the form of a tablet, a capsule, or a parenteral formulation, but the person of ordinary skill in the art will appreciate that the compound can be provided in a wide variety of pharmaceutical compositions.

As noted above, mutations that allow for increased and more efficient utilization of scarce nutrients are favored during tumor formation. Oncogenic Ras stimulates both glucose uptake via enhanced expression of GLUT1, and utilization of glucose by anabolic pathways and conversion into glutathione, a key cellular antioxidant. Ras also regulates glutamine metabolism, specifically directing glucose and glutamine carbon into pathways that support biosynthesis, redox homeostasis and ultimately cell survival and growth.

In addition to these effects on cellular metabolism, Ras has also been described to have effects on progression of the cell along the cell cycle. Specifically, Ras has been implicated as having a role in the transit across the restriction point in early G1 and again in G2. Ras activity at the G1 restriction point is particularly important as this event is the key integration point for growth factor signaling that commits the cell to further division or entry into the G0 or quiescent phase. Ras coordinates growth factor signaling to regulate levels of cyclins, cyclin dependent kinases and antagonistic cyclin dependent kinase inhibitors.

For additional information, see generally Hanahan D, Weinberg R A (2011) Hallmarks of cancer: the next generation. *Cell* 144(5):646-674; Ward P S, Thompson C B (2012) Metabolic Reprogramming: A Cancer Hallmark Even Warburg Did Not Anticipate. *Cancer Cell* 21(3):297-308; Prabakaran S (2016) Kras rewires metabolic networks. *Sci Signal* 9(418):ec56-ec56; Kerr E M, Gaude E, Turrell F K, Frezza C, Martins C P (2016) Mutant Kras copy number defines metabolic reprogramming and therapeutic susceptibilities. *Nature* 531(7592):110-113; Flier J S, Mueckler M M, Usher P, Lodish H F (1987) Elevated levels of glucose transport and transporter messenger RNA are induced by ras or src oncogenes. *Science* 235(4795):1492-1495; Yun J, et al. (2009) Glucose Deprivation Contributes to the Development of KRAS Pathway Mutations in Tumor Cells. *Science* 325(5947):1555-1559; Son J, et al. (2013) Glutamine supports pancreatic cancer growth through a KRAS-regulated metabolic pathway. *Nature* 496(7443):101-105; Kim M H, Kim H (2013) Oncogenes and tumor suppressors regulate glutamine metabolism in cancer cells. *J Cancer Prev* 18(3): 221-226; Gaglio D, et al. (2011) Oncogenic K-Ras decouples glucose and glutamine metabolism to support cancer cell growth. *Mol Syst Biol* 7:523; Hitomi M, Stacey D W (1999) Cellular ras and cyclin D1 are required during different cell cycle periods in cycling NIH 3T3 cells. *Mol Cell Biol* 19(7):4623-4632; Hitomi M, Stacey D W (2001) Ras-dependent cell cycle commitment during G2 phase. *FEBS Lett* 490(3):123-131; Foster D A, Yellen P, Xu L, Saqcena M (2010) Regulation of G1 Cell Cycle Progression: Distinguishing the Restriction Point from a Nutrient-Sensing Cell Growth Checkpoint(s). *Genes Cancer* 1(11):1124-1131; Massagué J (2004) G1 cell-cycle control and cancer. *Nature* 432(7015):298-306; Pardee A B (1974) A restriction point for control of normal animal cell proliferation. *Proc Natl Acad Sci USA* 71(4):1286-1290; Martinsson H-S, Starborg M, Erlandsson F, Zetterberg A (2005) Single cell analysis of G1 check points—the relationship between the restriction point and phosphorylation of pRb. *Exp Cell Res* 305(2):383-391; Larsson O, Zetterberg A (1995) Existence of a commitment program for mitosis in early G1 in tumour cells. *Cell Prolif* 28(1):33-43; Yen A, Pardee A B (1978) Exponential 3T3 cells escape in mid-G1 from their high serum requirement. *Exp Cell Res* 116(1):103-113; Novek B, Tyson J J (2004) A model for restriction point control of the mammalian cell cycle. *J Theor Biol* 230(4):563-579; Weber J D, Hu W, Jefcoat S C, Raben D M, Baldassare J J (1997) Ras-stimulated Extracellular Signal-related Kinase 1 and RhoA Activities Coordinate Platelet-derived Growth Factor-induced G1 Progression through the Independent Regulation of Cyclin D1 and p27KIP1. *J Biol Chem* 272(52):32966-32971; Kawada M, et al. (1997) Induction of p27Kip1 degradation and anchorage independence by Ras through the MAP kinase signaling pathway. Oncogene 15(6):629-637; Deng X, Mercer S E, Shah S, Ewton D Z, Friedman E (2004) The cyclin-dependent kinase inhibitor p27Kip1 is stabilized in G(0) by Mirk/dyrk1 B kinase. *J Biol Chem* 279(21): 22498-22504; Ladha M H, Lee K Y, Upton T M, Reed M F, Ewen M E (1998) Regulation of exit from quiescence by p27 and cyclin D1-CDK4. *Mol Cell Biol* 18(11):6605-6615; Fan J, Bertino J R (1997) K-ras modulates the cell cycle via both positive and negative regulatory pathways. *Oncogene* 14(21):2595-2607.

Ras-related oncogenes, KRAS (also known as k-Ras or V-Ki-ras2 Kirsten rat sarcoma viral oncogene homolog) in particular, have also been shown to have direct effects on cellular metabolism. The outcome is a global rewiring of the metabolic circuits. KRAS has been noted to have pleiotropic effects on glucose utilization, glutathione synthesis, and redox balance and glutamine metabolism. Glutathione, an ubiquitous intracellular peptide, has diverse functions including modulation of cell proliferation, detoxification, and antioxidant defense (Lu, Shelly C., *Mol Aspects Med.* 2009; 30(1-2): 42-59). Increased glutathione levels have been associated with an early proliferative response (for example, stimulating cells to shift from G0 to G1 phase of the cell cycle), and are essential for the cell to enter the S phase (Id.). Glutathione has also been implicated in the regulation of cell death, likely modulating both apoptosis and necrosis (Id.). In addition, increased leves of glutathione have been reported in many tumors and have been implicated to confer drug and/or radiation resistance and impede chemotherapy (Id.). Thus, inhibitors of glutathione synthesis present unique chemotherapeutic targets.

Without intending to be bound by theory, the inventors believe that the compounds described herein are active against cancer cells by arresting the cell cycle at the G0/G1 phase. Accordingly, as suggested above, the compounds described herein can be employed in a variety of methods and uses. For example, in certain embodiments of the disclosure, a method for treating a hyperproliferative disorder in a subject in need thereof includes administering to the subject an effective amount of a compound as described herein. In other embodiments of the disclosure, a compound as described herein is provided for use in the treatment of hyperproliferative disorder. Other embodiments of the disclosure provide a compound as described herein for the preparation of a medicament for the treatment of a hyperproliferative disorder. In each of these embodiments, the hyperproliferative disorder can be, for example, a cancer.

The inventors have determined that, in certain embodiments, the presently described compounds inhibit the progression of the cell cycle in cancer cells. Accordingly, another embodiment of the disclosure provides a method for inhibiting cell cycle progression in a cancer cell, the method comprising contacting the cancer cell with an effective amount of a compound as described herein. In certain such embodiments, the cell cycle progression is inhibited at the GO/G1 phase.

Inhibiting cell cycle progression at the GO/G1 phase can in certain embodiments induce apoptosis of a cancer cell. Accordingly, another embodiment of the disclosure provides a method for inducing apoptosis in a cancer cell, such as a hematopoietic cancer cell. The method includes contacting the cancer cell with an effective amount of a compound as described herein. However, in other embodiments, for example, in certain solid tumors, apoptosis may not be necessary for there to be an important therapeutic effect.

The inventors have determined that the compounds described herein can, in certain embodiments, induce a cytotoxic effect on a cancer cell (e.g., through the apoptotic mechanism described above, or through an alternative mechanism). Accordingly, another embodiment of the disclosure provides a method for inducing a cytotoxic effect on a cancer cell. The method includes contacting the cancer cell with an effective amount of a compound as described herein.

The inventors have determined that the compounds described herein can, in certain embodiments, inhibit glutathione synthesis in a cancer cell. Accordingly, another embodiment of the disclosure provides a method for inhibiting glutathione synthesis in a cancer cell. The method includes contacting the cancer cell with an effective amount of a compound as described herein.

The methods, compounds and uses described herein can be employed with respect to a variety of different cancers or with respect to cells of a variety of different types of cancer. For example, in certain embodiments of the methods, compounds and uses as otherwise described herein, the cancer is a hematopoietic cancer. In other embodiments, the cancer is a solid tumor.

In certain embodiments of the methods, compounds and uses as otherwise described herein, the cancer is a lymphoma (e.g., Burkitt's lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)). In other such embodiments, the cancer is a leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia). In other such embodiments, the cancer is a plasma cell neoplasm (e.g., multiple myeloma).

However, the person of ordinary skill in the art will appreciate from the disclosure provided herein that the methods, compounds and uses described herein can be employed with a variety of other types of cancer. For example, in certain embodiments of the methods, compounds and uses as otherwise described herein, the cancer is selected from appendix cancer, bone cancer (e.g., Ewing sarcoma, osteosarcoma and malignant fibrous histiocytoma), bronchial tumors, carcinoma of unknown primary, chronic myeloproliferative neoplasms, colon and rectal cancer, head and neck cancer (including head and neck squamous cell carcinoma (HNSCC)), leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), lymphoma (e.g., Burkitt lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)), plasma cell neoplasms (e.g., multiple myeloma), myelodysplastic syndrome, myelodysplastic/myeloproliferative neoplasms and chronic myeloproliferative neoplasms, pancreatic cancer and pancreatic neuroendocrine tumors (e.g., islet cell tumors), small intestine cancer, soft tissue sarcoma, and squamous cell carcinoma.

And in other embodiments of the methods, compounds and uses as otherwise described herein, the cancer is selected from adrenocortical carcinoma, adrenal cortex cancer, AIDS-related cancers (e.g., as Kaposi sarcoma, AIDS-related lymphoma, Burkitt lymphoma, and primary CNS lymphoma), anal cancer, appendix cancer, astrocytomas (e.g., childhood cerebellar or cerebral), bile duct cancer (e.g., cholangiocarcinoma), bladder cancer, bone cancer (e.g., Ewing sarcoma, osteosarcoma and malignant fibrous histiocytoma), brain tumors (e.g., glioblastoma multiforme, cerebellar astrocytoma, cerebral astrocytoma/malignant glioma, ependymoma, medulloblastoma, oligodendroglioma, supratentorial primitive neuroectodermal tumors, and visual pathway and hypothalamic glioma), brainstem glioma, breast cancer, bronchial tumors, gastrointestinal carcinoid tumor, carcinoid tumors, carcinoma of unknown primary, cardiac (heart) tumors, central nervous system caner (e.g., atypical teratoid/rhabdoid tumor, embryonal tumors, and germ cell tumors), cervical cancer, childhood cancers, chondrosarcoma, chronic myeloproliferative neoplasms, colon and rectal cancer, craniopharyngioma, desmoplastic small round cell tumor, ductal carcinoma in situ (DCIS), endometrial cancer, ependymoma, epitheliod hemangioendothelioma (EHE), esophageal cancer, esthesioneuroblastoma, extracranial germ cell tumor, extragonadal germ cell tumor, eye cancer (e.g., intraocular melanoma, and retinoblastoma), fallopian tube cancer, gallbladder cancer, gastric (stomach) cancer, gastrointestinal stromal tumors (GIST), gestational trophoblastic disease (GTD), gliomas, hairy cell leukemia, head and neck cancer (e.g., head and neck squamous cell carcinoma (HNSCC)), hepatocellular (liver) cancer, histiocytosis, langerhans cell, hypopharyngeal cancer, kidney cancer, langerhans cell histiocytosis, laryngeal cancer, laryngeal cancer and papillomatosis, leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), lip and oral cavity cancer, liver cancer, lung cancer (e.g., small cell lung cancer, non-small cell lung cancer (NSCLC), lung adenocarcinoma, carcinoma of the lung, and squamous carcinoma of the lung), lung carcinoid tumor, lymphoma (e.g., Burkitt lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)), male breast cancer, meningiomas, mesothelioma, midline tract carcinoma involving NUT gene, mouth cancer, multiple endocrine neoplasia syndrome, plasma cell neoplasm (e.g., multiple myeloma), mycosis fungoides, myelodysplastic syndrome, myelodysplastic/myeloproliferative neoplasms and chronic myeloproliferative neoplasms, nasal cavity and paranasal sinus cancer, nasopharyngeal cancer (NPC), neuroblastoma, oral cancer, lip and oral cavity cancer and oropharyngeal cancer, ovarian cancer, pancreatic cancer and pancreatic neuroendocrine tumors (e.g., islet cell tumors), paraganglioma, parathyroid cancer, penile cancer, pharyngeal cancer, pheochromocytoma, pituitary tumor, pleuropulmonary blastoma, primary peritoneal cancer, prostate cancer, retinoblastoma, rhabdomyosarcoma, salivary gland cancer, Sezary syndrome, skin cancer (e.g., basal and squamous cell carcinoma, merkel cell carcinoma, and melanoma), small intestine cancer, soft tissue sarcoma, squamous cell carcinoma, stomach (gastric) cancer, testicular cancer, throat cancer, thymoma and thymic carcinoma, thyroid cancer, transitional cell cancer of the renal pelvis and ureter, urethral cancer, uterine cancer and uterine Sarcoma, vaginal cancer, vascular tumors, vulvar cancer, and Wilms tumor.

For example, in a few particular embodiments of methods, compounds and uses as otherwise described herein, the cancer is a solid tumor. The solid tumor can be in various embodiments, for example, a lung cancer, a colorectal cancer, or a pancreatic cancer.

In one particular embodiment of the methods, compounds and uses as otherwise described herein, the cancer is diffuse large B-cell lymphoma.

The data provided herein demonstrates that the compounds are especially effective against cancers having a heterozygous mutant KRAS gene. KRAS mutations are found in >90% of pancreatic cancers, 50% of colon cancers and 25% of lung adenocarcinomas. Accordingly, in certain embodiments of the methods, compound and uses as otherwise described herein, the cancer has a mutant KRAS gene, e.g., a heterozygous mutant.

However, in certain embodiments of the methods, compounds and uses as otherwise described herein, the cancer or hyperproliferative disorder is not Burkitt lymphoma.

The person of ordinary skill in the art will determine effective amounts and dosages of the compounds described herein based on this disclosure in view of the current state of the art.

Definitions

Terms used herein may be preceded and/or followed by a single dash, "–", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-$(A)_a$, wherein a is 0 or 1. In such instances, when a is 0 the moiety is —B and when a is 1 the moiety is —B-A.

As used herein, the term "alkyl" includes a saturated hydrocarbon having a designed number of carbon atoms, such as 1 to 10 carbons (i.e., inclusive of 1 and 10), 1 to 8 carbons, 1 to 6 carbons, 1 to 3 carbons, or 1, 2, 3, 4, 5 or 6. Alkyl group may be straight or branched and depending on context, may be a monovalent radical or a divalent radical (i.e., an alkylene group). For example, the moiety "—($C_1$-$C_6$ alkyl)-O—" signifies connection of an oxygen through an alkylene bridge having from 1 to 6 carbons and $C_1$-$C_3$alkyl represents methyl, ethyl, and propyl moieties. Examples of "alkyl" include, for example, methyl, ethyl, propyl, isopropyl, butyl, iso-, sec- and tert-butyl, pentyl, and hexyl.

The term "alkoxy" represents an alkyl group of indicated number of carbon atoms attached to the parent molecular moiety through an oxygen bridge. Examples of "alkoxy" include, for example, methoxy, ethoxy, propoxy, and isopropoxy.

The term "alkenyl" as used herein, unsaturated hydrocarbon containing from 2 to 10 carbons (i.e., inclusive of 2 and 10), 2 to 8 carbons, 2 to 6 carbons, or 2, 3, 4, 5 or 6, unless otherwise specified, and containing at least one carbon-carbon double bond. Alkenyl group may be straight or branched and depending on context, may be a monovalent radical or a divalent radical (i.e., an alkenylene group). For example, the moiety "—($C_2$-$C_6$ alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" as used herein, unsaturated hydrocarbon containing from 2 to 10 carbons (i.e., inclusive of 2 and 10), 2 to 8 carbons, 2 to 6 carbons, or 2, 3, 4, 5 or 6 unless otherwise specified, and containing at least one carbon-carbon triple bond. Alkynyl group may be straight or branched and depending on context, may be a monovalent radical or a divalent radical (i.e., an alkynylene group). For example, the moiety "—($C_2$-$C_6$ alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The term "aryl" represents an aromatic ring system having a single ring (e.g., phenyl) which is optionally fused to other aromatic hydrocarbon rings or non-aromatic hydrocarbon or heterocycle rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. "Aryl" also includes ring systems having a first carbocyclic, aromatic ring fused to a nonaromatic heterocycle, for example, 1H-2,3-dihydrobenzofuranyl and tetrahydroisoquinolinyl. The aryl groups herein are unsubstituted or, when specified as "optionally substituted", can unless stated otherwise be substituted in one or more substitutable positions with various groups as indicated.

The terms "halogen" or "halo" indicate fluorine, chlorine, bromine, and iodine. In certain embodiments of each and every embodiment as otherwise described herein, the term "halogen" or "halo" refers to fluorine or chlorine. In certain embodiments of each and every embodiment described herein, the term "halogen" or "halo" refers to fluorine. The term "fluoroalkyl" indicates an alkyl group (i.e., as otherwise described herein) that is substituted with at least one fluorine. "Fluoroalkyl" includes alkyl groups substituted with multiple fluorines, such as perfluoroalkyl groups. Examples of fluoroalkyl groups include fluoromethyl, difluoromethyl, trifluoromethyl, pentafluoroethyl, 2,2,2-trifluoroethyl, 1,1,1,3,3,3-hexafluoroprop-2-yl and 2,2,3,3,3-pentafluoroprop-1-yl.

The term "heteroaryl" refers to an aromatic ring system containing at least one aromatic heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic rings, for example, cycloalkyl or heterocycloalkyl rings, wherein the cycloalkyl and heterocycloalkyl rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, isoindolinyl, isobenzothienyl, benzoxazolyl, pyridopyridinyl, purinyl, benzodioxolyl, triazinyl, pteridinyl, benzothiazolyl, imidazopyridinyl, imidazothiazolyl, benzisoxazinyl, benzoxazinyl, benzopyranyl, benzothiopyranyl, chromonyl, chromanonyl, pyridinyl-N-oxide, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as indicated.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as indicated.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane.

The cycloalkyl groups herein are unsubstituted or, when specified as "optionally substituted", may be substituted in one or more substitutable positions with various groups, as indicated.

The term "ring system" encompasses monocycles, as well as fused and/or bridged polycycles.

The term "oxo" means a doubly bonded oxygen, sometimes designated as =O or for example in describing a carbonyl "C(O)" may be used to show an oxo substituted carbon.

The term "substituted," when used to modify a specified group or radical, means that one or more hydrogen atoms of the specified group or radical are each, independently of one another, replaced with the same or different substituent groups as defined below, unless specified otherwise.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC—(CH_2)_n—COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease. Of course, in certain embodiments, the compound has substantially the same isotopic character as naturally-occurring materials.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" or "effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, an effective amount can be an amount suitable for (i) inhibiting the progression the disease;

(ii) prophylactic use for example, preventing or limiting development of a disease, condition or disorder in an individual who may be predisposed or otherwise at risk to the disease, condition or disorder but does not yet experience or display the pathology or symptomatology of the disease;

(iii) inhibiting the disease; for example, inhibiting a disease, condition or disorder in an individual who is experiencing or displaying the pathology or symptomatology of the disease, condition or disorder;

(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (v) eliciting the referenced biological effect.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof, or inhibiting the progression of disease; or (ii) eliciting the referenced biological effect (e.g., inducing apoptosis, or inhibiting glutathione synthesis).

Pharmaceutical Formulations and Dosage Forms

The compounds of the disclosure can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like. A medicament including a compound of the disclosure can be provided in any appropriate of the formulations and dosage forms as described herein.

Pharmaceutical compositions can be made using the presently disclosed compounds. For example, in one embodiment, a pharmaceutical composition includes a pharmaceutically acceptable carrier, diluent or excipient, and compound as described above with reference to any one of structural formulae.

In the pharmaceutical compositions disclosed herein, one or more compounds of the disclosure may be present in association with one or more pharmaceutically acceptable carriers, diluents or excipients, and, if desired, other active ingredients. The pharmaceutical compositions containing compounds of the disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of the disclosure can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of the disclosure can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The person of ordinary skill in the art will formulate a compound as described into pharmaceutical formulations herein. for example, based on the physicochemical properties of the compound, the amount of the compound needed for a pharmaceutically effective amount, and the desired route of administration.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art in view of the particular preparative procedures described herein. One of skill in the art can adapt the reaction sequences described in examples below to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

Compounds suitable for use in the presently disclosed pharmaceutical compositions include compounds of the table above. A variety of exemplary syntheses are provided below; the person of ordinary skill in the art will adapt the procedures described herein and/or other procedures familiar to the person of ordinary skill in the art, to make the compounds described herein.

The following synthetic examples and biochemical data are intended to further illustrate certain embodiments and are not intended to limit the scope of the presently disclosed compounds.

Compound 1: 1-(4-(4-chloro-2-(oxetan-3-yloxy)phenyl)-5-(isopropylthio)thiazol-2-yl)-3-methyl-1H-pyrazole-5-carboxylic acid 3-(2-bromo-5-chlorophenoxv)oxetane Diisopropyl diazocarboxylate (292 mg, 1.45 mmol) was added to a solution of 2-bromo-5-chlorophenol (200 mg, 0.964 mmol), oxetan-3-ol (89 mg, 1.2 mmol) and triphenylphosphine (379 mg, 1.45 mmol) in THF (4.2 mL). The reaction mixture was stirred at r.t. for 18 h. Ethyl acetate was added and the mixture was washed with 1N NaOH (3×). The organic layer was dried with sodium sulfate, filtered and evaporated under reduced pressure. The crude product was purified by flash chromatography on silica gel using a solution of ethyl acetate in hexanes (10%) to give the title compound (208 mg, 0.789 mmol, 82%).

2-(4-chloro-2-(oxetan-3-yloxy)phenyl)-4,4,5,5-tetramethyl-1,3,2-dioxaborolane

Degassed dioxane was added to a mixture of 3-(2-bromo-5-chlorophenoxy)oxetane (100 mg, 0.379 mmol), pinacol diborane (116 mg, 0.455 mmol), [1,1'-Bis(diphenylphosphino)ferrocene]palladium(II) dichloride (28 mg, 0.038 mmol) and potassium acetate (112 mg, 1.14 mmol). The reaction mixture was heated at 85° C. for 18 hours. The mixture was filtered on celite and the pad was washed with dioxane. The filtrate was evaporated to give the title compound (219 mg, 186%, 50% w/w from NMR analysis) that was used as is.

2-chloro-5-(isopropylthio)thiazole

A 2.5 M solution of n-BuLi in hexanes (20.5 mL, 51.2 mmol) was added to a THF solution (117 mL) of 2-chlorothiazole (4.9 g, 41.0 mmol) at −78° C. The reaction mixture was stirred at the same temperature for 30 min. Diisopropyl disulfide (13.1 mL, 82.0 mmol) was added to the reaction and was stirred at the same temperature for 1.5 h. Water was added to quench the reaction and then $Et_2O$. The reaction mixture was transferred into a separation funnel and the aqueous layer was extracted with $Et_2O$ (3×). The combined organic layers were dried over $Na_2SO_4$ and concentrated under vacuum. The crude product was purified by flash chromatography on silica gel (dry packing) using a solution of EtOAc in hexanes (0 to 5% gradient) and afforded the title compound (2.31 g, 11.9 mmol, 29%) as yellow liquid.

4-bromo-2-chloro-5-(isopropylthio)thiazole

A 2 M solution of bromine (72.7 μL, 1.42 mmol) in dichloromethane ("DCM") was added dropwise to a solution of 2-chloro-5-(isopropylthio)thiazole (250 mg, 1.29 mmol) in DCM. The reaction was stirred for 3 hours at room temperature. A solution of $Na_2SO_3$ was added and the aqueous layer was extracted with DCM (3×). The combined organic layers were washed with brine, dried over $Na_2SO_4$, filtered and concentrated under vacuum. The crude product was purified by flash chromatography on silica gel using a solution of DCM in hexanes (50 to 100% gradient) and afforded the title compound (271 mg, 0.99 mmol, 77%) as colorless liquid.

4-bromo-2-hydrazinyl-5-(isopropylthio)thiazole

DIPEA (64 μL, 0.37 mmol) was added to a solution of hydrazine hydrochloride (13.0 mg, 0.18 mmol) and 4-bromo-2-chloro-5-(isopropylthio)thiazole (50.0 mg, 0.18 mmol) to NMP (2 mL) in a glass microwave vial. The vial was sealed and was heated to 150° C. for 1 h with microwave radiation. The crude product was purified by reverse flash chromatography (C18, using a gradient 0 to 40 to 70% MeCN in $H_2O$ with 10 mM $NH_4CO_2H$ buffer) and afforded the title compound (29.0 mg, 0.11 mmol, 59%) as yellow solid after extraction with $Et_2O$ and concentration under vacuum.

methyl 2-(methoxyimino)-3-(2-nitrobenzyl)-4-oxopentanoate

Methyl acetopyruvate (1.0 g, 6.94 mmol), methoxyhydroxylamine hydrochloride (0.58 g, 6.94 mmol) and molecular sieves (2.5 g) were placed in a flame dried round bottom flask equipped with a nitrogen inlet. Dry DMF (23 mL) was added and the round bottom flask was covered with foil and stirred overnight at room temperature. The reaction mixture was diluted with EtOAc (150 mL) and the organic phase was washed with water (3×50 mL) and brine (1×50 mL), dried with $Na_2SO_4$, filtered and concentrated under vacuum to afford the title compound (1.07 g, 6.16 mmol, 89%) as red liquid.

methyl 1-(4-bromo-5-(isopropylthio)thiazol-2-yl)-3-methyl-1H-pyrazole-5-carboxylate Methyl 2-(methoxyimino)-3-(2-nitrobenzyl)-4-oxopentanoate (4.00 g, 23.1 mmol) was dissolved in MeOH (115 mL).4-bromo-2-hydrazinyl-5-(isopropylthio)thiazole (6.19 g, 23.1 mmol) was added and then HCl 12 N (7.70 mL, 92.4 mmol) was added dropwise to the reaction mixture. The reaction mixture was heated to reflux overnight. The crude product was concentrated under vacuum and was purified by flash chromatography on silica gel (dry packing) using a solution of EtOAc in hexanes (5 to 20% gradient) and was purified a second time by flash chromatography on silica gel (dry packing) using a solution of DCM in hexanes (10 to 50% gradient) and afforded the title compound (1.89 g, 5.02 mmol, 22%) as orange oil.

methyl 4-bromo-1-(4-bromo-5-(isopropylthio)thiazol-2-yl)-3-methyl-1H-pyrazole-5-carboxylate A 2 M solution of bromine (3.32 mL, 6.64 mmol) in MeCN was added dropwise to a solution of methyl 1-(4-bromo-5-(isopropylthio)thiazol-2-yl)-3-methyl-1H-pyrazole-5-carboxylate (500 mg, 1.33 mmol) in a solution of DCM/MeCN (7 mL, 1:1). The reaction was stirred for 5 hours at room temperature. A solution of $Na_2SO_3$ was added and the aqueous layer was extracted with $Et_2O$ (3×). The combined organic layers were washed with brine, dried over $Na_2SO_4$, filtered and concentrated under vacuum. The crude product was purified by flash chromatography on silica gel using a solution of DCM in hexanes (20%) and afforded the title compound (421 mg, 0.93 mmol, 70%) as orange solid.

methyl 1-(4-(4-chloro-2-(oxetan-3-yloxy)phenyl)-5-(isopropylthio)thiazol-2-yl)-3-methyl-1H-pyrazole-5-carboxylate Degassed THF (2 mL) was added to a mixture of methyl 4-bromo-1-(4-bromo-5-(isopropylthio)thiazol-2-yl)-3-methyl-1H-pyrazole-5-carboxylate (100 mg, 0.220 mmol), 2-(4-chloro-2-(oxetan-3-yloxy)phenyl)-4,4,5,5-tetramethyl-1,3,2-dioxaborolane (137 mg, 0.220 mmol, 50% w/w), [1,1'-bis(di-tert-butylphosphino)ferrocene]dichloropalladium(II) (11 mg, 0.022 mmol) and potassium carbonate (152 mg, 1.10 mmol). The reaction mixture was heated at 90° C. for 18 hours. The mixture was mixed with silica and the solvent was evaporated for flash chromatography on silica gel purification using a solution of ethyl acetate in hexanes (2 to 40%) to give the title compound (17 mg, 0.035 mmol, 16%) as a pale yellow oil.

1-(4-(4-chloro-2-(oxetan-3-yloxy)phenyl)-5-(isopropylthio)thiazol-2-yl)-3-methyl-1H-pyrazole-5-carboxylic acid Methyl 1-(4-(4-chloro-2-(oxetan-3-yloxy)phenyl)-5-(isopropylthio)thiazol-2-yl)-3-methyl-1H-pyrazole-5-carboxylate (17 mg, 0.035 mmol) was diluted in a 1:1 solution of THF and MeOH (0.35 mL). 1M NaOH (0.070 mL, 0.070 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (50 to 70%). The product was lyophilysed to give the title compound (2 mg, 0.004 mmol, 12%) as a pale yellow solid.

$^1H$ NMR (500 MHz, DMSO) δ 7.34 (d, J=8.2 Hz, 1H), 7.14 (dd, J=8.1, 1.9 Hz, 1H), 6.83 (d, J=1.9 Hz, 1H), 6.64 (s, 1H), 5.38-5.31 (m, 1H), 4.89 (t, J=6.8 Hz, 2H), 4.49 (dd, J=7.3, 5.1 Hz, 2H), 3.21 (d, J=6.6 Hz, 1H), 2.25 (s, 3H), 1.14 (d, J=6.7 Hz, 6H); MS (m/z): 466.1 $[M+1]^+$.

Compound 2: 1-(4-(4-chloro-3-(oxetan-3-yloxy)phenyl)-5-(isopropylthio)thiazol-2-yl)-3-methyl-1H-pyrazole-5-carboxylic acid 3-(5-bromo-2-chlorophenoxv)oxetane Diisopropyl diazocarboxylate (292 mg, 1.45 mmol) was added to a solution of 5-bromo-2-chlorophenol (200 mg, 0.964 mmol), oxetan-3-ol (89 mg, 1.2 mmol) and triphenylphosphine (379 mg, 1.45 mmol) in THF (4.2 mL). The reaction mixture was stirred at r.t. for 18 h. Ethyl acetate was added and the mixture was washed with 1N NaOH (3×). The organic layer was dried with sodium sulfate, filtered and evaporated under reduced pressure. The crude product was purified by flash chromatography on silica gel using a solution of ethyl acetate in hexanes (10%) to give the title compound (222 mg, 0.842 mmol, 87%).

2-(4-chloro-3-(oxetan-3-yloxy)phenyl)-4,4,5,5-tetramethyl-1,3,2-dioxaborolane

Degassed dioxane was added to a mixture of 3-(5-bromo-2-chlorophenoxy)oxetane (100 mg, 0.379 mmol), pinacol diborane (116 mg, 0.455 mmol), [1,1'-Bis(diphenylphosphino)ferrocene]palladium(II) dichloride (28 mg, 0.038 mmol) and potassium acetate (112 mg, 1.14 mmol). The reaction mixture was heated at 85° C. for 18 hours. The mixture was filtered on celite and the pad was washed with dioxane. The filtrate was evaporated to give the title compound (238 mg, 202%, 50% w/w from NMR analysis) that was used as is.

methyl 1-(4-(4-chloro-3-(oxetan-3-yloxy)phenyl)-5-(isopropylthio)thiazol-2-yl)-3-methyl-1H-pyrazole-5-carboxylate Degassed THF (2 mL) was added to a mixture of methyl 4-bromo-1-(4-bromo-5-(isopropylthio)thiazol-2-yl)-3-methyl-1H-pyrazole-5-carboxylate (100 mg, 0.220 mmol) prepared in example 27, 2-(4-chloro-3-(oxetan-3-yloxy)phenyl)-4,4,5,5-tetramethyl-1,3,2-dioxaborolane (137 mg, 0.220 mmol, 50% w/w), [1,1'-bis(di-tert-butylphosphino)ferrocene]dichloropalladium(II) (11 mg, 0.022 mmol) and potassium carbonate (152 mg, 1.10 mmol). The reaction mixture was heated at 90° C. for 18 hours. The mixture was mixed with silica and the solvent was evaporated for flash chromatography on silica gel purification using a solution of ethyl acetate in hexanes (2 to 40%) to give the title compound (6.2 mg, 0.013 mmol, 66%) as a pale orange oil.

1-(4-(4-chloro-3-(oxetan-3-yloxy)phenyl)-5-(isopropylthio)thiazol-2-yl)-3-methyl-1H-pyrazole-5-carboxylic acid methyl 1-(4-(4-chloro-3-(oxetan-3-yloxy)phenyl)-5-(isopropylthio)thiazol-2-yl)-3-methyl-1H-pyrazole-5-carboxylate (6.2 mg, 0.013 mmol) was diluted in a 1:1 solution of THF and MeOH (0.13 mL). 1M NaOH (0.026 mL, 0.026 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (50 to 70%). The product was lyophilysed to give the title compound (1.2 mg, 0.003 mmol, 20%) as a pale yellow solid.

$^1H$ NMR (500 MHz, DMSO) δ 7.71-7.66 (m, 1H), 7.57 (d, J=8.3 Hz, 1H), 7.36 (d, J=1.8 Hz, 1H), 6.71 (s, 1H), 5.43-5.35 (m, 1H), 5.04 (t, J=6.8 Hz, 2H), 4.62 (dd, J=7.9, 4.9 Hz, 2H), 3.33 (sept, J=6.7 Hz, 1H), 2.27 (s, 3H), 1.22 (d, J=6.7 Hz, 6H); MS (m/z): 466.1 $[M+1]^+$.

Compound 3: 4-(3-fluorophenyl)-1-(5-(isopropylthio)-4-(4-(5-methyl-1,3,4-oxadiazol-2-yl)phenyl)thiazol-2-yl)-3-methyl-1H-pyrazole-5-carboxylic acid methyl 4-bromo-1-(5-(isopropylthio)-4-(4-(5-methyl-1,3,4-oxadiazol-2-yl)phenyl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), (4-(5-methyl-1,3,4-oxadiazol-2-yl)phenyl)boronic acid (38.1 mg, 0.187 mmol) and $K_2CO_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)$Cl_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (0 to 50% gradient) and afforded the title compound (57.8 mg, 0.108 mmol, 49%) as brown oil.

methyl 4-(3-fluorophenyl)-1-(5-(isopropylthio)-4-(4-(5-methyl-1,3,4-oxadiazol-2-yl)phenyl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(5-(isopropylthio)-4-(4-(5-methyl-1,3,4-oxadiazol-2-yl)phenyl)thiazol-2-yl)-3-methyl-1H-pyrazole-5-carboxylate (57.8 mg, 0.108 mmol), 3-fluorophenylboronic acid (18.2 mg, 0.130 mmol) and $Na_2CO_3$ (57.3 mg, 0.541 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd($PPh_3$)$_4$ (12.5 mg, 0.011 mmol). The vial was capped and placed in an oil bath at 85° C. for 16 h. The crude product was purified by flash chromatography on silica gel (dry packing) using a solution of EtOAc in hexanes (5 to 40% gradient), affording the title compound (25.4 mg, 0.046 mmol, 43%) as yellow solid.

4-(3-fluorophenyl)-1-(5-(isopropylthio)-4-(4-(5-methyl-1,3,4-oxadiazol-2-yl)phenyl)thiazol-2-yl)-3-methyl-1H-pyrazole-5-carboxylic acid Into a 25 mL round bottom flask, methyl 4-(3-fluorophenyl)-1-(5-(isopropylthio)-4-(4-(5-methyl-1,3,4-oxadiazol-2-yl)phenyl)thiazol-2-yl)-3-methyl-1H-pyrazole-5-carboxylate (25.4 mg, 0.046 mmol) was diluted with THF/MeOH (2 mL, 1:1). A solution of NaOH 1 M (92.4 µL, 0.092 mmol) was added and the reaction was stirred 16 h at rt. The reaction mixture was acidified with HCl 1 M and the crude product was concentrated under vacuum. The product was purified using a semi prep HPLC-MS (column X-Bridge 30×50, eluted with 40-60% MeCN/$NH_4CO_2H$ 10 mM, pH 3.8/Flow 45 ml/min/11 min), resulting in the title compound (3.99 mg, 0.007 mmol, 16%) as a white solid after lyophilisation.

$^1$H NMR (500 MHz, DMSO) δ 8.26 (d, J=8.2 Hz, 2H), 8.06 (d, J=8.5 Hz, 2H), 7.52-7.33 (m, 3H), 7.12 (s, 2H), 3.37-3.24 (m, 1H), 2.61 (s, 3H), 2.30 (s, 3H), 1.24 (d, J=6.7 Hz, 6H); MS (m/z): 536.1 $[M+1]^+$.

Compound 4: 4-(3-fluorophenyl)-1-(5-(isopropylthio)-4-(4-methylcyclohex-1-en-1-yl)thiazol-2-yl)-3-methyl-1H-pyrazole-5-carboxylic acid methyl 4-bromo-1-(5-(isopropylthio)-4-(4-methylcyclohex-1-en-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), 4,4,5,5-tetramethyl-2-(4-methylcyclohex-1-en-1-yl)-1,3,2-dioxaborolane (41.5 mg, 0.187 mmol) and $K_2CO_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)$Cl_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (0 to 10% gradient) and afforded the title compound (45.6 mg, 0.097 mmol, 44%) as yellow oil.

methyl 4-(3-fluorophenyl)-1-(5-(isopropylthio)-4-(4-methylcyclohex-1-en-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(5-(isopropylthio)-4-(4-methylcyclohex-1-en-1-yl)thiazol-2-yl)-3-methyl-1H-pyrazole-5-carboxylate (44.6 mg, 0.085 mmol), 3-fluorophenylboronic acid (14.3 mg, 0.102 mmol) and $Na_2CO_3$ (45.2 mg, 0.427 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd($PPh_3$)$_4$ (9.86 mg, 0.009 mmol). The vial was capped and placed in an oil bath at 85° C. for 16 h. The crude product was purified by flash chromatography on silica gel (wet loading with DCM) using a solution of EtOAc in hexanes (1% isochratic), affording the title compound (40.0 mg, 0.082 mmol, 97%) as yellow oil.

4-(3-fluorophenyl)-1-(5-(isopropylthio)-4-(4-methylcyclohex-1-en-1-yl)thiazol-2-yl)-3-methyl-1H-pyrazole-5-carboxylic acid Into a round bottom flask, methyl 4-(3-fluorophenyl)-1-(5-(isopropylthio)-4-(4-methylcyclohex-1-en-1-yl)thiazol-2-yl)-3-methyl-1H-pyrazole-5-carboxylate (40.0 mg, 0.082 mmol) was diluted with THF/MeOH (2 mL, 1:1). A solution of NaOH 1 M (165 µL, 0.165 mmol) was added and the reaction was stirred 16 h at rt. The reaction mixture was acidified with HCl 1 M and the crude product was concentrated under vacuum. The product was purified using a semi prep HPLC-MS (column X-Bridge 30×50, eluted with 60-80% MeCN/$NH_4CO_2H$ 10 mM, pH 3.8/Flow 45 ml/min/11 min), resulting in the title compound (2.55 mg, 0.005 mmol, 7%) as yellow solid after lyophilisation.

$^1$H NMR (500 MHz, DMSO) δ 7.50 (dd, J=14.9, 7.8 Hz, 1H), 7.35-7.27 (m, 2H), 7.21 (s, 1H), 6.35 (s, 1H), 3.32-3.16 (m, 1H), 2.57 (s, 1H), 2.45-2.35 (m, 1H), 2.32 (s, 1H), 2.28 (s, 3H), 1.86-1.74 (m, 2H), 1.67 (s, 1H), 1.33-1.26 (m, 1H), 1.24 (d, J=6.6 Hz, 6H), 0.98 (d, J=6.6 Hz, 3H); MS (m/z): 472.1 $[M+1]^+$.

Compound 5: 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid methyl 4-bromo-1-(5-(isopropylthio)-4-(4-(trifluoromethyl)cyclohex-1-en-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), 4,4,5,5-tetramethyl-2-(4-(trifluoromethyl)cyclohex-1-en-1-yl)-1,3,2-dioxaborolane (51.6 mg, 0.187 mmol) and $K_2CO_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)$Cl_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (0 to 10% gradient) and afforded the title compound (47.4 mg, 0.090 mmol, 41%) as yellow oil.

4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid In a 5 mL glass microwave vial equipped with a magnetic stirring bar and nitrogen flow at room temperature was placed methyl 4-bromo-1-(5-(isopropylthio)-4-(4-(trifluoromethyl)cyclohex-1-en-1-yl)thiazol-2-yl)-3-methyl-1H-pyrazole-5-carboxylate (47.4 mg, 0.090 mmol), 3-fluorophenylboronic acid (15.2 mg, 0.108 mmol) and $Na_2CO_3$ (47.9 mg, 0.452 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd($PPh_3$)$_4$ (10.4 mg, 0.009 mmol). The vial was capped and placed in an oil bath at 85° C. for 16 h. The reaction mixture was diluted with EtOAc and transferred into an extraction funnel. The layers were separated and the aqueous layer was extracted with EtOAc (3×). The combined organic layers were dried over $Na_2SO_4$, filtered and concentrated under vacuum. THF/MeOH (2 mL, 1:1) and NaOH 1M (181 μL, 0.181 mmol) were added and the reaction was stirred 16 h at rt. The product was purified using a semi prep HPLC-MS (column X-Bridge 30×50, eluted with 55-75% MeCN/$NH_4CO_2H$ 10 mM, pH 3.8/Flow 45 ml/min/11 min), resulting in the title compound (12.8 mg, 0.024 mmol, 27%) as yellow solid after lyophilisation.

$^1$H NMR (500 MHz, DMSO) δ 7.53-7.42 (m, 1H), 7.30-7.23 (m, 2H), 7.22-7.15 (m, 1H), 6.41 (s, 1H), 3.32-3.22 (m, 1H), 2.74-2.60 (m, 1H), 2.50-2.33 (m, 3H), 2.26 (s, 3H), 2.23-2.15 (m, 1H), 2.07-1.97 (m, 1H), 1.57-1.46 (m, 1H), 1.23 (dd, J=6.7, 3.4 Hz, 6H); MS (m/z): 526.3 [M+1]$^+$.

Compound 6: 1-(4-(4,4-dimethylcyclohex-1-en-1-yl)-5-(isopropylthio)thiazol-2-yl)-4-(3-fluorophenyl)-3-methyl-1H-pyrazole-5-carboxylic acid methyl 4-bromo-1-(4-(4,4-dimethylcyclohex-1-en-1-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), the 2-(4,4-dimethylcyclohex-2-en-1-yl)-4,4,5,5-tetramethyl-1,3,2-dioxaborolane (52 mg, 0.22 mmol), $K_2CO_3$ (152 mg, 1.10 mmol) and THF (2 mL). Nitrogen was bubbled in the solvent for 10 minutes followed by the addition of the catalyst Pd(dtbpf)$Cl_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (57 mg, 0.12 mmol, 54%) as a yellow oil. MS (m/z): 484.0 [M+1]+.

1-(4-(4,4-dimethylcyclohex-1-en-1-yl)-5-(isopropylthio)thiazol-2-yl)-4-(3-fluorophenyl)-3-methyl-1H-pyrazole-5-carboxylic acid In a 5 mL glass microwave vial equipped with a magnetic stirring bar and nitrogen flow at room temperature was placed the methyl 4-bromo-1-(4-(4,4-dimethylcyclohex-1-en-1-yl)-5-(isopropylthio)thiazol-2-yl)-3-methyl-1H-pyrazole-5-carboxylate (53 mg, 0.11 mmol), (3-fluorophenyl)boronic acid (18 mg, 0.13 mmol) and $Na_2CO_3$ (58 mg, 0.55 mmol). Nitrogen gas was bubbled through a solution of dioxane/water (2 mL, 4:1) and then the solution was added to the microwave vial, followed by the addition of the catalyst Pd($PPh_3$)$_4$ (13 mg, 0.011 mmol). The vial was capped and placed in an oil bath at 85° C. for 16 h. LiOH (13 mg, 0.55 mmol) was added to the reaction mixture and stirred under microwave radiation at 110° C. for 15 min. The solvent was evaporated under vacuum and the product was purified using a semi prep HPLC-MS (column X-Bridge 30×50, eluted with 70-90% MeCN/$NH_4CO_2H$ 10 mM, pH 3.8/Flow 45 ml/min/10 min), resulting in the title compound (13 mg, 0.027 mmol, 24%) as yellow solid after lyophilization.

$^1$H NMR (500 MHz, DMSO) δ 7.52-7.44 (m, 1H), 7.35-7.27 (m, 2H), 7.23-7.15 (m, 1H), 6.33-6.27 (m, 1H), 3.28-3.19 (m, 1H), 2.48-2.42 (m, 2H), 2.28 (s, 3H), 2.00-1.95 (m, 2H), 1.43 (t, J=6.4 Hz, 2H), 1.23 (d, J=6.7 Hz, 6H), 0.94 (s, 6H). MS (m/z): 486.1 [M+1]$^+$.

Compound 7: 4-(3-fluorophenyl)-1-(5-(isopropylthio)-4-(1,4-dioxaspiro[4.5]dec-7-en-8-yl)thiazol-2-yl)-3-methyl-1H-pyrazole-5-carboxylic acid methyl 4-bromo-1-(5-(isopropylthio)-4-(1,4-dioxaspiro[4.5]dec-7-en-8-yl)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), the 4,4,5,5-tetramethyl-2-(1,4-dioxaspiro[4.5]dec-6-en-8-yl)-1,3,2-dioxaborolane (59 mg, 0.22 mmol), $K_2CO_3$ (152 mg, 1.10 mmol) and THF (2 mL). Nitrogen was bubbled in the solvent for 10 minutes followed by the addition of the catalyst Pd(dtbpf)$Cl_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 20% EtOAc in hexanes to give the title compound (55 mg, 0.11 mmol, 49%) as a yellow oil. MS (m/z): 514.0 [M+1]+.

4-(3-fluorophenyl)-1-(5-(isopropylthio)-4-(1,4-dioxaspiro[4.5]dec-7-en-8-yl)thiazol-2-yl)-3-methyl-1H-pyrazole-5-carboxylic acid In a 5 mL glass microwave vial equipped with a magnetic stirring bar and nitrogen flow at room temperature was placed the methyl 4-bromo-1-(5-(isopropylthio)-4-(1,4-dioxaspiro[4.5]dec-7-en-8-yl)thiazol-2-yl)-3-methyl-1H-pyrazole-5-carboxylate (53 mg, 0.10 mmol), (3-fluorophenyl)boronic acid (17 mg, 0.12 mmol) and $Na_2CO_3$ (54 mg, 0.51 mmol). Nitrogen gas was bubbled through a solution of dioxane/water (2 mL, 4:1) and then the solution was added to the microwave vial, followed by the addition of the catalyst $Pd(PPh_3)_4$ (12 mg, 0.010 mmol). The vial was capped and placed in an oil bath at 85° C. for 16 h. The reaction mixture was diluted with EtOAc, washed with water and brine. Dried $MgSO_4$, filtered and concentrated in vacuo. The reaction mixture was dissolved in a 1/1 mixture of THF/MeOH (2 mL) and treated with 1N NaOH (102 μL, 0.204 mmol). After 1 h, more 1N NaOH (102 μL, 0.204 mmol) was added and stirring was continued for 16 h. The solvent was evaporated under vacuum and the product was purified using a semi prep HPLC-MS (column X-Bridge 30×50, eluted with 55-75% $MeCN/NH_4CO_2H$ 10 mM, pH 3.8/Flow 45 ml/min/10 min), resulting in the title compound (14 mg, 0.027 mmol, 26%) as yellow solid after lyophilization.

$^1H$ NMR (500 MHz, DMSO) δ 7.53-7.45 (m, 1H), 7.34-7.27 (m, 2H), 7.25-7.16 (m, 1H), 6.34-6.28 (m, 1H), 3.92 (s, 4H), 3.32-3.19 (m, 1H), 2.67-2.60 (m, 2H), 2.43-2.36 (m, 2H), 2.28 (s, 3H), 1.77 (t, J=6.5 Hz, 2H), 1.25 (d, J=6.7 Hz, 6H). MS (m/z): 516.1[M+1]$^+$.

Compound 8: 1-(4-(4-chloro-3-(morpholine-4-carbonyl)phenyl)-5-(isopropylthio)thiazol-2-yl)-4-(3-fluorophenyl)-3-methyl-1H-pyrazole-5-carboxylic acid methyl 4-bromo-1-(4-(4-chloro-3-(morpholine-4-carbonyl)phenyl)-5-(isopropylthio)thiazol-2-yl)-3-methyl-1H-pyrazole-5-carboxylate Degassed THF (2 mL) was added to a mixture of methyl 4-bromo-1-(4-bromo-5-(isopropylthio)thiazol-2-yl)-3-methyl-1H-pyrazole-5-carboxylate (75.0 mg, 0.165 mmol) prepared described above with respect to Compound 1, (4-chloro-3-(morpholine-4-carbonyl)phenyl)boronic acid (44 mg, 0.16 mmol), [1,1'-bis(di-tert-butylphosphino)ferrocene]dichloropalladium(II) (8.2 mg, 0.016 mmol) and potassium carbonate (114 mg, 0.824 mmol). The reaction mixture was heated at 90° C. for 18 hours. Water was added and the mixture was extracted with ethyl acetate (2×). The combined organic layers were dried with sodium sulfate, filtered and evaporated. The crude product was purified by flash chromatography on silica gel using a solution of ethyl acetate in hexanes (2 to 10%) to give the title compound (47 mg, 0.078 mmol, 47%) as a pale orange oil.

1-(4-(4-chloro-3-(morpholine-4-carbonyl)phenyl)-5-(isopropylthio)thiazol-2-yl)-4-(3-fluorophenyl)-3-methyl-1H-pyrazole-5-carboxylic acid A solution of methyl 4-bromo-1-(4-(4-chloro-3-(morpholine-4-carbonyl)phenyl)-5-(isopropylthio)thiazol-2-yl)-3-methyl-1H-pyrazole-5-carboxylate (47 mg, 0.078 mmol), (3-fluorophenyl)boronic acid (13 mg, 0.094 mmol), $Pd(PPh_3)_4$ (9 mg, 0.008 mmol), $Na_2CO_3$ (41 mg, 0.39 mmol) in degassed 1,4-dioxane and $H_2O$ (4:1, 1.6 mL) was heated at 85° C. for 18 hours. LiOH hydrate (16 mg, 0.39 mmol) was added and the reaction was heated at 95° C. under microwave radiation for 45 minutes. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (45 to 65%). The product was lyophylised to give the title compound (2 mg, 0.003 mmol, 4%) as an off white solid.

$^1H$ NMR (500 MHz, DMSO) δ 8.06 (d, J=8.1 Hz, 1H), 7.99 (s, 1H), 7.65 (d, J=8.5 Hz, 1H), 7.52-7.44 (m, 1H), 7.41-7.31 (m, 2H), 7.22-7.13 (m, 1H), 3.75-3.62 (m, 4H), 3.61-3.51 (m, 2H), 3.33 (1H, below water signal), 3.22-3.15 (m, 2H), 2.30 (s, 3H), 1.22 (d, J=5.8 Hz, 6H); MS (m/z): 552.1 [M+1]$^+$.

Compound 9: 4-(3,4-dichlorophenyl)-2-(4-(2,6-dimethylpyridin-4-yl)-3-methyl-1H-pyrazol-1-yl)-5-(isopropylthio)thiazole 1-(4-(3,4-dichlorophenyl)-5-(isopropylthio)thiazol-2-yl)-4-(2,6-dimethylpyridin-4-yl)-3-methyl-1H-pyrazole-5-carboxylic acid (38.0 mg, 0.071 mmol), copper chromite (12.0 mg, 0.085 mmol) and Quinoline (0.6 ml) was heated at 230° C. for 15 min under microwave radiation. The crude product was purified by reverse chromatography on C-18 column with a solution of MeCN in water (containing 10 mM of $NH_4CO_2H$) (55 to 80 to 100%), affording the title compound (24.7 mg, 0.050 mmol, 71%) as beige solid after lyophilisation.

$^1H$ NMR (500 MHz, DMSO) δ 9.05 (s, 1H), 8.32 (d, J=2.0 Hz, 1H), 8.14 (dd, J=8.4, 2.1 Hz, 1H), 7.79 (d, J=8.5 Hz, 1H), 7.34 (s, 2H), 3.38-3.32 (m, J=13.4, 6.7 Hz, 1H), 3.29 (s, 3H), 2.47 (s, 6H), 1.23 (d, J=6.7 Hz, 6H); MS (m/z): 489.2 [M+1]$^+$.

Compound 10: 2-(4-(3-fluorophenyl)-3,5-dimethyl-1H-pyrazol-1-yl)-5-(isopropylthio)-4-(4-(trifluoromethyl)phenyl)thiazole 4-iodo-3,5-dimethyl-1H-pyrazole 3,5-dimethyl-1H-pyrazole (100 mg, 1.04 mmol) was dissolved in 1.0 mL of TFA. N-iodosuccinimide (234 mg, 1.04 mmol) was added in one portion. The reaction was stirred at rt for 1h. LCMS showed clean reaction. Water and EtOAc were added and the phases were separated. The organic phase was washed with a aqueous saturated solution of sodium sulfite and was dried over sodium sulfate, filtered and concentrated. Afforded 230 mg of crude product (1.04 mmol, 99%) as a white solid.

4-(3-fluorophenyl)-3,5-dimethyl-1H-pyrazole 4-iodo-3,5-dimethyl-1H-pyrazole (231 mg, 1.04 mmol), boronic acid (281 mg, 2.01 mmol), sodium carbonate (551 mg, 5.20 mmol), dioxane (5.2 ml) and water (1.3 ml) were charged to a screw-cap type tube. The mixture was degassed for 10 min and $Pd(PPh_3)_4$ (60 mg, 0.05 mmol) was added. The tube was sealed and the mixture was heated to 85° C. After 1h there was no reaction. After 16 h the ratio of iodopyrazole:product was 1:6. The mixture was heated to 110° C. After 6h there was no iodopyrazole starting material remaining, so the mixture was cooled to rt, diluted with water and EtOAc. The phases were separated and the aqueous phase was washed with brine. SiO2 was added to the organic phase and it was concentrated to dryness. The crude on silica was purified on Isco using a gradient of hexanes to EtOAc. Afforded 144 mg (0.76 mmol, 73%) of product as a colorless oil.

2-thiocyanato-1-(4-(trifluoromethyl)phenyl)ethanone

Potassium thiocyanate (9.55 g, 98.3 mmol) was added to a stirred solution of 2-bromo-1-(4-(trifluoromethyl)phenyl) ethanone (25.0 g, 93.6 mmol) in MeCN (178 mL) at rt. The reaction mixture was heated to reflux (90° C.) for 2 h, then cooled to room temperature and diluted with water and EtOAc. The aqueous layer was extracted with EtOAc (3×) The combined organic layers were washed with brine, dried over $MgSO_4$, filtered and concentrated in vacuo to give the title compound (23.3 g, 94.9 mmol, 97%), which was used without further purification.

2-chloro-4-(4-(trifluoromethyl)phenyl)thiazole

A mixture of 2-thiocyanato-1-(4-(trifluoromethyl)phenyl) ethanone (23.3 g, 94.9 mmol) and 4 M HCl in dioxane (142 mL, 569 mmol) in dioxane (95 mL) was stirred for 16 h at rt. The reaction mixture was concentrated in vacuo and the residue was diluted with sat. aq. $NaHCO_3$ and extracted with EtOAc (2×). The combined organic layers were washed with brine, dried over $MgSO_4$, filtered and concentrated in vacuo and afforded the title compound (25.0 g, 94.8 mmol, 100%) as brown solid.

2-chloro-5-(isopropylthio)-4-(4-(trifluoromethyl) phenyl)thiazole

A 2.5 M solution of n-BuLi in hexanes (18.8 mL, 40.3 mmol) was added to a THF solution (107 mL) of 2-chloro-4-(4-(trifluoromethyl)phenyl)thiazole (10.0 g, 32.3 mmol) at −78° C. The reaction mixture was stirred at the same temperature for 30 min. Diisopropyl disulfide (10.3 mL, 64.5 mmol) was added to the reaction and was stirred at the same temperature for 2 h. Water was added to quench the reaction and then $Et_2O$. The reaction mixture was transferred into a separation funnel and the layers were separated. The aqueous layer was extracted with $Et_2O$ (2×). The combined organic layers were dried over $Na_2SO_4$ and concentrated under vacuum. The crude product was purified by flash chromatography on silica gel (dry packing) using a solution of EtOAc in hexanes (0 to 1% gradient) and afforded the title compound (3.05 g, 9.03 mmol, 28%) as yellow oil.

2-(4-(3-fluorophenyl)-3,5-dimethyl-1H-pyrazol-1-yl)-5-(isopropylthio)-4-(4-(trifluoromethyl)phenyl) thiazole Into a 10 mL microwave vial, was placed 4-(3-fluorophenyl)-3,5-dimethyl-1H-pyrazole (140 mg, 1.0 mmol), the thiazole prepared above (372 mg, 1.1 mmol), $K_2CO_3$ (690 mg, 5.0 mmol) and DMSO (3.3 ml). Nitrogen was bubbled into DMSO for 10 minutes. And then CuI (57 mg, 0.30 mmol) was added. The resulting solution was cap and heated with a microwave at 100° C. 3 hours. LCMS showed 40% conversion (ratio pyrazole:product) and clean reaction. The mixture was heated in an oil bath for 3h. LCMS showed 74% conversion. Heating was continued for 16h. LCMS showed complete conversion. The mixture was diluted with EtOAc and water, the phases were separated and the organic phase was washed with water 3×, then brine. Silica was added to the organic phase and it was concentrated to dryness. The crude on SiO2 was purified on Isco using a gradient of hexanes to 10% DCM. Afforded 151 mg (0.307 mmol, 31%) of a yellow oil. This mixture was repurified on reverse phase Isco using C18 column, eluting with a gradient of 50-100% MeCN/water (10 mM ammonium formate, pH 3.8). The fractions containing the product were concentrated to remove most of the acetonitrile, water was added and the flask was frozen and lyophilized. The product (99 mg, 0.201 mmol, 20% yield) was afforded as a pale yellow solid.

$^1H$ NMR (500 MHz, DMSO) δ 8.24 (d, J=8.2 Hz, 2H), 7.87 (d, J=8.4 Hz, 2H), 7.53 (dd, J=14.2, 7.9 Hz, 1H), 7.29-7.18 (m, 3H), 3.39-3.33 (m, 1H), 2.69 (s, 3H), 2.25 (s, 3H), 1.23 (d, J=6.7 Hz, 6H); MS (m/z): 492.3 $[M+1]^+$.

Compound 11: 4-(3-fluorophenyl)-1-(5-(isopropylthio)-4-(piperidin-1-yl)thiazol-2-yl)-3-methyl-1H-pyrazole-5-carboxylic acid methyl 4-bromo-1-(5-(isopropylthio)-4-(piperidin-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), XantPhos (12.7 mg, 0.022 mmol) and $Cs_2CO_3$ (358 mg, 1.10 mmol), nitrogen and vacuum cycles were performed (2×). Nitrogen gas was bubbled through a solution of dioxane (2 mL) and piperidine (21.7 uL, 0.220 mmol) then the solution was added to the microwave vial, followed by the addition of the catalyst RuPhos Palladacycle (17.9 mg, 0.022 mmol). The vial was capped and placed in an oil bath at 105° C. for 16 h. The solvent was evaporated under vacuum and the crude product was purified by flash chromatography on silica gel (dry packing) using a solution of EtOAc in hexanes (1% isochratic), affording the title compound (41.0 mg, 0.089 mmol, 41%) as yellow oil.

4-(3-fluorophenyl)-1-(5-(isopropylthio)-4-(piperidin-1-yl)thiazol-2-yl)-3-methyl-1H-pyrazole-5-carboxylic acid In a 5 mL glass microwave vial equipped with a magnetic stirring bar and nitrogen flow at room temperature was placed methyl 4-bromo-1-(5-(isopropylthio)-4-(piperidin-1-yl)thiazol-2-yl)-3-methyl-1H-pyrazole-5-carboxylate (41.0 mg, 0.089 mmol), 3-fluorophenylboronic acid (15.0 mg, 0.108 mmol) and $Na_2CO_3$ (47.3 mg, 0.446 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$(10.3 mg, 0.009 mmol). The vial was capped and placed in an oil bath at 85° C. for 16 h. LiOH (18.7 mg, 0.446 mmol) was added to the reaction mixture and stirred under microwave radiation at 120° C. for 10 min. The reaction mixture was diluted with EtOAc and HCl 0.1 M. The aqueous layer was extracted with EtOAc (2×) and the combined organic layers were washed with brine, dried over $Na_2SO_4$, filtered and concentrated under vacuum. The product was purified using a semi prep HPLC-MS (column X-Bridge 30×50, eluted with 55-75% $MeCN/NH_4CO_2H$ 10 mM, pH 3.8/Flow 45 ml/min/11 min), resulting in the title compound (3.24 mg, 0.007 mmol, 8%) as yellow solid after lyophilisation.

$^1H$ NMR (500 MHz, DMSO) δ 7.55-7.40 (m, 1H), 7.41-7.24 (m, 2H), 7.23-7.05 (m, 1H), 3.59-3.49 (m, 4H), 3.18-3.06 (m, 1H), 2.27 (s, 3H), 1.55 (s, 6H), 1.23 (d, J=6.7 Hz, 6H); MS (m/z): 461.2 $[M+1]^+$.

Compound 12: 4-(3-fluorophenyl)-1-(5-(isopropylthio)-4-(4-(trifluoromethyl)piperidin-1-yl)thiazol-2-yl)-3-methyl-1H-pyrazole-5-carboxylic acid methyl 4-bromo-1-(5-(isopropylthio)-4-(4-(trifluoromethyl)piperidin-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (100 mg, 0.220 mmol), 4-(trifluoromethyl)piperidine (41.7 mg, 0.220 mmol), XantPhos (12.7 mg, 0.022 mmol) and $Cs_2CO_3$ (358 mg, 1.10 mmol), nitrogen and vacuum cycles were performed (2×). Nitrogen gas was bubbled through dioxane (2 mL), which was then added to the microwave vial, followed by the addition of the catalyst RuPhos Palladacycle (17.9 mg, 0.022 mmol). The vial was capped and placed in an oil bath at 105° C. for 16 h. The solvent was evaporated under vacuum and the crude product was purified by flash chromatography on silica gel (dry packing) using a solution of EtOAc in hexanes (1% isochratic), affording the title compound (52.0 mg, 0.099 mmol, 45%) as yellow oil.

4-(3-fluorophenyl)-1-(5-(isopropylthio)-4-(4-(trifluoromethyl)piperidin-1-yl)thiazol-2-yl)-3-methyl-1H-pyrazole-5-carboxylic acid In a 5 mL glass microwave vial equipped with a magnetic stirring bar and nitrogen flow at room temperature was placed methyl 4-bromo-1-(5-(isopropylthio)-4-(4-(trifluoromethyl)piperidin-1-yl)thiazol-2-yl)-3-methyl-1H-pyrazole-5-carboxylate (52.0 mg, 0.099 mmol), 3-fluorophenylboronic acid (16.6 mg, 0.118 mmol) and $Na_2CO_3$ (52.3 mg, 0.493 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$(11.4 mg, 0.010 mmol). The vial was capped and placed in an oil bath at 85° C. for 16 h. LiOH (42.0 mg, 0.493 mmol) was added to the reaction mixture and stirred under microwave radiation at 120° C. for 10 min. The reaction mixture was diluted with EtOAc and HCl 0.1 M. The aqueous layer was extracted with EtOAc (2×) and the combined organic layers were washed with brine, dried over $Na_2SO_4$, filtered and concentrated under vacuum. The product was purified using a semi prep HPLC-MS (column X-Bridge 30×50, eluted with 55-75% $MeCN/NH_4CO_2H$ 10 mM, pH 3.8/Flow 45 ml/min/11 min), resulting in the title compound (3.41 mg, 0.007 mmol, 7%) as yellow solid after lyophilisation.

$^1H$ NMR (500 MHz, DMSO) δ 7.52-7.43 (m, 1H), 7.36-7.26 (m, 2H), 7.19 (t, J=7.6 Hz, 1H), 4.38 (d, J=12.8 Hz, 2H), 3.19-3.07 (m, 1H), 2.95-2.86 (m, 2H), 2.58-2.51 (m, 1H), 2.28 (s, 3H), 1.80 (d, J=10.7 Hz, 2H), 1.49 (qd, J=12.6, 4.1 Hz, 2H), 1.24 (d, J=6.7 Hz, 6H); MS (m/z): 529.1 $[M+1]^+$.

Compound 13: 4-(3-fluorophenyl)-1-(5-(isopropylthio)-4-(4-(trifluoromethyl)phenyl)thiazol-2-yl)-3-methoxy-1H-pyrazole-5-carboxylic acid 2-thiocyanato-1-(4-(trifluoromethyl)phenyl)ethanone Potassium thiocyanate (9.55 g, 98.3 mmol) was added to a stirred solution of 2-bromo-1-(4-(trifluoromethyl)phenyl)ethanone (25.0 g, 93.6 mmol) in MeCN (178 mL) at rt. The reaction mixture was heated to reflux (90° C.) for 2 h, then cooled to room temperature and diluted with water and EtOAc. The aqueous layer was extracted with EtOAc (3×) The combined organic layers were washed with brine, dried over $MgSO_4$, filtered and concentrated in vacuo to give the title compound (23.3 g, 94.9 mmol, 97%), which was used without further purification.

2-chloro-4-(4-(trifluoromethyl)phenyl)thiazole

A mixture of 2-thiocyanato-1-(4-(trifluoromethyl)phenyl)ethanone (23.3 g, 94.9 mmol) and 4 M HCl in dioxane (142 mL, 569 mmol) in dioxane (95 mL) was stirred for 16 h at rt. The reaction mixture was concentrated in vacuo and the residue was diluted with sat. aq. $NaHCO_3$ and extracted with EtOAc (2×). The combined organic layers were washed with brine, dried over $MgSO_4$, filtered and concentrated in vacuo and afforded the title compound (25.0 g, 94.8 mmol, 100%) as brown solid.

2-chloro-5-(isopropylthio)-4-(4-(trifluoromethyl)phenyl)thiazole

A 2.5 M solution of n-BuLi in hexanes (18.8 mL, 40.3 mmol) was added to a THF solution (107 mL) of 2-chloro-4-(4-(trifluoromethyl)phenyl)thiazole (10.0 g, 32.3 mmol) at −78° C. The reaction mixture was stirred at the same temperature for 30 min. Diisopropyl disulfide (10.3 mL, 64.5 mmol) was added to the reaction and was stirred at the same temperature for 2 h. Water was added to quench the reaction and then $Et_2O$. The reaction mixture was transferred into a separation funnel and the layers were separated. The aqueous layer was extracted with $Et_2O$ (2×). The combined organic layers were dried over $Na_2SO_4$ and concentrated under vacuum. The crude product was purified by flash chromatography on silica gel (dry packing) using a solution of EtOAc in hexanes (0 to 1% gradient) and afforded the title compound (3.05 g, 9.03 mmol, 28%) as yellow oil.

2-hydrazinyl-5-(isopropylthio)-4-(4-(trifluoromethyl)phenyl)thiazole

DIPEA (3.2 mL, 18.2 mmol) was added to a solution of hydrazine hydrochloride (1.2 g, 18.2 mmol) and 2-chloro-5-(isopropylthio)-4-(4-(trifluoromethyl)phenyl)thiazole (3.1 g, 9.1 mmol) to NMP (18 mL) in a round bottom flask. The flask was heated to 135° C. for 2 h in an oil bath. The reaction mixture was diluted with water and extracted with $Et_2O$. The combined organic layers were washed with brine (3×), and dried over $Na_2SO_4$, filtered and concentrated under vacuum. This afforded the title compound (2.85 g, 8.55 mmol, 95%) as blue oil.

methyl 3-hydroxy-1-(5-(isopropylthio)-4-(4-(trifluoromethyl)phenyl)thiazol-2-yl)-1H-pyrazole-5-carboxylate A solution of 2-hydrazinyl-5-(isopropylthio)-4-(4-(trifluoromethyl)phenyl)thiazole (1.9 g, 5.76 mmol) in toluene (5 mL) was slowly added to a solution of dimethyl 2,5-dioxohex-3-ynedioate (900 mg, 6.33 mmol) in toluene (3 mL) and AcOH (4 mL) at 0° C. The reaction was stirred at rt for 1 h and was refluxed for 4 h. The reaction mixture was concentrated under vacuum and The crude product was purified by flash chromatography on silica gel (dry packing)

using a solution of EtOAc in hexanes (5 to 30% gradient), affording the title compound (714 mg, 1.61 mmol, 28%) as yellow oil.

methyl 1-(5-(isopropylthio)-4-(4-(trifluoromethyl) phenyl)thiazol-2-yl)-3-methoxy-1H-pyrazole-5-carboxylate In a round bottom flask equipped with a magnetic stirring bar and nitrogen flow at room temperature was placed ADDP (171 mg, 0.677 mmol) and tributylphosphine (205 mg, 1.02 mmol) in THF (7 mL), followed by the addition of methyl 3-hydroxy-1-(5-(isopropylthio)-4-(4-(trifluoromethyl)phenyl)thiazol-2-yl)-1H-pyrazole-5-carboxylate (150 mg, 0.338 mmol) and MeOH (20.6 μL, 0.507 mmol). The reaction mixture was heated to 80° C. for 3 h. The reaction mixture was concentrated under vacuum and dissolved in $Et_2O$ to filtrate the tributylphosphine oxide. The filtrate was concentrated under vacuum and the crude product was purified by flash chromatography on silica gel (dry packing) using a solution of EtOAc in hexanes (10 to 30% gradient), affording the title compound (115 mg, 0.251 mmol, 74%) as yellow oil.

methyl 4-bromo-1-(5-(isopropylthio)-4-(4-(trifluoromethyl)phenyl)thiazol-2-yl)-3-methoxy-1H-pyrazole-5-carboxylate A 2 M solution of bromine in acetonitrile (0.45 mL, 0.900 mmol) was added to a solution of methyl 1-(5-(isopropylthio)-4-(4-(trifluoromethyl)phenyl)thiazol-2-yl)-3-methoxy-1H-pyrazole-5-carboxylate (137 mg, 0.300 mmol) in MeCN/DCM (4 mL, 1:1 mL). The reaction was stirred for 3 hours at room temperature. A saturated aqueous solution of $Na_2SO_3$ was added and the reaction mixture was extracted with EtOAc (3×). The combined organic layers were dried with sodium sulfate, filtered and evaporated under reduced pressure. The crude product was purified by flash chromatography (dry packing) on silica gel using a solution of EtOAc in hexanes (2 to 10%), affording the title compound (98.0 mg, 0.183 mmol, 61%) as yellow oil.

4-(3-fluorophenyl)-1-(5-(isopropylthio)-4-(4-(trifluoromethyl)phenyl)thiazol-2-yl)-3-methoxy-1H-pyrazole-5-carboxylic acid In a 5 mL glass microwave vial equipped with a magnetic stirring bar and nitrogen flow at room temperature was placed methyl 4-bromo-1-(5-(isopropylthio)-4-(4-(trifluoromethyl)phenyl)thiazol-2-yl)-3-methoxy-1H-pyrazole-5-carboxylate (98.0 mg, 0.183 mmol), 3-fluorophenylboronic acid (60.7 mg, 0.219 mmol) and $Na_2CO_3$ (96.8 mg, 0.914 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (21.1 mg, 0.018 mmol). The vial was capped and placed in an oil bath at 85° C. for 16 h. LiOH (38.3 mg, 0.914 mmol) was added to the reaction mixture and stirred under microwave radiation at 120° C. for 10 min. The reaction mixture was diluted with EtOAc and HCl 0.1 M. The aqueous layer was extracted with EtOAc (2×) and the combined organic layers were washed with brine, dried over $Na_2SO_4$, filtered and concentrated under vacuum. The product was purified using a semi prep HPLC-MS (column X-Bridge 30×50, eluted with 40-60% $MeCN/NH_4CO_2H$ 10 mM, pH 3.8/Flow 45 ml/min/11 min), resulting in the title compound (2.95 mg, 0.005 mmol, 3%) as yellow solid after lyophilisation.

$^1H$ NMR (500 MHz, MeOD) δ 8.31 (d, J=8.1 Hz, 2H), 7.76 (d, J=8.3 Hz, 2H), 7.60-7.55 (m, 2H), 7.40-7.34 (m, 1H), 7.02-6.97 (m, 1H), 3.95 (s, 3H), 3.29-3.21 (m, 1H), 1.25 (d, J=6.7 Hz, 6H); MS (m/z): 538.2 $[M+1]^+$.

Compound 14: 4-(3-fluorophenyl)-1-(5-(isopropylthio)-4-morpholinothiazol-2-yl)-3-methyl-1H-pyrazole-5-carboxylic acid methyl 4-bromo-1-(5-(isopropylthio)-4-morpholinothiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (300 mg, 0.659 mmol), XantPhos (38.1 mg, 0.066 mmol) and $Cs_2CO_3$ (1.07 g, 3.30 mmol), nitrogen and vacuum cycles were performed (2×). Nitrogen gas was bubbled through a solution of dioxane (3 mL) and morpholine (57.4 μL, 0.659 mmol), which was then added to the microwave vial, followed by the addition of the catalyst RuPhos Palladacycle (53.8 mg, 0.066 mmol). The vial was capped and placed in an oil bath at 105° C. for 16 h. The solvent was evaporated under vacuum and the crude product was purified by flash chromatography on silica gel (dry packing) using a solution of EtOAc in hexanes (5 to 20% gradient), affording the title compound (108 mg, 0.234 mmol, 36%) as yellow oil.

4-(3-fluorophenyl)-1-(5-(isopropylthio)-4-morpholinothiazol-2-yl)-3-methyl-1H-pyrazole-5-carboxylic acid In a 5 mL glass microwave vial equipped with a magnetic stirring bar and nitrogen flow at room temperature was placed methyl 4-bromo-1-(5-(isopropylthio)-4-morpholinothiazol-2-yl)-3-methyl-1H-pyrazole-5-carboxylate (108 mg, 0.234 mmol), 3-fluorophenylboronic acid (39.3 mg, 0.281 mmol) and $Na_2CO_3$ (124 mg, 1.17 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (27.0 mg, 0.023 mmol). The vial was capped and placed in an oil bath at 85° C. for 16 h. LiOH (49.1 mg, 1.17 mmol) was added to the reaction mixture and stirred under microwave radiation at 110° C. for 15 min. The reaction mixture was diluted with EtOAc and HCl 0.1 M. The aqueous layer was extracted with EtOAc (2×) and the combined organic layers were washed with brine, dried over $Na_2SO_4$, filtered and concentrated under vacuum. The product was purified using a semi prep HPLC-MS (column X-Bridge 30×50, eluted with 30-50% $MeCN/NH_4CO_2H$ 10 mM, pH 3.8/Flow 45 ml/min/11 min), resulting in the title compound (18.0 mg, 0.039 mmol, 16%) as yellow solid after lyophilisation.

$^1H$ NMR (500 MHz, DMSO) δ 7.46 (dd, J=14.4, 7.6 Hz, 1H), 7.39-7.29 (m, 2H), 3.70-3.63 (m, 4H), 3.58-3.51 (m, 4H), 3.16-3.07 (m, J=13.4, 6.7 Hz, 1H), 2.27 (s, 3H), 1.24 (d, J=6.7 Hz, 6H); MS (m/z): 463.2 $[M+1]^+$.

Compound 15: 4-(3-fluorophenyl)-3-hydroxy-1-(5-(isopropylthio)-4-(4-(trifluoromethyl)phenyl)thiazol-2-yl)-1H-pyrazole-5-carboxylic acid 2-thiocyanato-1-(4-(trifluoromethyl)phenyl)ethanone Potassium thiocyanate (9.55 g, 98.3 mmol) was added to a stirred solution of 2-bromo-1-(4-(trifluoromethyl)phenyl)

ethanone (25.0 g, 93.6 mmol) in MeCN (178 mL) at rt. The reaction mixture was heated to reflux (90° C.) for 2 h, then cooled to room temperature and diluted with water and EtOAc. The aqueous layer was extracted with EtOAc (3×) The combined organic layers were washed with brine, dried over $MgSO_4$, filtered and concentrated in vacuo to give the title compound (23.3 g, 94.9 mmol, 97%), which was used without further purification.

2-chloro-4-(4-(trifluoromethyl)phenyl)thiazole

A mixture of 2-thiocyanato-1-(4-(trifluoromethyl)phenyl) ethanone (23.3 g, 94.9 mmol) and 4 M HCl in dioxane (142 mL, 569 mmol) in dioxane (95 mL) was stirred for 16 h at rt. The reaction mixture was concentrated in vacuo and the residue was diluted with sat. aq. $NaHCO_3$ and extracted with EtOAc (2×). The combined organic layers were washed with brine, dried over $MgSO_4$, filtered and concentrated in vacuo and afforded the title compound (25.0 g, 94.8 mmol, 100%) as brown solid.

2-chloro-5-(isopropylthio)-4-(4-(trifluoromethyl) phenyl)thiazole

A 2.5 M solution of n-BuLi in hexanes (18.8 mL, 40.3 mmol) was added to a THF solution (107 mL) of 2-chloro-4-(4-(trifluoromethyl)phenyl)thiazole (10.0 g, 32.3 mmol) at −78° C. The reaction mixture was stirred at the same temperature for 30 min. Diisopropyl disulfide (10.3 mL, 64.5 mmol) was added to the reaction and was stirred at the same temperature for 2 h. Water was added to quench the reaction and then $Et_2O$. The reaction mixture was transferred into a separation funnel and the layers were separated. The aqueous layer was extracted with $Et_2O$ (2×). The combined organic layers were dried over $Na_2SO_4$ and concentrated under vacuum. The crude product was purified by flash chromatography on silica gel (dry packing) using a solution of EtOAc in hexanes (0 to 1% gradient) and afforded the title compound (3.05 g, 9.03 mmol, 28%) as yellow oil.

2-hydrazinyl-5-(isopropylthio)-4-(4-(trifluoromethyl)phenyl)thiazole

Diisopropylethyamine (3.2 mL, 18.2 mmol) was added to a solution of hydrazine hydrochloride (1.2 g, 18.2 mmol) and 2-chloro-5-(isopropylthio)-4-(4-(trifluoromethyl)phenyl)thiazole (3.1 g, 9.1 mmol) in N-methylpyrrolidine ("NMP") (18 mL) in a round bottom flask. The flask was heated to 135° C. for 2 h in an oil bath. The reaction mixture was diluted with water and extracted with $Et_2O$. The combined organic layers were washed with brine (3×), and dried over $Na_2SO_4$, filtered and concentrated under vacuum. This afforded the title compound (2.85 g, 8.55 mmol, 95%) as blue oil.

methyl 3-hydroxy-1-(5-(isopropylthio)-4-(4-(trifluoromethyl)phenyl)thiazol-2-yl)-1H-pyrazole-5-carboxylate A solution of 2-hydrazinyl-5-(isopropylthio)-4-(4-(trifluoromethyl)phenyl)thiazole (1.9 g, 5.76 mmol) in toluene (5 mL) was slowly added to a solution of dimethyl 2,5-dioxohex-3-ynedioate (900 mg, 6.33 mmol) in toluene (3 mL) and AcOH (4 mL) at 0° C. The reaction was stirred at rt for 1 h and was refluxed for 4 h. The reaction mixture was concentrated under vacuum and The crude product was purified by flash chromatography on silica gel (dry packing)

using a solution of EtOAc in hexanes (5 to 30% gradient), affording the title compound (714 mg, 1.61 mmol, 28%) as yellow oil.

methyl 4-bromo-3-hydroxy-1-(5-(isopropylthio)-4-(4-(trifluoromethyl)phenyl)thiazol-2-yl)-1H-pyrazole-5-carboxylate N-bromosuccinimide (188 mg, 1.06 mmol) was added portion wise to a solution of methyl 3-hydroxy-1-(5-(isopropylthio)-4-(4-(trifluoromethyl)phenyl)thiazol-2-yl)-1H-pyrazole-5-carboxylate (469 mg, 1.06 mmol) in MeCN/DCM (8 mL, 1:1). The reaction was stirred for 5 min at room temperature. And was then quenched with water and drops of $Na_2S_2O_3$. The aqueous layer was extracted with EtOAc (2×) and the combined organic layers were dried over $Na_2SO_4$, filtered and concentrated under vacuum. The crude product was purified by flash chromatography on silica gel (dry packing) using a solution of EtOAc in hexanes (0 to 30% gradient), affording the title compound (139 mg, 0.266 mmol, 25%) as pink solid.

methyl 3-acetoxy-4-bromo-1-(5-(isopropylthio)-4-(4-(trifluoromethyl)phenyl)thiazol-2-yl)-1H-pyrazole-5-carboxylate methyl 4-bromo-3-hydroxy-1-(5-(isopropylthio)-4-(4-(trifluoromethyl)phenyl)thiazol-2-yl)-1H-pyrazole-5-carboxylate (89 mg, 0.17 mmol) was placed in acetic anhydride (5.00 mL), followed by the addition of pyridine (2 drops). The reaction was stirred 1 h at rt and was then evaporated to dryness. The crude product was purified by flash chromatography on silica gel (dry packing) using a solution of EtOAc in hexanes (5% isochratic), affording the title compound (50 mg, 0.089 mmol, 52%) as white solid.

methyl 4-(3-fluorophenyl)-3-hydroxy-1-(5-(isopropylthio)-4-(4-(trifluoromethyl)phenyl)thiazol-2-yl)-1H-pyrazole-5-carboxylate In a 5 mL glass microwave vial equipped with a magnetic stirring bar and nitrogen flow at room temperature was placed methyl 3-acetoxy-4-bromo-1-(5-(isopropylthio)-4-(4-(trifluoromethyl)phenyl)thiazol-2-yl)-1H-pyrazole-5-carboxylate (30.0 mg, 0.053 mmol), 3-fluorophenylboronic acid (8.93 mg, 0.064 mmol) and KF (10.2 mg, 0.175 mmol), nitrogen and vacuum cycles were performed (2×). Nitrogen gas was bubbled through THF (0.5 mL) and then the solution was added to the microwave vial, followed by the addition of the catalyst $Pd(P^tBu_3)_2$ (2.72 mg, 0.005 mmol). The vial was capped and stirred at rt for 72 h. The crude product was purified by reverse chromatography on C-18 column with a solution of MeCN in water (containing 10 mM of $NH_4CO_2H$) (40 to 80%), affording the title compound (4.00 mg, 0.007 mmol, 14%) as white solid.

4-(3-fluorophenyl)-3-hydroxy-1-(5-(isopropylthio)-4-(4-(trifluoromethyl)phenyl)thiazol-2-yl)-1H-pyrazole-5-carboxylic acid Into a 10 mL round bottom flask, methyl 4-(3-fluorophenyl)-3-hydroxy-1-(5-(isopropylthio)-4-(4-(trifluoromethyl) phenyl)thiazol-2-yl)-1H-pyrazole-5-carboxylate (4.00 mg, 0.007 mmol) was diluted with THF/MeOH (2 mL, 1:1). A solution of NaOH 1 M (15 μL, 0.015 mmol) was added and the reaction was stirred overnight at rt. The crude product was purified by reverse chromatography on C-18 column with a solution of MeCN in water (containing 10 mM of $NH_4CO_2H$) (35 to 65%), affording the title compound (0.548 mg, 0.001 mmol, 14%) as pale green powder after lyophilisation.

$^1$H NMR (500 MHz, MeOD) δ 8.33-8.28 (m, 2H), 7.74-7.70 (m, 2H), 7.54-7.48 (m, 2H), 7.29-7.20 (m, 1H), 6.82-6.75 (m, 1H), 4.57 (br s, 1H), 3.25-3.17 (m, 1H), 1.22 (d, J=6.7 Hz, 6H); MS (m/z): 524.2 $[M+1]^+$.

Compounds 16 and 17: 1-(5-(3,4-dichlorophenyl)-1-isobutyl-1H-1,2,4-triazol-3-yl)-4-(3-fluorophenyl)-3-methyl-1H-pyrazole-5-carboxylic acid and 1-(3-(3,4-dichlorophenyl)-1-isobutyl-1H-1,2,4-triazol-5-yl)-4-(3-fluorophenyl)-3-methyl-1H-pyrazole-5-carboxylic acid

3,4-dichlorobenzohydrazide

Hydrazine hydrate (20.2 ml, 324 mmol) was added to methyl 3,4-dichlorobenzoate (4.52 g, 21.6 mmol) in EtOH (108 ml). The reaction was refluxed for 1.5 h. LCMS indicated completion of the reaction. Most of the ethanol was evaporated and the product was triturated in water. After drying on high vacuum the product (4.42 g, 21.6 mmol) was afforded as a white solid.

N-(5-(3,4-dichlorophenyl)-1H-1,2,4-triazol-3-yl)nitramide

Nitroguanidine (3.04 g, 29.3 mmol) was suspended in 1 N NaOH (19.5 ml, 19.5 mmol). 3,4-dichlorobenzohydrazide (2.00 g, 9.75 mmol) was added (it stayed on the surface but enter in solution when heating). The reaction was heated at 75° C. for 3h. Added 1 N HCl (20 mL) to acidify the mixture (the product crashes). The mixture was filtered and washed with water. LCMS showed the product as major. The product (2.36 g, 6.80 mmol, 70%) was afforded as an off-white solid after drying under high vacuum.

5-(3,4-dichlorophenyl)-3-hydrazinyl-1H-1,2,4-triazole

In a flask containing the N-(5-(3,4-dichlorophenyl)-1H-1,2,4-triazol-3-yl)nitramide (250 mg, 0.91 mmol) was added acetic acid (4.56 mL). The suspension was stirred to 10° C. and a suspension of zinc powder (298 mg, 4.56 mmol) in water (4.56 mL) was added. After 16 h the mixture was cooled to 0° C. and a solution of 8 M aqueous sodium hydroxide (15 mL) was added and the pH was checked to be basic (pH>10). The mixture was used for the next step.

tert-Butyl 2-(5-(3,4-dichlorophenyl)-1H-1,2,4-triazol-3-yl)hydrazinecarboxylate In a flask containing the crude solution of 5-(3,4-dichlorophenyl)-3-hydrazinyl-1H-1,2,4-triazole in water (pH<10, aqueous phase from the previous step, theorical amount of 223 mg, 0.91 mmol) was added THF (9 mL). Di-tert-butyldicarbonate (499 mg, 2.28 mmol) was added. After 16h, LCMS showed no s.m. and many products. The mixture was transferred to a separatory funnel EtOAc and the phases were separated. The aqueous phase was extracted EtOAc. The combined organic phase was washed with brine and was dried over sodium sulfate, filtered and concentrated. Afforded a mixture of Boc-product and Boc-impurities as pale brown oil. Used directly in the next step.

Methyl 1-(5-(3,4-dichlorophenyl)-1H-1,2,4-triazol-3-yl)-3-methyl-1H-pyrazole-5-carboxylate In a flask containing the crude Boc-protected material of the previous step (theorical amount of 314 mg, 0.91 mmol) was added MeOH (9.1 mL). The keto-oxime (332 mg, 1.92 mmol) was added, followed by conc. HCl 37% in water (0.33 ml, 4.0 mmol). The mixture was heated to 80° C. in an oil bath and after 1 h and 3h LCMS showed only a trace of product. More conc. HCl 37% in water (0.33 mL, 4.0 mmol) was added and after 4h heating there was no s.m. The mixture was transferred to a separatory funnel using EtOAc and the organic phase was washed with a saturated solution of sodium bicarbonate, then brine. The organic phase was dried over sodium sulfate, filtered and concentrated. The crude was purified on Isco using a C18 column, loading with DMSO, eluting with a gradient of 35-55% MeCN/water (containing 10 mM ammonium formate, pH 3.8). The fractions containing the product were lyophilized, affording the product (72 mg, 0.20 mmol, 22%) as off-white solid.

Methyl 1-(5-(3,4-dichlorophenyl)-1H-1,2,4-triazol-3-yl)-4-iodo-3-methyl-1H-pyrazole-5-carboxylate In a flask containing the triazolylpyrazole of the previous step (72 mg, 0.20 mmol) was added TFA (1 mL). N-iodosuccinimide (115 mg, 0.51 mmol) was added and after stirring for 16h LCMS showed no starting material and clean product. The mixture was transferred to a separatory funnel using EtOAc and the organic phase was washed water, then with a saturated solution of sodium bicarbonate, then brine. The organic phase was dried over sodium sulfate, filtered and concentrated. The crude product (98 mg, 0.20 mmol, 100%) was afforded as an pale yellow oil and was used as is in the next step.

Methyl 1-(3-(3,4-dichlorophenyl)-1-isobutyl-1H-1,2,4-triazol-5-yl)-4-iodo-3-methyl-1H-pyrazole-5-carboxylate and methyl 1-(5-(3,4-dichlorophenyl)-1-isobutyl-1H-1,2,4-triazol-3-yl)-4-iodo-3-methyl-1H-pyrazole-5-carboxylate In a flask containing the product of the previous step (98 mg, 0.205 mmol) were added cesium carbonate (200 mg, 0.61 mmol), DMF (2 mL), then isobutyliodide (189 uL, 302 mg, 1.64 mmol). After 16h there was no s.m. pyrazole and the ratio of products was 77:13 product. The mixture was added to a C18 column, eluting with a gradient of 65-100% MeCN/water (containing 10 mM ammonium formate, pH 3.8). The fractions containing the products were combined and lyophilized to afford the mixture of product of esters (110 mg, 0.205 mmol, 100%) as an off-white solid.

1-(5-(3,4-dichlorophenyl)-1-isobutyl-1H-1,2,4-triazol-3-yl)-4-(3-fluorophenyl)-3-methyl-1H-pyrazole-5-carboxylic acid and 1-(3-(3,4-dichlorophenyl)-1-isobutyl-1H-1,2,4-triazol-5-yl)-4-(3-fluorophenyl)-3-methyl-1H-pyrazole-5-carboxylic acid The mixture of the previous step (5:1 ratio, 110 mg, 0.21 mmol), boronic acid (58 mg, 0.41 mmol), sodium carbonate (109 mg, 1.03 mmol), dioxane (2.1 ml) and water (0.5 mL) were charged to a screw-cap type tube. The mixture was degassed for 10 min and Pd(PPh3)4 (24 mg, 0.021 mmol) was added. The tube was sealed and the mixture was heated to 85° C. After 16 h LCMS showed no product so more boronic acid (58 mg, 0.41 mmol), sodium carbonate (109 mg, 1.03 mmol), and degassed water (0.5 mL) were added. The mixture was degassed for 10 min and Pd(PPh3)4 (24 mg, 0.021 mmol) was added. After 4h LCMS showed no iodopyrazole s.m. so the mixture was cooled to rt, neutralized with 2 mL of HCl 1M in water and added to a C18 column with DMSO. The mixture purified on Isco using a gradient of 25-100% MeCN/water (containing 10 mM ammonium formate, pH 3.8). Lyophilization of the esters fractions afforded a mixture of the esters (38 mg, 0.076 mmol, 37%) as an off-white solid.

1-(5-(3,4-dichlorophenyl)-1-isobutyl-1H-1,2,4-triazol-3-yl)-4-(3-fluorophenyl)-3-methyl-1H-pyrazole-5-carboxylic acid and 1-(3-(3,4-dichlorophenyl)-1-isobutyl-1H-1,2,4-triazol-5-yl)-4-(3-fluorophenyl)-3-methyl-1H-pyrazole-5-carboxylic acid In a microwave vial containing a mixture of the esters of the previous step (1:3 ratio of isomers, 35 mg, 70 umol) were added dioxane (0.70 mL), methanol (70 uL) and a solution of NaOH 1M in water (0.70 mL, 0.70 mmol). The mixture was heated in a microwave reactor to 100° C. for 20 min. LCMS showed complete reaction. A solution of HCl 1M in water (0.70 mL, 0.70 mmol) was added and the mixture was purified on reverse phase Isco using C18 column, eluting with a gradient of 30-70% MeCN/water (10 mM ammonium formate, pH 3.8). The pure fractions containing the $1^{st}$ eluting product were combined, concentrated to remove most of the acetonitrile, frozen and lyophilized. 1-(5-(3,4-dichlorophenyl)-1-isobutyl-1H-1,2,4-triazol-3-yl)-4-(3-fluorophenyl)-3-methyl-1H-pyrazole-5-carboxylic acid (5 mg, 0.010 mmol, 15% yield) was afforded as an off-white solid. The pure fractions containing the $2^{nd}$eluting product were combined, concentrated to remove most of the acetonitrile, frozen and lyophilized. 1-(3-(3,4-dichlorophenyl)-1-isobutyl-1H-1,2,4-triazol-5-yl)-4-(3-fluorophenyl)-3-methyl-1H-pyrazole-5-carboxylic acid (8 mg, 0.016 mmol, 24% yield) was afforded as a white solid.

$^1$H NMR (500 MHz, $CDCl_3$) δ 7.75 (s, 1H), 7.58 (d, J=8.2 Hz, 1H), 7.47 (d, J=7.1 Hz, 1H), 7.33 (dd, J=14.1, 7.7 Hz, 1H), 7.08 (d, J=7.4 Hz, 1H), 7.06-6.98 (m, 2H), 4.03 (d, J=7.2 Hz, 2H), 2.38-2.31 (m, 1H), 2.28 (s, 3H), 0.87 (d, J=6.6 Hz, 6H). Carboxylic acid OH signal not seen or hidden under water signal (br s, 3.7-2.5 ppm); MS (m/z): 488.12 $[M+1]^+$.

$^1$H NMR (500 MHz, $CDCl_3$) δ 8.07 (d, J=2.0 Hz, 1H), 7.77 (dd, J=8.4, 2.0 Hz, 1H), 7.42 (d, J=8.4 Hz, 1H), 7.32 (td, J=8.0, 6.0 Hz, 1H), 7.06-6.92 (m, 3H), 4.03 (d, J=7.3 Hz, 2H), 2.31-2.22 (m, 1H), 2.20 (s, 3H), 0.88 (d, J=6.7 Hz, 6H); MS (m/z): 488.12 $[M+1]^+$.

Compound 18: 1-(4-(4,4-difluoropiperidin-1-yl)-5-(isopropylthio)thiazol-2-yl)-4-(3-fluorophenyl)-3-methyl-1H-pyrazole-5-carboxylic acid methyl 4-bromo-1-(4-(4,4-difluoropiperidin-1-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared described above (300 mg, 0.659 mmol), 4,4-difluoropiperidine (104 mg, 0.659 mmol), XantPhos (38.1 mg, 0.066 mmol) and $Cs_2CO_3$ (1.07 g, 3.30 mmol), nitrogen and vacuum cycles were performed (2×). Nitrogen gas was bubbled through dioxane (3 mL), which was then added to the microwave vial, followed by the addition of the catalyst RuPhos Palladacycle (53.8 mg, 0.066 mmol). The vial was capped and placed in an oil bath at 105° C. for 16 h. The solvent was evaporated under vacuum and the crude product was purified by flash chromatography on silica gel (dry packing) using hexanes (100% isochratic), affording the title compound (173 mg, 0.350 mmol, 53%) as yellow oil.

methyl 1-(4-(4,4-difluoropiperidin-1-yl)-5-(isopropylthio)thiazol-2-yl)-4-(3-fluorophenyl)-3-methyl-1H-pyrazole-5-carboxylate In a 5 mL glass microwave vial equipped with a magnetic stirring bar and nitrogen flow at room temperature was placed methyl 4-bromo-1-(4-(4,4-difluoropiperidin-1-yl)-5-(isopropylthio)thiazol-2-yl)-3-methyl-1H-pyrazole-5-carboxylate (173 mg, 0.349 mmol), 3-fluorophenylboronic acid (58.6 mg, 0.419 mmol) and $Na_2CO_3$ (185 mg, 1.75 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (40.4 mg, 0.035 mmol). The vial was capped and placed in an oil bath at 85° C. for 16 h. The reaction mixture was diluted with EtOAc. The aqueous layer was extracted with EtOAc (2×) and the combined organic layers were washed with brine, dried over $Na_2SO_4$, filtered and concentrated under vacuum. The crude product was purified by flash chromatography on silica gel (dry packing) using a solution of EtOAc in hexanes (0 to 1% gradient) to give the title compound (150 mg, 0.294 mmol, 84%) as yellow oil.

1-(4-(4,4-difluoropiperidin-1-yl)-5-(isopropylthio)thiazol-2-yl)-4-(3-fluorophenyl)-3-methyl-1H-pyrazole-5-carboxylic acid Into a 25 mL round bottom flask, methyl 1-(4-(4,4-difluoropiperidin-1-yl)-5-(isopropylthio)thiazol-2-yl)-4-(3-fluorophenyl)-3-methyl-1H-pyrazole-5-carboxylate (150 mg, 0.294 mmol) was diluted with THF/MeOH (2 mL, 1:1). A solution of NaOH 1 M (588 uL, 0.588 mmol) was added and the reaction was stirred 16 h at rt. A solution of HCl 1 M (588 uL, 0.588 mmol) and water (2 mL) were added. The reaction mixture was directly purified by reverse chromatography on C-18 column with a solution of MeCN in water (containing 10 mM of $NH_4CO_2H$) (40 to 70%), affording the title compound (31.5 mg, 0.064 mmol, 22%) as yellow powder after lyophilisation.

$^1$H NMR (500 MHz, DMSO) δ 7.50 (dd, J=14.6, 7.9 Hz, 1H), 7.34-7.27 (m, 2H), 7.25-7.18 (m, 1H), 3.74-3.66 (m, 4H), 3.22-3.13 (m, 1H), 2.28 (s, 3H), 2.07-1.95 (m, 4H), 1.25 (d, J=6.7 Hz, 6H); MS (m/z): 497.1 $[M+1]^+$.

Compound 19: methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (Enantipure—Unknown Stereochemistry)

Into a 25 mL round bottom flask, methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (made as described above and resolved enantiopure (12.7 mg, 0.024 mmol) was diluted with THF/MeOH (2 mL, 1:1). A solution of NaOH 1 M (235 uL, 0.235 mmol) was added and the reaction was stirred 16 h at 60° C. A solution of HCl 1 M (235 uL, 0.235 mmol) and water (10 mL) were added. The reaction mixture was diluted with EtOAc and transferred into an extraction funnel. The layers were separated and the aqueous layer was extracted with EtOAc (3×). The combined organic layers were dried over $Na_2SO_4$, filtered and concentrated under vacuum, affording the title compound (9.00 mg, 0.017 mmol, 73%) as yellow solid after lyophilisation.

$^1$H NMR (500 MHz, MeOD) δ 7.49-7.42 (m, 1H), 7.28-7.23 (m, 1H), 7.22-7.17 (m, 1H), 7.15-7.09 (m, 1H), 6.53-6.44 (m, 1H), 3.30-3.21 (m, 1H), 2.80 (d, J=18.1 Hz, 1H), 2.59-2.40 (m, 3H), 2.31 (s, 3H), 2.18-2.10 (m, 1H), 1.71-1.56 (m, 2H), 1.30 (dd, J=6.7, 1.9 Hz, 6H); MS (m/z): 526.1 $[M+1]^+$.

Compound 19: methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (Enantipure—Unknown Stereochemistry)

Into a 25 mL round bottom flask, methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate enantiopure (30.7 mg, 0.057 mmol) (made as described above and resolved) was diluted with THF/MeOH (2 mL, 1:1). A solution of NaOH 1 M (569 uL, 0.569 mmol) was added and the reaction was stirred 16 h at 60° C. A solution of HCl 1 M (569 uL, 0.569 mmol) and water (10 mL) were added. The reaction mixture was diluted with EtOAc and transferred into an extraction funnel. The layers were separated and the aqueous layer was extracted with EtOAc (3×). The combined organic layers were dried over $Na_2SO_4$, filtered and concentrated under vacuum, affording the title compound (20.0 mg, 0.038 mmol, 67%) as yellow solid after lyophilisation.

$^1$H NMR (500 MHz, MeOD) δ 7.36 (td, J=8.0, 6.0 Hz, 1H), 7.18-7.13 (m, 1H), 7.11-7.07 (m, 1H), 7.05-6.99 (m, 1H), 6.41-6.34 (m, 1H), 3.21-3.11 (m, 1H), 2.70 (d, J=18.3 Hz, 1H), 2.50-2.30 (m, 3H), 2.21 (s, 3H), 2.08-1.99 (m, 1H), 1.59-1.42 (m, 2H), 1.20 (dd, J=6.7, 1.9 Hz, 6H); MS (m/z): 526.1 $[M+1]^+$.

Compound 20: 4-(3-fluorophenyl)-3-methyl-1-(4-(4-(trifluoromethyl)cyclohexyl)thiazol-2-yl)-1H-pyrazole-5-carboxylic acid In a 10 mL glass vial equipped with a magnetic stirring bar was dissolved Compound 5 (20.0 mg, 0.037 mmol) in acetic acid (4 mL). Pd on activated carbon (3.94 mg, 0.004 mmol) was added and the reaction mixture was stirred at 80° C. under a hydrogen atmosphere for 16 h. The crude product was purified by reverse chromatography on C-18 column with a solution of MeCN in water (containing 10 mM of $NH_4CO_2H$) (35 to 65%), affording the title compound (3.00 mg, 0.007 mmol, 18%) as white powder after lyophilisation.

$^1$H NMR (500 MHz, MeOD) δ 7.47-7.40 (m, 1H), 7.30-7.25 (m, 1H), 7.24-7.18 (m, 1H), 7.13-7.06 (m, 2H), 3.09-3.01 (m, 1H), 2.36-2.28 (m, 4H), 2.27-2.16 (m, 1H), 2.05 (d, J=11.6 Hz, 1H), 1.89-1.72 (m, 3H), 1.67-1.56 (m, 2H), 1.54-1.41 (m, 1H), 1.35-1.20 (m, 1H); MS (m/z): 454.1 $[M+1]^+$.

Compound 22: 4-(3-fluorophenyl)-1-(5-isobutyl-4-(4-(trifluoromethyl)phenyl)thiazol-2-yl)-3-methyl-1H-pyrazole-5-carboxylic acid methyl 1-(5-iodo-4-(4-(trifluoromethyl)phenyl)thiazol-2-yl)-3-methyl-1H-pyrazole-5-carboxylate Methyl 3-methyl-1-(4-(4-(trifluoromethyl)phenyl)thiazol-2-yl)-1H-pyrazole-5-carboxylate prepared generally as described above with respect to the butylthio analog (100 mg, 0.272 mmol) was dissolved in TFA (1.4 ml) and N-iodosuccinimide (73 mg, 0.33 mmol) was added. The reaction mixture was stirred 45 min at rt. The reaction mixture was poured in water and extracted with EtOAc. The organic layer was washed successively with an aqueous solution saturated in $NaHCO_3$, a 10% aqueous solution of $Na_2S_2O_3$ and brine. The organic layers was dried over magnesium sulfate, filtered, and concentrated. The product was purified by flash chromatography (dry packing) on silica gel using a gradient 0 to 10% EtOAc in hexanes to give the title compound (79 mg, 0.16 mmol, 59%) as a pink solid. MS (m/z): 493.9 [M+1]+.

methyl 3-methyl-1-(5-(2-methylprop-1-en-1-yl)-4-(4-(trifluoromethyl)phenyl)thiazol-2-yl)-1H-pyrazole-5-carboxylate In a 5 mL glass microwave vial equipped with a magnetic stirring bar and nitrogen flow at room temperature was placed the methyl 1-(5-iodo-4-(4-(trifluoromethyl)phenyl)thiazol-2-yl)-3-methyl-1H-pyrazole-5-carboxylate (200 mg, 0.405 mmol), the (2-methylprop-1-en-1-yl)boronic acid (49 mg, 0.49 mmol), $K_2CO_3$ (280 mg, 2.03 mmol), and THF (3 mL). Nitrogen was bubbled in the solvent for 10 minutes followed by the addition of the catalyst Pd(dtbpf) (26 mg, 0.041 mmol). The vial was capped and placed in an oil bath at 90° C. for 16 h. The product was purified by flash chromatography (dry packing) on silica gel using a gradient 0 to 10% EtOAc in hexanes to give the title compound (64 mg, 0.059 mmol, 38%) as a yellow oil. MS (m/z): 422.3 [M+1]+.

methyl 1-(5-isobutyl-4-(4-(trifluoromethyl)phenyl)thiazol-2-yl)-3-methyl-1H-pyrazole-5-carboxylate The methyl 3-methyl-1-(5-(2-methylprop-1-en-1-yl)-4-(4-(trifluoromethyl)phenyl)thiazol-2-yl)-1H-pyrazole-5-carboxylate (64 mg, 0.15 mmol) was dissolved in MeOH/AcOH (3 ml) and 20% $Pd(OH)_2/C$ (16 mg) was added. The reaction mixture was purged and stirred under a hydrogen atmosphere for 16 h. The reaction mixture was filtered over a pad of Celite® and concentrated in vacuo. The crude reaction mixture was resubmitted to the reaction conditions for two additional cycles to give after evaporation the title compound (36 mg, 0.084 mmol, 55%) as a yellowish solid. MS (m/z): 424.2 [M+1]+.

methyl 4-bromo-1-(5-isobutyl-4-(4-(trifluoromethyl)phenyl)thiazol-2-yl)-3-methyl-1H-pyrazole-5-carboxylate The methyl 1-(5-isobutyl-4-(4-(trifluoromethyl)phenyl)thiazol-2-yl)-3-methyl-1H-pyrazole-5-carboxylate (36 mg, 0.084 mmol) was dissolved in MeCN/DCM (1 mL) and a 2 M solution of bromine in MeCN (210 μL, 0.420 mmol) was added drop wise. The reaction mixture was stirred 16 h at rt. and quench with 10% aqueous solution of $Na_2S_2O_3$. The reaction mixture was diluted with EtOAc, washed with water and brine. The organic layer was dried over magnesium sulfate, filtered, and concentrated to give the title compound (36 mg, 0.072 mmol, 85%) as a yellow solid. MS (m/z): 502.0 [M+1]+.

4-(3-fluorophenyl)-1-(5-isobutyl-4-(4-(trifluoromethyl)phenyl)thiazol-2-yl)-3-methyl-1H-pyrazole-5-carboxylic acid In a 5 mL glass microwave vial equipped with a magnetic stirring bar and nitrogen flow at room temperature was placed the methyl 4-bromo-1-(5-isobutyl-4-(4-(trifluoromethyl)phenyl)thiazol-2-yl)-3-methyl-1H-pyrazole-5-carboxylate (36 mg, 0.072 mmol), (3-fluorophenyl)boronic acid (12 mg, 0.086 mmol) and $Na_2CO_3$ (38 mg, 0.36 mmol). Nitrogen gas was bubbled through a solution of dioxane/water (2 mL, 4:1) and then the solution was added to the microwave vial, followed by the addition of the catalyst $Pd(PPh_3)_4$ (8.3 mg, 0.0072 mmol). The vial was capped and placed in an oil bath at 85° C. for 16 h. LiOH (8.5 mg, 0.36 mmol) was added to the reaction mixture and stirred under microwave radiation at 110° C. for 15 min. The product was purified using a semi prep HPLC-MS (column X-Bridge 30×50, eluted with 60-80% MeCN/$NH_4CO_2H$ 10 mM, pH 3.8/Flow 45 ml/min/10 min), resulting in the title compound (7.5 mg, 0.015 mmol, 21%) as white solid after lyophilization.

$^1$H NMR (500 MHz, DMSO) δ 7.83 (s, 4H), 7.53-7.47 (m, 1H), 7.34-7.28 (m, 2H), 7.25-7.18 (m, 1H), 2.89 (d, J=7.2 Hz, 2H), 2.30 (s, 3H), 1.96-1.83 (m, 1H), 0.93 (d, J=6.6 Hz, 6H). MS (m/z): 504.0 $[M+1]^+$.

Compound 23: 4-(3-fluorophenyl)-1-(5-(isopropylthio)-4-(4-(2,2,2-trifluoroethyl)piperazin-1-yl)thiazol-2-yl)-3-methyl-1H-pyrazole-5-carboxylic acid tert-butyl 4-(2,2,2-trifluoroethyl)piperazine-1-carboxylate Trifluoroiodoethane (0.794 mL, 8.05 mmol) was added to a stirred mixture of boc-piperazine (1.25 g, 6.71 mmol), DIPEA (6.25 mL, 33.6 mmol) and DMF (7 mL). The reaction mixture was stirred at rt for the 72 h. The reaction was filtered and the filtrate was evaporated. The crude product was purified by flash chromatography on silica gel (dry packing) using a solution of EtOAc in hexanes (20 to 100% gradient) to give the title compound (253 mg, 0.943 mmol, 14%) as yellow solid.

1-(2,2,2-trifluoroethyl)piperazine hydrochloride tert-butyl 4-(2,2,2-trifluoroethyl)piperazine-1-carboxylate (253 mg, 0.94 mmol) was dissolve in DCM (9 mL) and a solution of 4 M HCl in dioxane (4.72 mL, 18.9 mmol) was added. The reaction was stirred 3 h at rt. The product was then concentrated in vacuum and co evaporated with DCM 3 times, affording the title compound (200 mg, 0.977 mmol, 100%) as beige solid.

methyl 4-bromo-1-(5-(isopropylthio)-4-(4-(2,2,2-trifluoroethyl)piperazin-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate prepared as described above with respect to Compound 1 (300 mg, 0.659 mmol), 1-(2,2,2-trifluoroethyl)piperazine hydrochloride (135 mg, 0.659 mmol), XantPhos (38.1 mg, 0.066 mmol) and $Cs_2CO_3$ (1.07 g, 3.30 mmol), nitrogen and vacuum cycles were performed (2×). Nitrogen gas was bubbled through dioxane (3 mL), which was then added to the microwave vial, followed by the addition of the catalyst RuPhos Palladacycle (53.8 mg, 0.066 mmol). The vial was capped and placed in an oil bath at 105° C. for 16 h. The solvent was evaporated under vacuum and the crude product was purified by flash chromatography on silica gel (dry packing) using a solution of EtOAc in hexanes (10 to 30% gradient), affording the title compound (123 mg, 0.227 mmol, 34%) as yellow oil.

methyl 4-(3-fluorophenyl)-1-(5-(isopropylthio)-4-(4-(2,2,2-trifluoroethyl)piperazin-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(5-(isopropylthio)-4-(4-(2,2,2-trifluoroethyl)piperazin-1-yl)thiazol-2-yl)-3-methyl-1H-pyrazole-5-carboxylate (123 mg, 0.227 mmol), 3-fluorophenylboronic acid (38.1 mg, 0.272 mmol) and $Na_2CO_3$ (120 mg, 1.13 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$(26.2 mg, 0.023 mmol). The vial was capped and placed in an oil bath at 85° C. for 16 h. The reaction mixture was diluted with EtOAc. The aqueous layer was extracted with EtOAc (2×) and the combined organic layers were washed with brine, dried over $Na_2SO_4$, filtered and concentrated under vacuum. The crude product was purified by flash chromatography on silica gel (dry packing) using a solution of EtOAc in hexanes (0 to 15% gradient) to give the title compound (41.3 mg, 0.074 mmol, 33%) as yellow oil.

4-(3-fluorophenyl)-1-(5-(isopropylthio)-4-(4-(2,2,2-trifluoroethyl)piperazin-1-yl)thiazol-2-yl)-3-methyl-1H-pyrazole-5-carboxylic acid Into a 25 mL round bottom flask, methyl 4-(3-fluorophenyl)-1-(5-(isopropylthio)-4-(4-(2,2,2-trifluoroethyl)piperazin-1-yl)thiazol-2-yl)-3-methyl-1H-pyrazole-5-carboxylate (41.3 mg, 0.076 mmol) was diluted with THF/MeOH (2 mL, 1:1). A solution of NaOH 1 M (381 uL, 0.381 mmol) was added and the reaction was stirred 16 h at rt. A solution of HCl 1 M (381 uL, 0.381 mmol) and water (2 mL) were added. The reaction mixture was directly purified by reverse chromatography on C-18 column with a solution of MeCN in water (containing 10 mM of $NH_4CO_2H$) (40 to 70%), affording the title compound (32.0 mg, 0.059 mmol, 77%) as yellow powder after lyophilisation.

$^1$H NMR (500 MHz, DMSO) δ 7.56-7.46 (m, J=14.4, 8.0 Hz, 1H), 7.28 (d, J=8.4 Hz, 2H), 7.26-7.19 (m, J=9.0 Hz, 1H), 3.59-3.53 (m, 4H), 3.21 (dd, J=20.5, 10.2 Hz, 2H), 3.17-3.07 (m, J=13.4, 6.7 Hz, 1H), 2.73-2.66 (m, 4H), 2.28 (s, 3H), 1.24 (d, J=6.7 Hz, 6H); MS (m/z): 544.1 $[M+1]^+$.

Compound 24: 1-(4-(4-cyanopiperidine-1-yl)-5-(isopropylthio)thiazol-2-yl)-4-(3-fluorophenyl)-3-methyl-1H-pyrazole-5-carboxylic acid methyl 4-bromo-1-(4-(4-cyanopiperidin-1-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (150 mg, 0.330 mmol), the piperidine-4-carbonitrile (36 mg, 0.33 mmol), $Cs_2CO_3$ (537 mg, 1.65 mmol), XantPhos (19 mg, 0.033 mmol) and dioxane (3 mL). Nitrogen was bubbled in the solvent for 10 minutes followed by the addition of the catalyst RuPhos Pd G1 (27 mg, 0.033 mmol). The vial was capped and placed in an oil bath at 105° C. for 16 h. The product was purified using a semi prep HPLC-MS (column X-Bridge 30×50, eluted with 70-90% MeCN/$NH_4CO_2H$ 10 mM, pH 3.8/Flow 45 ml/min/10 min), resulting in the title compound (29 mg, 0.059 mmol, 18%) as yellow solid after evaporation. MS (m/z): 484.0 [M+1]+.

1-(4-(4-cyanopiperidin-1-yl)-5-(isopropylthio)thiazol-2-yl)-4-(3-fluorophenyl)-3-methyl-1H-pyrazole-5-carboxylic acid In a 5 mL glass microwave vial equipped with a magnetic stirring bar and nitrogen flow at room temperature was placed the methyl 4-bromo-1-(4-(4-cyanopiperidin-1-yl)-5-(isopropylthio)thiazol-2-yl)-3-methyl-1H-pyrazole-5-carboxylate (29 mg, 0.059 mmol), (3-fluorophenyl)boronic acid (9.9 mg, 0.071 mmol) and $Na_2CO_3$ (31 mg, 0.29 mmol). Nitrogen gas was bubbled through a solution of dioxane/water (2 mL, 4:1) and then the solution was added to the microwave vial, followed by the addition of the catalyst $Pd(PPh_3)_4$ (6.8 mg, 0.0059 mmol). The vial was capped and placed in an oil bath at 85° C. for 16 h. LiOH (7.0 mg, 0.29 mmol) was added to the reaction mixture and stirred under microwave radiation at 110° C. for 15 min. The product was purified using a semi prep HPLC-MS (column X-Bridge 30×50, eluted with 50-70% MeCN/$NH_4CO_2H$ 10 mM, pH 3.8/Flow 45 ml/min/10 min), resulting in the title compound (2.3 mg, 0.0047 mmol, 8%) as yellowish solid after lyophilization.

$^1H$ NMR (500 MHz, MeOD) δ 7.41 (td, J=8.0, 6.1 Hz, 1H), 7.37-7.34 (m, 1H), 7.33-7.28 (m, 1H), 7.07-7.01 (m, 1H), 4.02-3.95 (m, 2H), 3.54-3.47 (m, 2H), 3.22-3.10 (m, 1H), 3.01-2.91 (m, 1H), 2.32 (s, 3H), 2.09-1.98 (m, 2H), 1.93-1.80 (m, 2H), 1.30 (d, J=6.7 Hz, 6H). MS (m/z): 486.1 $[M+1]^+$.

Compound 25: 1-(4-(4-cyclopropylpiperazin-1-yl)-5-(isopropylthio)thiazol-2-yl)-4-(3-fluorophenyl)-3-methyl-1H-pyrazole-5-carboxylic acid methyl 4-bromo-1-(4-(4-cyclopropylpiperazin-1-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (150 mg, 0.330 mmol), the 1-cyclopropylpiperazine (42 mg, 0.33 mmol), $Cs_2CO_3$ (537 mg, 1.65 mmol), XantPhos (19 mg, 0.033 mmol) and dioxane (3 mL). Nitrogen was bubbled in the solvent for 10 minutes followed by the addition of the catalyst RuPhos Pd G1 (27 mg, 0.033 mmol). The vial was capped and placed in an oil bath at 105° C. for 16 h. The product was purified by flash chromatography (dry packing) on silica gel using a gradient 0 to 10% EtOAc in hexanes to give the title compound (28 mg, 0.055 mmol, 17%) as a yellow oil. MS (m/z): 500.0 [M+1]+.

1-(4-(4-cyclopropylpiperazin-1-yl)-5-(isopropylthio)thiazol-2-yl)-4-(3-fluorophenyl)-3-methyl-1H-pyrazole-5-carboxylic acid In a 5 mL glass microwave vial equipped with a magnetic stirring bar and nitrogen flow at room temperature was placed the methyl 4-bromo-1-(4-(4-cyclopropylpiperazin-1-yl)-5-(isopropylthio)thiazol-2-yl)-3-methyl-1H-pyrazole-5-carboxylate (28 mg, 0.055 mmol), (3-fluorophenyl)boronic acid (9.2 mg, 0.066 mmol) and $Na_2CO_3$ (29 mg, 0.28 mmol). Nitrogen gas was bubbled through a solution of dioxane/water (2 mL, 4:1) and then the solution was added to the microwave vial, followed by the addition of the catalyst $Pd(PPh_3)_4$(6.3 mg, 0.0055 mmol). The vial was capped and placed in an oil bath at 85° C. for 16 h. LiOH (6.6 mg, 0.28 mmol) was added to the reaction mixture and stirred under microwave radiation at 110° C. for 15 min. The product was purified using a semi prep HPLC-MS (column X-Bridge 30×50, eluted once with 35-55% MeCN/$NH_4CO_2H$ 10 mM, pH 3.8/Flow 45 ml/min/10 min and then with 35-55% MeCN/$NH_4CO_3H$ 10 mM, pH 10/Flow 45 ml/min/10 min), resulting in the title compound (3.0 mg, 0.0060 mmol, 11%) as yellow solid after lyophilization.

$^1H$ NMR (500 MHz, MeOD) δ 7.46-7.40 (m, 1H), 7.39-7.35 (m, 1H), 7.35-7.31 (m, 1H), 7.09-7.03 (m, 1H), 3.93-3.75 (m, 4H), 3.40-3.32 (m, 4H), 3.26-3.15 (m, 1H), 2.76-2.60 (m, 1H), 2.34 (s, 3H), 1.31 (d, J=6.7 Hz, 6H), 0.95-0.81 (s, 4H). MS (m/z): 502.1 $[M+1]^+$.

Compound 26: 1-(4-(4-ethylpiperazin-1-yl)-5-(isopropylthio)thiazol-2-yl)-4-(3-fluorophenyl)-3-methyl-1H-pyrazole-5-carboxylic acid methyl 4-bromo-1-(4-(4-ethylpiperazin-1-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (150 mg, 0.330 mmol), the 1-ethylpiperazine (38 mg, 0.33 mmol), $Cs_2CO_3$ (537 mg, 1.65 mmol), XantPhos (19 mg, 0.033 mmol) and dioxane (3 mL). Nitrogen was bubbled in the solvent for 10 minutes followed by the addition of the catalyst RuPhos Pd G1 (27 mg, 0.033 mmol). The vial was capped and placed in an oil bath at 105° C. for 16 h. The product was purified using a semi prep HPLC-MS (column X-Bridge 30×50, eluted once with 50-70% MeCN/$NH_4CO_2H$ 10 mM, pH 3.8/Flow 45 ml/min/10 min), resulting in the title compound (49 mg, 0.10 mmol, 31%) as yellow solid after evaporation. MS (m/z): 488.0 [M+1]+.

1-(4-(4-ethylpiperazin-1-yl)-5-(isopropylthio)thiazol-2-yl)-4-(3-fluorophenyl)-3-methyl-1H-pyrazole-5-carboxylic acid In a 5 mL glass microwave vial equipped with a magnetic stirring bar and nitrogen flow at room temperature was placed the methyl 4-bromo-1-(4-(4-ethylpiperazin-1-yl)-5-(isopropylthio)thiazol-2-yl)-3-methyl-1H-pyrazole-5-carboxylate (49 mg, 0.10 mmol), (3-fluorophenyl)boronic acid (17 mg, 0.12 mmol) and $Na_2CO_3$ (53 mg, 0.50 mmol). Nitrogen gas was bubbled through a solution of dioxane/water (2 mL, 4:1) and then the solution was added to the microwave vial, followed by the addition of the catalyst $Pd(PPh_3)_4$ (12 mg, 0.010 mmol). The vial was capped and placed in an oil bath at 85° C. for 16 h. LiOH (12 mg, 0.50 mmol) was added to the reaction mixture and stirred under microwave radiation at 110° C. for 15 min. The product was purified using a semi prep HPLC-MS (column X-Bridge 30×50, eluted once with 35-55% MeCN/$NH_4CO_2H$ 10 mM, pH 3.8/Flow 45 ml/min/10 min), resulting in the title compound (1.1 mg, 0.0022 mmol, 2%) as white solid after lyophilization.

$^1$H NMR (500 MHz, MeOD) δ 8.49 (s, 1H), 7.43 (td, J=7.9, 6.0 Hz, 1H), 7.40-7.32 (m, 2H), 7.09-7.02 (m, 1H), 4.06-3.63 (m, 4H), 3.40-3.27 (m, 4H), 3.27-3.12 (m, 3H), 2.34 (s, 3H), 1.36 (t, J=7.3 Hz, 3H), 1.31 (d, J=6.7 Hz, 6H). Ammonium formate salt. MS (m/z): 490.1 $[M+1]^+$.

Compound 27: 1-(4-(4-acetylpiperazin-1-yl)-5-(isopropylthio)thiazol-2-yl)-4-(3-fluorophenyl)-3-methyl-1H-pyrazole-5-carboxylic acid methyl 1-(4-(4-acetylpiperazin-1-yl)-5-(isopropylthio)thiazol-2-yl)-4-bromo-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (150 mg, 0.330 mmol), the 1-(piperazin-1-yl)ethanone (42 mg, 0.33 mmol), $Cs_2CO_3$ (537 mg, 1.65 mmol), XantPhos (19 mg, 0.033 mmol) and dioxane (3 mL). Nitrogen was bubbled in the solvent for 10 minutes followed by the addition of the catalyst RuPhos Pd G1 (27 mg, 0.033 mmol). The vial was capped and placed in an oil bath at 105° C. for 16 h. The product was purified using a semi prep HPLC-MS (column X-Bridge 30×50, eluted once with 65-85% MeCN/$NH_4CO_2H$ 10 mM, pH 3.8/Flow 45 ml/min/10 min), resulting in the title compound (30 mg, 0.059 mmol, 18%) as yellow oil after evaporation.

MS (m/z): 502.0 [M+1]+.

1-(4-(4-acetylpiperazin-1-yl)-5-(isopropylthio)thiazol-2-yl)-4-(3-fluorophenyl)-3-methyl-1H-pyrazole-5-carboxylic acid In a 5 mL glass microwave vial equipped with a magnetic stirring bar and nitrogen flow at room temperature was placed the methyl 1-(4-(4-acetylpiperazin-1-yl)-5-(isopropylthio)thiazol-2-yl)-4-bromo-3-methyl-1H-pyrazole-5-carboxylate (30 mg, 0.059 mmol), (3-fluorophenyl)boronic acid (10 mg, 0.071 mmol) and $Na_2CO_3$ (31 mg, 0.30 mmol). Nitrogen gas was bubbled through a solution of dioxane/water (2 mL, 4:1) and then the solution was added to the microwave vial, followed by the addition of the catalyst $Pd(PPh_3)_4$ (12 mg, 0.010 mmol). The vial was capped and placed in an oil bath at 85° C. for 16 h. LiOH (7.1 mg, 0.30 mmol) was added to the reaction mixture and stirred under microwave radiation at 110° C. for 15 min. The product was purified using a semi prep HPLC-MS (column X-Bridge 30×50, eluted once with 40-60% MeCN/$NH_4CO_2H$ 10 mM, pH 3.8/Flow 45 ml/min/10 min), resulting in the title compound (4.1 mg, 0.0081 mmol, 14%) as yellow solid after lyophilization.

$^1$H NMR (500 MHz, MeOD) δ 7.43 (td, J=8.0, 6.1 Hz, 1H), 7.36-7.32 (m, 1H), 7.31-7.27 (m, 1H), 7.09-7.03 (m, 1H), 3.74-3.60 (m, 8H), 3.26-3.13 (m, 1H), 2.34 (s, 3H), 2.14 (s, 3H), 1.31 (d, J=6.7 Hz, 6H). MS (m/z): 504.1 $[M+1]^+$.

Compound 28: 4-(3-fluorophenyl)-1-(5-(isopropylthio)-4-(4-methylpiperidin-1-yl)thiazol-2-yl)-3-methyl-1H-pyrazole-5-carboxylic acid methyl 4-bromo-1-(5-(isopropylthio)-4-(4-methylpiperidin-1-yl)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate prepared as described above with respect to Compound 1 (150 mg, 0.330 mmol), the 4-methylpiperidine (33 mg, 0.33 mmol), $Cs_2CO_3$ (537 mg, 1.65 mmol), XantPhos (19 mg, 0.033 mmol) and dioxane (3 mL). Nitrogen was bubbled in the solvent for 10 minutes followed by the addition of the catalyst RuPhos Pd G1 (27 mg, 0.033 mmol). The vial was capped and placed in an oil bath at 105° C. for 16 h. The product was purified using a semi prep HPLC-MS (column X-Bridge 30×50, eluted once with 80-100% MeCN/$NH_4CO_2H$ 10 mM, pH 3.8/Flow 45 ml/min/10 min), resulting in the title compound (9.5 mg, 0.020 mmol, 6%) as yellow oil after evaporation. MS (m/z): 473.1 [M+1]+.

4-(3-fluorophenyl)-1-(5-(isopropylthio)-4-(4-methylpiperidin-1-yl)thiazol-2-yl)-3-methyl-1H-pyrazole-5-carboxylic acid In a 5 mL glass microwave vial equipped with a magnetic stirring bar and nitrogen flow at room temperature was placed the methyl 4-bromo-1-(5-(isopropylthio)-4-(4-methylpiperidin-1-yl)thiazol-2-yl)-3-methyl-1H-pyrazole-5-carboxylate (9.5 mg, 0.020 mmol), (3-fluorophenyl)boronic acid (3.4 mg, 0.024 mmol) and $Na_2CO_3$ (11 mg, 0.10 mmol). Nitrogen gas was bubbled through a solution of dioxane/water (2 mL, 4:1) and then the solution was added to the microwave vial, followed by the addition of the catalyst $Pd(PPh_3)_4$ (2.3 mg, 0.0020 mmol). The vial was capped and placed in an oil bath at 85° C. for 16 h. LiOH (2.4 mg, 0.10 mmol) was added to the reaction mixture and stirred under microwave radiation at 110° C. for 15 min. The product was purified using a semi prep HPLC-MS (column X-Bridge 30×50, eluted once with 65-85% MeCN/$NH_4CO_2H$ 10 mM, pH 3.8/Flow 45 ml/min/10 min), resulting in the title compound (1.6 mg, 0.0034 mmol, 17%) as yellow solid after lyophilization.

$^1$H NMR (500 MHz, MeOD) δ 7.45-7.39 (m, 1H), 7.35-7.31 (m, 1H), 7.31-7.26 (m, 1H), 7.010-7.03 (m, 1H), 4.43-4.34 (m, 2H), 3.23-3.10 (m, 1H), 2.95-2.86 (m, 2H), 2.32 (s, 3H), 1.74-1.62 (m, 2H), 1.61-1.49 (m, 1H), 1.38-1.19 (m, 2H) 1.29 (d, J=6.7 Hz, 6H), 0.98 (d, J=6.6 Hz, 3H). MS (m/z): 475.2 $[M+1]^+$.

Compound 29: 4-(3-fluorophenyl)-1-(5-(isopropylthio)-4-(4-methylpiperazin-1-yl)thiazol-2-yl)-3-methyl-1H-pyrazole-5-carboxylic acid The title compound was made in a manner analogous to Compound 12 as described above. $^1$H NMR (500 MHz, MeOD) δ 7.43 (td, J=7.9, 6.1 Hz, 1H), 7.40-7.37 (m, 1H), 7.37-7.32 (m, 1H), 7.09-7.03 (m, 1H), 4.43-3.50 (m, 4H), 3.42-3.31 (m, 4H), 3.29-3.14 (m, 1H), 2.91 (s, 3H), 2.35 (s, 3H), 1.31 (d, J=6.7 Hz, 6H). MS (m/z): 476.1 $[M+1]^+$ Compound 30: 4-(3-fluorophenyl)-3-methyl-1-(5-(4-(trifluoromethyl)phenyl)-1,3,4-thiadiazol-2-yl)-1H-pyrazole-5-carboxylic acid 5-(4-(trifluoromethyl)phenyl)-1,3,4-thiadiazol-2-amine Thiosemicarbazide (480 mg, 5.26 mmol) and 4-(trifluoromethyl)benzoic acid (1.00 g, 5.26 mmol) were suspended in phosphorus oxychloride (1.40 mL) and heated at 75° C. for 30 min. After cooling down to rt., water (5.5 mL) was added and the reaction mixture was reflux for 4 h. The reaction mixture was cooled to rt. and basicified to pH 8 by dropwise addition of 6 N NaOH solution under stirring. The precipitate was filtered and washed with water to give the title compound (1.09 g, 4.44 mmol, 85%) as white solid.

2-chloro-5-(4-(trifluoromethyl)phenyl)-1,3,4-thiadiazole

A stirred suspension of 5-(4-(trifluoromethyl)phenyl)-1,3,4-thiadiazol-2-amine (700 mg, 2.85 mmol) and copper (18 mg, 0.29 mmol) in conc. hydrochloric acid (2.8 mL) and acetic acid (14 mL) was cooled to 0° C. To the suspension was added portion wise a solution of sodium nitrite (206 mg, 2.99 mmol) in water (0.94 mL) and the reaction mixture was then stirred at rt. for 16 h. After cooling to 0° C., more solution of sodium nitrite (41 mg, 0.59 mmol) in water (0.20 mL) was added and stirring was continued at rt for 3 h. The reaction mixture was added drop wise to a cold solution of water (150 mL) and the precipitate was filtered to afford the title compound (627 mg, 2.37 mmol, 83%) as yellow solid.

2-hydrazinyl-5-(4-(trifluoromethyl)phenyl)-1,3,4-thiadiazole

The 2-chloro-5-(4-(trifluoromethyl)phenyl)-1,3,4-thiadiazole (425 mg, 1.61 mmol) and the hydrazine hydrate (176 mg, 1.93 mmol) were stirred in dioxane at 82° C. After 3 h, more hydrazine hydrate (65 mg, 0.71 mmol) was added and stirring at 82° C. was continued for 16 h. More hydrazine hydrate (60 mg, 0.66 mmol) was added to the suspension and another 4 h was required to complete the reaction. The yellow precipitate was filtered and rinsed with $Et_2O$ to give the title compound (346 mg, 1.33 mmol, 83%) as yellow solid.

Methyl 3-methyl-1-(5-(4-(trifluoromethyl)phenyl)-1,3,4-thiadiazol-2-yl)-1H-pyrazole-5-carboxylate Methyl 2-(methoxyimino)-4-oxopentanoate (127 mg, 0.734 mmol) was dissolved in MeOH (4 mL) and 2-hydrazinyl-5-(4-(trifluoromethyl)phenyl)-1,3,4-thiadiazole (191 mg, 0.734 mmol) was added followed by HCl 12 N (245 μL, 2.94 mmol) dropwise. The reaction mixture was heated to reflux for 5 h. The reaction mixture was concentrated. The residual starting material was removed by triturating in DCM. The filtrate was concentrated and the crude product was purified by flash chromatography on silica gel using a solution of ethyl acetate in hexanes (0 to 50% gradient) to give the title compound (55.6 mg, 0.151 mmol, 21%) as yellow oil.

Methyl 4-bromo-3-methyl-1-(5-(4-(trifluoromethyl)phenyl)-1,3,4-thiadiazol-2-yl)-1H-pyrazole-5-carboxylate Methyl 3-methyl-1-(5-(4-(trifluoromethyl)phenyl)-1,3,4-thiadiazol-2-yl)-1H-pyrazole-5-carboxylate (88 mg, 0.24 mmol) was dissolved in TFA (1.2 ml) and N-bromosuccinimide (47 mg, 0.26 mmol) was added. The reaction mixture was stirred 2 h at rt. followed by the addition of more N-bromosuccinimide (12 mg, 0.067 mmol) and stirring was continued for 16 h. More N-bromosuccinimide (12 mg, 0.067 mmol) and stirring was continued another 16 h. The reaction mixture was slowly added to ice water and the solid was filtered, washed with water and dried to give the title compound (84 mg, 0.19 mmol, 78%) as a yellow solid.

4-(3-fluorophenyl)-3-methyl-1-(5-(4-(trifluoromethyl)phenyl)-1,3,4-thiadiazol-2-yl)-1H-pyrazole-5-carboxylic acid In a 5 mL glass microwave vial equipped with a magnetic stirring bar and nitrogen flow at room temperature was placed the Methyl 4-bromo-3-methyl-1-(5-(4-(trifluoromethyl)phenyl)-1,3,4-thiadiazol-2-yl)-1H-pyrazole-5-carboxylate (42 mg, 0.094 mmol), (3-fluorophenyl)boronic acid (16 mg, 0.11 mmol) and $Na_2CO_3$ (50 mg, 0.47 mmol). Nitrogen gas was bubbled through a solution of dioxane/water (1.2 mL, 4:1) and then the solution was added to the microwave vial, followed by the addition of the catalyst $Pd(PPh_3)_4$ (11 mg, 0.00095 mmol). The vial was capped and placed in an oil bath at 85° C. for 16 h. LiOH (11 mg, 0.47 mmol) was added to the reaction mixture and stirred under microwave radiation at 115° C. for 15 min. The product was purified using a semi prep HPLC-MS (column X-Bridge 30×50, eluted with 40-60% MeCN/$NH_4CO_2H$ 10 mM, pH 3.8/Flow 45 ml/min/10 min), resulting in the title compound (6.4 mg, 0.014 mmol, 15%) as a white solid after lyophilization.

$^1H$ NMR (500 MHz, DMSO) δ 8.23 (d, J=8.2 Hz, 2H), 7.95 (d, J=8.2 Hz, 2H), 7.48-7.36 (m, 3H), 7.18-7.09 (m, 1H), 2.32 (s, 3H); MS (m/z): 448.9 $[M+1]^+$

Compound 31: 4-(3-fluorophenyl)-1-(5-((2-methoxyethyl)(methyl)amino)-4-(4-(trifluoromethyl)phenyl)thiazol-2-yl)-3-methyl-1H-pyrazole-5-carboxylic acid methyl 1-(4-(3,4-dichlorophenyl)thiazol-2-yl)-3-methyl-1H-pyrazole-5-carboxylate Methyl 2-(methoxyimino)-4-oxopentanoate (1.00 g, 5.77 mmol) was dissolved in MeOH (60 mL) and 4-(3,4-dichlorophenyl)-2-hydrazinylthiazole as prepared as described (1.52 g, 5.77 mmol) was added followed by HCl 12 N (1.82 mL, 23.1 mmol) dropwise. The reaction mixture was heated to reflux overnight. The reaction mixture was diluted with EtOAc and transferred into an extraction funnel. The layers were separated and the aqueous layer was extracted with EtOAc (3×). The combined organic layers were dried over $Na_2SO_4$, filtered and concentrated under vacuum. The crude product was purified by flash chromatography on silica gel (dry packing) using a solution of 1:2:18 EtOAc/DCM/hexanes in 1:9 DCM/hexanes (0 to 100% gradient), affording the title compound (1.23 g, 2.19 mmol, 38%) as yellow solid.

methyl 1-(4-(3,4-dichlorophenyl)-5-fluorothiazol-2-yl)-3-methyl-1H-pyrazole-5-carboxylate methyl 1-(4-(3,4-dichlorophenyl)thiazol-2-yl)-3-methyl-1H-pyrazole-5-carboxylate (500 mg, 1.36 mmol) was dissolve in MeCN/DCE (4 mL, 1:1). SelectFluor (577 mg, 1.63 mmol) was added and the reaction was stirred 18 h at 80° C. The crude product was concentrated under vacuum and was purified by flash chromatography on silica gel (wet loading with DCM) using a solution of EtOAc in hexanes (5 to 20% gradient), affording the title compound (190 mg, 0.492 mmol, 36%) as white solid.

methyl 4-bromo-1-(4-(3,4-dichlorophenyl)-5-fluorothiazol-2-yl)-3-methyl-1H-pyrazole-5-carboxylate Bromine (0.126 mL, 2.46 mmol) was added to a solution of methyl 1-(4-(3,4-dichlorophenyl)-5-fluorothiazol-2-yl)-3-methyl-1H-pyrazole-5-carboxylate (190 mg, 0.492 mmol) in MeCN/DCM (5 mL, 1:1 mL). The reaction was stirred for 5 hours at room temperature. A saturated aqueous solution of $Na_2SO_3$ was added and the reaction mixture was extracted with EtOAc (3×). The combined organic layers were dried with sodium sulfate, filtered and evaporated under reduced pressure. The crude product was purified by flash chromatography (dry packing) on silica gel using a solution of DCM in hexanes (10 to 40%), affording the title compound (42.6 mg, 0.092 mmol, 19%) as a white solid.

1-(4-(3,4-dichlorophenyl)-5-fluorothiazol-2-yl)-4-(3-fluorophenyl)-3-methyl-1H-pyrazole-5-carboxylic acid In a 5 mL glass microwave vial equipped with a magnetic stirring bar and nitrogen flow at room temperature was placed methyl 4-bromo-1-(4-(3,4-dichlorophenyl)-5-fluorothiazol-2-yl)-3-methyl-1H-pyrazole-5-carboxylate (42.6 mg, 0.092 mmol), 3-fluorophenylboronic acid (15.4 mg, 0.110 mmol) and $Na_2CO_3$ (48.5 mg, 0.458 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (10.6 mg, 0.009 mmol). The vial was capped and placed in an oil bath at 85° C. for 16 h. LiOH (19.2 mg, 0.458 mmol) was added to the reaction mixture and stirred under microwave radiation at 120° C. for 10 min. The product was purified using a semi prep HPLC-MS (column X-Bridge 30×50, eluted with 55-75% MeCN/$NH_4CO_2H$ 10 mM, pH 3.8/Flow 45 ml/min/11 min), resulting in the title compound (8.93 mg, 0.019 mmol, 21%) as white solid after lyophilisation.

$^1$H NMR (500 MHz, DMSO) δ 7.92 (t, J=1.1 Hz, 1H), 7.76 (d, J=1.1 Hz, 2H), 7.48 (dd, J=14.4, 8.0 Hz, 1H), 7.41-7.30 (m, J=15.4, 9.1 Hz, 2H), 7.19 (t, J=7.6 Hz, 1H), 3.33 (1H, below water signal), 2.29 (s, 3H); MS (m/z): 466.9 $[M+1]^+$.

4-(3-fluorophenyl)-1-(5-((2-methoxyethyl)(methyl)amino)-4-(4-(trifluoromethyl)phenyl)thiazol-2-yl)-3-methyl-1H-pyrazole-5-carboxylic acid In a 5 mL glass microwave vial equipped with a magnetic stirring bar was placed 1-(5-fluoro-4-(4-(trifluoromethyl)phenyl)thiazol-2-yl)-4-(3-fluorophenyl)-3-methyl-1H-pyrazole-5-carboxylic acid (10 mg, 0.021 mmol) and (2-methoxyethyl)methylamine (246 mg, 2.75 mmol). The vial was capped and placed in an oil bath at 80° C. for 16 h. The reaction mixture was warmed to 90° C. and stirred for another 3 days. The product was purified using a semi prep HPLC-MS (column X-Bridge 30×50, eluted with 55-75% MeCN/$NH_4CO_2H$ 10 mM, pH 3.8/Flow 45 ml/min/10 min), resulting in the title compound (3.3 mg, 0.0062 mmol, 29%) as yellowish solid after lyophilization.

$^1$H NMR (500 MHz, MeOD) δ 8.38 (d, J=8.3 Hz, 2H), 7.68 (d, J=8.3 Hz, 2H), 7.50-7.44 (m, 1H), 7.33-7.29 (m, 1H), 7.28-7.23 (m, 1H), 7.16-7.09 (m, 1H), 3.56 (t, J=5.3 Hz, 2H), 3.28 (s, 3H), 3.20 (t, J=5.3 Hz, 2H), 2.89 (s, 3H), 2.35 (s, 3H); MS (m/z): 535.1 $[M+1]^+$

Compound 32: 1-(4-(4,4-dimethylpiperidin-1-yl)-5-(isopropylthio)thiazol-2-yl)-4-(3-fluorophenyl)-3-methyl-1H-pyrazole-5-carboxylic acid The title compound was made in a manner analogous to Compound 12 as described above. $^1$H NMR (500 MHz, DMSO) δ 7.47-7.46 (m, 1H), 7.34-7.30 (m, 2H), 7.17 (bs, 1H), 3.59-3.53 (m, 4H), 3.11 (q, J=5.0 Hz, 1H), 2.27 (s, 3H), 1.38-1.34 (m, 4H), 1.23 (d, J=6.7 Hz, 6H), 0.95 (s, 6H). MS (m/z): 489.2 $[M+1]^+$.

Compound 33: 1-(4-(4-(tert-butoxycarbonyl)piperazin-1-yl)-5-(isopropylthio)thiazol-2-yl)-4-(3-fluorophenyl)-3-methyl-1H-pyrazole-5-carboxylic acid The title compound was made in a manner analogous to Compound 12 as described above. $^1$H NMR (500 MHz, DMSO) δ 7.53-7.48 (m, 1H), 7.30-7.28 (m, 2H), 7.24-7.21 (m, 1H), 3.53-3.51 (m, 4H), 3.40 (bs, 4H), 3.19-3.14 (m, 1H), 2.28 (s, 3H), 1.41 (s, 9H), 1.24 (d, J=6.7 Hz, 6H). MS (m/z): 562.2 $[M+1]^+$.

Compound 34: 4-(3-fluorophenyl)-1-(5-(isopropylthio)-4-(3-(trifluoromethyl)pyrrolidin-1-yl)thiazol-2-yl)-3-methyl-1H-pyrazole-5-carboxylic acid The title compound was made in a manner analogous to Compound 12 as described above. $^1$H NMR (500 MHz, DMSO) δ 7.53-7.49 (m, 1H), 7.30-7.27 (m, 2H), 7.25-7.21 (m, 1H), 3.82-3.70 (m, 3H), 3.64-3.59 (m, 1H), 3.06-3.01 (m, 1H), 2.28 (s, 3H), 2.25-2.18 (m, 1H), 2.06-1.99 (m, 1H), 1.22 (d, J=6.7, Hz, 6H). MS (m/z): 515.1 $[M+1]^+$.

Compound 35: 4-(3-fluorophenyl)-1-(5-(isopropylthio)-4-(piperazin-1-yl)thiazol-2-yl)-3-methyl-1H-pyrazole-5-carboxylic acid hydrochloric acid salt The title compound was made in a manner analogous to Compound 12 as described above. $^1$H NMR (500 MHz, MeOD) δ 8.45 (bs, 1H), 7.44-7.39 (m, 1H), 7.37-7.31 (m, 2H), 7.06-7.03 (m, 1H), 3.85-3.83 (m, 4H), 3.28-3.26 (m, 4H), 3.23-3.17 (m, 1H), 2.33 (s, 3H), 1.29 (d, J=6.7 Hz, 6H). MS (m/z): 462.1 $[M+1]^+$.

Compound 36: 4-(3-fluorophenyl)-3-methyl-1-(5-(2-methylprop-1-en-1-yl)-4-(4-(trifluoromethyl)phenyl)thiazol-2-yl)-1H-pyrazole-5-carboxylic acid Methyl 4-iodo-1-(5-iodo-4-(4-(trifluoromethyl)phenyl)thiazol-2-yl)-3-methyl-1H-pyrazole-5-carboxylate The methyl 3-methyl-1-(4-(4-(trifluoromethyl)phenyl)thiazol-2-yl)-1H-pyrazole-5-carboxylate prepared as described above (1.86 g, 5.06 mmol) was dissolved in TFA (25 ml) and N-iodosuccinimide (2.39 g, 10.6 mmol) was added. The reaction mixture was stirred 1h 30 at rt. followed by the addition of more N-iodosuccinimide (190 mg, 0.844 mmol) and stirring was continued for 4 h. The reaction mixture was slowly added to ice water and the solid was filtered, washed with water and dried to give the title compound (2.45 g, 3.96 mmol, 78%) as a pink solid.

Methyl 4-iodo-3-methyl-1-(5-(2-methylprop-1-en-1-yl)-4-(4-(trifluoromethyl)phenyl)thiazol-2-yl)-1H-pyrazole-5-carboxylate In a glass microwave vial equipped with a magnetic stirring bar and nitrogen flow at room temperature was placed methyl 4-iodo-1-(5-iodo-4-(4-(trifluoromethyl)phenyl)thiazol-2-yl)-3-methyl-1H-pyrazole-5-carboxylate (800 mg, 1.29 mmol), (2-methylprop-1-en-1-yl)boronic acid (129 mg, 1.29 mmol) and $K_2CO_3$ (893 mg, 6.46 mmol), nitrogen and vacuum cycles were performed (2×). Nitrogen gas was bubbled through a solution of THF (13 mL) and then the solution was added to the microwave vial, followed by the addition of the catalyst Pd(dtbpf)$Cl_2$ (84.2 mg, 0.129 mmol). The vial was capped and placed in an oil bath at 90° C. for 16 h. The reaction mixture was diluted with EtOAc, washed with water and brine. The organic layer was dried with magnesium sulfate, filtered and evaporated under reduced pressure. The crude product was purified by flash chromatography on silica gel using a solution of ethyl acetate in hexanes (0 to 10% gradient) to give the title compound (172 mg, 0.314 mmol, 24%) as a yellow solid.

Methyl 4-(3-fluorophenyl)-3-methyl-1-(5-(2-methylprop-1-en-1-yl)-4-(4-(trifluoromethyl)phenyl)thiazol-2-yl)-1H-pyrazole-5-carboxylate In a 5 mL glass microwave vial equipped with a magnetic stirring bar and nitrogen flow at room temperature was placed methyl 4-iodo-3-methyl-1-(5-(2-methylprop-1-en-1-yl)-4-(4-(trifluoromethyl)phenyl)thiazol-2-yl)-1H-pyrazole-5-carboxylate (172 mg, 0.314 mmol), 3-fluorophenylboronic acid (52.8 mg, 0.377 mmol) and $Na_2CO_3$ (167 mg, 1.57 mmol), nitrogen and vacuum cycles were performed (2×). Nitrogen gas was bubbled through a solution of dioxane/water (3 mL, 4:1) and then the solution was added to the microwave vial, followed by the addition of the catalyst Pd($PPh_3$)$_4$ (36.3 mg, 0.0314 mmol). The vial was capped and placed in an oil bath at 85° C. for 16 h. The crude product was purified by flash chromatography on silica gel using a solution of EtOAc in hexanes (0 to 10% gradient), affording the title compound (111 mg, 0.215 mmol, 69%) as yellow solid.

4-(3-fluorophenyl)-3-methyl-1-(5-(2-methylprop-1-en-1-yl)-4-(4-(trifluoromethyl)phenyl)thiazol-2-yl)-1H-pyrazole-5-carboxylic acid Into a 5 mL glass microwave vial, was placed methyl 4-(3-fluorophenyl)-3-methyl-1-(5-(2-methylprop-1-en-1-yl)-4-(4-(trifluoromethyl)phenyl)thiazol-2-yl)-1H-pyrazole-5-carboxylate (20 mg, 0.039 mmol) and LiOH (4.6 mg, 0.19 mmol). A solution of dioxane/water (2 mL, 4:1) was added. The vial was heated to 110° C. under microwave radiation for 15 minutes. The crude product was purified using a semi prep HPLC-MS (X-Bridge 30×50, eluted with 60-80% MeCN/AmForm 10 mM, pH 3.8/Flow 45 ml/min/10 min), resulting in the title compound (8.2 mg, 0.016 mmol, 42%) as yellow solid after lyophilisation.

$^1H$ NMR (500 MHz, DMSO) δ 7.89 (d, J=8.3 Hz, 2H), 7.81 (d, J=8.3 Hz, 2H), 7.51-7.44 (m, 1H), 7.39-7.30 (m, 2H), 7.22-7.14 (m, 1H), 6.41-6.36 (m, 1H), 2.30 (s, 3H), 1.95 (s, 3H), 1.90 (s, 3H); MS (m/z): 502.0 $[M+1]^+$.

Compound 37: 4-(3-fluorophenyl)-3-Methyl-1-(4-(2-methylprop-1-en-1-yl)-5-(4-(trifluoromethyl)phenyl)thiazol-2-yl)-1H-pyrazole-5-carboxylic acid Methyl 4-bromo-1-(4,5-dibromothiazol-2-yl)-3-methyl-1H-pyrazole-5-carboxylate To a solution of methyl 1-(4-bromo-5-(isopropylthio)thiazol-2-yl)-3-methyl-1H-pyrazole-5-carboxylate prepared as described above with respect to Compound 1 (27.9 g, 74.07 mmol) in MeCN (570 mL) at 0° C. was added a solution of $Br_2$ (21 mL) in MeCN (170 mL). The reaction mixture was allowed to warm up to room temperature and was stirred for 2.5 h. The reaction mixture was filtrated and the mother liquor was transferred in an extraction funnel. The layers were separated the aqueous layer was extracted with DCM (3×). The combined organic layers were dried over $MgSO_4$, filtrated and concentrated under vacuum, affording the title compound product (8.76 g, 19.0 mmol, 26%) as yellow solid.

Methyl 4-bromo-1-(4-bromo-5-(4-(trifluoromethyl)phenyl)thiazol-2-yl)-3-methyl-1H-pyrazole-5-carboxylate In a 20 mL glass microwave vial equipped with a magnetic stirring bar and nitrogen flow at room temperature was placed methyl 4-bromo-1-(4,5-dibromothiazol-2-yl)-3-methyl-1H-pyrazole-5-carboxylate (1.50 g, 3.26 mmol), (4-(trifluoromethyl)phenyl)boronic acid (619 mg, 3.26 mmol) and $K_2CO_3$ (2.25 g, 16.3 mmol), nitrogen and vacuum cycles were performed (2×). Nitrogen gas was bubbled through a solution of THF (11 mL) and then the solution was added to the microwave vial, followed by the addition of the catalyst Pd(dtbpf)$Cl_2$ (212 mg, 0.326 mmol). The vial was capped and placed in an oil bath at 90° C. for 16 h. The solvent was evaporated under vacuum and the crude product was purified by flash chromatography on silica gel (dry packing) using a solution of EtOAc in hexanes (1 to 5% gradient) and was then purified again by reverse chromatography on C-18 column with a solution of MeCN in water (containing 10 mM of $NH_4CO_2H$) (60 to 100%), affording the title compound (490 mg, 0.933 mmol, 29%) as white powder after lyophilisation.

Methyl 4-bromo-3-methyl-1-(4-(2-methylprop-1-en-1-yl)-5-(4-(trifluoromethyl)phenyl)thiazol-2-yl)-1H-pyrazole-5-carboxylate In a 5 mL glass microwave vial equipped with a magnetic stirring bar and nitrogen flow at room temperature was placed methyl 4-bromo-1-(4-bromo-5-(4-(trifluoromethyl)phenyl)thiazol-2-yl)-3-methyl-1H-pyrazole-5-carboxylate (200 mg, 0.381 mmol), (2-methylprop-1-en-1-yl)boronic acid (38.0 mg, 0.381 mmol) and $K_2CO_3$ (263 mg, 1.90 mmol), nitrogen and vacuum cycles were performed (2×). Nitrogen gas was bubbled through a solution of THF (2 mL) and then the solution was added to the microwave vial, followed by the addition of the catalyst Pd(dtbpf)$Cl_2$ (24.8 mg, 0.0381 mmol). The vial was capped and placed in an oil bath at 90° C. for 16 h. The solvent was evaporated under vacuum and the crude product was purified by flash chromatography on silica gel (dry packing) using a solution of EtOAc in hexanes (0 to 5% gradient), affording the title compound (62.0 mg, 0.124 mmol, 33%) as white solid.

Methyl 4-(3-fluorophenyl)-3-methyl-1-(4-(2-methylprop-1-en-1-yl)-5-(4-(trifluoromethyl)phenyl)thiazol-2-yl)-1H-pyrazole-5-carboxylate In a 5 mL glass microwave vial equipped with a magnetic stirring bar and nitrogen flow at room temperature was placed methyl 4-bromo-3-methyl-1-(4-(2-methylprop-1-en-1-yl)-5-(4-(trifluoromethyl)phenyl)thiazol-2-yl)-1H-pyrazole-5-carboxylate (62.0 mg, 0.124 mmol), 3-fluorophenylboronic acid (20.8 mg, 0.149 mmol) and $Na_2CO_3$ (65.7 mg, 0.620 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (13.8 mg, 0.012 mmol). The vial was capped and placed in an oil bath at 85° C. for 16 h. The crude product was purified by flash chromatography on silica gel using a solution of EtOAc in hexanes (1% isochratic), affording the title compound (27.0 mg, 0.052 mmol, 42%) as colorless oil.

4-(3-fluorophenyl)-3-Methyl-1-(4-(2-methylprop-1-en-1-yl)-5-(4-(trifluoromethyl)phenyl)thiazol-2-yl)-1H-pyrazole-5-carboxylic acid Into a 25 mL round bottom flask, methyl 4-(3-fluorophenyl)-3-methyl-1-(4-(2-methylprop-1-en-1-yl)-5-(4-(trifluoromethyl)phenyl)thiazol-2-yl)-1H-pyrazole-5-carboxylate (27.0 mg, 0.052 mmol) was diluted with THF/MeOH (2 mL, 1:1). A solution of NaOH 1 M (262 μL, 0.262 mmol) was added and the reaction was stirred 16 h at rt. A solution of HCl 1 M (262 μL, 0.262 mmol) and water (2 mL) were added. The reaction mixture was directly purified by reverse chromatography on C-18 column with a solution of MeCN in water (containing 10 mM of $NH_4CO_2H$) (35 to 75%), affording the title compound (3.00 mg, 0.006 mmol, 11%) as white powder after lyophilisation.

$^1$H NMR (500 MHz, MeOD) δ 7.75 (d, J=8.3 Hz, 2H), 7.69 (d, J=8.2 Hz, 2H), 7.43-7.30 (m, 3H), 7.06-6.99 (m, 1H), 6.14-6.09 (m, 1H), 2.33 (s, 3H), 2.14 (d, J=1.0 Hz, 3H), 1.88 (d, J=1.1 Hz, 3H); MS (m/z): 502.1 $[M+1]^+$.

Compound 38: 1-(4,5-bis(4-(trifluoromethyl)phenyl)thiazol-2-yl)-4-(3-fluorophenyl)-3-methyl-1H-pyrazole-5-carboxylic acid The title compound was made in a manner analogous to Compound 37 as described above. $^1$H NMR (500 MHz, DMSO) δ 7.82 (d, J=8.2 Hz, 2H), 7.73 (d, J=8.4 Hz, 2H), 7.65 (dd, J=8.1, 3.6 Hz, 4H), 7.53-7.46 (m, 1H), 7.40-7.33 (m, 2H), 7.23-7.17 (m, 1H), 2.32 (s, 3H). MS (m/z): 592.2 $[M+1]^+$.

Compound 39: 2-(4-(3-fluorophenyl)-3-methyl-1H-pyrazol-1-yl)-4,5-bis(4-(trifluoromethyl)phenyl)thiazole The title compound was made in a manner analogous to Compound 37 as described above. $^1$H NMR (500 MHz, DMSO) δ 8.94 (s, 1H), 7.82 (d, J=8.3 Hz, 2H), 7.78 (d, J=8.3 Hz, 2H), 7.73 (d, J=8.2 Hz, 2H), 7.66 (d, J=8.0 Hz, 2H), 7.54-7.48 (m, 3H), 7.22-7.15 (m, 1H), 2.48 (s, 3H). MS (m/z): 548.2 $[M+1]^+$.

Compound 40: 1-(4-(4-(tert-butyl)piperidin-1-yl)-5-(isopropylthio)thiazol-2-yl)-4-(3-fluorophenyl)-3-methyl-1H-pyrazole-5-carboxylic acid The title compound was made in a manner analogous to Compound 12 as described above. $^1$H NMR (500 MHz, DMSO) δ 7.53-7.48 (m, 1H), 7.29-7.21 (m, 3H), 4.37 (d, J=12.9 Hz, 2H), 3.15-3.10 (m, 1H), 2.76 (t, J=11.6 Hz, 2H), 2.28 (s, 3H), 1.66 (d, J=12.6 Hz, 2H), 1.27-1.20 (m, 8H), 1.18-1.14 (m, 1H), 0.85 (s, 9H). MS (m/z): 517.2 $[M+1]^+$.

Compound 41: 4-(3-fluorophenyl)-1-(5-(isopropylthio)-4-(6-azaspiro[2.5]octan-6-yl)thiazol-2-yl)-3-methyl-1H-pyrazole-5-carboxylic acid The title compound was made in a manner analogous to Compound 12 as described above. $^1$H NMR (500 MHz, DMSO) δ 7.47 (bs, 1H), 7.31 (bs, 2H), 7.18 (bs, 1H), 3.62-3.60 (m, 4H), 3.16-3.11 (m, 1H), 2.27 (s, 3H), 1.40-1.38 (m, 4H), 1.24 (d, J=6.7 Hz, 6H), 0.32 (s, 4H). MS (m/z): 487.2 $[M+1]^+$.

Compound 42: 4-(3-fluorophenyl)-1-(5-(isopropylthio)-4-(4-methoxy-4-(trifluoromethyl)piperidin-1-yl)thiazol-2-yl)-3-methyl-1H-pyrazole-5-carboxylic acid The title compound was made in a manner analogous to Compound 12 as described above. $^1$H NMR (500 MHz, DMSO) δ 7.50-7.46 (m, 1H), 7.32-7.29 (m, 2H), 7.21-7.18 (m, 1H), 4.24 (d, J=13.1 Hz, 2H), 3.39 (s, 3H), 3.18-3.13 (m, 1H), 3.05 (t, J=11.9 Hz, 2H), 2.28 (s, 3H), 1.91 (d, J=12.6 Hz, 2H), 1.76 (td, J=13.5, 4.4 Hz, 2H), 1.24 (d, J=6.7 Hz, 6H). MS (m/z): 559.1 $[M+1]^+$.

Compound 43: 4-(3-fluorophenyl)-1-(4-(4-methoxyphenyl)-5-(4-(trifluoromethyl)phenyl)thiazol-2-yl)-3-methyl-1H-pyrazole-5-carboxylic acid The title compound was made in a manner analogous to Compound 37 as described above. $^1$H NMR (500 MHz, DMSO) δ 7.79 (d, J=8.2 Hz, 2H), 7.64 (d, J=8.2 Hz, 2H), 7.54-7.46 (m, 1H), 7.41-7.36 (m, 2H), 7.36-7.31 (m, 2H), 7.26-7.17 (m, 1H), 6.95-6.90 (m, 2H), 3.77 (s, 3H), 2.32 (s, 3H). MS (m/z): 554.0 $[M+1]^+$.

Compound 44: 1-(4,5-bis(4-methoxyphenyl)thiazol-2-yl)-4-(3-fluorophenyl)-3-methyl-1H-pyrazole-5-carboxylic acid The title compound was made in a manner analogous to Compound 37 as described above. $^1$H NMR (500 MHz, DMSO) δ 7.56-7.46 (m, 1H), 7.43-7.29 (m, 6H), 7.27-7.14 (m, 1H), 7.03-6.97 (m, 2H), 6.92-6.85 (m, 2H), 3.80 (s, 3H), 3.75 (s, 3H), 2.30 (s, 3H). MS (m/z): 516.4 $[M+1]^+$.

Compound 45: 4-(3-fluorophenyl)-1-(5-(4-methoxyphenyl)-4-(4-(trifluoromethyl)phenyl)thiazol-2-yl)-3-methyl-1H-pyrazole-5-carboxylic acid The title compound was made in a manner analogous to Compound 37 as described above. $^1$H NMR (500 MHz, DMSO) δ 7.70 (d, J=8.4 Hz, 2H), 7.65 (d, J=8.4 Hz, 2H), 7.54-7.47 (m, 1H), 7.340-7.30 (m, 4H), 7.27-7.18 (m, 1H), 7.05-7.00 (m, 2H), 3.81 (s, 3H), 2.32 (s, 3H). MS (m/z): 553.9 $[M+1]^+$.

Compound 46: 1-(4-(4-(tert-butyl)-3-oxopiperazin-1-yl)-5-(isopropylthio)thiazol-2-yl)-4-(3-fluorophenyl)-3-methyl-1H-pyrazole-5-carboxylic acid The title compound was made in a manner analogous to Compound 12 as described above. $^1H$ NMR (500 MHz, DMSO) δ 7.44-7.40 (m, 2H), 7.36-7.34 (m, 1H), 7.12-7.09 (m, 1H), 4.19 (s, 2H), 3.77-3.75 (m, 2H), 3.46-3.44 (m, 2H), 3.12-3.07 (m, 1H), 2.26 (s, 3H), 1.38 (s, 9H), 1.23 (d, J=6.7 Hz, 6H). MS (m/z): 532.1 $[M+1]^+$.

Compound 47: 4-(3-fluorophenyl)-3-methyl-1-(5-(3-(methylamino)-3-oxopropyl)-4-(4-(trifluoromethyl)phenyl)thiazol-2-yl)-1H-pyrazole-5-carboxylic acid Methyl 1-(5-(3-(tert-butoxy)-3-oxoprop-1-en-1-yl)-4-(4-(trifluoromethyl)phenyl)thiazol-2-yl)-4-iodo-3-methyl-1H-pyrazole-5-carboxylate In a 5 mL glass microwave vial equipped with a magnetic stirring bar at room temperature was placed the methyl 4-iodo-1-(5-iodo-4-(4-(trifluoromethyl)phenyl)thiazol-2-yl)-3-methyl-1H-pyrazole-5-carboxylate prepared as in Compound 36 (500 mg, 0.807 mmol), the tert-butyl acrylate (113 μL, 0.888 mmol), $K_2CO_3$ (558 mg, 4.035 mmol) and the catalyst Pd(dtbpf)$Cl_2$ (53 mg, 0.0807 mmol). THF (8.1 mL, 0.1 M) was added to the microwave tube and a flow of nitrogen was bubbled through the brown mixture for 5 minutes. The vial was capped and stirred in an oil bath at 90° C. for 16 h. After 16 h, the reaction was purified on a silica gel column using a mobile phase of 0-5% EtOAc in hexanes. The fractions containing the product were evaporated under reduced pressure to afford the title compound (215 mg, 0.347 mmol, 43%) as an off-white foam.

Methyl 1-(5-(3-(tert-butoxy)-3-oxoprop-1-en-1-yl)-4-(4-(trifluoromethyl)phenyl)thiazol-2-yl)-4-(3-fluorophenyl)-3-methyl-1H-pyrazole-5-carboxylate In a 5 mL glass microwave vial equipped with a magnetic stirring bar at room temperature was placed the methyl 1-(5-(3-(tert-butoxy)-3-oxoprop-1-en-1-yl)-4-(4-(trifluoromethyl)phenyl)thiazol-2-yl)-4-iodo-3-methyl-1H-pyrazole-5-carboxylate (105 mg, 0.169 mmol), the (3-fluorophenyl)boronic acid (24 mg, 0.169 mmol), $Na_2CO_3$ (90 mg, 0.845 mmol) and the catalyst $Pd(PPh_3)_4$ (20 mg, 0.0169 mmol). THF:water (1.7 mL, 4:1, 0.1 M) which was deoxygenated with a flow of nitrogen for 5 minutes was added to the microwave tube. The vial was capped and stirred in an oil bath at 90° C. for 16 h. After 16 h, the reaction was purified on a silica gel column using a mobile phase of 0-5% EtOAc in hexanes. The fractions containing the product were evaporated under reduced pressure to afford the title compound (69 mg, 0.117 mmol, 70%) as a colorless oil.

methyl 1-(5-(3-(tert-butoxy)-3-oxopropyl)-4-(4-(trifluoromethyl)phenyl)thiazol-2-yl)-4-(3-fluorophenyl)-3-methyl-1H-pyrazole-5-carboxylate In a 10 mL round bottom flask equipped with a magnetic stirring bar at room temperature was placed the methyl 1-(5-(3-(tert-butoxy)-3-oxoprop-1-en-1-yl)-4-(4-(trifluoromethyl)phenyl)thiazol-2-yl)-4-(3-fluorophenyl)-3-methyl-1H-pyrazole-5-carboxylate (68 mg, 0.115 mmol), the catalyst $Pd(OH)_2$ (15 mg) and MeOH:AcOH (1 mL, 1:1, 0.1 M). The flask was equipped with a balloon of hydrogen. The reaction was purged three times with hydrogen and vacuum. The reaction was stirred at room temperature under hydrogen atmosphere for 16 h. After 16 h, the reaction was filtered over celite and the filter cake was washed with methanol. The reaction was purified on a silica gel column using a mobile phase of 0-5% EtOAc in hexanes. The fractions containing the product were evaporated under reduced pressure to afford the title compound (50 mg, 0.0848 mmol, 75%) as a yellow oil.

3-(2-(4-(3-fluorophenyl)-5-(methoxycarbonyl)-3-methyl-1H-pyrazol-1-yl)-4-(4-(trifluoromethyl)phenyl)thiazol-5-yl)propanoic acid In a 10 mL round bottom flask equipped with a magnetic stirring bar at room temperature was placed the methyl 1-(5-(3-(tert-butoxy)-3-oxopropyl)-4-(4-(trifluoromethyl)phenyl)thiazol-2-yl)-4-(3-fluorophenyl)-3-methyl-1H-pyrazole-5-carboxylate (50 mg, 0.0848 mmol), the $CeCl_3.7H_2O$ (47 mg, 0.127 mmol) NaI (16 mg, 0.110 mmol) and MeCN (0.7 mL, 0.1 M). The reaction was heated at reflux for 2 h. After 2 h, the reaction was diluted with EtOAc and treated with 0.5 M HCl. The compound was extracted three times with EtOAc. The combined organic layers were dried over $Na_2SO_4$, filtered and evaporated under reduced pressure to afford the title compound (38 mg, 0.0729 mmol, 86%) as an orange solid.

4-(3-fluorophenyl)-3-methyl-1-(5-(3-(methylamino)-3-oxopropyl)-4-(4-(trifluoromethyl)phenyl)thiazol-2-yl)-1H-pyrazole-5-carboxylic acid In a 10 mL round bottom flask equipped with a magnetic stirring bar at room temperature was placed the 3-(2-(4-(3-fluorophenyl)-5-(methoxycarbonyl)-3-methyl-1H-pyrazol-1-yl)-4-(4-(trifluoromethyl)phenyl)thiazol-5-yl)propanoic acid (48 mg, 0.0899 mmol), HATU (51 mg, 0.134 mmol), $MeNH_2$ (67 μL, 0.134 mmol), and Hunig's base (39 μL, 0.224 mmol) in DMF (0.9 mL, 0.1 M). The orange solution turned yellowish within 5 minutes. After 5 min, analysis of the reaction mixture with HPLC-MS indicated that the reaction was complete. The compound was evaporated to dryness. The yellowish residue was transferred into a microwave vial which was added LiOH (21 mg, 0.899 mmol) and THF:water (4:1, 2 mL, 0.04 M). The microwave vial was capped and heated at 110° C. for 15 minutes under microwave radiation. Reaction was filtered and the crude product was purified using a semi prep HPLC-MS (X-Bridge 30×50, eluted with 40-60% MeCN/$NH_4CO_2H$ 10 mM, pH 3.8/Flow 45 mL/min/11 min), resulting in the title compound (8 mg, 0.015 mmol, 17%) as a white solid after lyophilization.

$^1H$ NMR (500 MHz, DMSO) δ 7.93-7.87 (m, 3H), 7.83-7.81 (m, 2H), 7.46-7.39 (m, 2H), 7.36-7.34 (m, 1H), 7.13-7.10 (m, 1H), 3.19 (t, J=7.2 Hz, 2H), 2.58 (d, J=4.6 Hz, 3H), 2.53-2.51 (m, 2H), 2.28 (s, 3H); MS (m/z): 533.0 $[M+1]^+$.

Compound 48: 4-(3-fluorophenyl)-1-(5-(isopropylthio)-4-(4-(2-methoxyethoxy)-4-(trifluoromethyl)piperidin-1-yl)thiazol-2-yl)-3-methyl-1H-pyrazole-5-carboxylic acid The title compound was made in a manner analogous to Compound 11 as described above. $^1H$ NMR (500 MHz, DMSO) δ 14.16 (s, 1H), 7.54-7.47 (m, 1H), 7.28 (d, J=7.7 Hz, 2H), 7.24 (t, J=8.1 Hz, 1H), 4.22 (d, J=13.2 Hz, 2H), 3.72-3.67 (m, 2H), 3.53-3.48 (m, 2H), 3.28 (s, 3H), 3.20-

3.08 (m, 3H), 2.29 (s, 3H), 1.93 (d, J=12.8 Hz, 2H), 1.77 (td, J=13.4, 4.4 Hz, 2H), 1.24 (d, J=6.7 Hz, 6H). MS (m/z): 603.3 $[M+1]^+$.

Compound 49: 4-(3-fluorophenyl)-1-(5-(4-((2-methoxyethyl)carbamoyl)phenyl)-4-(4-(trifluoromethyl)phenyl)thiazol-2-yl)-3-methyl-1H-pyrazole-5-carboxylic acid The title compound was made in a manner analogous to compound Compound 36 as described above. $^1$H NMR (500 MHz, DMSO) δ 8.56 (t, J=5.3 Hz, 1H), 7.87-7.81 (m, 2H), 7.65 (d, J=8.3 Hz, 2H), 7.58 (d, J=8.3 Hz, 2H), 7.49-7.40 (m, 3H), 7.33-7.25 (m, 2H), 7.19-7.10 (m, 1H), 3.42-3.34 (m, 4H), 3.21 (s, 3H), 2.26 (s, 3H). MS (m/z): 625.2 $[M+1]^+$.

Compound 50: 4-(3-fluorophenyl)-1-(5-(4-((2-methoxyethyl)(methyl)carbamoyl)phenyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 7.75-7.62 (m, 4H), 7.54-7.42 (m, 5H), 7.41-7.32 (m, 2H), 7.26-7.16 (m, 1H), 3.69-3.35 (m, 4H), 3.17 (s, 3H), 2.98 (s, 3H), 2.32 (s, 3H). MS (m/z): 639.2 $[M+1]^+$.

Compound 51: 4-(3-fluorophenyl)-1-(5-(4-(2-methoxyacetamido)phenyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 9.92 (s, 1H), 7.72-7.66 (m, 2H), 7.66-7.57 (m, 4H), 7.44-7.36 (m, 1H), 7.36-7.27 (m, 4H), 7.13-7.05 (m, 1H), 3.96 (s, 2H), 3.32 (s, 3H), 2.24 (s, 3H). MS (m/z): 611.2 [M+1]

Compound 52: 4-(3-fluorophenyl)-1-(5-(4-(2-(2-methoxyethoxy)acetamido)phenyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 9.87 (s, 1H), 7.77-7.65 (m, 6H), 7.49-7.36 (m, 5H), 7.17-7.07 (m, 1H), 4.11 (s, 2H), 3.72-3.65 (m, 2H), 3.57-3.51 (m, 2H), 3.31 (s, 3H), 2.31 (s, 3H). MS (m/z): 655.1 $[M+1]^+$ Compound 53: 4-(3-fluorophenyl)-1-(5-(3-((2-methoxyethyl)amino)-3-oxopropyl)-4-(4-(trifluoromethyl)phenyl)thiazol-2-yl)-3-methyl-1H-pyrazole-5-carboxylic acid The title compound was made in a manner analogous to Compound 47 as described above. $^1$H NMR (500 MHz, DMSO) δ 8.49 (bs, 1H), 7.97-7.95 (m, 2H), 7.73-7.71 (m, 2H), 7.42-7.30 (m, 3H), 7.04-7.00 (m, 1H), 3.44-3.42 (m, 2H), 3.38-3.32 (m, 4H), 3.32 (s, 3H), 2.64 (t, J=7.4 Hz, 2H), 2.33 (s, 3H). MS (m/z): 577.1 $[M+1]^+$.

Compound 54: 4-(3-fluorophenyl)-1-(5-(3-((2-methoxyethyl)(methyl)amino)-3-oxopropyl)-4-(4-(trifluoromethyl)phenyl)thiazol-2-yl)-3-methyl-1H-pyrazole-5-carboxylic acid The title compound was made in a manner analogous to Compound 47 as described above. $^1$H NMR (500 MHz, MeOD) δ 7.91-7.90 (m, 2H), 7.75-7.74 (m, 2H), 7.47-7.42 (m, 1H), 7.29-7.27 (m, 1H), 7.24-7.22 (m, 1H), 7.12-7.08 (m, 1H), 3.58-3.49 (m, 4H), 3.35-3.32 (m, 2H), 3.33-3.29 (m, 3H), 3.07-2.96 (m, 3H), 2.91 (t, J=7.1 Hz, 1H), 2.85 (t, J=7.0 Hz, 1H), 2.32 (d, J=1.3 Hz, 3H). MS (m/z): 591.1 $[M+1]^+$.

Compound 55: 4-(3-fluorophenyl)-1-(5-(4-(2-methoxy-N-methylacetamido)phenyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 7.73-7.64 (m, 4H), 7.52-7.32 (m, 7H), 7.22-7.15 (m, 1H), 4.02-3.86 (m, 2H), 3.23 (s, 3H), 3.22 (s, 3H), 2.33 (s, 3H). MS (m/z): 625.2 $[M+1]^+$ Compound 56: 4-(3-fluorophenyl)-1-(5-(4-(2-(2-methoxyethoxy)-N-methylacetamido)phenyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 7.72-7.63 (m, 4H), 7.51-7.33 (m, 7H), 7.21-7.13 (m, 1H), 4.08-3.91 (m, 2H), 3.55-3.44 (m, 2H), 3.42-3.35 (m, 2H), 3.22 (s, 3H), 3.20 (s, 3H), 2.31 (s, 3H). MS (m/z): 669.4 $[M+1]^+$ Compound 57: 4-(3-fluorophenyl)-1-(5-(methoxymethyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 7.90-7.81 (m, 4H), 7.56-7.46 (m, 1H), 7.36-7.28 (m, 2H), 7.25-7.18 (m, 1H), 4.77 (s, 2H), 3.42 (s, 3H), 2.31 (s, 3H). MS (m/z): 492.0 $[M+1]^+$ Compound 58: 1-(5-(4-(2-(2-ethoxyethoxy)ethoxy)phenyl)-4-(4-(trifluoromethyl)phenyl)thiazol-2-yl)-4-(3-fluorophenyl)-3-methyl-1H-pyrazole-5-carboxylic acid The title compound was made in a manner analogous to Compound 36 as described above. $^1$H NMR (500 MHz, DMSO) δ 7.66-7.56 (m, 4H), 7.48-7.41 (m, 1H), 7.32-7.24 (m, 4H), 7.20-7.11 (m, 1H), 7.00-6.94 (m, 2H), 4.08 (dd, J=5.4, 3.8 Hz, 2H), 3.69 (dd, J=5.4, 3.8 Hz, 2H), 3.52 (dd, J=5.8, 3.8 Hz, 2H), 3.43 (dd, J=5.8, 3.9 Hz, 2H), 3.37 (q, J=7.0 Hz, 2H), 2.25 (s, 3H), 1.03 (t, J=7.0 Hz, 3H). MS (m/z): 656.3 [M+1]+

Compound 59: 4-(3-fluorophenyl)-1-(5-(3-fluorophenyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 7.70 (d, J=8.4 Hz, 2H), 7.65 (d, J=8.4 Hz, 2H), 7.54-7.45 (m, 2H), 7.41-7.34 (m, 2H), 7.33-7.28 (m, 2H), 7.27-7.24 (m, 1H), 7.23-7.17 (m, 1H), 2.32 (s, 3H). MS (m/z): 542.0 $[M+1]^+$ Compound 60: 4-(3-fluorophenyl)-1-(5-(hydroxymethyl)-4-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, DMSO) δ 7.91-7.80 (m, 4H), 7.57-7.45 (m, 1H), 7.36-7.27 (m, 2H), 7.26-7.16 (m, 1H), 6.13 (s, 1H), 4.85 (d, J=4.0 Hz, 2H), 2.31 (s, 3H). MS (m/z): 478.1 [M+1]+

Compound 61: 4-(3-fluorophenyl)-3-methyl-1-(5-(4-(trifluoromethyl)phenyl)-4-(4-(trifluoromethyl)piperidin-1-yl)thiazol-2-yl)-1H-pyrazole-5-carboxylic acid Methyl 4-bromo-3-methyl-1-(5-(4-(trifluoromethyl) phenyl)-4-(4-(trifluoromethyl)piperidin-1-yl)thiazol-2-yl)-1H-pyrazole-5-carboxylate In a 5 mL glass microwave vial equipped with a magnetic stirring bar and nitrogen flow at room temperature was placed the methyl 4-bromo-1-(4-bromo-5-(4-(trifluoromethyl)phenyl)thiazol-2-yl)-3-methyl-1H-pyrazole-5-carboxylate prepared as described above with respect to Compound 37 (131 mg, 0.249 mmol), the 4-(trifluoromethyl) piperidine (47.3 mg, 0.249 mmol), $Cs_2CO_3$ (406 mg, 1.25 mmol), XantPhos (14 mg, 0.025 mmol) and dioxane (2.5 mL). Nitrogen was bubbled in the solvent for 10 minutes followed by the addition of the catalyst RuPhos Pd G1 (20 mg, 0.025 mmol). The vial was capped and placed in an oil bath at 105° C. for 16 h. The crude product was purified by flash chromatography on silica gel using a solution of ethyl acetate in hexanes (0 to 10% gradient) to give the title compound (74 mg, 0.12 mmol, 50%) as yellow oil.

4-(3-fluorophenyl)-3-methyl-1-(5-(4-(trifluoromethyl)phenyl)-4-(4-(trifluoromethyl)piperidin-1-yl) thiazol-2-yl)-1H-pyrazole-5-carboxylic acid In a 5 mL glass microwave vial equipped with a magnetic stirring bar and nitrogen flow at room temperature was placed the methyl 4-bromo-3-methyl-1-(5-(4-(trifluoromethyl)phenyl)-4-(4-(trifluoromethyl)piperidin-1-yl)thiazol-2-yl)-1H-pyrazole-5-carboxylate (74 mg, 0.12 mmol), (3-fluorophenyl)boronic acid (21 mg, 0.15 mmol) and $Na_2CO_3$ (66 mg, 0.62 mmol). Nitrogen gas was bubbled through a solution of dioxane/water (2 mL, 4:1) and then the solution was added to the microwave vial, followed by the addition of the catalyst $Pd(PPh_3)_4$(14 mg, 0.012 mmol). The vial was capped and placed in an oil bath at 85° C. for 16 h. LiOH (15 mg, 0.62 mmol) was added to the reaction mixture and stirred under microwave radiation at 115° C. for 15 min. The product was purified using a semi prep HPLC-MS (column X-Bridge 30×50, eluted with 60-80% MeCN/ $NH_4CO_2H$ 10 mM, pH 3.8/Flow 45 ml/min/10 min), resulting in the title compound (4.2 mg, 0.0070 mmol, 6%) as yellowish solid after lyophilization.

$^1$H NMR (500 MHz, MeOD) δ 7.91 (d, J=8.2 Hz, 2H), 7.74 (d, J=8.2 Hz, 2H), 7.50-7.43 (m, 1H), 7.38-7.32 (m, 1H), 7.32-7.27 (m, 1H), 7.15-7.08 (m, 1H), 3.59-3.50 (m, 2H), 3.00-2.91(m, 2H), 2.36 (s, 3H), 2.39-2.25 (m, 1H), 1.95-1.88 (m, 2H), 1.81-1.68 (m, 2H); MS (m/z): 599.1 [M+1]+

Compound 62: 4-(3-fluorophenyl)-1-(4-(3-fluorophenyl)-5-(4-(trifluoromethyl)phenyl)thiazol-2-yl)-3-methyl-1H-pyrazole-5-carboxylic acid The title compound was made in a manner analogous to Compound 36 as described above. $^1$H NMR (500 MHz, MeOD) δ 7.76 (d, J=8.2 Hz, 2H), 7.66 (d, J=8.2 Hz, 2H), 7.51-7.45 (m, 1H), 7.38-7.28 (m, 5H), 7.15-7.10 (m, 1H), 7.09-7.04 (m, 1H), 2.38 (s, 3H). MS (m/z): 542.1 $[M+1]^+$ Compound 63: 4-(3-fluorophenyl)-1-(5-(1-hydroxyethyl)-4-(4-(trifluoromethyl)phenyl)thiazol-2-yl)-3-methyl-1H-pyrazole-5-carboxylic acid The title compound was made in a manner analogous to Compound 64 as described below. $^1$H NMR (500 MHz, MeOD) δ 8.52 (bs, 1H), 7.96 (d, J=8.1 Hz, 2H), 7.72 (d, J=8.0 Hz, 2H), 7.43-7.31 (m, 3H), 7.05-7.01 (m, 1H), 5.30 (q, J=6.2 Hz, 1H), 2.34 (s, 3H), 1.61 (d, J=6.3 Hz, 3H). MS (m/z): 492.1 $[M+1]^+$.

Compound 64: 4-(3-fluorophenyl)-1-(5-(2-hydroxyethyl)-4-(4-(trifluoromethyl)phenyl)thiazol-2-yl)-3-methyl-1H-pyrazole-5-carboxylic acid methyl 4-bromo-3-methyl-1-(4-(4-(trifluoromethyl) phenyl)-5-vinylthiazole-2-yl)-1H-pyrazole-5-carboxylate In a 5 mL glass microwave vial equipped with a magnetic stirring bar at room temperature was placed methyl 4-bromo-1-(5-bromo-4-(4-(trifluoromethyl)phenyl)thiazol-2-yl)-3-methyl-1H-pyrazole-5-carboxylate prepared as described above with respect to Compound 36 (200 mg, 0.380 mmol), the potassium vinyltrifluoroborate (51 mg, 0.380 mmol), $K_2CO_3$ (158 mg, 1.14 mmol) and the catalyst $Pd(dtbpf)Cl_2$ (25 mg, 0.0380 mmol). THF (1.9 mL, 0.2 M) was added to the microwave tube and a flow of nitrogen was bubbled through the brown mixture for 5 minutes. The vial was capped and stirred in an oil bath at 90° C. for 16 h. After 16 h, the reaction was purified on a silica gel column using a mobile phase of 0-5% EtOAc in hexanes. The fractions containing the product were evaporated under reduced pressure to afford the title compound (104 mg, 0.220 mmol, 58%) as an off-white solid.

methyl 4-(3-fluorophenyl)-3-methyl-1-(4-(4-(trifluoromethyl)phenyl)-5-vinylthiazole-2-yl)-1H-pyrazole-5-carboxylate In a 5 mL glass microwave vial equipped with a magnetic stirring bar at room temperature was placed the methyl 4-bromo-3-methyl-1-(4-(4-(trifluoromethyl)phenyl)-5-vinylthiazol-2-yl)-1H-pyrazole-5-carboxylate (101 mg, 0.213 mmol), the (3-fluorophenyl)boronic acid (30 mg, 0.213 mmol), $Na_2CO_3$ (68 mg, 0.639 mmol) and the catalyst $Pd(PPh_3)_4$ (25 mg, 0.0213 mmol). THF:water (2.1 mL, 4:1, 0.1 M) which was deoxygenated with a flow of nitrogen for 5 minutes was added to the microwave tube. The vial was capped and stirred in an oil bath at 90° C. for 16 h. After 16 h, the reaction was purified on a silica gel column using a mobile phase of 0-5% EtOAc in hexanes. The fractions containing the product were evaporated under reduced pressure to afford the title compound (77 mg, 0.159 mmol, 75%) as a white solid.

4-(3-fluorophenyl)-1-(5-(2-hydroxyethyl)-4-(4-(trifluoromethyl)Phenyl)thiazol-2-yl)-3-methyl-1H-pyrazole-5-carboxylic acid In a 10 mL round bottom flask equipped with a magnetic stirring bar at room temperature was placed the methyl 4-(3-fluorophenyl)-3-methyl-1-(4-(4-(trifluoromethyl)phenyl)-5-vinylthiazol-2-yl)-1H-pyrazole-5-carboxylate (22 mg, 0.0451 mmol) in dry THF (0.5 mL, 0.1 M). The solution was cooled to 0° C. and borane-DMS (225 μL, 0.451 mmol) was added dropwise. The reaction was warmed to room temperature and stirred for 16 h under nitrogen atmosphere. After 16 h, 30% peroxide in water (250 μL) and NaOH (18 mg, 0.451 mmol) in water (250 μL) at 0° C. Reaction was stirred at room temperature for 16 h. Reaction was extracted with EtOAc three times. The combined organic layers were dried over $Na_2SO_4$, filtered and evaporated. The white solid was transferred into a microwave vial which was added LiOH (11 mg, 0.451 mmol) and THF:water (1.5 mL; 4:1, 0.03 M). The microwave vial was capped and heated at 110° C. for 15 minutes under microwave radiation. Reaction was filtered and the crude product was purified using a semi prep HPLC-MS (X-Bridge 30×50, eluted with 40-60% MeCN/$NH_4CO_2H$ 10 mM, pH 3.8/Flow 45 mL/min/11 min), resulting in the title compound (1 mg, 0.002 mmol, 5%) as a white solid after lyophilization.

$^1H$ NMR (500 MHz, MeOD) δ 7.96 (d, J=8.1 Hz, 2H), 7.71 (d, J=7.7 Hz, 2H), 7.42-7.30 (m, 3H), 7.05-7.01 (m, 1H), 3.86 (t, J=6.2 Hz, 2H), 3.20 (t, J=6.2 Hz, 2H), 2.33 (s, 3H); MS (m/z): 492.1 $[M+1]^+$.

Compound 65: 4-(3-fluorophenyl)-1-(5-(4-(2-methoxyethoxy)phenyl)-4-(4-(trifluoromethyl)phenyl)thiazol-2-yl)-3-methyl-1H-pyrazole-5-carboxylic acid The title compound was made in a manner analogous to Compound 36 as described above. $^1H$ NMR (500 MHz, DMSO) δ 7.71-7.63 (m, 4H), 7.53-7.46 (m, 1H), 7.39-7.32 (m, 4H), 7.24-7.16 (m, 1H), 7.06-7.00 (m, 2H), 4.16-4.12 (m, 2H), 3.70-3.66 (m, 2H), 3.32 (s, 3H), 2.31 (s, 3H). MS (m/z): 598.2 $[M+1]^+$.

Compound 66: 4-(3-fluorophenyl)-1-(5-(1-methoxyethyl)-4-(4-(trifluoromethyl)phenyl)thiazol-2-yl)-3-methyl-1H-pyrazole-5-carboxylic acid The title compound was made in a manner analogous to Compound 64 as described above. $^1H$ NMR (500 MHz, MeOD) δ 7.88 (d, J=7.9 Hz, 2H), 7.74 (d, J=8.1 Hz, 2H), 7.44-7.39 (m, 1H), 7.36-7.34 (m, 1H), 7.31-7.29 (m, 1H), 7.07-7.03 (m, 1H), 4.89-4.87 (m, 1H), 3.26 (s, 3H), 2.34 (s, 3H), 1.63 (d, J=6.3 Hz, 3H). MS (m/z): 506.1 $[M+1]^+$.

Compound 67: 4-(3-fluorophenyl)-1-(4-(4-isopropylpiperidin-1-yl)-5-(isopropylthio)thiazol-2-yl)-3-methyl-1H-pyrazole-5-carboxylic acid The title compound was made in a manner analogous to Compound 12 as described above. $^1H$ NMR (500 MHz, MeOD) δ 7.44-7.40 (m, 1H), 7.29 (d, J=7.6 Hz, 1H), 7.24 (d, J=9.7 Hz, 1H), 7.08-7.05 (m, 1H), 4.41 (d, J=12.8 Hz, 2H), 3.17-3.12 (m, 1H), 2.82 (t, J=12.3 Hz, 2H), 2.30 (s, 3H), 1.71 (d, J=12.2 Hz, 2H), 1.48-1.40 (m, 1H), 1.37-1.31 (m, 2H), 1.28 (d, J=6.7 Hz, 6H), 1.23-1.18 (m, 1H), 0.91 (d, J=6.7 Hz, 6H). MS (m/z): 503.3 $[M+1]^+$.

Compound 68: 4-(3-fluorophenyl)-1-(5-(isopropylthio)-4-(3-methoxy-3-(trifluoromethyl)-8-azabicyclo[3.2.1]octan-8-yl)thiazol-2-yl)-3-methyl-1H-pyrazole-5-carboxylic acid The title compound was made in a manner analogous to Compound 47 as described above. $^1H$ NMR (500 MHz, DMSO) δ 7.50-7.41 (m, 1H), 7.38-7.27 (m, 2H), 7.24-7.08 (m, 1H), 4.77 (s, 2H), 3.37 (s, 3H), 3.16-3.07 (m, 1H), 2.28 (s, 3H), 2.09-1.82 (m, 8H), 1.23 (d, J=6.7 Hz, 6H). MS (m/z): 585.1 $[M+1]^+$.

BJAB Data

BJAB cells (DSMZ) were maintained in RPMI 1640 growth medium+10% FBS at 37° C./5% $CO_2$ and used prior to passage 34. Cells were seeded in white Corning Costar 96-well assay plates at 2500 cells/well in 50 μL of medium. Serial dilutions of test compounds were made in cell culture medium/FBS+0.2% DMSO, and transferred to assay plates in a volume of 50 μL (DMSO at 0.1% final). Plates were maintained at 37° C. for approximately 72 hours. The effect of compounds on cell proliferation was evaluated using the Cell Titer Glo reagent (Promega), according to the manufacturer's instructions. Briefly, 100 μL of reagent was added per well, and after a 10 minute incubation luminescence values were determined on a plate reader (Tecan F200PRO). The percent of luminescence signal relative to untreated controls was calculated for each compound concentration, and $EC_{50}$ values were determined from dose response data by non-linear regression analysis using Prism (GraphPad). Data are shown in the compound table above. The mTor inhibitor Torin1 (Liu, et al. (2010) J. Med. Chem. 53, 7146.) was used as a control. The data are summarized in the compound table provided above.

Further studies on various test compounds indicated that cell viability decreased in a dose-dependent manner, and that the test compounds induced cell death in a dose-dependent manner 48 hours post-treatment.

BIOLOGICAL EXAMPLES

The present inventors have determined that, despite initial data suggesting that they inhibit the initiation of translation of RNA, an important biological effect caused by the compounds as described herein is the inhibition of cell cycle progression, as described by the data provided herein. While not intending to be bound by theory, the present inventors surmise that the compounds disclosed herein disrupt the cell cycle at the GO/G1 phase, preventing a cancer cell from further proliferation.

The examples below provide four measures of the activity of the compounds of the present disclosure, specifically with respect to a test compound falling within the broad scope of the compounds described herein, having an IC5o value in the "A" range. The test compound is believed to be representative of the active compounds as described herein. First is the overall sensitivity of tumor cell lines to the test compound. Second is the role of KRAS genotype on the sensitivity of the cells to the test compound. Third is the effect of the test compound on a key cellular metabolite, glutathione. And fourth is the effect of the test compound on the cell cycle.

Example 1: Anticancer Activity

A panel of 96 tumor and 3 normal cell lines were tested for sensitivity to the test compound. The cell lines were cultured in standard media and pipetted into 96-well plates at the required plating densities. The cells were acclimated for 24 hours prior to compound testing. Compound was prepared as a stock of 20 mM in DMSO. To prepare dose response curves compound was serially diluted in DMSO and dispensed into the plate wells using a Tecan D300e digital dispenser. The final DMSO concentration was 0.15%. After 72 hours of incubation cell number was determined using the CellTiter-Glo® (Promega) protocol. In this assay, ATP is measured as a surrogate of cell number. The activity of the compound is determined by comparing untreated cells with treated cells and calculating the % of signal retained. Compound activity is measured as an $EC_{50}$ of maximum level of efficacy and the two are used to compute an activity area curve.

Out of the 96 tumor cell lines, 39 tumors (40%) demonstrated a significant response to the test compound (as defined by ability to estimate an $ICO_{50}$; Table 1). Of these, hematopoetic tumors demonstrated a great enrichment of response. More than 89% of all hematopoetic tumors responded to compound, while 28.5% of solid tumors responded in kind.

TABLE 1

| Summary of tumor responsiveness | | | |
|---|---|---|---|
| | Number Responsive | | Responsiveness |
| Tumor type | No | Yes | (%) |
| Hematopoetic | 2 | 17 | 89 |
| Solid | 55 | 22 | 28.5 |

Data for various of the cell lines are provided in Table 2 below:

TABLE 2

Specific tumor responses

| Cell Line | Tumor Type | Tumor Category | K-RAS | KRAS Zyygosity | Computed IC50 | Activty Area | Max Inhibition_ % |
|---|---|---|---|---|---|---|---|
| 143b | Solid | Sarcoma | MUT | HET | Y | 2.00 | 63.84 |
| 786-0 | Solid | Renal | WT | HOMO | N | 1.05 | 24.32 |
| A204 | Solid | Sarcoma | WT | HOMO | N | 1.37 | 34.89 |
| A2058 | Solid | Skin | WT | HOMO | N | −0.08 | 6.18 |
| A2780 | Solid | Ovarian | WT | HOMO | Y | 3.88 | 70.89 |
| A375 | Solid | Skin | WT | HOMO | N | 1.14 | 29.08 |
| A498 | Solid | Renal | WT | HOMO | N | 2.29 | 46.35 |
| A549 | Solid | Lung | MUT | HOMO | Y | 3.92 | 81.53 |
| A673 | Solid | Sarcoma | WT | HOMO | Y | 2.29 | 57.68 |
| AU565 | Solid | Breast | WT | HOMO | Y | 2.82 | 84.45 |
| BT-474 | Solid | Breast | WT | HOMO | N | −.12 | -1.00 |
| BT-483 | Solid | Breast | WT | HOMO | N | 0.22 | 6.13 |
| BxPC-3 | Solid | Pancreatic | WT | HOMO | N | 1.46 | 30.79 |
| CaCo-2 | Solid | Colorectal | WT | HOMO | N | 0.07 | 22.11 |
| CAL-27 | Solid | Head and Neck | WT | HOMO | N | −.05 | 23.28 |
| COLO 205 | Solid | Colorectal | WT | HOMO | N | 2.40 | 49.77 |
| COLO-824 | Solid | Breast | WT | HOMO | N | -0.06 | 29.16 |
| Daudi | Hematopoetic | Hematopoietic | WT | HOMO | Y | 4.33 | 92.47 |
| DOHH-2 | Hematopoetic | Hematopoietic | WT | HOMO | Y | 5.04 | 100.21 |
| DU-145 | Solid | Prostate | WT | HOMO | N | 1.48 | 33.20 |
| EFM-19 | Solid | Breast | WT | HOMO | N | 0.51 | 29.01 |
| FADU | Solid | Head and Neck | WT | HOMO | N | 2.88 | 49.81 |
| HCC1143 | Solid | Breast | WT | HOMO | N | 0.95 | 19.79 |
| HCC1187 | Solid | Breast | WT | HOMO | N | 1.38 | 31.76 |
| HCC1395 | Solid | Breast | WT | HOMO | N | 1.08 | 33.13 |
| HCC1419 | Solid | Breast | WT | HOMO | N | 0.25 | 5.82 |
| HCC1500 | Solid | Breast | WT | HOMO | N | 0.82 | 55.17 |
| HCC1569 | Solid | Breast | WT | HOMO | N | −1.27 | 26.60 |
| HCC1806 | Solid | Breast | WT | HOMO | N | 1.00 | 56.75 |
| HCC1937 | Solid | Breast | WT | HOMO | N | 1.12 | 40.02 |
| HCC1954 | Solid | Breast | WT | HOMO | N | 1.08 | 21.92 |
| HCC38 | Solid | Breast | WT | HOMO | N | 0.13 | 9.67 |
| HCT-116 | Solid | Colorectal | MUT | HET | Y | 4.13 | 86.23 |
| Hep 3B2.1-7 | Solid | Liver | WT | HOMO | N | 1.21 | 23.73 |
| HepG2 | Solid | Liver | WT | HOMO | N | 0.70 | 19.20 |
| HL-60 | Hematopoetic | Hematopoietic | WT | HOMO | Y | 2.45 | 103.55 |
| Hs-445 | Hematopoetic | Hematopoietic | WT | HOMO | Y | 2.76 | 57.67 |
| HT-1080 | Solid | Sarcoma | WT | HOMO | Y | 3.03 | 77.72 |
| HT-29 | Solid | Colorectal | WT | HOMO | N | 1.89 | 46.47 |
| Jurkat | Hematopoetic | Hematopoietic | WT | HOMO | Y | 4.91 | 94.46 |
| K-562 | Hematopoetic | Hematopoietic | WT | HOMO | N | 0.30 | 30.94 |
| Kasumi-1 | Hematopoetic | Hematopoietic | WT | HOMO | Y | 2.70 | 63.46 |
| KHOS/NP | Solid | Sarcoma | NA | NA | N | 1.43 | 32.83 |
| LoVo | Solid | Colorectal | MUT | HET | Y | 3.70 | 61.30 |
| Malme-3M | Solid | Skin | WT | HOMO | N | −1.41 | 29.79 |
| MCF7 | Solid | Breast | WT | HOMO | Y | 2.43 | 54.45 |
| MDA-MB-157 | Solid | Breast | WT | HOMO | N | 1.77 | 31.44 |
| MDA-MB-231 | Solid | Breast | MUT | HET | N | 0.92 | 32.97 |
| MDA-MB-435S | Solid | Breast | WT | HOMO | N | 0.02 | 32.16 |
| MDA-MB- | | | | | | | |

TABLE 2-continued

| Specific tumor responses | | | | | | | |
|---|---|---|---|---|---|---|---|
| Cell Line | Tumor Type | Tumor Category | K-RAS | KRAS Zyygosity | Computed IC50 | Activty Area | Max Inhibition_ % |
| 436 | Solid | Breast | WT | HOMO | N | 1.33 | 28.79 |
| MDA-MB-453 | Solid | Breast | WT | HOMO | N | 0.83 | 42.71 |
| MDA-MB-468 | Solid | Breast | WT | HOMO | Y | 2.85 | 60.30 |
| MFM-223 | Solid | Breast | WT | HOMO | N | 1.12 | 22.49 |
| MG-63 | Solid | Sarcoma | WT | HOMO | N | 0.59 | 55.53 |
| MIA PaCa-2 | Solid | Pancreatic | MUT | HOMO | Y | 2.56 | 53.12 |
| MOLT-4 | Hematopoetic | Hematopoietic | WT | HOMO | Y | 3.12 | 65.24 |
| MV-4-11 | Hematopoetic | Hematopoietic | WT | HOMO | Y | 2.97 | 74.31 |
| NALM-6 | Hematopoetic | Hematopoietic | WT | HOMO | Y | 2.95 | 66.29 |
| NAMALWA | Hematopoetic | Hematopoietic | WT | HOMO | Y | 4.32 | 88.24 |
| NCI-H1734 | Solid | Lung | MUT | HET | Y | 2.43 | 62.45 |
| NCI-H2122 | Solid | Lung | MUT | HET | Y | 3.73 | 71.82 |
| NCI-H2444 | Solid | Lung | MUT | HOMO | N | −0.45 | 15.70 |
| NCI-H460 | Solid | Lung | MUT | HET | Y | 3.52 | 64.86 |
| NCI-H929 | Hematopoetic | Hematopoietic | WT | HOMO | N | 1.22 | 31.23 |
| OCI-LY7 | Hematopoetic | Hematopoietic | NA | NA | Y | 5.40 | 99.53 |
| OVCAR-3 | Solid | Ovarian | WT | HOMO | Y | 2.44 | 59.46 |
| PANC-1 | Solid | Pancreatic | MUT | HET | Y | 2.73 | 60.76 |
| PC-3 | Solid | Prostate | WT | HOMO | N | 0.27 | 15.52 |
| PC-9 | Solid | Lung | WT | HOMO | Y | 3.37 | 67.08 |
| Raji | Hematopoetic | Hematopoietic | WT | HOMO | Y | 3.21 | 80.38 |
| RL95-2 | Solid | Endometrial | WT | HOMO | N | 2.38 | 45.56 |
| RPMI-2650 | Solid | Head and Neck | WT | HOMO | N | 2.34 | 45.63 |
| RPMI-8226 | Hematopoetic | Hematopoietic | MUT | HET | Y | 2.94 | 60.91 |
| SJSA-1 | Solid | Sarcoma | MUT | HOMO | N | 0.46 | 36.32 |
| SK-BR-3 | Solid | Breast | NA | NA | N | 0.98 | 70.35 |
| SK-ES-1 | Solid | Sarcoma | WT | HOMO | N | 1.24 | 33.95 |
| SK-HEP-1 | Solid | Liver | WT | HOMO | Y | 2.72 | 60.08 |
| SK-MEL-28 | Solid | Skin | WT | HOMO | N | −1.15 | 8.99 |
| SK-N-AS | Solid | Neuroblastoma | WT | HOMO | N | −0.08 | 30.60 |
| SK-NEP-1 | Solid | Renal | WT | HOMO | N | 1.22 | 36.63 |
| SK-OV-3 | Solid | Ovarian | WT | HOMO | N | 0.60 | 33.48 |
| SU-DHL-10 | Hematopoetic | Hematopoietic | MUT | HET | Y | 5.37 | 100.83 |
| SU-DHL-4 | Hematopoetic | Hematopoietic | WT | HOMO | Y | 4.08 | 99.94 |
| SU-DHL-6 | Hematopoetic | Hematopoietic | WT | HOMO | Y | 4.76 | 100.72 |
| SUM190PT | Solid | Breast | WT | HOMO | Y | 2.69 | 77.18 |
| SUP-B15 | Hematopoetic | Hematopoietic | WT | HOMO | Y | 4.21 | 100.03 |
| SW48 | Solid | Colorectal | WT | HOMO | N | 0.06 | 11.53 |
| SW480 | Solid | Colorectal | MUT | HOMO | N | 0.90 | 20.83 |
| SW620 | Solid | Colorectal | MUT | HOMO | N | 2.04 | 47.00 |
| T.Tn | Solid | Esophagus | NA | NA | Y | 2.26 | 65.75 |
| T47D | Solid | Breast | WT | HOMO | N | 1.41 | 26.52 |
| TC-71 | Solid | Sarcoma | WT | HOMO | Y | 4.23 | 80.00 |
| U-118-MG | Solid | Brain | WT | HOMO | N | −0.24 | 18.15 |
| U-2 OS | Solid | Sarcoma | WT | HOMO | Y | 1.80 | 55.04 |
| U-87-MG | Solid | Brain | WT | HOMO | N | 0.82 | 24.25 |
| ZR-75-30 | Solid | Breast | WT | HOMO | N | 1.04 | 23.13 |

Example 2: Role of KRAS on Activity

Next, the genotype of the KRAS allele for the solid tumor lines was determined. Using the COSMIC database, KRAS genotype and zygosity (homozygous or heterozygous) could be determined for 74 of 77 solid tumor cell lines (Table 3).

TABLE 3

| Tumor responsiveness with respect to KRAS genotype | | | |
|---|---|---|---|
| | Number Responsive | | Responsiveness |
| KRAS genotype | N | Y | (%) |
| MUT | 5 | 9 | 65 |
| NA | 2 | 1 | 33 |
| WT | 48 | 12 | 20 |

Only 20% of the cell types having the wild-type KRAS allele were responsive to the test compound. In contrast, 65% of the cell types harboring a mutation in the KRAS allele were responsive to the test compound. When the analysis is extended to whether the KRAS allele is homozygous or heterozygous there is a distinct split in the outcome (Table 4). Cell lines bearing a heterozygous mutation in the KRAS allele showed greatest responsiveness.

TABLE 4

| Tumor responsiveness with respect to KRAS zygosity | | | |
|---|---|---|---|
| | KRAS MUT | | Responsiveness |
| Number Responsive | N | Y | (%) |
| HET | 1 | 7 | 87.5 |
| HOMO | 4 | 2 | 30 |
| NA | 0 | 1 | |

A final analysis of the role of KRAS on the response to the test compound used pooled data based on compound activity area. Responses of all cell lines were included in the analysis using Tukey's All Pairs HSD test. The data are presented in FIG. 1 as a plot of activity area by KRAS genotype and KRAS zygosity. The average responsiveness of the test compound in cell lines containing the KRAS mutant heterozygous genotype were significantly higher than corresponding WT cells lines.

Example 3: Cellular Metabolism and Activity

Measurement of glutathione levels following treatment using three cell lines: BJAB, HCT116, and normal human lung fibroblasts (NHLF) were maintained in RPMI (Wisent), McCoy's (Wisent) or FGM-2 (Lonza) medium, respectively. For total glutathione measurement, 5000 cells/well (BJAB or HCT116) or 10,000 cells/well (NHLF) were transferred to clear-bottom 96-well assay plates (Thermo Fisher) in a volume of 50 μL. Plates were incubated overnight at 37° C. in 5% $CO_2$, in an unsealed plastic bag with damp paper. Test compound was serially diluted in medium plus 0.4% DMSO, and 50 μL/well of each dilution was transferred to the assay plate. Assay plates were incubated at 37° C. in 5% $CO_2$ in unsealed plastic bag with damp paper for the indicated time. For total glutathione measurement, GSH-Glo™ reagent (Promega) was prepared by diluting provided Luciferin-NT (1:100), Glutathione S-Transferase (1:100), and DTT (1 mM final) to GSH-Glo™ Reaction buffer, and 100 μL was added to assay plates, followed by 30 min incubation at room temperature, and then 100 μL Luciferin Detection Reagent was added. Plates were maintained in the dark at room temperature for 10 min. Luminescence was measured using Tecan Infinite 200Pro.

Figure 2:
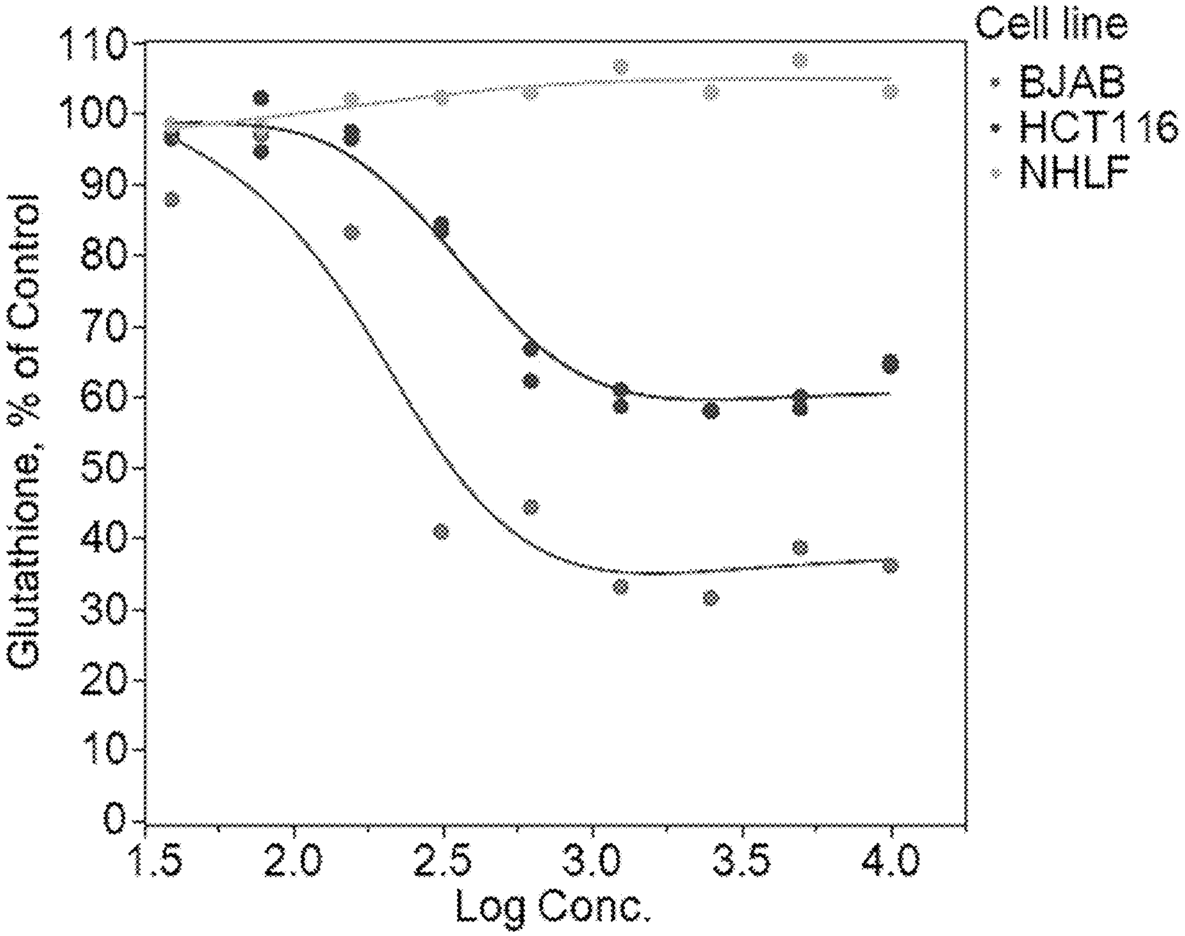
FIG. 2 is a graph showing glutathione levels in three cell lines (BJAB, HCT116, and NHFL) following treatment with the test compound. BJAB is represented by dark gray (bottom) line, HCT116 is represented by black (middle) line, and NHFL is represented by light gray (top) line.

FIG. 2 represents data from a typical experiment showing that the test compound reduced cellular glutathione levels in a dose dependent manner. Cell lines whose growth and survival are sensitive to the test compound (BJAB and HCT116) demonstrate a dose-dependent reduction in cellular glutathione levels while cell lines that are not sensitive (NHLF) fail to change.

To evaluate proliferation (in parallel with glutathione levels measurement), 50 μL/well of cells in the medium described above were added to clear 96-well plates (TPP). At the indicated times, cells were fixed by adding 50 μL cold 50% Trichloroacetic acid (TCA Sigma) and incubated at 4° C. for at least 45 minutes before rinsing with distilled water. A volume of 50 μL/well 0.4% (w/v) Sulforhodamine B (SRB, Sigma) in 1% acetic acid was added to the wells to determine total protein content. Plates were rinsed several times in a large volume of 1% acetic acid, to remove excess dye, then total protein was solubilized in 200 μl 10 mM unbuffered Tris base, agitating for 30 minutes. Absorbance was measured at 560 nm on Tecan Infinite 200Pro.

Effect on Glutathione levels: BJAB and HCT116 cells were maintained in RPMI medium (Wisent) or McCoy's medium (Wisent), respectively. 5000 cells/well were transferred to clear-bottom 96-well assay plates (Thermo Fisher) in a volume of 50 μL. Plates were incubated overnight at 37° C. in 5% $CO_2$, in an unsealed plastic bag with damp paper. Menadione (Sigma) was dissolved in DMSO and diluted in 10% heat inactivated FBS plus culture medium to 20 μM and 5 μM (0.2% DMSO for each). Culture medium was gently aspirated from cells and replaced by 50 μl diluted menadione or 0.2% DMSO for controls. Test compound was diluted to 80 μM (0.2% DMSO) in 10% heat inactivated FBS plus culture medium then diluted further to 5 μM, 1 μM, 0.5 μM and 0.05 μM (in 0.2% DMSO). 50 μL test compound solution was added to each well, with or without menadione. One μL of an N-acetyl cysteine (Sigma) solution at 100 mM in water was added where indicated. Assay plates were incubated for the times indicated at 37° C. 5% $CO_2$ in opened plastic bag with damp paper. Total glutathione levels were determined according to the procedure described above.

Figure 3:
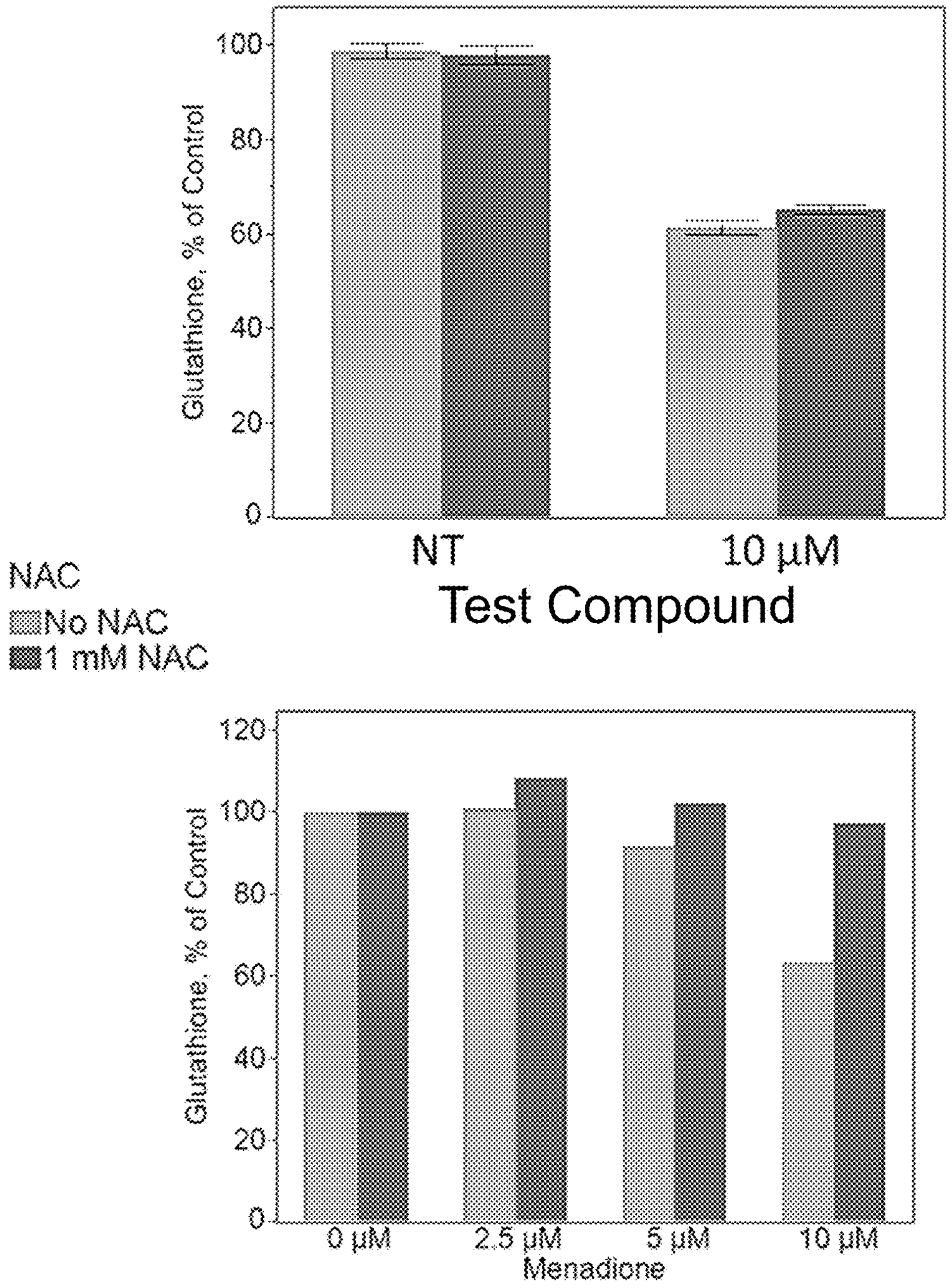
FIG. 3 is a pair of bar graphs demonstrating reduction in glutathione levels in HCT-116 cells after treatment with the test compound (top) and menadione treatment (bottom), both in the presence and absence of N-acetyl cysteine (NAC).

The inclusion of N-acetyl cysteine in the media prevents the reduction of glutathione caused by menadione. FIG. 3, top, represents the test compound-mediated reduction in glutathione levels in HCT116 cells. There was no difference in the levels of glutathione in the presence or absence of N-acetyl-cysteine. FIG. 3, bottom, demonstrates the menadione-mediated reduction in glutathione levels in HCT116 cells. This data suggests that the test compound reduces cellular glutathione in a manner distinct from agents that affect mitochondrial function and induce cellular ROS. Without being bound to particular theory, because N-acetyl cysteine fails to recover glutathione levels, it is believed that the defect in glutathione levels in treated cells is caused by an inability to synthesize glutathione after treatment with the test compound.

Example 3: Cell Cycle Analysis of Compound-Treated Cells

HCT116 cells ($3\times10^5$ cells) grown in McCoy media supplemented with heat inactivated fetal bovine serum were plated in 6-well plates and allowed to adhere overnight. Duplicate samples were prepared by treating cells for 24 hours with serum starvation (0% FBS), 5 μM test compound or DMSO vehicle control. Two hours prior to harvest, replicating DNA was labeled with EdU (5-Ethynyl-2'-deoxyuridine, Thermo Fisher) at 10 μM. Both adherent and floating cells were harvested and fixed in a solution of 4% paraformaldehyde in PBS for 15 minutes at room temperature. Next, cells were permeabilized in a solution of 0.25% v/v triton X-100/0.5% BSA/PBS for 20 minutes at room temperature. This was followed by click reaction with OG488-Azide to detect EdU incorporation as follows: cells were incubated for 30 minutes in a reaction mixture containing 100 mM Tris-HCl pH 7.6, 4 mM CuSO4, 10 μM OG488-azide, and 100 mM ascorbic acid. Excess reagent was removed by repeated washes in 0.5% BSA/PBS wash buffer. Cells were re-suspended in 500 μL of DAPI staining solution (1 μg/mL DAPI and 50 μg/mL RNAse A in PBS).

Flow cytometry analysis was performed in a LSRII flow cytometer (BD Biosciences) equipped with blue (488 nm), red (633 nm), and violet (405 nm) lasers. OG488 analysis was performed using 488 nm excitation and detection with a 505LP mirror and a 530/30BP filter. DAPI analysis was performed using a 405 nm excitation and detection with a 442/16BP filter. Voltage settings were: FSC=324, SSC=276, OG488=215, DAPI=351. Cell cycle analysis with DAPI was performed using a linear axis scale. Log scale was used for EdU. Data analysis was performed using FCS Express software version 6 (DeNovo Software).

Figure 4A:
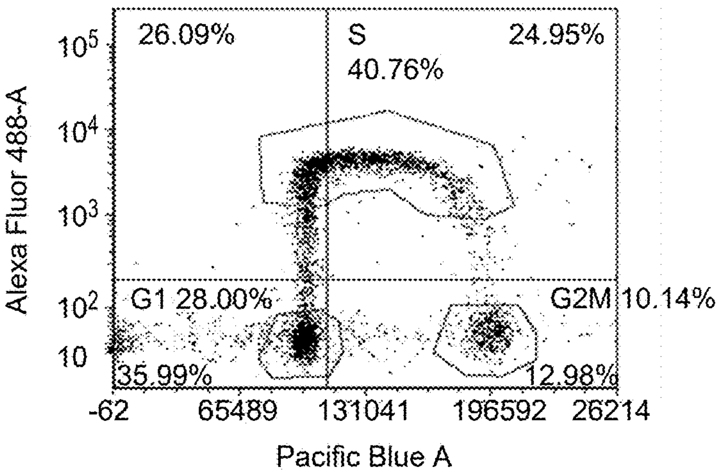
FIG. 4A is a set of graphs representing flow cytometry data collected from a representative cell cycle experiments in HCT116 cells after treatment with the test compound.
Figure 4A:
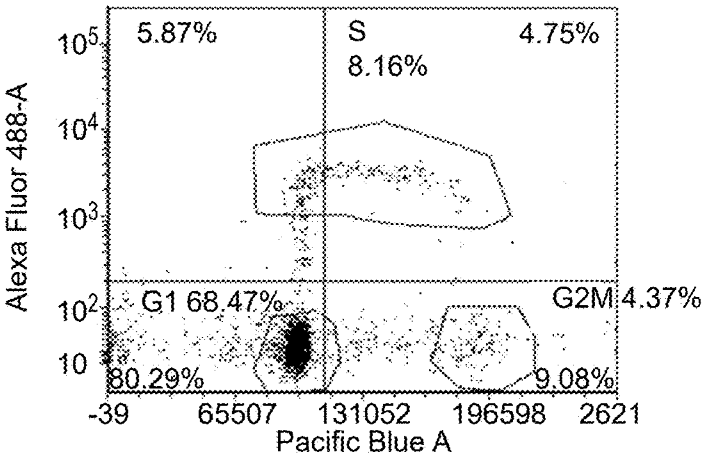
Figure 4A:
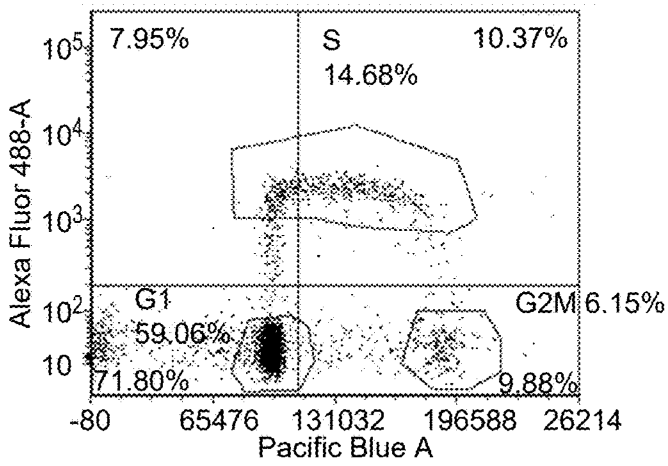
Figure 4B:
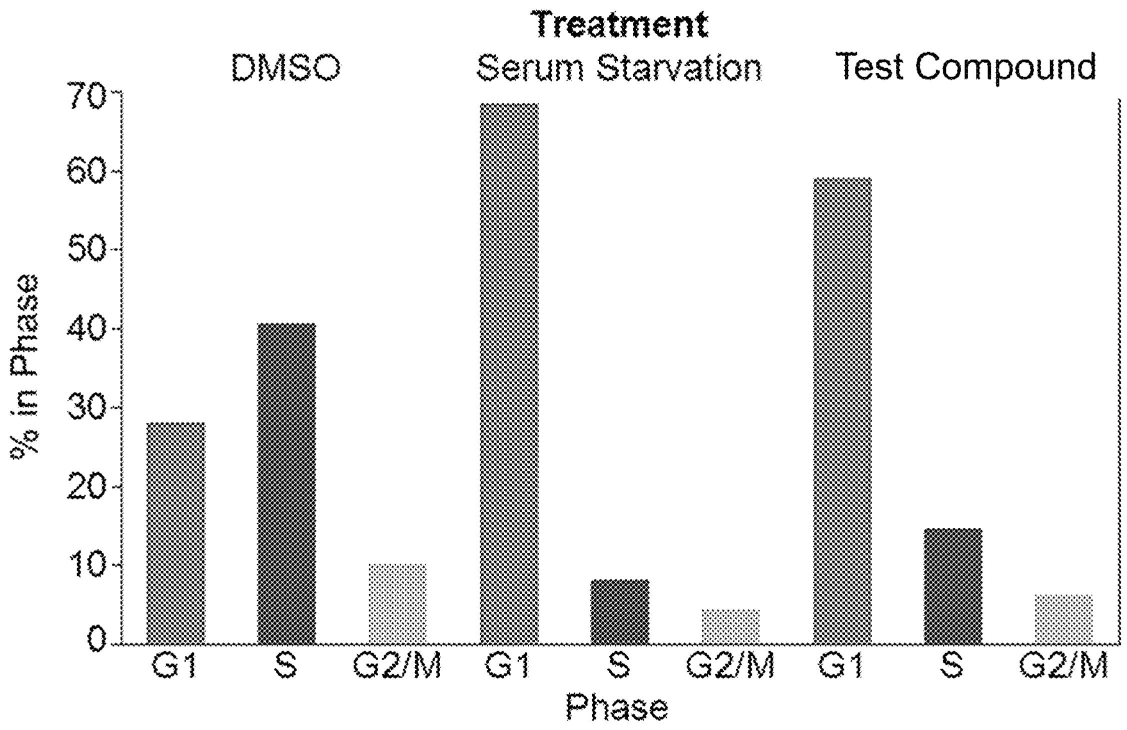
FIG. 4B is a bar representation of the data in FIG. 4A as the percentage of cells in each phase of the cell cycle.

FIG. 4A represents flow cytometry data collected from a representative cell cycle experiments in HCT116 cells after treatment with test compound. The data are presented as a dot plot of cell labeling data, with each channel being gated for detection and quantitation. FIG. 4B is bar representation of the data in FIG. 4A as the percentage of cells in each phase of the cell cycle. The data clearly demonstrate the effects of serum starvation on the cells by arresting cells in the G0/G1 phase. The test compound demonstrated a similar distribution of cells in G1, S and G2/M suggesting that the test compound is arresting cells in the GO/G1 phase.

It is understood that the examples and embodiments described herein are for illustrative purposes only and that various modifications or changes in light thereof will be suggested to persons skilled in the art and are to be incorporated within the spirit and purview of this application and scope of the appended claims.

We claim:

1. A compound having the structural formula (Ia):

(Ia)

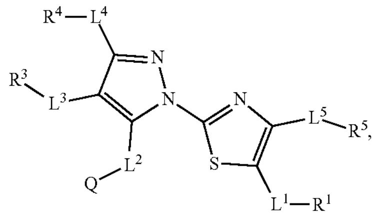

optionally in the form of a pharmaceutically acceptable salt, N-oxide, a solvate or hydrate thereof, wherein $L^1$ is —S— or a bond;

$R^1$ is selected from the group consisting of $C_1$-$C_8$ alkyl, $C_1$-$C_8$ alkenyl and $C_1$-$C_8$ alkynyl, each unsubstituted or fluorinated, $L^2$ is a bond or —$CH_2$—;

Q is —C(O)OH, —C(O)$OR^{2A}$, or —C(O)$NR^{2B}R^{2A}$, in which each $R^{2A}$ is independently selected from H and $C_1$-$C_3$ alkyl, and each $R^{2B}$ is independently selected from H and $C_1$-$C_3$ alkyl;

$L^3$ is a bond;

$R^3$ is phenyl or monocyclic heteroaryl, optionally substituted with 1-5 $R^{3E}$, in which each $R^{3E}$ is independently selected from oxo, optionally-substituted $C_1$-$C_4$ alkyl, $C_1$-$C_4$ fluoroalkyl, halogen, —CN, $SF_5$, —$N_3$, —C(O)$R^{3F}$, —$SR^{3F}$, —$S(O)_{1-2}R^{3F}$, —$OR^{3F}$, —$NR^{3G}R^{3F}$, —C(O)$R^{3F}$, —C(O)$NR^{3G}R^{3F}$, —$NR^{3G}$C(O)$R^{3F}$, —C(S)$NR^{3G}R^{3F}$, —$NR^{3G}$C(S)$R^{3F}$, —C(O)$OR^{3F}$, —OC(O)$R^{3F}$, —C(O)$SR^{3F}$, —SC(O)$R^{3F}$, —C(S)$OR^{3F}$, —OC(S)$R^{3F}$, —C(S)$SR^{3F}$, —SC(S)$R^{3F}$, —$S(O)_{1-2}OR^{3F}$, —$OS(O)_{1-2}R^{3F}$, —$S(O)_{1-2}NR^{3G}R^{3F}$, and —$NR^{3G}S(O)_{1-2}R^{3F}$;

each $R^{3F}$ is independently selected from H, $C_1$-$C_3$ alkyl and $C_1$-$C_3$ fluoroalkyl and each $R^{3G}$ is independently selected from H, $C_1$-$C_3$ alkyl, and $C_1$-$C_3$ fluoroalkyl;

$L^4$ is a bond, $R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl;

$L^5$ is a bond, $R^5$ is cycloalkyl or heterocycloalkyl, each optionally substituted with 1-5 $R^{5E}$, in which each $R^{5E}$ is independently selected from oxo, optionally-substituted $C_1$-$C_4$ alkyl, $C_1$-$C_4$ fluoroalkyl, halogen, —CN, —$SF_5$, —$N_3$, —C(O)$R^{5F}$, $SR^{5F}$, —$S(O)_{12}R^{5F}$, —$OR^{5F}$, —$NR^{5G}R^{5F}$, —C(O)$R^{5F}$, —C(O)$NR^{5G}R^{5F}$, —$NR^{5G}$C(O)$R^{5F}$, —C(S)$NR^{5G}R^{5F}$, —$NR^{1G}$C(S)$R^{5F}$, —C(O)$OR^{5F}$, —OC(O)$R^{5F}$, —C(O)$SR^{5F}$, —SC(O)$R^{5F}$, —C(S)$OR^{5F}$, —OC(S)$R^{5F}$, —C(S)$SR^{5F}$, —SC(S)$R^{5F}$, —$S(O)_{1-2}OR^{5F}$, —$OS(O)_{1-2}R^{5F}$, —$S(O)_{1-2}NR^{5G}R^{5F}$ and —$NR^{5G}S(O)_{1-2}R^{5F}$;

each $R^{5F}$ is independently selected from H, $C_1$-$C_3$ alkyl and $C_1$-$C_3$ fluoroalkyl and each $R^{5G}$ is independently selected from H and $C_1$-$C_3$ alkyl;

wherein each optionally substituted alkyl, alkenyl and alkynyl is unsubstituted, fluorinated or substituted with one or two hydroxyl groups;

each cycloalkyl has 3-10 ring carbons and is saturated or partially unsaturated, and optionally has one or two fused cycloalkyl rings, each fused ring having 3-8 ring members;

each heterocylcloalkyl has 3-10 ring members and 1-3 heteroatoms independently selected from nitrogen, oxygen and sulfur and is saturated or partially unsaturated, and optionally has one or two fused cycloalkyl rings, each having 3-8 ring members;

each monocyclic heteroaryl is a 5-6 membered monocyclic heteroaryl ring having 1-4 heteroatoms independently selected from nitrogen, oxygen and sulfur.

2. The compound according to claim 1, wherein $L^1$ is —S—.

3. The compound according to claim 1, wherein $R^1$ is unsubstituted.

4. The compound according to claim 1, wherein $R^1$ is $C_1$-$C_8$ alkyl.

5. The compound according to claim 1, wherein $R^1$ is propyl, butyl or butenyl.

6. The compound according to claim 1, wherein $L^2$ is a bond.

7. The compound according to claim 1, wherein Q is —C(O)OH wherein Q is —C(O)OH.

8. The compound according to claim 1, wherein Q is —C(O)O($C_1$-$C_3$alkyl).

9. The compound according to claim 1, wherein $R^3$ is phenyl optionally substituted with 1-5 $R^{3E}$.

10. The compound according to claim 1, wherein $R^4$ is unsubstituted $C_1$-$C_3$ alkyl.

11. The compound according to claim 1, wherein $R^5$ is heterocycloalkyl optionally substituted with 1-5 $R^{5E}$.

12. The compound according to claim 11, wherein the heterocycloalkyl is a monocyclic nitrogen-containing heterocycloalkyl, attached to the -$L^5$- through a nitrogen atom.

13. The compound according to claim 1, wherein $R^5$ is cycloalkyl optionally substituted with 1-5 $R^{5E}$.

14. The compound according to claim 13, wherein the cycloalkyl of $R^5$ is monocyclic and is partially unsaturated.

15. The compound according to claim 1, wherein each optionally substituted alkyl, alkenyl and alkynyl is unsubstituted or fluorinated.

16. The compound according to claim 1, wherein $L^1$ is —S—;

$R^1$ is propyl, butyl or butenyl;

$L_2$ is a bond;

Q is —C(O)OH;

$R^3$ is phenyl optionally substituted with 1-5 $R^{3E}$;

$R^4$ is unsubstituted $C_1$-$C_3$ alkyl; and each optionally substituted alkyl, alkenyl and alkynyl is unsubstituted or fluorinated.

17. The compound according to claim 16, wherein $R^5$ is monocyclic heterocycloalkyl optionally substituted with 1-5 $R^{5E}$, the monocyclic heterocycloalkyl being attached to the -$L^5$- through a nitrogen atom.

18. The compound according to claim 16, wherein $R^5$ is monocyclic cycloalkyl optionally substituted with 1-5 $R^{5E}$.

19. The compound according to claim 18, wherein the monocyclic cycloalkyl of $R^5$ is partially unsaturated.

20. The compound according to claim 1, wherein the compound is 4-(3-fluorophenyl)-1-(5-(isopropylthio)-4-(4-methylcyclohex-1-en-1-yl)thiazol-2-yl)-3-methyl-1H-pyrazole-5-carboxylic acid;

4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid;

1-(4-(4,4-dimethylcyclohex-1-en-1-yl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-(1,4-dioxaspiro[4.5]dec-7-en-8-yl)thiazol-2-yl)-3-methyl-1H-pyrazole-5-carboxylic acid;

4-(3-fluorophenyl)-1-(5-(isopropylthio)-4-(piperidin-1-yl)thiazol-2-yl)-3-methyl-1H-pyrazole-5-carboxylic acid;

4-(3-fluorophenyl)-1-(5-(isopropylthio)-4-(4-(trifluoromethyl)piperidin-1-yl)thiazol-2-yl)-3-methyl-1H-pyrazole-5-carboxylic acid;

4-(3-fluorophenyl)-1-(5-(isopropylthio)-4-morpholinothiazol-2-yl)-3-methyl-1H-pyrazole-5-carboxylic acid;

1-(4-(4,4-difluoropiperidin-1-yl)-5-(isopropylthio)thiazol-2-yl)-4-(3-fluorophenyl)-3-methyl-1H-pyrazole-5-carboxylic acid;

methyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;

4-(3-fluorophenyl)-1-(5-isobutyl-4-(4-(trifluoromethyl)phenyl)thiazol-2-yl)-3-methyl-1H-pyrazole-5-carboxylic acid;

4-(3-fluorophenyl)-1-(5-(isopropylthio)-4-(4-(2,2,2-trifluoroethyl)piperazin-1-yl)thiazol-2-yl)-3-methyl-1H-pyrazole-5-carboxylic acid;

1-(4-(4-cyanopiperidin-1-yl)-5-(isopropylthio)thiazol-2-yl)-4-(3-fluorophenyl)-3-methyl-1H-pyrazole-5-carboxylic acid;

1-(4-(4-cyclopropylpiperazin-1-yl)-5-(isopropylthio)thiazol-2-yl)-4-(3-fluorophenyl)-3-methyl-1H-pyrazole-5-carboxylic acid;

1-(4-(4-ethylpiperazin-1-yl)-5-(isopropylthio)thiazol-2-yl)-4-(3-fluorophenyl)-3-methyl-1H-pyrazole-5-carboxylic acid;

1-(4-(4-acetylpiperazin-1-yl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-(4-methylpiperidin-1-yl)thiazol-2-yl)-3-methyl-1H-pyrazole-5-carboxylic acid;

4-(3-fluorophenyl)-1-(5-(isopropylthio)-4-(4-methylpiperazin-1-yl)thiazol-2-yl)-3-methyl-1H-pyrazole-5-carboxylic acid;

1-(4-(4,4-dimethylpiperidin-1-yl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-(3-(trifluoromethyl)pyrrolidin-1-yl)thiazol-2-yl)-3-methyl-1H-pyrazole-5-carboxylic acid;

1-(4-(4-(tert-butyl)piperidin-1-yl)-5-(isopropylthio)thiazol-2-yl)-4-(3-fluorophenyl)-3-methyl-1H-pyrazole-5-carboxylic acid;

4-(3-fluorophenyl)-1-(5-(isopropylthio)-4-(6-azaspiro[2.5]octan-6-yl)thiazol-2-yl)-3-methyl-1H-pyrazole-5-carboxylic acid;

4-(3-fluorophenyl)-1-(5-(isopropylthio)-4-(4-methoxy-4-(trifluoromethyl)piperidin-1-yl)thiazol-2-yl)-3-methyl-1H-pyrazole-5-carboxylic acid; or 4-(3-fluorophenyl)-1-(4-(4-isopropylpiperidin-1-yl)-5-(isopropylthio)thiazol-2-yl)-3-methyl-1H-pyrazole-5-carboxylic acid, optionally in the form of a pharmaceutically acceptable salt, N-oxide, a solvate or hydrate thereof.

21. A method for treating a hyperproliferative disorder in a subject in need thereof, comprising administering to the subject an effective amount of a compound of claim 1.

22. A method for inhibiting cell cycle progression in, inducing apoptosis in, inducing a cytotoxic effect on, or inhibiting glutathione synthesis in a cancer cell, the method comprising contacting the cancer cell with an effective amount of a compound of claim 1.

* * * * *